United States Patent
Iyengar et al.

(10) Patent No.: US 7,119,205 B2
(45) Date of Patent: Oct. 10, 2006

(54) THIENOPYRIDONES AS AMPK ACTIVATORS FOR THE TREATMENT OF DIABETES AND OBESITY

(75) Inventors: Rajesh R. Iyengar, Lindenhurst, IL (US); Andrew S. Judd, Grayslake, IL (US); Gang Zhao, Northbrook, IL (US); Philip R. Kym, Libertyville, IL (US); Hing L. Sham, Vernon Hills, IL (US); Yugui Gu, Libertyville, IL (US); Gang Liu, Gurnee, IL (US); Mei Liu, Gurnee, IL (US); Hongyu Zhao, Buffalo Grove, IL (US); Richard F. Clark, Gurnee, IL (US); Ernst U. Frevert, Deerfield, IL (US); Barbara L. Cool, Highland Park, IL (US); Tianyuan Zhang, Gurnee, IL (US); Robert F. Keyes, Pleasant Prairie, WI (US); Todd M. Hansen, Grayslake, IL (US); Zhili Xin, Lake Bluff, IL (US)

(73) Assignee: Abbott Laboratories, Abbott Park, IL (US)

( * ) Notice: Subject to any disclaimer, the term of this patent is extended or adjusted under 35 U.S.C. 154(b) by 127 days.

(21) Appl. No.: 10/847,144

(22) Filed: May 17, 2004

(65) Prior Publication Data

US 2005/0038068 A1   Feb. 17, 2005

Related U.S. Application Data

(60) Provisional application No. 60/471,064, filed on May 16, 2003.

(51) Int. Cl.
*C07D 471/102* (2006.01)
*A61K 31/395* (2006.01)

(52) U.S. Cl. .................................. 546/114; 514/301
(58) Field of Classification Search .............. 546/114; 514/301
See application file for complete search history.

(56) References Cited

U.S. PATENT DOCUMENTS 5,378,679 A * 1/1995 Nuebling et al. ........... 504/246
5,602,144 A * 2/1997 Gottschlich et al. ........ 514/301

OTHER PUBLICATIONS

Buchstaller et al., Thieno[2,3-b]pyridinoes as Antagonists on the Glycine Site of the N-methyl-D-aspartate Receptor—Binding Studies, Molecular Modeling and Structure-Activity-Relationships, Scientia Pharmaceutica 68(1):3-14 (2000).*

Bergeron, R., et al., "Effect of 5-Aminoimidazole-4-Carboxamide-1-[beta]-D-Ribofuranoside Infusion on In Vivo Glucose and Lipid Metabolism in Lean and Obese Zucker Rats", *Diabetes*, 50(5):1076-1082 (2001).

Blázquez, C., et al., "The AMP_Activated Protein Kinase is Involved in the Regulation of Ketone Body Production by Astrocytes", *Journ of Neurochemistry*, 73:1674-1682 (1999).

Carling, D., et al., "A common bicyclic protein kinase cascade inactivates the regulatory enzymes of fatty acid and cholesterol biosynthesis", *FEB*, 223(2):217-222 (1987).

Corton, J. M., et al., "5-Aminoimidazole-4-carboxamide ribonucleoside—A specific method for activating AMP-activated protein kinase in intact cells?", *Eur. J. Biochem.*, 229:558-565 (1995).

Buhl, Esbes S., et al., "Long-Term AICAR administration Reduces Metabolic Disturbances and Lowers Blood Pressure in Rats Displaying Features of the Insulin Resistance Syndrome", *Diabetes*, 51(7):2199-2206 (2002).

Garton, A. J., et al., "Phosphorylation of bovine hormone-sensitive lipase by the AMP-activated protein kinase", *Eur. J. Biochem.*, 179:249-254 (1989).

Halseth, A. E., et al., "Acute and chronic treatment of ob/ob and db/db mice with AICAR decreases blood glucose concentrations", *Biochem & Biophys Res Comm.*, 294:798-805 (2002).

Hardie, D. G., & Hayley, S. A., "AMP-activated protein kinase: the energy charge hypothesis revisited", *BioEssays*, 23(12):1112-1119 (2001).

Hwang, K-J., et al., "4-Hydroxy-6-Oxo-6,7-Dihydro-Thieno[2,3-b] Pyrimidine Derivatives: Synthesis and Their Biological Evaluation for the Glyciine Site Acting on the *N*-Methyl-D-Aspartate (NMDA) Receptor", *Arch Pharm Res.*, 24(4):270-275 (2001).

Isabelle, L., et al., "Hepatocyte Nuclear Factor-4[alpha] Involved in Type 1 Maturity-Onset Diabetes of the Young Is a Novel Target of AMP-Activated Protein Kinase", *Diabetes*, 50(7):1515-1521 (2001).

Kemp et al., "AMP-activated protein kinase, super metabolic regulator," Biochem. Soc. Transactions 31:162-168 (2003).

Lockhead, P., et al., "5-Aminoimidazole-4-Carboxamide Riboside Mimics the Effects of Insulin on the Expression of the 2 Key Gluconeogenic Genes PEPCK and Glucose-6-Phosphatase", *Diabetes*, 49(6):896-903 (2000).

(Continued)

Primary Examiner—Celia Chang
(74) Attorney, Agent, or Firm—Andrew M. Parial; Johanna M. Corbin

(57) ABSTRACT

The present invention relates to compounds that activate AMP-activated protein kinase (AMPK), including the preparation of the compounds, compositions containing the compounds and the use of the compounds in the prevention or treatment of disorders such as diabetes, metabolic syndrome, and obesity.

14 Claims, No Drawings

OTHER PUBLICATIONS

Minokoshi, Y., et al., "Leptin stimulates fatty-acid oxidation by activating AMP-activated protein kinase", *Nature*, 415:339-343 (2002).

Mu, J., et al., "A Role of AMP-Activated Protein Kinase in Contraction and Hypoxia-Regulated Glucose Transport in Skeletal Muscle", *Molecular Cell*, 7:1085-1094 (2001).

Muoio, D. M., et al., "AMP-activated kinase reciprocally regulates triacylglycerol synthesis and fatty acid oxidation in liver and muscle: evidence that *sn*-glycerol-3-phosphate acyltransferase is a novel target", *Biochem J.*, 338:783-791 (1999).

Musi, N., & Goodyear, L. J., "Targeting the AMP-Activated Protein Kinase for the Treatment of Type 2 Diabetes", *Current Drug Targets-Imm. End & Metabo. Disor.*, 2:119-127 (2002).

Musi, N., et al., "Metformin Increases AMP-Activated Protein Kinase Activity in Skeletal Muscle of Subjects With Type 2 Diabetes", *Diabetes*, 51(7):2074-2081 (2002).

Saha, A. K., et al., "Activation of Malonyl-CoA Decarboxylase in Rat Skeletal Muscle by Contraction and the AMP-activated Protein Kinase Activator 5-Aminomidazole-4-carboxamide-1-B-$_D$-ribofuranoside", *J. Biol. Chem.*, 275(32):24279-24283 (2000).

Song, X. M., et al., "5-Aminoimidazole-4-carboxamide ribonucleoside treatment improves glucose homeostasis in insulin-resistant diabetic (*ob/ob*) mice", *Diabetologia*, 45:56-65 (2002).

Tomas, E., et al., "Enhanced muscle fat oxidation and glucose transport by ACRP30 globular domain: Acetyl-CoA carboxylase inhibition and AMP-activated protein kinase activation", *PNAS*, 99*25):16309-16313 (2002).

Yamauchi, T., et al., "Adiponectin stimulates glucose utilization and fatty-acid oxidation by activating AMP-activated protein kinase", *nature medicine*, 8(11):1288-1295 (2002.

Chen, Z-P., et al., "AMP-activated protein kinase phosphorylation of endothelial NO synthase", *FEBS Letters*, 443:285-289 (1999).

Zhou, G., et al., "Role of AMP-activated protein kinase in mechanism of metformin action", *The Journ of Clin Invest.*, 108(8):1167-1174 (2001).

Zhou, M., et al., "UCP-3 expression in skeletal muscle: effects, hypoxia, and AMP-activated protein kinase", *Am J Physiol Endoc Metab.*, 279:E622-E629 (2000).

* cited by examiner

THIENOPYRIDONES AS AMPK ACTIVATORS FOR THE TREATMENT OF DIABETES AND OBESITY

This application claims priority to the provisional application Ser. No. 60/471,064 filed on May 16, 2003.

TECHNICAL FIELD

The present invention relates to compounds that activate AMP-activated protein kinase (AMPK), including the preparation of the compounds, compositions containing the compounds and the use of the compounds in the prevention or treatment of disorders such as diabetes, metabolic syndrome, and obesity.

BACKGROUND OF THE INVENTION

AMPK is well established as a sensor and regulator of cellular energy homeostasis (Hardie, D. G. and Hawley, S. A. AMP-activated protein kinase: the energy charge hypothesis revisited. Bioessays 23: 1112 (2001), Kemp, B. E. et.al. AMP-activated protein kinase, super metabolic regulator. Biochem. Soc. Transactions 31:162 (2003)). Allosteric activation of this kinase due to rising AMP levels occurs in states of cellular energy depletion. The resulting serine/threonine phosphorylation of target enzymes leads to an adaptation of cellular metabolism to the low energy state. The net effect of AMPK activation induced changes is inhibition of ATP consuming processes and activation of ATP generating pathways, and therefore regeneration of ATP stores. Examples of AMPK substrates include acetyl-CoA-carboxylase (ACC) and HMG-CoA-reductase (Carling, D. et.al. A common bicyclic protein kinase cascade inactivates the regulatory enzymes of fatty acid and cholesterol biosynthesis. FEBS Letters 223:217 (1987)). Phosphorylation and therefore inhibition of ACC leads to a decrease in fatty acid synthesis (ATP-consuming) and at the same time to an increase in fatty acid oxidation (ATP-generating). Phosphorylation and resulting inhibition of HMG-CoA reductase leads to a decrease in cholesterol synthesis. Other substrates of AMPK include hormone sensitive lipase (Garton, A. J. et.al. Phosphorylation of bovine hormone-sensitive lipase by the AMP-activated protein kinase. A possible antilipolytic mechanism. Eur. J. Biochem. 179:249 (1989)), glycerol-3-phosphate acyltransferase (Muoio, D. M. et.al. AMP-activated kinase reciprocally regulates triacylglycerol synthesis and fatty acid oxidation in liver and muscle: evidence that sn-glycerol-3-phosphate acyltransferase is a novel target. Biochem. J. 338:783 (1999)), malonyl-CoA decarboxylase (Saha, A. K. et.al. Activation of malonyl-CoA decarboxylase in rat skeletal muscle by contraction and the AMP-activated protein kinase activator 5-aminoimidazole-4-carboxamide-1-β-D-ribofuranoside. J. Biol. Chem. 275:24279 (2000)), and hepatocyte nuclear factor-4α (Leclerc, I. et.al. Hepatocyte nuclear factor-4α involved in type-1 maturity-onset diabetes of the young is a novel target of AMP-activated protein kinase. Diabetes 50:1515 (2001)), some of which are potential drug targets for components of the metabolic syndrome. Additional processes that are believed to be regulated through AMPK activation, but for which the exact AMPK substrates have not been identified, include stimulation of glucose transport in skeletal muscle and expressional regulation of key genes in fatty acid and glucose metabolism in liver (Hardie, D. G. and Hawley, S. A. AMP-activated protein kinase: the energy charge hypothesis revisited. Bioessays 23: 1112 (2001), Kemp, B. E. et.al. AMP-activated protein kinase, super metabolic regulator. Biochem. Soc. Transactions 31:162 (2003), Musi, N. and Goodyear, L. J. Targeting the AMP-activated protein kinase for the treatment of type 2 diabetes. Current Drug Targets-Immune, Endocrine and Metabolic Disorders 2:119 (2002)). For example, decreased expression of glucose-6-phosphatase (Lochhead, P. A. et.al. 5-aminoimidazole-4-carboxamide riboside mimics the effects of insulin on the expression of the 2 key gluconeogenic genes PEPCK and glucose-6-phosphatase. Diabetes 49:896 (2000)), a key enzyme in hepatic glucose production, and SREBP-1c (Zhou, G. et.al. Role of AMP-activated protein kinase in mechanism of metformin action. The J. of Clin. Invest. 108: 1167 (2001)), a key lipogenic transcription factor, has been found following AMPK stimulation.

More recently an involvement of AMPK in the regulation of not only cellular but also whole body energy metabolism has become apparent. It was shown that the adipocyte-derived hormone leptin leads to a stimulation of AMPK and therefore to an increase in fatty acid oxidation in skeletal muscle (Minokoshi, Y. et.al. Leptin stimulates fatty-acid oxidation by activating AMP-activated protein kinase. Nature 415: 339 (2002)). Adiponectin, another adipocyte derived hormone leading to improved carbohydrate and lipid metabolism, has been demonstrated to stimulate AMPK in liver and skeletal muscle (Yamauchi,T. et.al. Adiponectin stimulates glucose utilization and fatty acid oxidation by activating AMP-activated protein kinase. Nature Medicine 8: 1288 (2002), Tomas, E. et.al. Enhanced muscle fat oxidation and glucose transport by ACRP30 globular domain: Acetyl-CoA carboxylase inhibition and AMP-activated protein kinase activation. PNAS 99: 16309(2002)). The activation of AMPK in these circumstances seems to be independent of increasing cellular AMP levels but rather due to phosphorylation by one or more yet to be identified upstream kinases.

Based on the knowledge of the above-mentioned consequences of AMPK activation, profound beneficial effects would be expected from in vivo activation of AMPK. In liver, decreased expression of gluconeogenic enzymes would reduce hepatic glucose output and improve overall glucose homeostasis, and both direct inhibition and/or reduced expression of key enzymes in lipid metabolism would lead to decreased fatty acid and cholesterol synthesis and increased fatty acid oxidation. Stimulation of AMPK in skeletal muscle would increase glucose uptake and fatty acid oxidation with resulting improvement of glucose homeostasis and, due to a reduction in intra-myocyte triglyceride accumulation, to improved insulin action. Finally, the increase in energy expenditure should lead to a decrease in body weight. The combination of these effects in the metabolic syndrome would be expected to significantly reduce the risk for acquiring cardiovascular diseases.

Several studies in rodents support this hypothesis (Bergeron, R. et.al. Effect of 5-aminoimidazole-4-carboxamide-1 (beta)-D-ribofuranoside infusion on in vivo glucose metabolism in lean and obese Zucker rats. Diabetes 50:1076 (2001), Song, S. M. et.al. 5-Aminoimidazole-4-darboxamide ribonucleoside treatment improves glucose homeostasis in insulin-resistant diabeted (ob/ob) mice. Diabetologia 45:56 (2002), Halseth, A. E. et.al. Acute and chronic treatment of ob/ob and db/db mice with AICAR decreases blood glucose concentrations. Biochem. and Biophys. Res. Comm. 294: 798 (2002), Buhl, E. S. et.al. Long-term AICAR administration reduces metabolic disturbances and lowers blood pressure in rats displaying feature of the insulin resistance syndrome. Diabetes 51: 2199 (2002)). Until recently most in vivo studies have relied on the AMPK activator AICAR, a cell permeable precursor of ZMP. ZMP acts as an intracellular AMP mimic, and, when accumulated to high enough levels, is able to stimulate AMPK activity (Corton, J. M. et.al. 5-Aminoimidazole-4-carboxamide ribonucleoside, a specific method for activating AMP-activated protein kinase in intact cells? Eur. J. Biochem. 229: 558 (1995)). However, ZMP also acts as an AMP mimic in the regulation of other enzymes, and is therefore not a specific AMPK activator (Musi, N. and Goodyear, L. J. Targeting the AMP-activated protein kinase for the treatment of type 2 diabetes. Current Drug Targets-Immune, Endocrine and Metabolic Disorders 2:119 (2002)). Several in vivo studies have demonstrated beneficial effects of both acute and chronic AICAR administration in rodent models of obesity and type 2 diabetes (Bergeron, R. et.al. Effect of 5-aminoimidazole-4-carboxamide-1(beta)-D-ribofuranoside infusion on in vivo glucose metabolism in lean and obese Zucker rats. Diabetes 50:1076 (2001), Song, S. M. et.al. 5-Aminoimidazole-4-darboxamide ribonucleoside treatment improves glucose homeostasis in insulin-resistant diabeted (ob/ob) mice. Diabetologia 45:56 (2002), Halseth, A. E. et.al. Acute and chronic treatment of ob/ob and db/db mice with AICAR decreases blood glucose concentrations. Biochem. and Biophys. Res. Comm. 294:798 (2002), Buhl, E. S. et.al. Long-term AICAR administration reduces metabolic disturbances and lowers blood pressure in rats displaying feature of the insulin resistance syndrome. Diabetes 51: 2199 (2002)). For example, 7 week AICAR administration in the obese Zucker (fa/fa) rat leads to a reduction in plasma triglycerides and free fatty acids, an increase in HDL cholesterol, and a normalization of glucose metabolism as assessed by an oral glucose tolerance test (Minokoshi, Y. et.al. Leptin stimulates fatty-acid oxidation by activating AMP-activated protein kinase. Nature 415: 339 (2002)). In both ob/ob and db/db mice, 8 day AICAR administration reduces blood glucose by 35% (Halseth, A. E. et.al. Acute and chronic treatment of ob/ob and db/db mice with AICAR decreases blood glucose concentrations. Biochem. and Biophys. Res. Comm. 294:798 (2002)). In addition to AICAR, more recently it was found that the diabetes drug metformin can activate AMPK in vivo at high concentrations (Zhou, G. et.al. Role of AMP-activated protein kinase in mechanism of metformin action. The J. of Clin. Invest. 108: 1167 (2001), Musi, N. et.al. Metformin increases AMP-activated protein kinase activity in skeletal muscle of subjects with type 2 diabetes. Diabetes 51: 2074 (2002)), although it has to be determined to what extent its antidiabetic action relies on this activation. As with leptin and adiponectin, the stimulatory effect of metformin is indirect via activation of an upstream kinase (Zhou, G. et.al. Role of AMP-activated protein kinase in mechanism of metformin action. The J. of Clin. Invest. 108: 1167 (2001)). In addition to pharmacologic intervention, several transgenic mouse models have been developed in the last years, and initial results are becoming available. Expression of dominant negative AMPK in skeletal muscle of transgenic mice has demonstrated that the AICAR effect on stimulation of glucose transport is dependent on AMPK activation (Mu, J. et.al. A role for AMP-activated protein kinase in contraction and hypoxia-regulated glucose transport in skeletal muscle. Molecular Cell 7: 1085 (2001)), and therefore likely not caused by non-specific ZMP effects. Similar studies in other tissues will help to further define the consequences of AMPK activation. It is expected that pharmacologic activation of AMPK will have benefits in the metabolic syndrome with improved glucose and lipid metabolism and a reduction in body weight. To qualify a patient as having metabolic syndrome, three out of the five following criteria must be met: elevated blood pressure above 130/85 mmHg, fasting blood glucose above 110 mg/dl, abdominal obesity above 40" (men) or 35" (women) waist circumference, and blood lipid changes as defined by an increase in triglycerides above 150 mg/dl or decreased HDL cholesterol below 40 mg/dl (men) or 50 mg/dl (women). Therefore, the combined effects that may be acheived through activation of AMPK in a patient who qualifies as having metabolic syndrome would raise the Lowering of blood pressure has been reported to be a consequence of AMPK activation (Buhl, E. S. et.al. Long-term AICAR administration reduces metabolic disturbances and lowers blood pressure in rats displaying feature of the insulin resistance syndrome. Diabetes 51: 2199 (2002)), therefore activation of AMPK might have beneficial effects in hypertension. Through combination of some or all of the above-mentioned effects stimulation of AMPK is expected to reduce the incidence of cardiovascular diseases (e.g. MI, stroke). Increased fatty acid synthesis is a characteristic of many tumor cells, therefore decreased synthesis of fatty acids through activation of AMPK can be useful as a cancer therapy. Stimulation of AMPK has been shown to stimulate production of ketone bodies from astrocytes (Blazquez, C. et.al. The AMP-activated protein kinase is involved in the regulation of ketone body production by astrocytes. J. Neurochem. 73: 1674 (1999)), and might therefore be a strategy to treat ischemic events in the brain. Stimulation of AMPK has been shown to stimulate expression of uncoupling protein 3 (UCP3) in skeletal muscle (Zhou, M. et.al. UCP-3 expression in skeletal muscle: effects of exercise, hypoxia, and AMP-activated protein kinase. Am. J. Physiol. Endocrinol. Metab. 279: E622 (2000)) and might therefore be a way to prevent damage from reactive oxygen species. Endothelial NO synthase (eNOS) has been shown to be activated through AMPK mediated phosphorylation (Chen, Z.-P., et.al. AMP-activated protein kinase phosphorylation of endothelial NO synthase. FEBS Letters 443: 285 (1999)), therefore AMPK activation can be used to improve local circulatory systems.

SUMMARY OF THE INVENTION

The present invention is directed to compounds of formula (I):

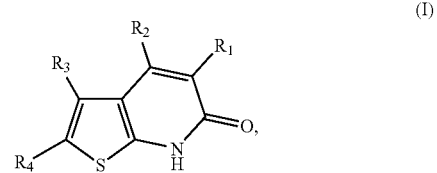

or a therapeutically suitable salt, or prodrug thereof, wherein
$R_1$ is selected from the group consisting of hydrogen, alkoxy, alkoxycarbonyl, alkyl, alkenyl, alkynyl, carboxy, carboxyalkyl, cyano, cyanoalkyl, halogen, haloalkyl, trihaloalkyl, heterocycle, hydroxyalkyl, $R_aR_bN-$, $R_aR_bN$alkyl, and $R_cR_dNC(O)-$, wherein alkyl may be optionally substituted with $O=$ and $R_f-N=$;
$R_2$ is selected from the group consisting of $R_fO-$, $HO-$, $R_fS-$, and $HS-$;
$R_3$ is selected from the group consisting of alkoxycarbonyl, substituted aryl, arylalkyl, arylalkenyl, arylalkynyl, cycloalkyl, carboxy, carboxylalkyl, halogen, heteroaryl, heterocycle, heterocyclealkyl, R$_g$R$_j$N—, and R$_g$R$_j$Nalkyl, wherein cycloalkyl may be fused to an aryl ring as defined herein;

R$_4$ is selected from the group consisting of hydrogen, alkyl, alkenyl, alkynyl, aryl, arylalkyl, arylcarbonyl, aryloxycarbonyl, carboxy, carboxyalkyl, carboxyalkynyl, halogen, haloalkyl, heteroaryl, heterocycle, heterocyclealkyl, heterocyclecarbonyl, heterocycleoxycarbonyl, hydroxyalkyl, HO—N=CH—(CH$_2$)$_u$—, and R$_m$R$_n$N—;

u is 0, 1 or 2;

R$_a$ and R$_b$ are each individually selected from the group consisting of hydrogen, alkyl, alkylcarbonyl, alkoxylcarbonyl, aryl, arylalkyl, arylcarbonyl, arylalkyloxycarbonyl, heteroaryl, heterocycle, heterocyclealkyl, heterocyclecarbonyl, and heterocycleoxycarbonyl;

R$_c$ and R$_d$ are each independently selected from the group consisting of hydrogen, alkyl, aryl, arylalkyl, haloalkyl, hydroxyalkyl, and heterocycle;

R$_f$ is selected from the group consisting of alkyl, cycloalkyl, cycloalkylalkyl, alkoxyalkyl, alkylthioalkyl, and haloalkyl;

R$_g$ and R$_j$ are each independently selected from the group consisting of hydrogen, alkyl, alkoxycarbonyl, aryl, arylalkyl, arylcarbonyl, aryloxycarbonyl, heteroaryl, heterocycle, heterocyclealkyl, heterocyclecarbonyl, heterocycleoxycarbonyl, and haloalkyl;

R$_m$ and R$_n$ are each independently selected from the group consisting of hydrogen, alkyl, alkoxycarbonyl, aryl, arylalkyl, heteroaryl, heterocycle, heterocyclealkyl, and haloalkyl; and R$_t$ is selected from the group consisting of hydrogen, alkyl and HO—.

According to one embodiment of the present invention there is provided a method of treating disorders regulated by activation of AMP-activated protein kinase (AMPK) which are useful for the prevention or treatment of diabetes, metabolic syndrome, and obesity comprising administering a therapeutically effective amount of a compound of formula (I).

According to still another embodiment, the present invention is directed to a pharmaceutical composition comprising a therapeutically effective amount of a compound of formula (I) in combination with a pharmaceutically suitable carrier.

DETAILED DESCRIPTION OF THE INVENTION

Accordingly, the principle embodiment of the present invention is directed to compounds of formula (I):

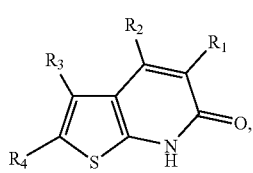

(I)

or a therapeutically suitable salt, or prodrug thereof, wherein

R$_1$ is selected from the group consisting of hydrogen, alkoxy, alkoxycarbonyl, alkyl, alkenyl, alkynyl, carboxy, carboxyalkyl, cyano, cyanoalkyl, halogen, haloalkyl, trihaloalkyl, heterocycle, hydroxyalkyl, R$_a$R$_b$N—, R$_a$R$_b$Nalkyl, and R$_c$R$_d$NC(O)—, wherein alkyl may be optionally substituted with O= and R$_t$—N=;

R$_2$ is selected from the group consisting of R$_f$O—, HO—, R$_f$S—, and HS—;

R$_3$ is selected from the group consisting of alkoxycarbonyl, substituted aryl, arylalkyl, arylalkenyl, arylalkynyl, cycloalkyl, carboxy, carboxylalkyl, halogen, heteroaryl, heterocycle, heterocyclealkyl, R$_g$R$_j$N—, and R$_g$R$_j$Nalkyl, wherein cycloalkyl may be fused to an aryl ring as defined herein;

R$_4$ is selected from the group consisting of hydrogen, alkyl, alkenyl, alkynyl, aryl, arylalkyl, arylcarbonyl, aryloxycarbonyl, carboxy, carboxyalkyl, carboxyalkynyl, halogen, haloalkyl, heteroaryl, heterocycle, heterocyclealkyl, heterocyclecarbonyl, heterocycleoxycarbonyl, hydroxyalkyl, HO—N=CH—(CH$_2$)$_u$—, and R$_m$R$_n$N—;

u is 0, 1 or 2;

R$_a$ and R$_b$ are each individually selected from the group consisting of hydrogen, alkyl, alkylcarbonyl, alkoxylcarbonyl, aryl, arylalkyl, arylcarbonyl, arylalkyloxycarbonyl, heteroaryl, heterocycle, heterocyclealkyl, heterocyclecarbonyl, and heterocycleoxycarbonyl;

R$_c$ and R$_d$ are each independently selected from the group consisting of hydrogen, alkyl, aryl, arylalkyl, haloalkyl, hydroxyalkyl, and heterocycle;

R$_f$ is selected from the group consisting of alkyl, cycloalkyl, cycloalkylalkyl, alkoxyalkyl, alkylthioalkyl, and haloalkyl;

R$_g$ and R$_j$ are each independently selected from the group consisting of hydrogen, alkyl, alkoxycarbonyl, aryl, arylalkyl, arylcarbonyl, aryloxycarbonyl, heteroaryl, heterocycle, heterocyclealkyl, heterocyclecarbonyl, heterocycleoxycarbonyl, and haloalkyl;

R$_m$ and R$_n$ are each independently selected from the group consisting of hydrogen, alkyl, alkoxycarbonyl, aryl, arylalkyl, heteroaryl, heterocycle, heterocyclealkyl, and haloalkyl; and R$_t$ is selected from the group consisting of hydrogen, alkyl and HO—.

According to another embodiment, the present invention is directed to compounds of formula (I), wherein R$_1$ is selected from the group consisting of hydrogen, alkoxy, alkoxycarbonyl, alkyl, alkenyl, alkynyl, carboxy, carboxyalkyl, cyano, cyanoalkyl, halogen, haloalkyl, trihaloalkyl, heterocycle, hydroxyalkyl, R$_a$R$_b$N—, R$_a$R$_b$Nalkyl, and R$_c$R$_d$NC(O)—, wherein alkyl may be optionally substituted with O= and R$_t$—N=; R$_2$ is selected from the group consisting of R$_f$O—, and HO—; R$_3$ is selected from the group consisting of alkoxycarbonyl, substituted aryl, arylalkyl, arylalkenyl, arylalkynyl, cycloalkyl, carboxy, carboxylalkyl, halogen, heteroaryl, heterocycle, heterocyclealkyl, R$_g$R$_j$N—, and R$_g$R$_j$Nalkyl, wherein cycloalkyl may be fused to an aryl ring as defined herein; R$_4$ is selected from the group consisting of hydrogen, alkyl, alkenyl, alkynyl, aryl, arylalkyl, arylcarbonyl, aryloxycarbonyl, carboxy, carboxyalkyl, carboxyalkynyl, halogen, haloalkyl, heteroaryl, heterocycle, heterocyclealkyl, heterocyclecarbonyl, heterocycleoxycarbonyl, hydroxyalkyl, HO—N=CH—(CH$_2$)$_u$—, and R$_m$R$_n$N—; u is 0, 1 or 2; R$_a$ and R$_b$ are each individually selected from the group consisting of hydrogen, alkyl, alkylcarbonyl, alkoxylcarbonyl, aryl, arylalkyl, arylcarbonyl, arylalkyloxycarbonyl, heteroaryl, heterocycle, heterocyclealkyl, heterocyclecarbonyl, and heterocycleoxycarbonyl; R$_c$ and R$_d$ are each independently selected from the group consisting of hydrogen, alkyl, aryl, arylalkyl, haloalkyl, hydroxyalkyl, and heterocycle; R$_f$ is selected from the group consisting of alkyl, cycloalkyl, cycloalkylalkyl, alkoxyalkyl, alkylthioalkyl, and haloalkyl; $R_g$ and $R_j$ are each independently selected from the group consisting of hydrogen, alkyl, alkoxycarbonyl, aryl, arylalkyl, arylcarbonyl, aryloxycarbonyl, heteroaryl, heterocycle, heterocyclealkyl, heterocyclecarbonyl, heterocycleoxycarbonyl, and haloalkyl; $R_m$ and $R_n$ are each independently selected from the group consisting of hydrogen, alkyl, alkoxycarbonyl, aryl, arylalkyl, heteroaryl, heterocycle, heterocyclealkyl, and haloalkyl; and $R_t$ is selected from the group consisting of hydrogen, alkyl and HO—.

According to another embodiment, the present invention is directed to compounds of formula (I), wherein $R_1$ is selected from the group consisting of hydrogen, alkoxy, alkoxycarbonyl, alkyl, alkynyl, carboxy, cyano, halogen, heterocycle, and hydroxyalkyl, wherein alkyl may be optionally substituted with O═ and $R_t$—N═; $R_2$ is selected from the group consisting of $R_fO$—, and HO—; $R_3$ is selected from the group consisting of alkoxycarbonyl, substituted aryl, arylalkyl, arylalkenyl, arylalkynyl, cycloalkyl, carboxy, carboxylalkyl, halogen, heteroaryl, heterocycle, heterocyclealkyl, $R_gR_jN$—, and $R_gR_jNalkyl$, wherein cycloalkyl may be fused to an aryl ring as defined herein; $R_4$ is selected from the group consisting of hydrogen, alkyl, carboxyalkynyl, halogen, haloalkyl, heteroaryl, heterocycle, heterocyclealkyl, and HO—N═CH—$(CH_2)_u$—; u is 0, 1 or 2; $R_f$ is selected from the group consisting of alkyl, cycloalkyl, cycloalkylalkyl, alkoxyalkyl, alkylthioalkyl, and haloalkyl; $R_g$ and $R_j$ are each independently selected from the group consisting of hydrogen, alkyl, alkoxycarbonyl, aryl, arylalkyl, arylcarbonyl, aryloxycarbonyl, heteroaryl, heterocycle, heterocyclealkyl, heterocyclecarbonyl, heterocycleoxycarbonyl, and haloalkyl; and $R_t$ is selected from the group consisting of hydrogen, alkyl and HO—.

According to another embodiment, the present invention is directed to compounds of formula (I), wherein $R_1$ is selected from the group consisting of hydrogen, alkoxy, alkoxycarbonyl, alkyl, alkynyl, carboxy, cyano, halogen, heterocycle, and hydroxyalkyl, wherein alkyl may be optionally substituted with O═ and $R_t$—N═; $R_2$ is selected from the group consisting of $R_fO$—, and HO—; $R_3$ is selected from the group consisting of alkoxycarbonyl, arylalkyl, arylalkenyl, arylalkynyl, cycloalkyl, carboxy, carboxylalkyl, halogen, heterocyclealkyl, $R_gR_jN$—, and $R_gR_jNalkyl$, wherein cycloalkyl may be fused to an aryl ring as defined herein; $R_4$ is selected from the group consisting of hydrogen, alkyl, carboxyalkynyl, halogen, haloalkyl, heteroaryl, heterocycle, heterocyclealkyl, and HO—N═CH—$(CH_2)_u$—; u is 0, 1 or 2; $R_f$ is selected from the group consisting of alkyl, cycloalkyl, cycloalkylalkyl, alkoxyalkyl, alkylthioalkyl, and haloalkyl; and $R_t$ is selected from the group consisting of hydrogen, alkyl and HO—.

According to another embodiment, the present invention is directed to compounds of formula (I), wherein $R_1$ is selected from the group consisting of hydrogen, alkoxy, alkoxycarbonyl, alkyl, alkynyl, carboxy, cyano, halogen, heterocycle, and hydroxyalkyl, wherein alkyl may be optionally substituted with O═ and $R_t$—N═; $R_2$ is selected from the group consisting of $R_fO$—, and HO—; $R_3$ is selected from the group consisting of heteroaryl and heterocycle; $R_4$ is selected from the group consisting of hydrogen, alkyl, carboxyalkynyl, halogen, haloalkyl, heteroaryl, heterocycle, heterocyclealkyl, and HO—N═CH—$(CH_2)_u$—; u is 0, 1 or 2; $R_f$ is selected from the group consisting of alkyl, cycloalkyl, cycloalkylalkyl, alkoxyalkyl, alkylthioalkyl, and haloalkyl; $R_g$ and $R_j$ are each independently selected from the group consisting of hydrogen, alkyl, alkoxycarbonyl, aryl, arylalkyl, arylcarbonyl, aryloxycarbonyl, heteroaryl, heterocycle, heterocyclealkyl, heterocyclecarbonyl, heterocycleoxycarbonyl, and haloalkyl; and $R_t$ is selected from the group consisting of hydrogen, alkyl and HO—.

According to another embodiment, the present invention is directed to compounds of formula (II)

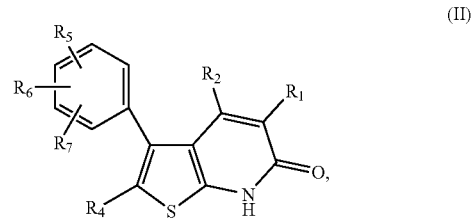

or a therapeutically suitable salt, ester or prodrug thereof, wherein $R_1$ is selected from the group consisting of hydrogen, alkyl, alkoxy, alkoxycarbonyl, alkynyl, carboxy, cyano, halogen, heterocycle, and hydroxyalkyl, wherein alkyl may be optionally substituted with O═ and $R_t$—N═; $R_2$ is selected from the group consisting of $R_fO$—, and HO—; $R_4$ is selected from the group consisting of hydrogen, alkyl, carboxyalkynyl, halogen, haloalkyl, heteroaryl, heterocycle, heterocyclealkyl, and HO—N═CH—$(CH_2)_u$—; $R_5$ is selected from the group consisting of alkenyl, alkenyloxy, alkoxy, alkoxyalkoxy, alkoxycarbonyl, alkyl, alkylcarbonyl, alkoxycarbonylalkoxy, alkynyl, aryl, aryloxy, carboxy, carboxyalkyl, carboxyalkoxy, cyano, cycloalkylalkoxy, formyl, halo, haloalkyl, trihaloalkyl, trihaloalkoxy, heteroaryl, heterocycle, hydroxy, hydroxyalkyl, hydroxyalkoxy, dihydroxyalkoxy, nitro, $R_pR_qN$—, $R_rR_sNC(O)$alkoxy, and $R_rR_sNSO_2$alkoxy; $R_6$ and $R_7$ are each individually selected from the group consisting of hydrogen, alkenyl, alkenyloxy, alkoxy, alkoxyalkoxy, alkoxycarbonyl, alkoxyalkynyl, alkyl, alkylcarbonyl, alkoxycarbonylalkoxy, alkynyl, aryl, aryloxy, carboxy, carboxyalkyl, carboxyalkoxy, carboxyalkynyl, cyano, cyanoalkoxy, cyanoalkynyl, cycloalkenylalkoxy, formyl, halo, haloalkyl, trihaloalkyl, trihaloalkoxy, heteroaryl, heterocycle, heterocyclealkenyl, heterocyclealkoxy, heterocycleoxyalkynyl, hydroxy, hydroxyalkenyl, hydroxyalkyl, hydroxyalkoxy, hydroxyalkynyl, dihydroxyalkoxy, nitro, $R_pR_qN$—, $R_rR_sNC(O)$alkoxy, $R_rR_sNC(O)$alkynyl, and $R_rR_sNSO_2$alkoxy, and $R_w$—O—N═CH—, $R_xR_yN$-alkynyl or $R_6$ and $R_7$ together with the atoms to which they are attached form a ring selected from the group consisting of cycloalkyl and heterocycle; u is 0, 1 or 2; $R_f$ is selected from the group consisting of alkyl, cycloalkyl, cycloalkylalkyl, alkoxyalkyl, alkylthioalkyl, and haloalkyl; $R_p$ is selected from the group consisting of hydrogen, alkenyl, alkenylcarbonyl, alkoxycarbonyl, alkoxycarbonylalkyl, alkoxycarbonylalkylcarbonyl, alkyl, alkylcarbonyl, alkynyl, aryl, arylalkenyl, arylalkyl, arylcarbonyl, haloalkyl, haloalkylcarbonyl, heteroaryl, heterocycle, heterocyclealkenyl, heterocyclealkyl, heterocyclealkylcarbonyl, heterocyclecarbonyl, trihaloalkyl, trihaloalkylcarbonyl, hydroxyalkyl, and hydroxyalkylcarbonyl; $R_q$ are each independently selected from the group consisting of hydrogen, alkyl, alkenyl; $R_r$ and $R_s$ are each independently selected from the group consisting of hydrogen, alkyl, arylalkyl, hydroxyalkyl, heterocyclealkyl; $R_t$ is selected from the group consisting of hydrogen, alkyl and HO—; $R_w$ is selected from the group consisting of hydrogen, alkylcarbonyl-NH-alkyl-NHC(O)-alkyl, alkyl, alkyl(alkyl)N-alkyl-NHC(O)-alkyl, hydroxyalkyl-NHC(O)-alkyl, heterocyclealkyl-NHC(O)-alkyl, heterocycle-NHC(O)-alkyl, heteroarylalkyl-NHC(O)- alkyl; and R$_x$ and R$_y$ are each individually selected fro the group consisting of hydrogen, alkyl and alkylsulfonyl.

According to another embodiment, the present invention is directed to compounds of formula (II), wherein R$_1$ is selected from the group consisting of hydrogen, alkyl, alkoxy, alkoxycarbonyl, carboxy, cyano, halogen, hydroxyalkyl, and heterocycle, wherein alkyl may be optionally substituted with O═ and R$_t$—N═; R$_2$ is selected from the group consisting of R$_t$O—, and HO—; R$_4$ is selected from the group consisting of hydrogen, alkyl, carboxyalkynyl, halogen, haloalkyl, and HO—N═CH—(CH$_2$)$_u$—; R$_5$ is selected from the group consisting of alkenyl, alkenyloxy, alkoxy, alkoxyalkoxy, alkoxycarbonyl, alkyl, alkylcarbonyl, alkoxycarbonylalkoxy, alkynyl, aryl, aryloxy, carboxy, carboxyalkyl, carboxyalkoxy, cyano, cycloalkylalkoxy, formyl, halo, haloalkyl, trihaloalkyl, trihaloalkoxy, heteroaryl, heterocycle, hydroxy, hydroxyalkyl, hydroxyalkoxy, dihydroxyalkoxy, nitro, R$_p$R$_q$N—, R$_r$R$_s$NC(O)alkoxy, and R$_r$R$_s$NSO$_2$alkoxy; R$_6$ and R$_7$ are each individually selected from the group consisting of hydrogen, alkenyl, alkenyloxy, alkoxy, alkoxyalkoxy, alkoxycarbonyl, alkoxyalkynyl, alkyl, alkylcarbonyl, alkoxycarbonylalkoxy, alkynyl, aryl, aryloxy, carboxy, carboxyalkyl, carboxyalkoxy, carboxyalkynyl, cyano, cyanoalkoxy, cyanoalkynyl, cycloalkenylalkoxy, formyl, halo, haloalkyl, trihaloalkyl, trihaloalkoxy, heteroaryl, heterocycle, heterocyclealkenyl, heterocyclealkoxy, heterocycleoxyalkynyl, hydroxy, hydroxyalkenyl, hydroxyalkyl, hydroxyalkoxy, hydroxyalkynyl, dihydroxyalkoxy, nitro, R$_p$R$_q$N—, R$_r$R$_s$NC(O)alkoxy, R$_r$R$_s$NC(O)alkynyl, and R$_r$R$_s$NSO$_2$alkoxy, and R$_w$—O—N═CH—, R$_x$R$_y$N-alkynyl or R$_6$ and R$_7$ together with the atoms to which they are attached form a ring selected from the group consisting of cycloalkyl and heterocycle; u is 0, 1 or 2; R$_f$ is selected from the group consisting of alkyl, cycloalkyl, cycloalkylalkyl, alkoxyalkyl, alkylthioalkyl, and haloalkyl; R$_p$ is selected from the group consisting of hydrogen, alkenyl, alkenylcarbonyl, alkoxycarbonyl, alkoxycarbonylalkyl, alkoxycarbonylalkylcarbonyl, alkyl, alkylcarbonyl, alkynyl, aryl, arylalkenyl, arylalkyl, arylcarbonyl, haloalkyl, haloalkylcarbonyl, heteroaryl, heterocycle, heterocyclealkenyl, heterocyclealkyl, heterocyclealkylcarbonyl, heterocyclecarbonyl, trihaloalkyl, trihaloalkylcarbonyl, hydroxyalkyl, and hydroxyalkylcarbonyl; R$_q$ are each independently selected from the group consisting of hydrogen, alkyl, alkenyl; R$_r$ and R$_s$ are each independently selected from the group consisting of hydrogen, alkyl, arylalkyl, hydroxyalkyl, heterocyclealkyl; R$_t$ is selected from the group consisting of hydrogen, alkyl and HO—; R$_w$ is selected from the group consisting of hydrogen, alkylcarbonyl-NH-alkyl-NHC(O)-alkyl, alkyl, alkyl(alkyl)N-alkyl-NHC(O)-alkyl, hydroxyalkyl-NHC(O)-alkyl, heterocyclealkyl-NHC(O)-alkyl, heterocycle-NHC(O)-alkyl, heteroarylalkyl-NHC(O)-alkyl; and R$_x$ and R$_y$ are each individually selected fro the group consisting of hydrogen, alkyl and alkylsulfonyl.

According to another embodiment, the present invention is directed to compounds of formula (II), wherein R$_1$ is selected from the group consisting of hydrogen, alkyl, alkoxy, alkoxycarbonyl, alkynyl, carboxy, cyano, halogen, heterocycle, and hydroxyalkyl, wherein alkyl may be optionally substituted with O═ and R$_t$—N═; R$_2$ is selected from the group consisting of R$_t$O—, and HO—; R$_4$ is selected from the group consisting of hydrogen, alkyl, carboxyalkynyl, halogen, haloalkyl, and HO—N═CH—(CH$_2$)$_u$—; R$_5$ is selected from the group consisting of aryl, aryloxy, and heterocycle; R$_6$ and R$_7$ are each individually selected from the group consisting of hydrogen, alkenyl, alkenyloxy, alkoxy, alkoxyalkoxy, alkoxycarbonyl, alkoxy- alkynyl, alkyl, alkylcarbonyl, alkoxycarbonylalkoxy, alkynyl, aryl, aryloxy, carboxy, carboxyalkyl, carboxyalkoxy, carboxyalkynyl, cyano, cyanoalkoxy, cyanoalkynyl, cycloalkenylalkoxy, formyl, halo, haloalkyl, trihaloalkyl, trihaloalkoxy, heteroaryl, heterocycle, heterocyclealkenyl, heterocyclealkoxy, heterocycleoxyalkynyl, hydroxy, hydroxyalkenyl, hydroxyalkyl, hydroxyalkoxy, hydroxyalkynyl, dihydroxyalkoxy, nitro, R$_p$R$_q$N—, R$_r$R$_s$NC(O)alkoxy, R$_r$R$_s$NC(O)alkynyl, and R$_r$R$_s$NSO$_2$alkoxy, and R$_w$—O—N═CH—, R$_x$R$_y$N-alkynyl or R$_6$ and R$_7$ together with the atoms to which they are attached form a ring selected from the group consisting of cycloalkyl and heterocycle; u is 0, 1 or 2; R$_f$ is selected from the group consisting of alkyl, cycloalkyl, cycloalkylalkyl, alkoxyalkyl, alkylthioalkyl, and haloalkyl; R$_p$ is selected from the group consisting of hydrogen, alkenyl, alkenylcarbonyl, alkoxycarbonyl, alkoxycarbonylalkyl, alkoxycarbonylalkylcarbonyl, alkyl, alkylcarbonyl, alkynyl, aryl, arylalkenyl, arylalkyl, arylcarbonyl, haloalkyl, haloalkylcarbonyl, heteroaryl, heterocycle, heterocyclealkenyl, heterocyclealkyl, heterocyclealkylcarbonyl, heterocyclecarbonyl, trihaloalkyl, trihaloalkylcarbonyl, hydroxyalkyl, and hydroxyalkylcarbonyl; R$_q$ are each independently selected from the group consisting of hydrogen, alkyl, alkenyl; R$_r$ and R$_s$ are each independently selected from the group consisting of hydrogen, alkyl, arylalkyl, hydroxyalkyl, heterocyclealkyl; R$_t$ is selected from the group consisting of hydrogen, alkyl and HO—; R$_w$ is selected from the group consisting of hydrogen, alkylcarbonyl-NH-alkyl-NHC(O)-alkyl, alkyl, alkyl(alkyl) N-alkyl-NHC(O)-alkyl, hydroxyalkyl-NHC(O)-alkyl, heterocyclealkyl-NHC(O)-alkyl, heterocycle-NHC(O)-alkyl, heteroarylalkyl-NHC(O)-alkyl; and R$_x$ and R$_y$ are each individually selected fro the group consisting of hydrogen, alkyl and alkylsulfonyl.

According to another embodiment, the present invention is directed to compound of formula (III)

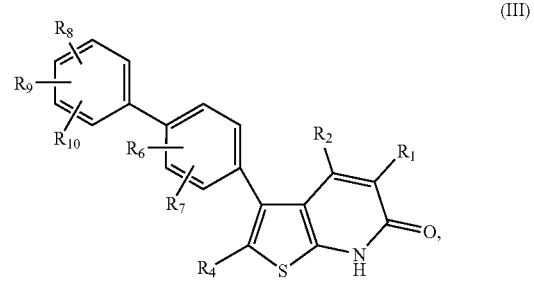

(III)

or a therapeutically suitable salt, ester or prodrug thereof, wherein R$_1$ is selected from the group consisting of hydrogen, alkyl, alkoxy, alkoxycarbonyl, alkynyl, carboxy, cyano, halogen, heterocycle, and hydroxyalkyl, wherein alkyl may be optionally substituted with O═ and R$_t$—N═; R$_2$ is selected from the group consisting of R$_t$O—, and HO—; R$_4$ is selected from the group consisting of hydrogen, alkyl, carboxyalkynyl, halogen, haloalkyl, heteroaryl, heterocycle, heterocyclealkyl, and HO—N═CH—(CH$_2$)$_u$—; R$_6$ and R$_7$ are each individually selected from the group consisting of hydrogen, alkenyl, alkenyloxy, alkoxy, alkoxyalkoxy, alkoxycarbonyl, alkoxyalkynyl, alkyl, alkylcarbonyl, alkoxycarbonylalkoxy, alkynyl, aryl, aryloxy, carboxy, carboxyalkyl, carboxyalkoxy, carboxyalkynyl, cyano, cyanoalkoxy, cyanoalkynyl, cycloalkenylalkoxy, formyl, halo, haloalkyl, trihaloalkyl, trihaloalkoxy, heteroaryl, heterocycle, heterocyclealkenyl, heterocyclealkoxy, heterocycleoxyalkynyl, hydroxy, hydroxyalkenyl, hydroxyalkyl, hydroxyalkoxy, hydroxyalkynyl, dihydroxyalkoxy, nitro, $R_pR_qN$—, $R_rR_sNC(O)$alkoxy, $R_rR_sNC(O)$alkynyl, and $R_rR_sNSO_2$alkoxy, and $R_w$—O—N=CH—, $R_xR_yN$-alkynyl or $R_6$ and $R_7$ together with the atoms to which they are attached form a ring selected from the group consisting of cycloalkyl and heterocycle; $R_8$, $R_9$ and $R_{10}$ are each individually selected from the group consisting of hydrogen, alkenyl, alkenyloxy, alkoxy, alkoxyalkoxy, alkoxycarbonyl, alkoxyalkynyl, alkyl, alkylcarbonyl, alkylSO$_2$—, alkoxycarbonylalkoxy, alkynyl, arylalkynyl, aryloxy, carboxy, carboxyalkyl, carboxyalkynyl, carboxyalkoxy, cyano, formyl, halo, haloalkyl, heterocyclealkoxy, heterocycleoxyalkynyl, trihaloalkyl, trihaloalkoxy, hydroxy, hydroxyalkyl, hydroxyalkenyl, hydroxyalkynyl, hydroxyalkoxy, dihydroxyalkoxy, nitro, $R_uR_vN$—, $R_uR_v$Nalkyl-, $R_uR_vN$—C(O)-alkyl-, $R_uR_v$Nalkynyl-, $R_uR_vN$—C(O)-alkynyl-, $R_rR_sNSO_2$—, or $R_8$ and $R_9$ taken together with the atoms to which they are attached form a 1,3-dioxolyl ring; u is 0, 1 or 2; $R_f$ is selected from the group consisting of alkyl, cycloalkyl, cycloalkylalkyl, alkoxyalkyl, alkylthioalkyl, and haloalkyl; $R_p$ is selected from the group consisting of hydrogen, alkenyl, alkenylcarbonyl, alkoxycarbonyl, alkoxycarbonylalkyl, alkoxycarbonylalkylcarbonyl, alkyl, alkylcarbonyl, alkynyl, aryl, arylalkenyl, arylalkyl, arylcarbonyl, haloalkyl, haloalkylcarbonyl, heteroaryl, heterocycle, heterocyclealkenyl, heterocyclealkyl, heterocyclealkylcarbonyl, heterocyclecarbonyl, trihaloalkyl, trihaloalkylcarbonyl, hydroxyalkyl, and hydroxyalkylcarbonyl; $R_q$ are each independently selected from the group consisting of hydrogen, alkyl; $R_r$ and $R_s$ are each independently selected from the group consisting of hydrogen, alkyl, arylalkyl, hydroxyalkyl, heterocyclealkyl; $R_t$ is selected from the group consisting of hydrogen, alkyl and HO—; $R_u$ and $R_v$ are each individually selected from the group consisting of hydrogen, alkylcarbonyl, alkyl, alkylSO$_2$—, alkenyl, arylalkyl, $R_w$ is selected from the group consisting of hydrogen, alkylcarbonyl-NH-alkyl-NHC(O)-alkyl, alkyl, alkyl(alkyl)N-alkyl-NHC(O)-alkyl, hydroxyalkyl-NHC(O)-alkyl, heterocyclealkyl-NHC(O)-alkyl, heterocycle-NHC(O)-alkyl, heteroarylalkyl-NHC(O)-alkyl; and $R_x$ and $R_y$ are each individually selected fro the group consisting of hydrogen, alkyl and alkylsulfonyl.

According to one embodiment of the present invention there is provided a method of treating method of treating diabetes in a mammal, comprising administration of a therapeutically effective amount of a compound of formula (I).

According to one embodiment of the present invention there is provided a method of treating method of treating diabetes in a mammal, comprising administration of a therapeutically effective amount of a compound of formula (II).

According to one embodiment of the present invention there is provided a method of treating metabolic syndrome in a mammal, comprising administration of a therapeutically effective amount of a compound of formula (I).

According to one embodiment of the present invention there is provided a method of treating metabolic syndrome in a mammal, comprising administration of a therapeutically effective amount of a compound of formula (II).

According to one embodiment of the present invention there is provided a method of treating obesity in a mammal, comprising administration of a therapeutically effective amount of a compound of formula (I).

According to one embodiment of the present invention there is provided a method of treating obesity in a mammal, comprising administration of a therapeutically effective amount of a compound of formula (II).

According to one embodiment of the present invention there is provided a pharmaceutical composition comprising a therapeutically effective amount of a compound of formula (I) in combination with a pharmaceutically suitable carrier.

According to one embodiment of the present invention there is provided a pharmaceutical composition comprising a therapeutically effective amount of a compound of formula (II) in combination with a pharmaceutically suitable carrier.

As set forth herein, the invention includes administering a therapeutically effective amount of any of the compounds of formula I–II and the salts and prodrugs thereof to a mamal. Preferably, the invention also includes administering a therapeutically effective amount of any of the compounds of formula I–II to a human, and more preferably to a human in need of being treated for or prophylactically treated for any of the respective disorders set forth herein.

DEFINITIONS

As used throughout this specification and the appended claims, the following terms have the following meanings:

The term "alkenyl," as used herein, refers to a straight or branched chain hydrocarbon containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkenyloxy," as used herein, refers to an alkenyl group as defined herein, appended to the parent molecular moiety through a oxy group, as defined herein. Representative examples of alkyl include, but are not limited to, ethoxy, 2-propoxy, 2-methyl-2-propoxy, 3-butoxy, and the like.

The term "alkoxy," as used herein, refers to an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkoxyalkyl," as used herein, refers to an alkoxy group, as defined herein, appended to the parent molecular moiety through an alkyl group, as defined herein. Representative examples of alkoxyalkyl include, but are not limited to, tert-butoxymethyl, 2-ethoxyethyl, 2-methoxyethyl, and methoxymethyl.

The term "alkoxyalkoxy," as used herein, refers to an alkoxy group, as defined herein, appended to the parent molecular moiety through an alkoxy group, as defined herein.

The term "alkoxyalkynyl," as used herein, refers to an alkoxy group, as defined herein, appended to the parent molecular moiety through an alkyne group, as defined herein.

The term "alkoxycarbonyl," as used herein, refers to an alkoxy group, as defined herein, appended to the parent molecular moiety through a carbonyl group, as defined herein. Representative examples of alkoxycarbonyl include, but are not limited to, methoxycarbonyl, ethoxycarbonyl, and tert-butoxycarbonyl.

The term "alkoxycarbonylalkoxy," as used herein, refers to an alkoxycarbonyl group, as defined herein, appended to the parent molecular moiety through an alkoxy group, as defined herein.

The term "alkyl," as used herein, refers to a straight or branched chain hydrocarbon containing from 1 to 10 carbon atoms. The term "alkyl," as related to the compounds of the present invention, refer to $C_1$-alkyl, $C_2$-alkyl, $C_3$-alkyl, $C_4$-alkyl, $C_5$-alkyl, $C_6$-alkyl, $C_7$-alkyl, $C_8$-alkyl, $C_9$-alkyl or $C_{10}$-alkyl. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkyl(alkyl)N—," as used herein, refers to an nitrogen atom, appended to the parent molecular moiety which is substituted with two alkyl group, as defined herein.

The term "alkyl(alkyl)N-alkyl-," as used herein, refers to an alkyl(alkyl)N—, as defined herein, appended to the parent molecular moiety through an alkyl group, as defined herein.

The term "alkyl(alkyl)N-alkyl-NHC(O)—," as used herein, refers to an alkyl(alkyl)N-alkyl-, as defined herein, appended to the parent molecular moiety through an NHC (O)— group, as defined herein.

The term "alkyl(alkyl)N-alkyl-NHC(O)-alkyl," as used herein, refers to an alkyl(alkyl)N-alkyl-NHC(O)—, as defined herein, appended to the parent molecular moiety through an alkyl group, as defined herein.

The term "alkylcarbonyl," as used herein, refers to an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, and 1-oxopentyl.

The term "alkylcarbonyl-NH—," as used herein, refers to an alkylcarbonyl group, as defined herein, appended to the parent molecular moiety through an unsubstituted nitrogen atom, as defined herein.

The term "alkylcarbonyl-NH-alkyl," as used herein, refers to an alkylcarbonyl-NH— group, as defined herein, appended to the parent molecular moiety through an alkyl group, as defined herein.

The term "alkylcarbonyl-NH-alkyl-NHC(O)—," as used herein, refers to an alkylcarbonyl-NH-alkyl group, as defined herein, appended to the parent molecular moiety through a —NHC(O)— group, as defined herein.

The term "alkylcarbonyl-NH-alkyl-NHC(O)-alkyl," as used herein, refers to an alkylcarbonyl-NH-alkyl-NHC(O)— group, as defined herein, appended to the parent molecular moiety through an alkyl group, as defined herein.

The term "alkylsulfonyl," as used herein, refers to an alkyl group, as defined herein, appended to the parent molecular moiety through a sulfonyl group, as defined herein. Representative examples of alkylsulfonyl include, but are not limited to, methylsulfonyl and ethylsulfonyl.

The term "alkylthio," as used herein, refers to an alkyl group, as defined herein, appended to the parent molecular moiety through a sulfur atom.

The term "alkylthioalkyl," as used herein, refers to an alkylthio group, as defined herein, appended to the parent molecular moiety through an alkyl group, as defined herein.

The term "alkynyl," as used herein, refers to a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "aryl," as used herein, means a phenyl group or a bicyclic aryl ring or a tricyclic aryl ring. The aryl groups of the present invention can be attached to the parent molecular moiety through any carbon atom within the aryl group while maintaining the proper valence. The bicyclic aryl ring consists of a phenyl group fused to a distal cycloalkyl group or a phenyl group fused to a distal cycloalkenyl group, or a phenyl group fused to a distal heteroaryl group, or a phenyl group fused to a distal heterocycle group. Representative examples of the bicyclic aryl ring include, but are not limited to, 2,3-dihydro-1H-indenyl, 1H-indenyl, naphthyl, 7,8-dihydronaphthalenyl, and 5,6,7,8-tetrahydronaphthalenyl. The tricyclic aryl ring consists of the bicyclic aryl ring fused to a cycloalkyl group or the bicyclic aryl ring fused to a cycloalkyl group or the bicyclic aryl ring fused to another phenyl group. Representative examples of tricyclic aryl ring include, but are not limited to, anthracenyl, azulenyl, 9,10-dihydroanthracenyl, fluorenyl, and 4b,8a,9,10-tetrahydrophenanthrenyl.

The aryl groups of the present invention can be substituted with 0, 1, 2, or 3 substituents independently selected from alkenyl, alkenyloxy, alkoxy, alkoxyalkoxy, alkoxyalkyl, alkoxycarbonyl, alkoxycarbonylalkyl, alkyl, alkylcarbonyl, alkylcarbonylalkyl, alkylcarbonyloxy, alkylsulfonyl, alkylthio, alkynyl, carboxy, carboxyalkyl, cyano, cyanoalkyl, formyl, halogen, haloalkyl, trichloroalkyl, trichloroalkoxy, heterocycle, heterocyclealkyl, heterocyclealkoxy, hydroxy, hydroxyalkyl, hydroxyalkoxy, dihydroxyalkoxy, mercapto, nitro, oxo, phenyl, $R_{ss}R_{tt}N$—, and $R_{rr}R_{pp}NSO_2$— wherein $R_{ss}$ and $R_{tt}$ are each independently selected from the group consisting of hydrogen, alkyl, alkylcarbonyl, alkoxycarbonyl, and alkylSO$_2$— and wherein $R_{rr}$ and $R_{pp}$ are each independently selected from the group consisting of hydrogen and alkyl.

The term "arylalkoxy," as used herein, refers to an aryl group, as defined herein, appended to the parent molecular moiety through an alkoxy group, as defined herein. Representative examples of arylalkoxy include, but are not limited to, 2-phenylethoxy, 3-naphth-2-ylpropoxy, and 5-phenylpentyloxy.

The term "arylalkyl," as used herein, refers to an aryl group, as defined herein, appended to the parent molecular moiety through an alkyl group, as defined herein. Representative examples of arylalkyl include, but are not limited to, benzyl, 2-phenylethyl, 3-phenylpropyl, and 2-naphth-2-ylethyl.

The term "arylalkynyl," as used herein, refers to an aryl group, as defined herein, appended to the parent molecular moiety through an alkyne group, as defined herein.

The term "arylalkyloxy," as used herein, refers to an arylalkyl group, as defined herein, appended to the parent molecular moiety through an oxy group, as defined herein. Representative examples of arylalkyloxy include, but are not limited to, benzyloxy, phenylpropoxy.

The term "arylalkyloxycarbonyl," as used herein, refers to an arylalkyloxy group, as defined herein, appended to the parent molecular moiety through an carbonyl group, as defined herein. Representative examples of arylalkyloxycarbonyl include, but are not limited to, benzyl carboxylate, phenylpropyl carboxylate.

The term "arylcarbonyl," as used herein, refers to an aryl group, as defined herein, appended to the parent molecular moiety through a carbonyl group, as defined herein. Representative examples of arylcarbonyl include, but are not limited to, benzoyl and naphthoyl.

The term "aryloxy," as used herein, refers to an aryl group, as defined herein, appended to the parent molecular moiety through an oxy group, as defined herein. Representative examples of aryloxy groups include, but are not limited to, phenoxy.

The term "aryloxycarbonyl," as used herein, refers to an aryloxy group, as defined herein appended to the parent molecular moiety through a carbonyl group, as defined herein. Representative examples of aryloxycarbonyl groups include, but are not limited to, phenoxycarbonyl.

The term "biaryl," as used herein, refers to an aryl group as defined herein, appended to the parent molecular moiety through an aryl group, as defined herein. Representative examples of biaryl include, but are not limited to 4 biphenyl, 3-biphenyl, 2-biphenyl.

The term "carbonyl," as used herein, refers to a —C(O)— group.

The term "carboxy," as used herein, refers to a —CO$_2$H group.

The term "carboxyalkyl," as used herein, refers to a carboxy group, as defined herein, appended to the parent molecular moiety through an alkyl group, as defined herein. Representative examples of carboxyalkyl include, but are not limited to, carboxymethyl, 2-carboxyethyl, and 3-carboxypropyl.

The term "carboxyalkoxy," as used herein, refers to a carboxy group, as defined herein, appended to the parent molecular moiety through an alkoxy group, as defined herein.

The term "carboxyalkynyl," as used herein, refers to a carboxy group, as defined herein, appended to the parent molecular moiety through an alkynyl group, as defined herein.

The term "cyano," as used herein, refers to a —CN group.

The term "cyanoalkyl," as used herein, refers to a cyano group, as defined herein, appended to the parent molecular moiety through an alkyl group, as defined herein. Representative examples of cyanoalkyl include, but are not limited to, cyanomethyl, 2-cyanoethyl, and 3-cyanopropyl.

The term "cyanoalkoxy," as used herein, refers to a cyano group, as defined herein, appended to the parent molecular moiety through an alkyoxy group, as defined herein.

The term "cyanoalkynyl," as used herein, refers to a cyano group, as defined herein, appended to the parent molecular moiety through an alkyne group, as defined herein.

The term "cycloalkyl," as used herein, refers to a monocyclic, bicyclic, or tricyclic ring system. Monocyclic ring systems are exemplified by a saturated cyclic hydrocarbon group containing from 3 to 8 carbon atoms. Examples of monocyclic ring systems include cyclopropyl, cyclobutyl, cyclopentyl, cyclohexyl, cycloheptyl, and cyclooctyl. Bicyclic ring systems are exemplified by a bridged monocyclic ring system in which two non-adjacent carbon atoms of the monocyclic ring are linked by an alkylene bridge of between one and three additional carbon atoms. Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane. Tricyclic ring systems are exemplified by a bicyclic ring system in which two non-adjacent carbon atoms of the bicyclic ring are linked by a bond or an alkylene bridge of between one and three carbon atoms. Representative examples of tricyclic-ring systems include, but are not limited to, tricyclo[3.3.1.0$^{3,7}$]nonane and tricyclo[3.3.1.1$^{3,7}$]decane (adamantane). The term "cycloalkyl," as related to the compounds of the present invention refer to $C_3$-cycloalkyl, $C_4$-cycloalkyl, $C_5$-cycloalkyl, $C_6$-cycloalkyl, $C_7$-cycloalkyl or $C_8$-cycloalkyl.

The cycloalkyl groups of this invention can be substituted with 0, 1, 2, or 3 substituents independently selected from alkenyl, alkoxy, alkoxyalkyl, alkoxycarbonyl, alkoxycarbonylalkyl, alkyl, alkylcarbonyl, alkylcarbonylalkyl, alkylcarbonyloxy, alkylsulfonyl, alkylthio, alkynyl, carboxy, carboxyalkyl, cyano, cyanoalkyl, formyl, halogen, haloalkyl, heterocycle, heterocyclealkyl, hydroxy, hydroxyalkyl, mercapto, nitro, oxo, phenyl and $R_{ss}R_{tt}N$— wherein $R_{ss}$ and $R_{tt}$ are defined herein.

The term "cycloalkylalkyl," as used herein, refers to a cycloalkyl group, as defined herein appended to the parent molecular moiety through an alkyl group, as defined herein. Representative examples of cycloalkylalkyl group include, but are not limited to cyclopentylpropyl, cyclohexyl 2-methylbutyl.

The term "cycloalkenyl," as used herein, refers to a monocyclic, bicyclic, or tricyclic ring system which contains 1 or 2 double bonds by is not aromatic. Monocyclic ring systems are exemplified by an unsaturated cyclic hydrocarbon group containing from 3 to 8 carbon atoms. Examples of monocyclic ring systems include cyclopropenyl, cyclobutenyl, cyclopentenyl, cyclohexenyl, cycloheptenyl, and cyclooctenyl. Bicyclic ring systems are exemplified by a bridged monocyclic ring system in which two non-adjacent carbon atoms of the monocyclic ring are linked by an alkylene bridge of between one and three additional carbon atoms.

The cycloalkenyl groups of this invention can be substituted with 1, 2, or 3 substituents independently selected from alkenyl, alkoxy, alkoxyalkyl, alkoxycarbonyl, alkoxycarbonylalkyl, alkyl, alkylcarbonyl, alkylcarbonylalkyl, alkylcarbonyloxy, alkylsulfonyl, alkylthio, alkynyl, carboxy, carboxyalkyl, cyano, cyanoalkyl, formyl, halogen, haloalkyl, heterocycle, heterocyclealkyl, hydroxy, hydroxyalkyl, mercapto, nitro, phenyl and $R_{ss}R_{tt}N$— wherein $R_{ss}$ and $R_{tt}$ are defined herein.

The term "cycloalkenylalkoxy," as used herein, refers to a cycloalkenyl group as defined herein appended to the parent molecular moiety through an alkoxy group, as defined herein.

The term "dihydroxyalkoxy," as used herein, refers to two hydroxy groups as defined herein, appended to the parent molecular moiety through an alkoxy group, as defined herein. Representative examples of alkyl include, but are not limited to, 2-dihydroxyethoxy, 2,3-dihydroxypropoxy, 3,4-dihydroxybutoxy and the like.

The term "formyl," as used herein, refers to a —C(O)H group.

The term "halo" or "halogen," as used herein, refers to —Cl, —Br, —I or —F.

The term "haloalkyl," as used herein, refers to at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, and 2-chloro-3-fluoropentyl.

The term "heteroaryl," as used herein, means a monocyclic heteroaryl ring or a bicyclic heteroaryl ring. The monocyclic heteroaryl ring is a 5 or 6 membered ring. The 5 membered ring has two double bonds and contains one, two, three or four heteroatoms independently selected from the group consisting of N, O, and S. The 6 membered ring has three double bonds and contains one, two, three or four heteroatoms independently selected from the group consisting of N, O, and S. The bicyclic heteroaryl ring consists of the 5 or 6 membered heteroaryl ring fused to a distal aryl group or the 5 or 6 membered heteroaryl ring fused to a distal cycloalkyl group or the 5 or 6 membered heteroaryl ring fused to a distal cycloalkenyl group or the 5 or 6 membered heteroaryl ring fused to a distal 5 or 6 membered heteroaryl ring, or the 5 or 6 membered heteroaryl ring fused to a distal 5 or 6 membered heterocycle ring. Nitrogen heteroatoms contained within the heteroaryl may be optionally oxidized to the N-oxide or optionally protected with a nitrogen protecting group known to those of skill in the art. The heteroaryl is connected to the parent molecular moiety through any carbon atom or any nitrogen atom contained within the heteroaryl. Representative examples of heteroaryl include, but are not limited to, benzothienyl, benzoxadiazolyl, cinnolinyl, 5,6-dihydroisoquinolinyl, 7,8-dihydroisoquinolinyl, 5,6-dihydroquinolinyl, 7,8-dihydroquinolinyl, furopyridinyl, furyl, imidazolyl, indazolyl, indolyl, isoxazolyl, isoquinolinyl, isothiazolyl, naphthyridinyl, oxadiazolyl, oxazolyl, pyridinyl, pyridazinyl, pyrimidinyl, pyrazinyl, pyrazolyl, pyrrolyl, pyridinium N-oxide, quinolinyl, 5,6,7,8-tetrahydroisoquinolinyl, 5,6,7,8-tetrahydroquinolinyl, tetrazolyl, thiadiazolyl, thiazolyl, thienopyridinyl, thienyl, triazolyl, and triazinyl.

According to the present invention, heteroaryls of the present invention can be substituted with 0, 1, 2, or 3 substituents independently selected from alkenyl, alkoxy, alkoxyalkyl, alkoxyalkynyl, alkoxycarbonyl, alkoxycarbonylalkyl, alkyl, alkylcarbonyl, alkylcarbonylalkyl, alkylcarbonyloxy, alkylsulfonyl, alkylthio, alkynyl, aryl, arylalkoxy, arylalkyl, arylcarbonyl, aryloxy, carboxy, carboxyalkyl, cyano, cyanoalkyl, formyl, halogen, haloalkyl, heterocycle, hydroxy, hydroxyalkyl, hydroxyalkynyl, hydroxycycloalkyl, mercapto, nitro, oxo, phenyl, piperazinyl, pyridinyl, pyrazinyl, thiophen-yl, tetrahydropyridinyl, alkoxy-N=C(alkyl)alkyl-, HO—N=C(alkyl)-, $R_{ss}R_{tt}N-$, $R_{ss}R_{tt}Ncarbonyl$, $R_{ss}R_{tt}Nalkyl$, $R_{ss}R_{tt}NalkylNHcarbonyl$, $R_{ss}R_{tt}Nalkynyl$ wherein $R_{ss}$ and $R_{tt}$ are defined herein.

The term "heteroarylalkyl," as used herein, refers to a heteroaryl, as defined herein, appended to the parent molecular moiety through an alkyl group, as defined herein.

The term "heteroaryl-NHC(O)—," as used herein, refers to an heteroaryl-, as defined herein, appended to the parent molecular moiety through an NHC(O)— group, as defined herein.

The term "heteroaryl-NHC(O)-alkyl," as used herein, refers to an heteroaryl-NHC(O)—, as defined herein, appended to the parent molecular moiety through an alkyl-group, as defined herein.

The term "heteroarylalkyl-NHC(O)—," as used herein, refers to an heteroarylalkyl-, as defined herein, appended to the parent molecular moiety through an NHC(O)— group, as defined herein.

The term "heteroarylalkyl-NHC(O)-alkyl," as used herein, refers to an heteroarylalkyl-NHC(O)—, as defined herein, appended to the parent molecular moiety through an alkyl-group, as defined herein.

The term "heterocycle" or "heterocyclic" as used herein, means a monocyclic heterocyclic ring or a bicyclic heterocyclic ring or a tricyclic heterocyclic ring. The monocyclic heterocyclic ring consists of a 3, 4, 5, 6 or 7 membered ring containing at least one heteroatom independently selected from oxygen, nitrogen and sulfur. The 3 or 4 membered ring contains 1 heteroatom selected from the group consisting of O, N and S. The 5 membered ring contains zero or one double bond and one, two or three heteroatoms selected from the group consisting of O, N and S. The 6 or 7 membered ring contains zero, one or two double bonds and one, two or three heteroatoms selected from the group consisting of O, N and S. Representative examples of the monocyclic heterocyclic ring include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The bicyclic heterocyclic ring consists of the monocyclic heterocyclic ring fused to a distal aryl ring or the monocyclic heterocyclic ring fused to a distal cycloalkyl ring or the monocyclic heterocyclic ring fused to a distal cycloalkenyl ring or the monocyclic heterocyclic ring fused to a distal monocyclic heterocyclic ring, or the monocyclic heterocyclic ring fused to a distal monocyclic heteroaryl ring. Representative examples of the bicyclic heterocyclic ring include, but are not limited to, 1,3-benzodioxolyl, 1,3-benzodithiolyl, 2,3-dihydro-1,4-benzodioxinyl, 2,3-dihydro-1-benzofuranyl, 2,3-dihydro-1-benzothienyl, 2,3-dihydro-1H-indolyl, and 1,2,3,4-tetrahydroquinolinyl. The tricyclic heterocyclic ring consists of the bicyclic heterocyclic ring fused to a phenyl group or the bicyclic heterocyclic ring fused to a cycloalkyl group or the bicyclic heterocyclic ring fused to a cycloalkenyl group or the bicyclic heterocyclic ring fused to another monocyclic heterocyclic ring. Representative examples of tricyclic heterocyclic ring include, but are not limited to, 2,3,4,4a,9,9a-hexahydro-1H-carbazolyl, 5a,6,7,8,9,9a-hexahydrodibenzo[b,d]furanyl, and 5a,6,7,8,9,9a-hexahydrodibenzo[b,d]thienyl.

According to the present invention, heterocycles of the present invention can be substituted with 0, 1, 2, or 3 substituents independently selected from alkenyl, alkoxy, alkoxyalkyl, alkoxyalkynyl, alkoxycarbonyl, alkoxycarbonylalkyl, alkoxy-NH=C(alkyl)—, alkyl, alkylcarbonyl, alkylcarbonylalkyl, alkylcarbonyloxy, alkylsulfonyl, alkylthio, alkynyl, aryl, arylalkoxy, arylalkyl, arylcarbonyl, aryloxy, carboxy, carboxyalkyl, cyano, cyanoalkyl, cycloalkyl, cycloalkylalkyl, formyl, halogen, haloalkyl, hydroxy, hydroxyalkyl, hydroxycycloalkyl, mercapto, nitro, oxo, phenyl, and $R_{ss}R_{tt}N-$, $R_sR_tNcarbonyl$, $R_{ss}R_{tt}Nalkyl$, wherein $R_{ss}$ and $R_{tt}$ are defined herein.

The term "heterocyclealkyl," as used herein, refers to a heterocycle, as defined herein, appended to the parent molecular moiety through an alkyl group, as defined herein. Representative examples of heterocyclealkyl include, but are not limited to, pyridin-3-ylmethyl and 2-pyrimidin-2-ylpropyl and the like.

The term "heterocyclealkyl-NHC(O)—," as used herein, refers to an heterocyclealkyl-, as defined herein, appended to the parent molecular moiety through an NHC(O)— group, as defined herein.

The term "heterocyclealkyl-NHC(O)-alkyl," as used herein, refers to an heterocyclealkyl-NHC(O)—, as defined herein, appended to the parent molecular moiety through an alkyl-group, as defined herein.

The term "heterocycle-NHC(O)—," as used herein, refers to an heterocycle, as defined herein, appended to the parent molecular moiety through an NHC(O)— group, as defined herein.

The term "heterocycle-NHC(O)-alkyl," as used herein, refers to an heterocycle-NHC(O)—, as defined herein, appended to the parent molecular moiety through an alkyl-group, as defined herein.

The term "heterocyclealkenyl," as used herein, refers to a heterocycle, as defined herein, appended to the parent molecular moiety through an alkenyl group, as defined herein.

The term "heterocyclealkoxy," as used herein, refers to a heterocycle, as defined herein, appended to the parent molecular moiety through an alkoxy group, as defined herein.

The term "heterocyclecarbonyl," as used herein, refers to a heterocycle, as defined herein, appended to the parent molecular moiety through a carbonyl group, as defined herein. Representative examples of heterocyclecarbonyl include, but are not limited to, pyridin-4-ylethanone, pyridin-4-ylpropanone.

The term "heterocycleoxy," as used herein, refers to a heterocycle, as defined herein, appended to the parent molecular moiety through an oxy group, as defined herein. Representative examples of heterocycleoxy include, but are not limited to, pyridin-2-ol, pyridin-4-ol, thiophen-2-ol.

The term "heterocycleoxycarbonyl," as used herein, refers to a heterocycleoxy, as defined herein, appended to the parent molecular moiety through a carbonyl group, as defined herein. Representative examples of heterocyclecarbonyl include, but are not limited to, pyridin-4-ylcarboxylate, thiophene-2-ylcarboxylate.

The term "heterocycleoxyalkynyl," as used herein, refers to a heterocycleoxy, as defined herein, appended to the parent molecular moiety through an alkyne group, as defined herein.

The term "hydroxy," as used herein, refers to an —OH group.

The term "hydroxyalkyl," as used herein, refers to a hydroxy group, as defined herein, appended to the parent molecular moiety through an alkyl group, as defined herein. Representative examples of hydroxyalkyl include, but are not limited to, 2-hydroxyethyl, 2-hydroxypropyl, 3-hydroxybutyl and the like.

The term "hydroxyalkyl-NHC(O)—," as used herein, refers to an hydroxyalkyl-, as defined herein, appended to the parent molecular moiety through an NHC(O)— group, as defined herein.

The term "hydroxyalkyl-NHC(O)-alkyl," as used herein, refers to an hydroxyalkyl-NHC(O)—, as defined herein, appended to the parent molecular moiety through an alkyl-group, as defined herein.

The term "hydroxyalkenyl," as used herein, refers to a hydroxy group, as defined herein, appended to the parent molecular moiety through an alkenyl group, as defined herein.

The term "hydroxyalkynyl," as used herein, refers to a hydroxy group, as defined herein, appended to the parent molecular moiety through an alkyne group, as defined herein.

The term "hydroxyalkoxy," as used herein, refers to a hydroxy group as defined herein, appended to the parent molecular moiety through a alkoxy group, as defined herein. Representative examples of alkyl include, but are not limited to, 2-hydroxyethoxy, 2-hydroxypropoxy, 3-hydroxybutoxy and the like.

The term "hydroxycycloalkyl," as used herein, refers to a hydroxy group, as defined herein, appended to the parent molecular moiety through an cycloalkyl group, as defined herein.

The term "—NHC(O)—," as used herein, refers to an unsubstituted nitrogen atom, as defined herein, appended to the parent molecular moiety through a carbonyl group, as defined herein.

The term "trihaloalkyl," as used herein, refers to three halogen atoms, appended to the parent molecular moiety through an alkyl group, as defined herein.

The term "trihaloalkoxy," as used herein, refers to three halogen atoms, appended to the parent molecular moiety through an alkoxy group, as defined herein.

Specific compounds of formula (I) include, but are not limited to:

3-(3,5-dimethylphenyl)-4-hydroxy-6-oxo-6,7-dihydrothieno[2,3-b]pyridine-5-carbonitrile;

3-(4-fluorophenyl)-4-hydroxy-6-oxo-6,7-dihydrothieno[2,3-b]pyridine-5-carbonitrile;

3-(4-chlorophenyl)-4-hydroxy-6-oxo-6,7-dihydrothieno[2,3-b]pyridine-5-carbonitrile;

4-hydroxy-6-oxo-3-[4-(trifluoromethyl)phenyl]-6,7-dihydrothieno[2,3-b]pyridine-5-carbonitrile;

2-bromo-3-(4-chlorophenyl)-4-hydroxy-6-oxo-6,7-dihydrothieno[2,3-b]pyridine-5-carbonitrile;

2-bromo-4-hydroxy-6-oxo-3-[4-(trifluoromethyl)phenyl]-6,7-dihydrothieno[2,3-b]pyridine-5-carbonitrile;

3-(4-bromophenyl)-4-hydroxy-6-oxo-6,7-dihydrothieno[2,3-b]pyridine-5-carbonitrile;

2-bromo-3-(4-fluorophenyl)-4-hydroxy-6-oxo-6,7-dihydrothieno[2,3-b]pyridine-5-carbonitrile;

3-(4'-fluoro-1,1'-biphenyl-4-yl)-4-hydroxy-6-oxo-6,7-dihydrothieno[2,3-b]pyridine-5-carbonitrile;

4-hydroxy-6-oxo-3-[4'-(trifluoromethyl)-1,1'-biphenyl-4-yl]-6,7-dihydrothieno[2,3-b]pyridine-5-carbonitrile;

3-[4-(1,3-benzodioxol-5-yl)phenyl]-4-hydroxy-6-oxo-6,7-dihydrothieno[2,3-b]pyridine-5-carbonitrile;

2,5-dibromo-3-(4-chlorophenyl)-4-hydroxythieno[2,3-b]pyridin-6(7H)-one;

2,5-dichloro-3-(4-chlorophenyl)-4-hydroxythieno[2,3-b]pyridin-6(7H)-one;

4-hydroxy-3-(4-nitrophenyl)-6-oxo-6,7-dihydrothieno[2,3-b]pyridine-5-carbonitrile;

2-bromo-4-hydroxy-3-(4-nitrophenyl)-6-oxo-6,7-dihydrothieno[2,3-b]pyridine-5-carbonitrile;

3-(1,1'-biphenyl-4-yl)-4-hydroxy-6-oxo-6,7-dihydrothieno[2,3-b]pyridine-5-carbonitrile;

4-hydroxy-3-(2'-methyl-1,1'-biphenyl-4-yl)-6-oxo-6,7-dihydrothieno[2,3-b]pyridine-5-carbonitrile;

4-hydroxy-3-(3'-methyl-1,1'-biphenyl-4-yl)-6-oxo-6,7-dihydrothieno[2,3-b]pyridine-5-carbonitrile;

4-hydroxy-3-(2'-hydroxy-1,1'-biphenyl-4-yl)-6-oxo-6,7-dihydrothieno[2,3-b]pyridine-5-carbonitrile;

4-hydroxy-3-(3'-hydroxy-1,1'-biphenyl-4-yl)-6-oxo-6,7-dihydrothieno[2,3-b]pyridine-5-carbonitrile;

4-hydroxy-3-(2'-methoxy-1,1'-biphenyl-4-yl)-6-oxo-6,7-dihydrothieno[2,3-b]pyridine-5-carbonitrile;

4-hydroxy-3-(3'-methoxy-1,1'-biphenyl-4-yl)-6-oxo-6,7-dihydrothieno[2,3-b]pyridine-5-carbonitrile;

4-hydroxy-3-(4'-methoxy-1,1'-biphenyl-4-yl)-6-oxo-6,7-dihydrothieno[2,3-b]pyridine-5-carbonitrile;

3-(2'-fluoro-1,1'-biphenyl-4-yl)-4-hydroxy-6-oxo-6,7-dihydrothieno[2,3-b]pyridine-5-carbonitrile;

3-(3'-fluoro-1,1'-biphenyl-4-yl)-4-hydroxy-6-oxo-6,7-dihydrothieno[2,3-b]pyridine-5-carbonitrile;

3-(2'-chloro-1,1'-biphenyl-4-yl)-4-hydroxy-6-oxo-6,7-dihydrothieno[2,3-b]pyridine-5-carbonitrile;

3-(3'-chloro-1,1'-biphenyl-4-yl)-4-hydroxy-6-oxo-6,7-dihydrothieno[2,3-b]pyridine-5-carbonitrile;

3-(4'-chloro-1,1'-biphenyl-4-yl)-4-hydroxy-6-oxo-6,7-dihydrothieno[2,3-b]pyridine-5-carbonitrile;

3-(4'-cyano-1,1'-biphenyl-4-yl)-4-hydroxy-6-oxo-6,7-dihydrothieno[2,3-b]pyridine-5-carbonitrile;

3-(3'-acetyl-1,1'-biphenyl-4-yl)-4-hydroxy-6-oxo-6,7-dihydrothieno[2,3-b]pyridine-5-carbonitrile;

3-[4'-(dimethylamino)-1,1'-biphenyl-4-yl]-4-hydroxy-6-oxo-6,7-dihydrothieno[2,3-b]pyridine-5-carbonitrile;

4-hydroxy-6-oxo-3-(4'-phenoxy-1,1'-biphenyl-4-yl)-6,7-dihydrothieno[2,3-b]pyridine-5-carbonitrile;
3-(4'-acetyl-1,1'-biphenyl-4-yl)-4-hydroxy-6-oxo-6,7-dihydrothieno[2,3-b]pyridine-5-carbonitrile;
3-(2',3'-dimethyl-1,1'-biphenyl-4-yl)-4-hydroxy-6-oxo-6,7-dihydrothieno[2,3-b]pyridine-5-carbonitrile;
4-hydroxy-6-oxo-3-[4'-(trifluoromethoxy)-1,1'-biphenyl-4-yl]-6,7-dihydrothieno[2,3-b]pyridine-5-carbonitrile;
3-(3',4'-dimethyl-1,1'-biphenyl-4-yl)-4-hydroxy-6-oxo-6,7-dihydrothieno[2,3-b]pyridine-5-carbonitrile;
3-(2',3'-dichloro-1,1'-biphenyl-4-yl)-4-hydroxy-6-oxo-6,7-dihydrothieno[2,3-b]pyridine-5-carbonitrile;
3-(2',4'-dichloro-1,1'-biphenyl-4-yl)-4-hydroxy-6-oxo-6,7-dihydrothieno[2,3-b]pyridine-5-carbonitrile;
2-bromo-3-(4'-fluoro-1,1'-biphenyl-4-yl)-4-hydroxy-6-oxo-6,7-dihydrothieno[2,3-b]pyridine-5-carbonitrile;
3-(4-aminophenyl)-4-hydroxy-6-oxo-6,7-dihydrothieno[2,3-b]pyridine-5-carbonitrile;
2-chloro-4-hydroxy-6-oxo-3-[4-(trifluoromethyl)phenyl]-6,7-dihydrothieno[2,3-b]pyridine-5-carbonitrile;
4-hydroxy-3-(4'-hydroxy-1,1'-biphenyl-4-yl)-6-oxo-6,7-dihydrothieno[2,3-b]pyridine-5-carbonitrile;
3-(4'-acetyl-1,1'-biphenyl-4-yl)-2-bromo-4-hydroxy-6-oxo-6,7-dihydrothieno[2,3-b]pyridine-5-carbonitrile;
2-bromo-4-hydroxy-3-(2'-hydroxy-1,1'-biphenyl-4-yl)-6-oxo-6,7-dihydrothieno[2,3-b]pyridine-5-carbonitrile;
2-bromo-3-(4'-cyano-1,1'-biphenyl-4-yl)-4-hydroxy-6-oxo-6,7-dihydrothieno[2,3-b]pyridine-5-carbonitrile;
2-chloro-4-hydroxy-3-(2'-hydroxy-1,1'-biphenyl-4-yl)-6-oxo-6,7-dihydrothieno[2,3-b]pyridine-5-carbonitrile;
2-bromo-3-(5'-bromo-2'-hydroxy-1,1'-biphenyl-4-yl)-4-hydroxy-6-oxo-6,7-dihydrothieno[2,3-b]pyridine-5-carbonitrile;
4-hydroxy-3-[2'-(hydroxymethyl)-1,1'-biphenyl-4-yl]-6-oxo-6,7-dihydrothieno[2,3-b]pyridine-5-carbonitrile;
4-hydroxy-3-[4-(methoxymethoxy)phenyl]-6-oxo-6,7-dihydrothieno[2,3-b]pyridine-5-carbonitrile;
4-hydroxy-6-oxo-3-{2'-[({2-[4-(trifluoromethyl)phenyl]ethyl}amino)methyl]-1,1'-biphenyl-4-yl}-6,7-dihydrothieno[2,3-b]pyridine-5-carbonitrile;
4-hydroxy-3-[2'-({[2-(4-hydroxy-3,5-dimethoxyphenyl)ethyl]amino}methyl)-1,1'-biphenyl-4-yl]-6-oxo-6,7-dihydrothieno[2,3-b]pyridine-5-carbonitrile;
3-[4-(2-formylthien-3-yl)phenyl]-4-hydroxy-6-oxo-6,7-dihydrothieno[2,3-b]pyridine-5-carbonitrile;
3-(2'-amino-1,1'-biphenyl-4-yl)-4-hydroxy-6-oxo-6,7-dihydrothieno[2,3-b]pyridine-5-carbonitrile;
4-hydroxy-3-(4-hydroxyphenyl)-6-oxo-6,7-dihydrothieno[2,3-b]pyridine-5-carbonitrile;
2-bromo-3-(3-bromo-4-hydroxyphenyl)-4-hydroxy-6-oxo-6,7-dihydrothieno[2,3-b]pyridine-5-carbonitrile;
2-chloro-3-(4'-chloro-1,1'-biphenyl-4-yl)-4-hydroxy-6-oxo-6,7-dihydrothieno[2,3-b]pyridine-5-carbonitrile;
N-[4'-(2-chloro-5-cyano-4-hydroxy-6-oxo-6,7-dihydrothieno[2,3-b]pyridin-3-yl)-1,1'-biphenyl-3-yl]acetamide;
2-chloro-3-(4'-chloro-1,1'-biphenyl-4-yl)-4-hydroxy-6-oxo-6,7-dihydrothieno[2,3-b]pyridine-5-carbonitrile;
{[4'-(5-cyano-4-hydroxy-6-oxo-6,7-dihydrothieno[2,3-b]pyridin-3-yl)-1,1'-biphenyl-2-yl]oxy}acetic acid;
2-bromo-4-hydroxy-3-(4-hydroxyphenyl)-6-oxo-6,7-dihydrothieno[2,3-b]pyridine-5-carbonitrile;
2-bromo-3-(3,5-dibromo-4-hydroxyphenyl)-4-hydroxy-6-oxo-6,7-dihydrothieno[2,3-b]pyridine-5-carbonitrile;
3-(3-bromophenyl)-4-hydroxy-6-oxo-6,7-dihydrothieno[2,3-b]pyridine-5-carbonitrile;
2-chloro-4-hydroxy-3-(2'-methyl-1,1'-biphenyl-4-yl)-6-oxo-6,7-dihydrothieno[2,3-b]pyridine-5-carbonitrile;
2-chloro-4-hydroxy-3-(3'-hydroxy-1,1'-biphenyl-4-yl)-6-oxo-6,7-dihydrothieno[2,3-b]pyridine-5-carbonitrile;
3-{4-[bis(3,3-dimethylbutyl)amino]phenyl}-4-hydroxy-6-oxo-6,7-dihydrothieno[2,3-b]pyridine-5-carbonitrile;
2,5-dichloro-3-(3,5-dichloro-4-hydroxyphenyl)-4-hydroxythieno[2,3-b]pyridin-6(7H)-one;
3-(2',6'-dihydroxy-1,1'-biphenyl-4-yl)-4-hydroxy-6-oxo-6,7-dihydrothieno[2,3-b]pyridine-5-carbonitrile;
3-[5-(4-aminophenyl)thien-2-yl]-4-hydroxy-6-oxo-6,7-dihydrothieno[2,3-b]pyridine-5-carbonitrile;
N-{4-[5-(2-chloro-5-cyano-4-hydroxy-6-oxo-6,7-dihydrothieno[2,3-b]pyridin-3-yl)thien-2-yl]phenyl}methanesulfonamide;
2-bromo-3-(3,5-dibromo-4-hydroxyphenyl)-4-hydroxy-6-oxo-6,7-dihydrothieno[2,3-b]pyridine-5-carbonitrile;
3-(2',3'-dihydroxy-1,1'-biphenyl-4-yl)-4-hydroxy-6-oxo-6,7-dihydrothieno[2,3-b]pyridine-5-carbonitrile;
2,5-dibromo-3-(3,5-dibromo-4-hydroxyphenyl)-4-hydroxythieno[2,3-b]pyridin-6(7H)-one;
3-(2',4'-dihydroxy-1,1'-biphenyl-4-yl)-4-hydroxy-6-oxo-6,7-dihydrothieno[2,3-b]pyridine-5-carbonitrile;
N-{4-[5-(5-cyano-4-hydroxy-6-oxo-6,7-dihydrothieno[2,3-b]pyridin-3-yl)thien-2-yl]phenyl}methanesulfonamide;
4-hydroxy-3-[5-(4-hydroxyphenyl)thien-2-yl]-6-oxo-6,7-dihydrothieno[2,3-b]pyridine-5-carbonitrile;
2-chloro-3-[4-(2,3-dihydroxypropoxy)phenyl]-4-hydroxy-6-oxo-6,7-dihydrothieno[2,3-b]pyridine-5-carbonitrile;
4-[5-(5-cyano-4-hydroxy-6-oxo-6,7-dihydrothieno[2,3-b]pyridin-3-yl)thien-2-yl]benzenesulfonamide;
3-(2'-amino-1,1'-biphenyl-4-yl)-4-hydroxy-6-oxo-6,7-dihydrothieno[2,3-b]pyridine-5-carbonitrile;
4-hydroxy-6-oxo-3-(5-pyridin-4-ylthien-2-yl)-6,7-dihydrothieno[2,3-b]pyridine-5-carbonitrile;
2-chloro-4-hydroxy-3-[5-(4-hydroxyphenyl)thien-2-yl]-6-oxo-6,7-dihydrothieno[2,3-b]pyridine-5-carbonitrile;
4-hydroxy-3-{5-[4-(hydroxymethyl)phenyl]thien-2-yl}-6-oxo-6,7-dihydrothieno[2,3-b]pyridine-5-carbonitrile;
2-chloro-4-hydroxy-3-{4-[(1-hydroxycyclopent-3-en-1-yl)methoxy]phenyl}-6-oxo-6,7-dihydrothieno[2,3-b]pyridine-5-carbonitrile;
2-chloro-4-hydroxy-3-(4-hydroxyphenyl)-6-oxo-6,7-dihydrothieno[2,3-b]pyridine-5-carbonitrile;
4-hydroxy-3-{5-[4-(methylsulfonyl)phenyl]thien-2-yl}-6-oxo-6,7-dihydrothieno[2,3-b]pyridine-5-carbonitrile;
N-{4-[5-(5-cyano-4-hydroxy-6-oxo-6,7-dihydrothieno[2,3-b]pyridin-3-yl)thien-2-yl]phenyl}acetamide;
4-hydroxy-6-oxo-3-(5-phenylthien-2-yl)-6,7-dihydrothieno[2,3-b]pyridine-5-carbonitrile; 3-(2,2'-bithien-5-yl)-4-hydroxy-6-oxo-6,7-dihydrothieno[2,3-b]pyridine-5-carbonitrile;
3-(3'-fluoro-2'-hydroxy-1,1'-biphenyl-4-yl)-4-hydroxy-6-oxo-6,7-dihydrothieno[2,3-b]pyridine-5-carbonitrile;
3-[5-(2-aminophenyl)thien-2-yl]-4-hydroxy-6-oxo-6,7-dihydrothieno[2,3-b]pyridine-5-carbonitrile;
3-[5-(4-fluorophenyl)thien-2-yl]-4-hydroxy-6-oxo-6,7-dihydrothieno[2,3-b]pyridine-5-carbonitrile;
3-[5-(2,4-difluorophenyl)thien-2-yl]-4-hydroxy-6-oxo-6,7-dihydrothieno[2,3-b]pyridine-5-carbonitrile;
4-hydroxy-6-oxo-3-(4-thien-3-ylphenyl)-6,7-dihydrothieno[2,3-b]pyridine-5-carbonitrile;
4-hydroxy-3-[5-(3-methoxyprop-1-ynyl)-4-methylthien-2-yl]-6-oxo-6,7-dihydrothieno[2,3-b]pyridine-5-carbonitrile;
4-hydroxy-3-(4-hydroxyphenyl)-6-oxo-6,7-dihydrothieno[2,3-b]pyridine-5-carbonitrile;

2-bromo-3-(3-bromo-4-hydroxyphenyl)-4-hydroxy-6-oxo-6,7-dihydrothieno[2,3-b]pyridine-5-carbonitrile;

2,5-dichloro-4-hydroxy-3-(4-hydroxyphenyl)thieno[2,3-b]pyridin-6(7H)-one;

methyl 4-[5-(5-cyano-4-hydroxy-6-oxo-6,7-dihydrothieno[2,3-b]pyridin-3-yl)thien-2-yl]phenylcarbamate;

2-chloro-4-hydroxy-3-[4-(2-hydroxy-2-methylpropoxy)phenyl]-6-oxo-6,7-dihydrothieno[2,3-b]pyridine-5-carbonitrile;

2-chloro-4-hydroxy-3-{4-[(1-hydroxycyclopentyl)methoxy]phenyl}-6-oxo-6,7-dihydrothieno[2,3-b]pyridine-5-carbonitrile;

2-bromo-4-hydroxy-3-(4-hydroxyphenyl)-6-oxo-6,7-dihydrothieno[2,3-b]pyridine-5-carbonitrile;

2-chloro-4-hydroxy-3-[4-(hydroxymethyl)phenyl]-6-oxo-6,7-dihydrothieno[2,3-b]pyridine-5-carbonitrile;

4-hydroxy-3-[5-(4-methoxyphenyl)thien-2-yl]-6-oxo-6,7-dihydrothieno[2,3-b]pyridine-5-carbonitrile;

4-hydroxy-2-methyl-6-oxo-3-(phenylethynyl)-6,7-dihydrothieno[2,3-b]pyridine-5-carbonitrile;

2-chloro-3-{4-[(1-ethyl-4-hydroxypiperidin-4-yl)methoxy]phenyl}-4-hydroxy-6-oxo-6,7-dihydrothieno[2,3-b]pyridine-5-carbonitrile;

4-hydroxy-3-[5-(3-methoxyprop-1-ynyl)thien-2-yl]-6-oxo-6,7-dihydrothieno[2,3-b]pyridine-5-carbonitrile;

4-hydroxy-3-[5-(5-hydroxypent-1-ynyl)thien-2-yl]-6-oxo-6,7-dihydrothieno[2,3-b]pyridine-5-carbonitrile;

3-{4-[(1-acetyl-4-hydroxypiperidin-4-yl)methoxy]phenyl}-2-chloro-4-hydroxy-6-oxo-6,7-dihydrothieno[2,3-b]pyridine-5-carbonitrile;

2-bromo-4-hydroxy-3-[4-(4-hydroxybut-1-ynyl)phenyl]-6-oxo-6,7-dihydrothieno[2,3-b]pyridine-5-carbonitrile;

4-hydroxy-3-[5-(3-hydroxyprop-1-ynyl)thien-2-yl]-6-oxo-6,7-dihydrothieno[2,3-b]pyridine-5-carbonitrile;

2-chloro-4-hydroxy-3-{4-[(4-hydroxy-1-isobutylpiperidin-4-yl)methoxy]phenyl}-6-oxo-6,7-dihydrothieno[2,3-b]pyridine-5-carbonitrile;

4-hydroxy-3-{4-[(1E)-4-hydroxybut-1-enyl]phenyl}-6-oxo-6,7-dihydrothieno[2,3-b]pyridine-5-carbonitrile;

4-hydroxy-6-oxo-3-[5-(1,2,3,6-tetrahydropyridin-4-yl)thien-2-yl]-6,7-dihydrothieno[2,3-b]pyridine-5-carbonitrile;

4-hydroxy-6-oxo-3-(5-phenyl-4-pyridin-3-ylthien-2-yl)-6,7-dihydrothieno[2,3-b]pyridine-5-carbonitrile;

3-[4-(allyloxy)phenyl]-2-chloro-4-hydroxy-6-oxo-6,7-dihydrothieno[2,3-b]pyridine-5-carbonitrile;

7-[4-(5-cyano-4-hydroxy-6-oxo-6,7-dihydrothieno[2,3-b]pyridin-3-yl)phenyl]-N,N-diethylhept-6-ynamide;

4-hydroxy-6-oxo-3-[5-(2-oxo-2,3-dihydro-1H-indol-5-yl)thien-2-yl]-6,7-dihydrothieno[2,3-b]pyridine-5-carbonitrile;

3-[5-(4-cyanophenyl)thien-2-yl]-4-hydroxy-6-oxo-6,7-dihydrothieno[2,3-b]pyridine-5-carbonitrile;

2-chloro-3-{4-[(1-cyclopropyl-4-hydroxypiperidin-4-yl)methoxy]phenyl}-4-hydroxy-6-oxo-6,7-dihydrothieno[2,3-b]pyridine-5-carbonitrile;

3-(4'-fluoro-2'-hydroxy-1,1'-biphenyl-4-yl)-4-hydroxy-6-oxo-6,7-dihydrothieno[2,3-b]pyridine-5-carbonitrile;

4-hydroxy-3-[4-(methoxymethoxy)phenyl]-6-oxo-6,7-dihydrothieno[2,3-b]pyridine-5-carbonitrile;

4-[5-(5-cyano-4-hydroxy-6-oxo-6,7-dihydrothieno[2,3-b]pyridin-3-yl)thien-2-yl]benzoic acid;

3-[5-(3-aminophenyl)thien-2-yl]-4-hydroxy-6-oxo-6,7-dihydrothieno[2,3-b]pyridine-5-carbonitrile;

4-hydroxy-3-(2'-hydroxy-1,1'-biphenyl-4-yl)thieno[2,3-b]pyridin-6(7H)-one;

methyl 4-(2-chloro-5-cyano-4-hydroxy-6-oxo-6,7-dihydrothieno[2,3-b]pyridin-3-yl)benzoate;

2-chloro-4-hydroxy-6-oxo-3-(2-phenylcyclopropyl)-6,7-dihydrothieno[2,3-b]pyridine-5-carbonitrile;

3-[5-(4-acetylphenyl)thien-2-yl]-4-hydroxy-6-oxo-6,7-dihydrothieno[2,3-b]pyridine-5-carbonitrile;

4-hydroxy-6-oxo-3-(4-vinylphenyl)-6,7-dihydrothieno[2,3-b]pyridine-5-carbonitrile;

3-[5-(2,4-dihydroxyphenyl)thien-2-yl]-4-hydroxy-6-oxo-6,7-dihydrothieno[2,3-b]pyridine-5-carbonitrile;

3-[3-(allyloxy)phenyl]-2-bromo-4-hydroxy-6-oxo-6,7-dihydrothieno[2,3-b]pyridine-5-carbonitrile;

3-{5-[3-(dimethylamino)prop-1-ynyl]thien-2-yl}-4-hydroxy-6-oxo-6,7-dihydrothieno[2,3-b]pyridine-5-carbonitrile;

4-hydroxy-3-[2'-(hydroxymethyl)-1,1'-biphenyl-4-yl]-6-oxo-6,7-dihydrothieno[2,3-b]pyridine-5-carbonitrile;

3-(4-bromophenyl)-2-chloro-4-hydroxy-6-oxo-6,7-dihydrothieno[2,3-b]pyridine-5-carbonitrile;

4-hydroxy-3-[4-(4-hydroxybut-1-ynyl)phenyl]-6-oxo-6,7-dihydrothieno[2,3-b]pyridine-5-carbonitrile;

4-hydroxy-6-oxo-3-(5-pyridin-2-ylthien-2-yl)-6,7-dihydrothieno[2,3-b]pyridine-5-carbonitrile;

4-hydroxy-3-(2'-hydroxy-1,1'-biphenyl-4-yl)-6-oxo-6,7-dihydrothieno[2,3-b]pyridine-5-carbaldehyde oxime;

3-[3-(allyloxy)phenyl]-2-chloro-4-hydroxy-6-oxo-6,7-dihydrothieno[2,3-b]pyridine-5-carbonitrile;

3-(5'-bromo-2',4'-dihydroxy-1,1'-biphenyl-4-yl)-4-hydroxy-6-oxo-6,7-dihydrothieno[2,3-b]pyridine-5-carbonitrile;

4-hydroxy-3-(2'-hydroxy-4',6'-dimethyl-1,1'-biphenyl-4-yl)-6-oxo-6,7-dihydrothieno[2,3-b]pyridine-5-carbonitrile;

N-{4-[5-(5-cyano-4-hydroxy-6-oxo-6,7-dihydrothieno[2,3-b]pyridin-3-yl)thien-2-yl]-2-fluorophenyl}acetamide;

2-[({(1E)-[4-(5-cyano-4-hydroxy-6-oxo-6,7-dihydrothieno[2,3-b]pyridin-3-yl)phenyl]methylene}amino)oxy]-N-(pyridin-2-ylmethyl)acetamide;

2-chloro-4-hydroxy-3-(5-methyl-2-furyl)-6-oxo-6,7-dihydrothieno[2,3-b]pyridine-5-carbonitrile;

4-hydroxy-3-(3-hydroxyphenyl)-6-oxo-6,7-dihydrothieno[2,3-b]pyridine-5-carbonitrile;

2-chloro-3-{4-[(1-cyclopentyl-4-hydroxypiperidin-4-yl)methoxy]phenyl}-4-hydroxy-6-oxo-6,7-dihydrothieno[2,3-b]pyridine-5-carbonitrile;

3-(2',5'-dihydroxy-1,1'-biphenyl-4-yl)-4-hydroxy-6-oxo-6,7-dihydrothieno[2,3-b]pyridine-5-carbonitrile;

3-(2'-formyl-1,1'-biphenyl-4-yl)-4-hydroxy-6-oxo-6,7-dihydrothieno[2,3-b]pyridine-5-carbonitrile;

3-[4-(2,3-dihydroxypropoxy)phenyl]-4-hydroxy-2-methyl-6-oxo-6,7-dihydrothieno[2,3-b]pyridine-5-carbonitrile;

3-[4-(allyloxy)phenyl]-2-bromo-4-hydroxy-6-oxo-6,7-dihydrothieno[2,3-b]pyridine-5-carbonitrile;

3-[5-(1-acetyl-1,2,3,6-tetrahydropyridin-4-yl)thien-2-yl]-4-hydroxy-6-oxo-6,7-dihydrothieno[2,3-b]pyridine-5-carbonitrile;

3-{5-[4-(allyloxy)phenyl]thien-2-yl}-4-hydroxy-6-oxo-6,7-dihydrothieno[2,3-b]pyridine-5-carbonitrile;

7-[3-(5-cyano-4-hydroxy-6-oxo-6,7-dihydrothieno[2,3-b]pyridin-3-yl)phenyl]hept-6-ynoic acid;

4-hydroxy-3-[5-(3-methoxyprop-1-ynyl)-4-vinylthien-2-yl]-6-oxo-6,7-dihydrothieno[2,3-b]pyridine-5-carbonitrile;

3-(2'-chloro-6'-hydroxy-1,1'-biphenyl-4-yl)-4-hydroxy-6-oxo-6,7-dihydrothieno[2,3-b]pyridine-5-carbonitrile;

2-chloro-4-hydroxy-3-(3'-hydroxy-1,1'-biphenyl-4-yl)-6-oxo-6,7-dihydrothieno[2,3-b]pyridine-5-carbonitrile;

2-chloro-3-{4-[(1-cyclobutyl-4-hydroxypiperidin-4-yl)methoxy]phenyl}-4-hydroxy-6-oxo-6,7-dihydrothieno[2,3-b]pyridine-5-carbonitrile;
7-[4-(5-cyano-4-hydroxy-6-oxo-6,7-dihydrothieno[2,3-b]pyridin-3-yl)phenyl]hept-6-ynoic acid;
3-(3,5-dichloro-4-hydroxyphenyl)-4-hydroxy-6-oxo-6,7-dihydrothieno[2,3-b]pyridine-5-carbonitrile;
2-[({(1E)-[4-(5-cyano-4-hydroxy-6-oxo-6,7-dihydrothieno[2,3-b]pyridin-3-yl)phenyl]methylene}amino)oxy]-N-[(2S)-2,3-dihydroxypropyl]acetamide;
4-hydroxy-6-oxo-3-[4-(1H-pyrazol-3-yl)phenyl]-6,7-dihydrothieno[2,3-b]pyridine-5-carbonitrile;
3-{5-[4-(2,3-dihydroxypropoxy)phenyl]thien-2-yl}-4-hydroxy-6-oxo-6,7-dihydrothieno[2,3-b]pyridine-5-carbonitrile;
2-bromo-4-hydroxy-3-[4-(5-hydroxypent-1-ynyl)phenyl]-6-oxo-6,7-dihydrothieno[2,3-b]pyridine-5-carbonitrile;
4-hydroxy-6-oxo-3-(5,6,7,8-tetrahydronaphthalen-2-yl)-6,7-dihydrothieno[2,3-b]pyridine-5-carbonitrile;
2-[({(1E)-[4-(5-cyano-4-hydroxy-6-oxo-6,7-dihydrothieno[2,3-b]pyridin-3-yl)phenyl]methylene}amino)oxy]-N-[2-(4-methylpiperazin-1-yl)ethyl]acetamide;
N-{3-chloro-4-[5-(5-cyano-4-hydroxy-6-oxo-6,7-dihydrothieno[2,3-b]pyridin-3-yl)thien-2-yl]phenyl}acetamide;
4-hydroxy-3-[4-(5-hydroxypent-1-ynyl)phenyl]-6-oxo-6,7-dihydrothieno[2,3-b]pyridine-5-carbonitrile;
3-[4-bromo-5-(3-methoxyprop-1-ynyl)thien-2-yl]-4-hydroxy-6-oxo-6,7-dihydrothieno[2,3-b]pyridine-5-carbonitrile;
2-[4-(2-chloro-5-cyano-4-hydroxy-6-oxo-6,7-dihydrothieno[2,3-b]pyridin-3-yl)phenoxy]-N-(3-hydroxypropyl)acetamide;
2-chloro-3-[4-(cyanomethoxy)phenyl]-4-hydroxy-6-oxo-6,7-dihydrothieno[2,3-b]pyridine-5-carbonitrile;
4-hydroxy-3-[4-(3-methoxyprop-1-ynyl)phenyl]-6-oxo-6,7-dihydrothieno[2,3-b]pyridine-5-carbonitrile;
4-hydroxy-6-oxo-3-{4-[(1E)-4-pyrrolidin-1-ylbut-1-enyl]phenyl}-6,7-dihydrothieno[2,3-b]pyridine-5-carbonitrile;
tert-butyl 4-[5-(5-cyano-4-hydroxy-6-oxo-6,7-dihydrothieno[2,3-b]pyridin-3-yl)thien-2-yl]phenylcarbamate;
4-hydroxy-3-[5-(4-hydroxyphenyl)-4-methylthien-2-yl]-6-oxo-6,7-dihydrothieno[2,3-b]pyridine-5-carbonitrile;
2-chloro-3-[4-(diallylamino)phenyl]-4-hydroxy-6-oxo-6,7-dihydrothieno[2,3-b]pyridine-5-carbonitrile;
4-hydroxy-3-[5-(1H-indol-5-yl)thien-2-yl]-6-oxo-6,7-dihydrothieno[2,3-b]pyridine-5-carbonitrile;
2-bromo-3-(5'-bromo-2'-hydroxy-1,1'-biphenyl-4-yl)-4-hydroxy-6-oxo-6,7-dihydrothieno[2,3-b]pyridine-5-carbonitrile;
3-[4-(5-cyanopent-1-ynyl)phenyl]-4-hydroxy-6-oxo-6,7-dihydrothieno[2,3-b]pyridine-5-carbonitrile;
2-[4-(2-chloro-5-cyano-4-hydroxy-6-oxo-6,7-dihydrothieno[2,3-b]pyridin-3-yl)phenoxy]acetamide;
2-[({(1E)-[4-(5-cyano-4-hydroxy-6-oxo-6,7-dihydrothieno[2,3-b]pyridin-3-yl)phenyl]methylene}amino)oxy]-N-(2-pyridin-2-ylethyl)acetamide;
2-chloro-4-hydroxy-3-{4-[(4-hydroxypiperidin-4-yl)methoxy]phenyl}-6-oxo-6,7-dihydrothieno[2,3-b]pyridine-5-carbonitrile;
3-(2'-amino-1,1'-biphenyl-4-yl)-2-chloro-4-hydroxy-6-oxo-6,7-dihydrothieno[2,3-b]pyridine-5-carbonitrile;
4-hydroxy-6-oxo-3-(1,2,3,4-tetrahydronaphthalen-2-yl)-6,7-dihydrothieno[2,3-b]pyridine-5-carbonitrile;
3-(5-bromothien-2-yl)-4-hydroxy-6-oxo-6,7-dihydrothieno[2,3-b]pyridine-5-carbonitrile;
4-hydroxy-3-[5-(4-nitrophenyl)thien-2-yl]-6-oxo-6,7-dihydrothieno[2,3-b]pyridine-5-carbonitrile;
6-[4-(5-cyano-4-hydroxy-6-oxo-6,7-dihydrothieno[2,3-b]pyridin-3-yl)phenyl]hex-5-ynoic acid;
3-[4-(4-cyanobut-1-ynyl)phenyl]-4-hydroxy-6-oxo-6,7-dihydrothieno[2,3-b]pyridine-5-carbonitrile;
2-[({(1E)-[4-(5-cyano-4-hydroxy-6-oxo-6,7-dihydrothieno[2,3-b]pyridin-3-yl)phenyl]methylene}amino)oxy]-N-(pyridin-3-ylmethyl)acetamide;
3-(2,3-dihydro-1,4-benzodioxin-6-yl)-4-hydroxy-6-oxo-6,7-dihydrothieno[2,3-b]pyridine-5-carbonitrile;
N-{4-[5-(5-cyano-4-hydroxy-6-oxo-6,7-dihydrothieno[2,3-b]pyridin-3-yl)-2-phenylthien-3-yl]phenyl}methanesulfonamide;
4-hydroxy-6-oxo-3-(5-vinylthien-2-yl)-6,7-dihydrothieno[2,3-b]pyridine-5-carbonitrile;
4-hydroxy-6-oxo-3-(5-pyrazin-2-ylthien-2-yl)-6,7-dihydrothieno[2,3-b]pyridine-5-carbonitrile;
2-[({(1E)-[4-(5-cyano-4-hydroxy-6-oxo-6,7-dihydrothieno[2,3-b]pyridin-3-yl)phenyl]methylene}amino)oxy]-N-[(1R)-1-(hydroxymethyl)-3-methylbutyl]acetamide;
3-[4-(2-formylthien-3-yl)phenyl]-4-hydroxy-6-oxo-6,7-dihydrothieno[2,3-b]pyridine-5-carbonitrile;
4-hydroxy-3-{4-[(E)-({2-[(2R)-2-(hydroxymethyl)pyrrolidin-1-yl]-2-oxoethoxy}imino)methyl]phenyl}-6-oxo-6,7-dihydrothieno[2,3-b]pyridine-5-carbonitrile;
3-(2,3-dihydro-1H-inden-5-yl)-4-hydroxy-6-oxo-6,7-dihydrothieno[2,3-b]pyridine-5-carbonitrile;
4-hydroxy-3-[5-(4-hydroxybut-1-ynyl)thien-2-yl]-6-oxo-6,7-dihydrothieno[2,3-b]pyridine-5-carbonitrile;
2-[({(1E)-[4-(5-cyano-4-hydroxy-6-oxo-6,7-dihydrothieno[2,3-b]pyridin-3-yl)phenyl]methylene}amino)oxy]-N-[3-(dimethylamino)propyl]acetamide;
2-[4-(2-chloro-5-cyano-4-hydroxy-6-oxo-6,7-dihydrothieno[2,3-b]pyridin-3-yl)phenoxy]-N-methylacetamide;
3-[4-(allyloxy)phenyl]-4-hydroxy-6-oxo-6,7-dihydrothieno[2,3-b]pyridine-5-carbonitrile;
{[4'-(5-cyano-4-hydroxy-6-oxo-6,7-dihydrothieno[2,3-b]pyridin-3-yl)-1,1'-biphenyl-2-yl]oxy}acetic acid;
4-hydroxy-3-(4-methylthien-2-yl)-6-oxo-6,7-dihydrothieno[2,3-b]pyridine-5-carbonitrile;
N-{4-[5-(5-cyano-4-hydroxy-6-oxo-6,7-dihydrothieno[2,3-b]pyridin-3-yl)-3-methylthien-2-yl]phenyl}methanesulfonamide;
4-hydroxy-3-[4-(3-hydroxy-3-methylbut-1-ynyl)phenyl]-6-oxo-6,7-dihydrothieno[2,3-b]pyridine-5-carbonitrile;
N-[2-(acetylamino)ethyl]-2-[({(1E)-[4-(5-cyano-4-hydroxy-6-oxo-6,7-dihydrothieno[2,3-b]pyridin-3-yl)phenyl]methylene}amino)oxy]acetamide;
2-[({(1E)-[4-(5-cyano-4-hydroxy-6-oxo-6,7-dihydrothieno[2,3-b]pyridin-3-yl)phenyl]methylene}amino)oxy]-N-(pyrimidin-4-ylmethyl)acetamide;
4-hydroxy-3-(5-iodo-4-methylthien-2-yl)-6-oxo-6,7-dihydrothieno[2,3-b]pyridine-5-carbonitrile;
5-(5-cyano-4-hydroxy-6-oxo-6,7-dihydrothieno[2,3-b]pyridin-3-yl)-N-[2-(dimethylamino)ethyl]thiophene-2-carboxamide;
4-hydroxy-3-{4-[3-(methylamino)prop-1-ynyl]phenyl}-6-oxo-6,7-dihydrothieno[2,3-b]pyridine-5-carbonitrile;
2-[({(1E)-[4-(5-cyano-4-hydroxy-6-oxo-6,7-dihydrothieno[2,3-b]pyridin-3-yl)phenyl]methylene}amino)oxy]-N-[3-(1H-imidazol-1-yl)propyl]acetamide;
3-{5-[(1E)-N-ethoxyethanimidoyl]thien-2-yl}-4-hydroxy-6-oxo-6,7-dihydrothieno[2,3-b]pyridine-5-carbonitrile;
4-hydroxy-6-oxo-3-(5-pyridin-3-ylthien-2-yl)-6,7-dihydrothieno[2,3-b]pyridine-5-carbonitrile;

7-(5-cyano-4-hydroxy-6-oxo-3-phenyl-6,7-dihydrothieno[2,3-b]pyridin-2-yl)hept-6-ynoic acid;
3-[4-(allyloxy)phenyl]-4-hydroxy-2-methyl-6-oxo-6,7-dihydrothieno[2,3-b]pyridine-5-carbonitrile;
2-[4-(2-chloro-5-cyano-4-hydroxy-6-oxo-6,7-dihydrothieno[2,3-b]pyridin-3-yl)phenoxy]-N-[3-(2-oxopyrrolidin-1-yl)propyl]acetamide;
4-hydroxy-3-[4-(4-hydroxyphenyl)-5-phenylthien-2-yl]-6-oxo-6,7-dihydrothieno[2,3-b]pyridine-5-carbonitrile;
3-(3,5-dibromo-4-hydroxyphenyl)-4-hydroxy-6-oxo-6,7-dihydrothieno[2,3-b]pyridine-5-carbonitrile;
2-[({(1E)-[4-(5-cyano-4-hydroxy-6-oxo-6,7-dihydrothieno[2,3-b]pyridin-3-yl)phenyl]methylene}amino)oxy]-N-[2-(1-methylpyrrolidin-2-yl)ethyl]acetamide;
4-hydroxy-6-oxo-3-{4-[3-(tetrahydrofuran-3-yloxy)prop-1-ynyl]phenyl}-6,7-dihydrothieno[2,3-b]pyridine-5-carbonitrile;
2-[4-(2-chloro-5-cyano-4-hydroxy-6-oxo-6,7-dihydrothieno[2,3-b]pyridin-3-yl)phenoxy]-N-[3-(1H-imidazol-1-yl)propyl]acetamide;
3-(1,3-benzodioxol-5-yl)-4-hydroxy-6-oxo-6,7-dihydrothieno[2,3-b]pyridine-5-carbonitrile;
5-ethanimidoyl-4-hydroxy-3-(2'-hydroxy-1,1'-biphenyl-4-yl)thieno[2,3-b]pyridin-6(7H)-one;
4-hydroxy-3-{5-[(1E)-N-hydroxyethanimidoyl]thien-2-yl}-6-oxo-6,7-dihydrothieno[2,3-b]pyridine-5-carbonitrile;
4-hydroxy-3-(3-methyl-1-benzothien-2-yl)-6-oxo-6,7-dihydrothieno[2,3-b]pyridine-5-carbonitrile;
4-hydroxy-6-oxo-3-[(E)-2-phenylvinyl]-6,7-dihydrothieno[2,3-b]pyridine-5-carbonitrile;
4-hydroxy-6-oxo-3-(phenylethynyl)-6,7-dihydrothieno[2,3-b]pyridine-5-carbonitrile;
N-{3-[4-(5-cyano-4-hydroxy-6-oxo-6,7-dihydrothieno[2,3-b]pyridin-3-yl)phenyl]prop-2-ynyl}methanesulfonamide;
4-hydroxy-3-[4-(4-hydroxybutyl)phenyl]-6-oxo-6,7-dihydrothieno[2,3-b]pyridine-5-carbonitrile;
3-[4-(4-azidobut-1-ynyl)phenyl]-4-hydroxy-6-oxo-6,7-dihydrothieno[2,3-b]pyridine-5-carbonitrile;
4-hydroxy-3-[4-(5-hydroxypentyl)phenyl]-6-oxo-6,7-dihydrothieno[2,3-b]pyridine-5-carbonitrile;
ethyl 4-hydroxy-3-(2'-hydroxy-1,1'-biphenyl-4-yl)-6-oxo-6,7-dihydrothieno[2,3-b]pyridine-5-carboxylate; and
3-(2'-fluoro-6'-hydroxy-1,1'-biphenyl-4-yl)-4-hydroxy-6-oxo-6,7-dihydrothieno[2,3-b]pyridine-5-carbonitrile.

The present compounds can exist as therapeutically suitable salts. The term "therapeutically suitable salt," refers to salts or zwitterions of the compounds which are water or oil-soluble or dispersible, suitable for treatment of disorders without undue toxicity, irritation, and allergic response, commensurate with a reasonable benefit/risk ratio, and effective for their intended use. The salts can be prepared during the final isolation and purification of the compounds or separately by reacting an amino group of the compounds with a suitable acid. Representative salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, formate, isethionate, fumarate, lactate, maleate, methanesulfonate, naphthylenesulfonate, nicotinate, oxalate, pamoate, pectinate, persulfate, 3-phenylpropionate, picrate, oxalate, maleate, pivalate, propionate, succinate, tartrate, trichloroacetic, trifluoroacetic, glutamate, para-toluenesulfonate, undecanoate, hydrochloric, hydrobromic, sulfuric, phosphoric, and the like. The amino groups of the compounds can also be quaternized with alkyl chlorides, bromides, and iodides such as methyl, ethyl, propyl, isopropyl, butyl, lauryl, myristyl, stearyl, and the like.

Basic addition salts can be prepared during the final isolation and purification of the present compounds by reaction of a carboxyl group with a suitable base such as the hydroxide, carbonate, or bicarbonate of a metal cation such as lithium, sodium, potassium, calcium, magnesium, or aluminum, or an organic primary, secondary, or tertiary amine. Quaternary amine salts derived from methylamine, dimethylamine, trimethylamine, triethylamine, diethylamine, ethylamine, tributlyamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N'-dibenzylethylenediamine, ethylenediamine, ethanolamine, diethanolamine, piperidine, piperazine, and the like, are contemplated as being within the scope of the present invention.

The present compounds can also exist as therapeutically suitable prodrugs. The term "therapeutically suitable prodrug," refers to those prodrugs or zwitterions which are suitable for use in contact with the tissues of patients without undue toxicity, irritation, and allergic response, are commensurate with a reasonable benefit/risk ratio, and are effective for their intended use. The term "prodrug," refers to compounds which are rapidly transformed in vivo to the parent compounds of formula (I) for example, by hydrolysis in blood.

Asymmetric centers can exist in the present compounds. Individual stereoisomers of the compounds are prepared by synthesis from chiral starting materials or by preparation of racemic mixtures and separation by conversion to a mixture of diastereomers followed by separation or recrystallization, chromatographic techniques, or direct separation of the enantiomers on chiral chromatographic columns. Starting materials of particular stereochemistry are either commercially available or are made by the methods described hereinbelow and resolved by techniques well-known in the art.

Geometric isomers can exist in the present compounds The invention contemplates the various geometric isomers and mixtures thereof resulting from the disposal of substituents around a carbon-carbon double bond, a cycloalkyl group, or a heterocycloalkyl group. Substituents around a carbon-carbon double bond are designated as being of Z or E configuration and substituents around a cycloalkyl or heterocycloalkyl are designated as being of cis or trans configuration.

SYNTHETIC METHODS

Abbreviations which have been used in the descriptions of the scheme and the examples that follow are: $CH_2Cl_2$ for dichloromethane; DCC for 1,3-dicyclohexylcarbodiimide; DMF for N,N-dimethylformamide; DMSO for dimethylsulfoxide; EDAC for 1-(3-dimethylaminopropyl)-3-ethylcarbodiimide hydrochloride; HOBT for 1-hydroxybenzotriazole hydrate; HMDS for hexamethyl disilazide, NaH for sodium hydride; $NaCNBH_3$ for sodium cyanoborohydride; NMP for N-methylpyrrolidinone; $PCl_5$ for phosphorous pentachloride; $Pd(PPh_3)_4$ for tetrakis triphenylphosphine palladium; $POCl_3$ for phosphorous oxychloride; THF for tetrahydrofuran; TFA for trifluoroacetic acid.

Scheme 1

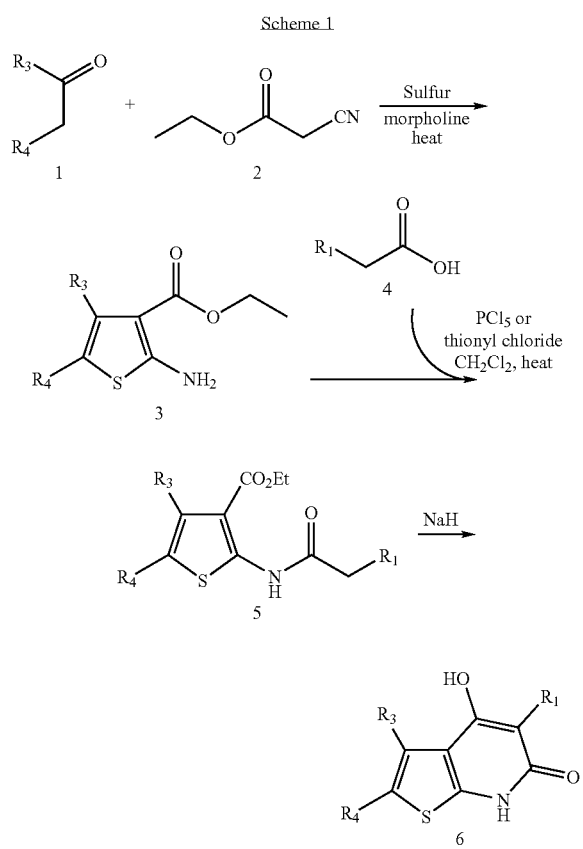

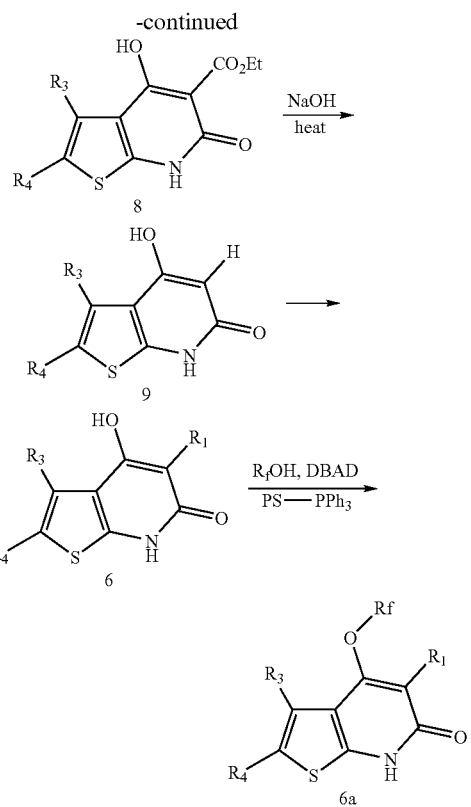

As shown in Scheme 1, compounds of general formula 1 when treated with compounds of general formula 2, sulfur and morpholine under heating conditions will provide compounds of general formula 3. Compounds of general formula 4 (wherein $R_1$ is defined in formula (I) of the present invention), when pretreated with $PCl_5$, thionyl chloride or oxalyl chloride in dichloromethane (reaction conditions may require a catalytic amount of DMF) under heating conditions followed by treatment with compounds of general formula 3 will provide compounds of general formula 5. Alternatively, compounds of general formula 3 can be treated with diethylmalonate under heated conditions to provide compounds of general formula 5. Compounds of general formula 5 when treated with reagents such as but not limited to sodium hydride in solvents such as but not limited to tetrahydrofuran and dioxane will provide compounds of general formula 6 which are representative of the compounds of the present invention.

Scheme 2

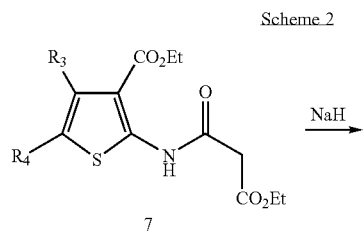

Compounds of general formula 7 can be obtained using the methods described in Scheme 1 when compounds of general formula 4 contain an $R_1$ group that is alkoxycarbonyl (particularity ethoxycarbonyl) and is treated with phosphorous pentachloride followed by treatment with compounds of general formula 3. Compounds of general formula 7 can be treated with reagents such as, but not limited to sodium hydride in solvents such as, but not limited to tetrahydrofuran to provide compounds of general formula 8, which are representative of compounds of the present invention where $R_1$ is alkoxycarbonyl. Compounds of general formula 8 can be treated with reagents known to hydrolize alkoxycarbonyl compounds to provide the corresponding carboxylic acid such as sodium hydroxide, lithium hydroxide or potassium hydroxide in solvents such as but not limited to aqueous ethanol, aqueous tetrahydrofuran, aqueous acetonitrile or through other methods as described in Greene, T. W. and Wuts, G. M. "Protective groups in Organic Synthesis", third ed. John Wiley & Sons, 1999. When the hydrolysis conditions are conducted with heating, decarboxylation may occur to provide compounds of general formula 9 which are representative of compounds of the present invention which lack the carboxy group at the $R_1$ position. Compounds of general formula 9 can be treated with electrophilic reagents such as but not limited to pyridinium hydrobromide perbromide and N-chlorosuccinimide to provide compounds of general formula 6 where $R_1$ is a halogen which are representative of compounds of the present invention. Compounds of general formula 6 can be treated with compounds of formula $R_fOH$, polystyrene supported triphenylphosphine and a reagent such as but not-limited to diethylazodicarboxylate, dimethylazodicarboxylate or dibutylazodicarboxylate to provide compounds of general formula 6a.

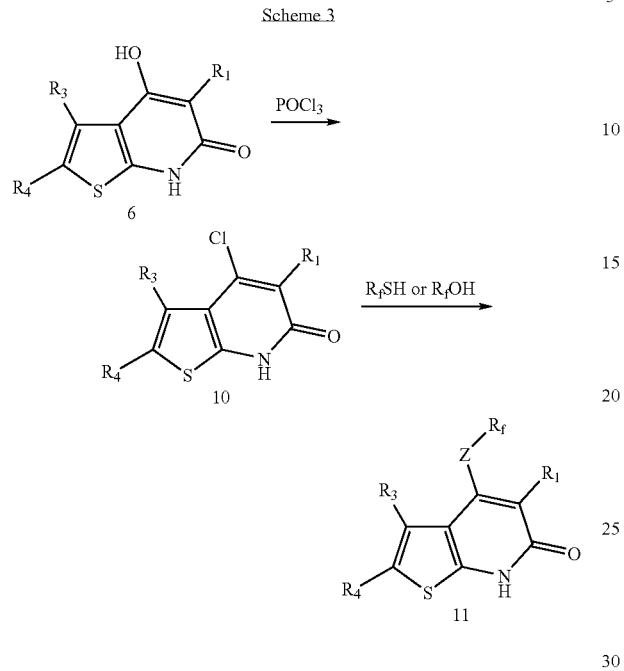

As shown in Scheme 3, compounds of general formula 6 may be treated with reagents such as but not limited to phosphorous oxychloride in solvents such as but not limited to toluene to provide compounds of general formula 10 which are representative of compounds of the present invention. Compounds of general formula 10 can be treated with compounds of formula $R_eNH_2$ with or without heating conditions to provide compounds of general formula 11. When $R_e$ is arylalkyl, such as benzyl, the removal of the benzyl group can be effected using condition known to those skilled in the art to remove such groups. For example, one such method commonly used to remove benzyl groups from amines consists of stirring the compound and palladium on carbon in solvents such as but not limited to methanol or ethanol under an atmosphere of hydrogen for 16–30 hours or until the transformation is complete. The conversion of compounds of general formula 11 to compounds of general formula 13 can be achieved utilizing this method. Alternatively, compound of general formula 10 can be treated with compounds of formula $R_fSH$ or $R_fOH$ and a base such as but not limited to triethylamine or diisopropylethylamine in solvents such as THF to provide compounds of general formula 12 where Z is S or O.

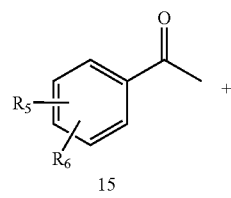

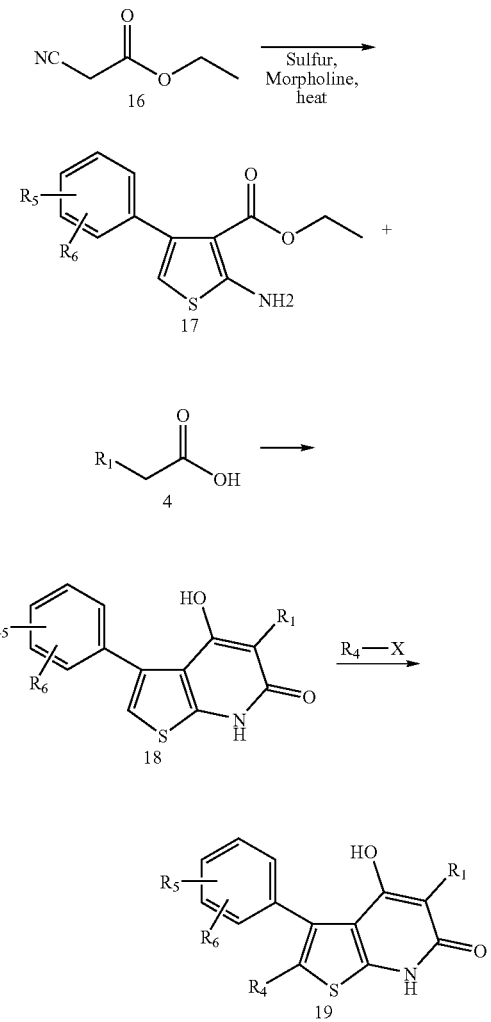

A shown in Scheme 4, compounds of general formula 15 when treated with compounds of general formula 16 in the presence of sulfur and morpholine in solvents such as but not limited to ethanol under heated conditions will provide compounds of general formula 17. Compounds of general formula 17 when treated with compounds of general formula 4 using conditions described in Scheme 1 will provide compounds of formula 18 which are representative of compounds of the present invention where $R_3$ is aryl. Compounds of general formula 18 can be treated with electrophilic reagents containing $R_4$ to provide compounds of general formula 19 which are representative of compounds of the present invention where $R_3$ is aryl and $R_4$ is selected from the group consisting of alkyl, alkylcarbonyl, alkenyl, alkynyl, arylalkyl, heterocyclealkyl, nitro, haloalkyl and halogen, specifically bromine and chlorine. Some reactions between compounds of general formula 18 with compounds of formula $R_4$—X may require the addition of a mild lewis acid catalysis reagent as know to those skilled in the art to get the desired compounds.

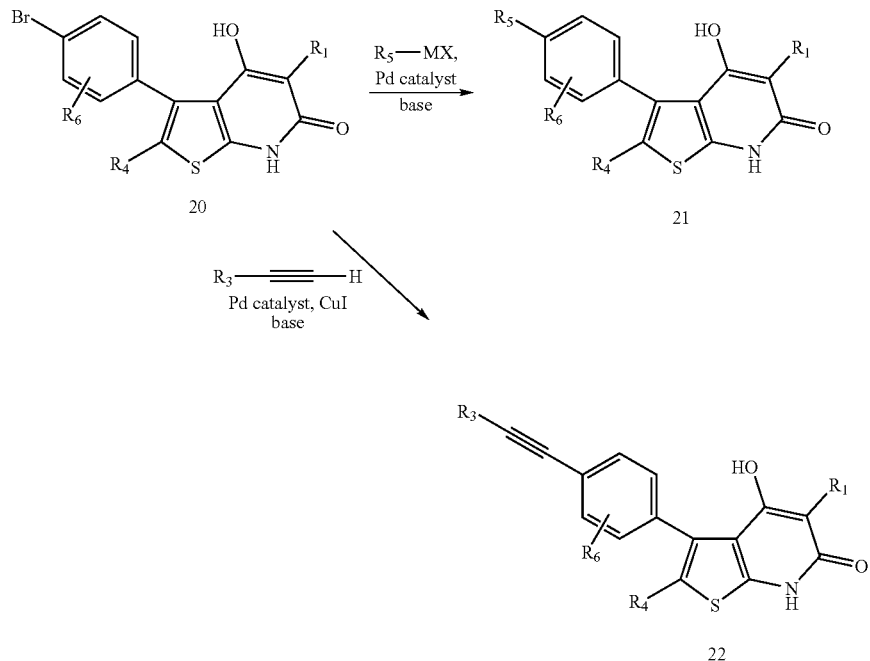

The compounds of general formula 20 that are shown in Scheme 5, can be obtained through the methodology described in Scheme 4 when compounds of general formula 15 containing an aryl group substituted with a halogen are treated according to the conditions described within Scheme 4. Compounds of general formula 20 can be treated with reagents of formula $R_5$-MX where $R_5$ is alkenyl, alkoxy, alkoxyalkoxy, alkoxycarbonyl, alkyl, alkylcarbonyl, alkynyl, aryl, haloalkyl, trihaloalkyl or heterocycle, M is boron, tin or zinc and X is halogen, hydroxy or alkyl in the presence of a palladium catalyst such as but not limited to palladium tetrakistriphenylphosphine with or without a base such as but not limited to cesium carbonate to provide compounds of general formula 21 which are representative of compounds of the present invention. Alternatively, compounds of general formula 20 can be treated with reagents of formula $R_{13}$≡—H where $R_{13}$ is alkyl, hydroxyalkyl, alkoxyalkyl, aryl, haloalkyl, aminoalkyl, alkylaminoalkyl, heterocyclealkyl, or heterocycle in the presence of a palladium catalyst such as but not limited to dichlorobis(triphenylphosphine)palladium(II), copper(I) iodide, and a base such as but not limited to diisopropylamine to provide compounds of general formula 22.

-continued

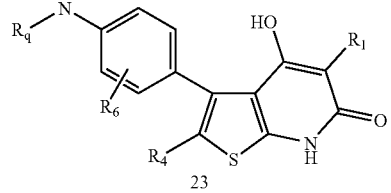

As shown in Scheme 6, compounds of general formula 20 when treated with compounds of formula $R_pR_qNH$, wherein $R_p$ and $R_q$ are hydrogen or alkyl, a palladium catalyst and a base such as triethylamine, diisopropylamine and the like in solvents such as but not limited to acetonitrile, DMF and dioxane under heated conditions will provide compounds of general formula 23 which are representative of compounds of the present invention.

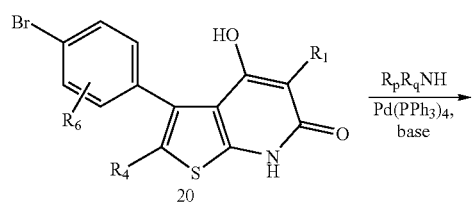

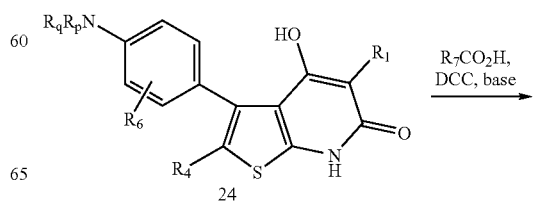

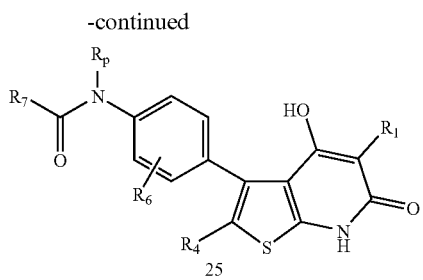

As shown in Scheme 7, compounds of general formula 24 which are representative of compounds of the present invention, can be made through the methods described in Scheme 6 where $R_p$ and $R_q$ are both hydrogen. Alternatively, compounds of general formula 24 can be made through methods described in Scheme 6, wherein $R_p$ is a benzyl group. The benzyl group may be removed under conditions know to remove a benzyl group such as stirring in the presence of a palladium catalyst such as but not limited to 5% palladium on barium sulfate in a solvent such as methanol under an atmosphere of hydrogen or as otherwise stated in Greene, T. W. and Wuts, G. M. "Protective groups in Organic Synthesis", third ed. John Wiley & Sons, 1999. Compound of general formula 24 can be treated with acid chlorides $R_7COCl$ or anhydrides of formula $(R_7CO)_2O$ in the presence of a base such as but not limited to triethylamine or diisopropylamine in solvents such as tetrahydrofuran or dichloromethane or with a carboxylic acid and a coupling reagent such as but not limited to dicyclohexylcarbodiimide, ethyldimethylazodicarboxylate and the like to provide compounds of general formula 25 which are representative of compounds of the present invention.

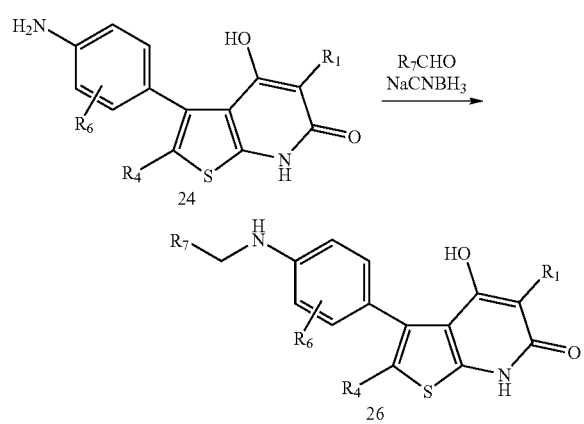

As shown in Scheme 8, compounds of general formula 24 can be treated with aldehydes of general formula $R_7CHO$ and sodium cyanoborohydride in solvents such as but not limited to tetrahydrofuran, dioxane and the like to provide compounds of general formula 26 which are representative of compounds of the present invention.

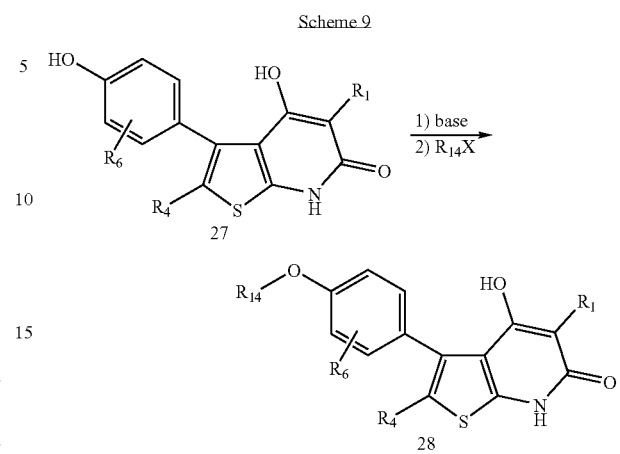

As shown in Scheme 9, compounds of general formula 27 can be obtained through the pathway described in Scheme 4 when compounds of general formula 15 containing a hydroxyl group are used in the pathway described. Compounds of general formula 27 can be treated with base such as but not limited to sodium hydride in solvents such as but not limited to DMF followed by treatment with $R_{14}$-halides wherein $R_{14}$ is alkyl, alkenyl, alkynyl, cycloalkylalkyl, hydroxyalkyl, alkoxyalkyl, arylalkyl, haloalkyl, alkylN-Halkyl, heterocyclealkyl, or heterocycle, and halide is chloro, bromo or iodo, to provide compounds of general formula 28 which are representative of compounds of present invention.

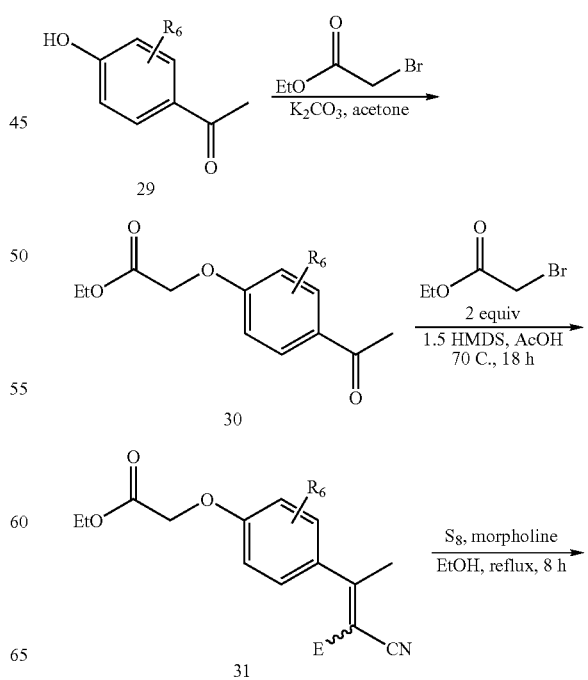

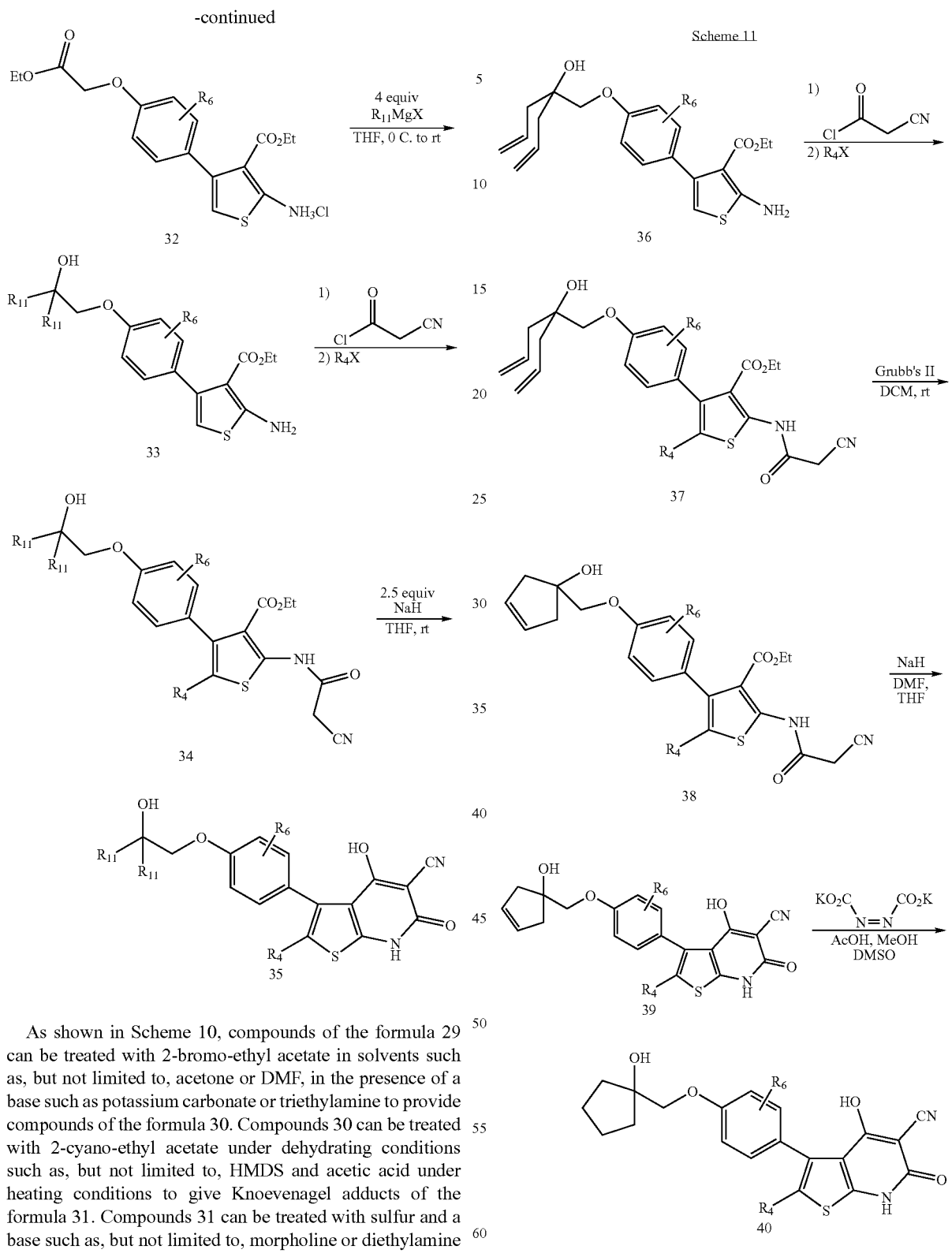

As shown in Scheme 10, compounds of the formula 29 can be treated with 2-bromo-ethyl acetate in solvents such as, but not limited to, acetone or DMF, in the presence of a base such as potassium carbonate or triethylamine to provide compounds of the formula 30. Compounds 30 can be treated with 2-cyano-ethyl acetate under dehydrating conditions such as, but not limited to, HMDS and acetic acid under heating conditions to give Knoevenagel adducts of the formula 31. Compounds 31 can be treated with sulfur and a base such as, but not limited to, morpholine or diethylamine in solvents such as ethanol to provide compounds 32 that may be treated with an excess of Grignard reagent, $R_{11}MgX$, to provide compounds of the formula 33. Compounds 33 may be transformed, according to the procedure described in Scheme 4 to provide compounds of the formula 35, which represent compounds of the present invention.

As shown in Scheme 11, compounds of the formula 37, which may be obtained through the procedure described in Scheme 10, may be treated with the Grubb's II catalyst ([1,3-bis-(2,4,6-trimethylphenyl)-2-imidazolidinylidene) dichloro(phenylmethylene)-(tricyclohexylphosphine)ruthe nium]) in solvents such as, but not limited to, DCM or acetonitrile to provide compounds of the formula 38 that may be treated with sodium hydride in solvents such as, but not limited to, THF or DMF to provide compounds of the formula 39, which are representative of compounds of the present invention. Compounds of the formula 39 can be treated under reducing conditions such as diimide (potassium diazodicarboxylate which is obtained as described in Groves, J. T.; Ma, K. W. *J. Am. Chem. Soc.* 1977, 99, 4076) or Pd/C/$H_2$ to provide compounds 40, which are representative of compounds of the present invention.

As shown in Scheme 12, compound 42 can be treated with the sulfur ylide derived from the reaction of trimethylsulfonium iodide with sodium hydride to provide compound 43. Reaction of 43 with variously substituted 4-hydroxyacetophenones provides compounds of the formula 44, which can be transformed to compounds 47 via the protocol described in Scheme 10. Treatment of compounds of the formula 47 with sodium hydride in solvents such as, but not limited to, THF or DMF, followed by reaction with TFA or some other suitable Lewis acid as described in Greene, T. W. and Wuts, G. M. "Protective groups in Organic Synthesis", third ed. John Wiley & Sons, 1999, for the removal of a Boc group from nitrogen yields compounds 48, which are representative of compounds of the present invention. Treatment of the compounds 48 with an aldehyde, $R_{12}$CHO, wherein $R_{12}$ is alkyl, aryl, arylalkyl, alkoxyalkyl, heteroaryl, heterocycle, alkenyl, and alkynyl in the presence of a reducing agent such as, but not limited to, NaCNBH$_3$ and NaBH(OAc)$_3$, or treatment of the compounds 48 with alkylating agents, $R_{12}$X, wherein X is chloro, bromo, and iodo will provide compounds of the formula 49, which are examples of the present invention.

Scheme 13

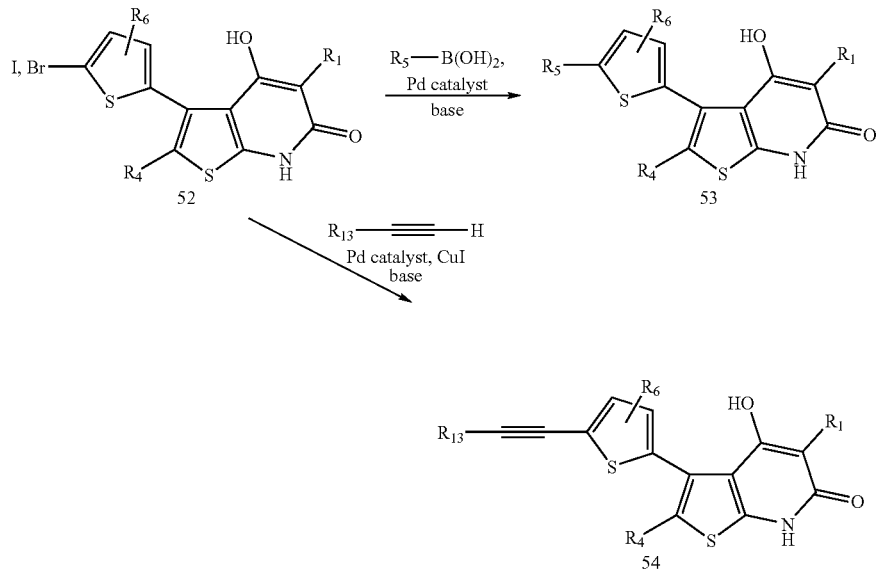

As shown in Scheme 13, compounds of formula 52 which contain a bromine or iodide on the heteroaryl ring when treated with a boronic acid of formula $R_5$—B(OH) in the presence of a palladium catalyst such as but not limited to palladium tetrakistriphenylphosphine with or without a base such as but not limited to cesium carbonate will produce compounds of formula 53 which are representative of the compounds of the present invention. Also, as shown in Scheme 13, compounds of formula 52 when treated with $R_{13}$ substituted alkynes ($R_{13}$≡—H) wherein $R_{13}$ is alkyl, hydroxyalkyl, alkoxyalkyl, aryl, haloalkyl, aminoalkyl, alkylaminoalkyl, heterocyclealkyl, or heterocycle in the presence of a palladium catalyst such as but not limited to dichlorobis(triphenylphosphine)-palladium(II), copper(I) iodide, and a base such as but not limited to diisopropylamine will produce compounds of formula 54 which are representative of the compounds of the present invention which contain $R_{13}$ substituted alkynes on the heteroaryl ring as described by formula 54.

Scheme 14

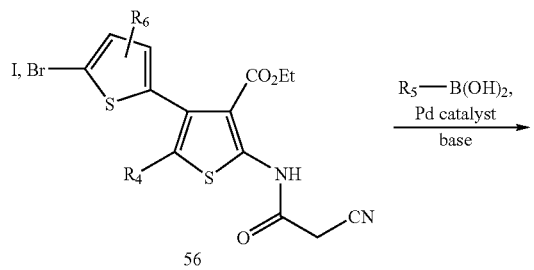

-continued

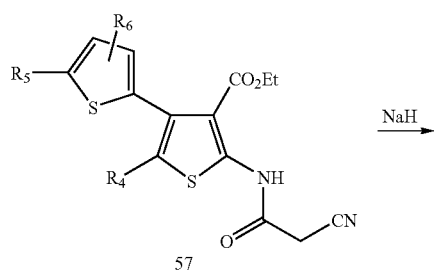

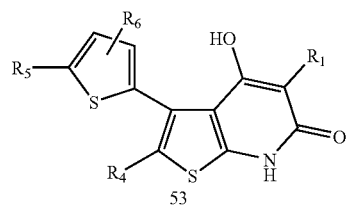

As shown in Scheme 14, compounds of formula 56 which contain a bromine or iodide on the heteroaryl ring when treated with a boronic acid of formula $R_5$—B(OH) in the presence of a palladium catalyst such as but not limited to palladium tetrakistriphenylphosphine with or without a base such as but not limited to cesium carbonate will provide compounds of formula 57. Compounds of formula 57 when treated with sodium hydride will provide compounds of formula 53 which are representative of compounds of the present invention.

Scheme 15

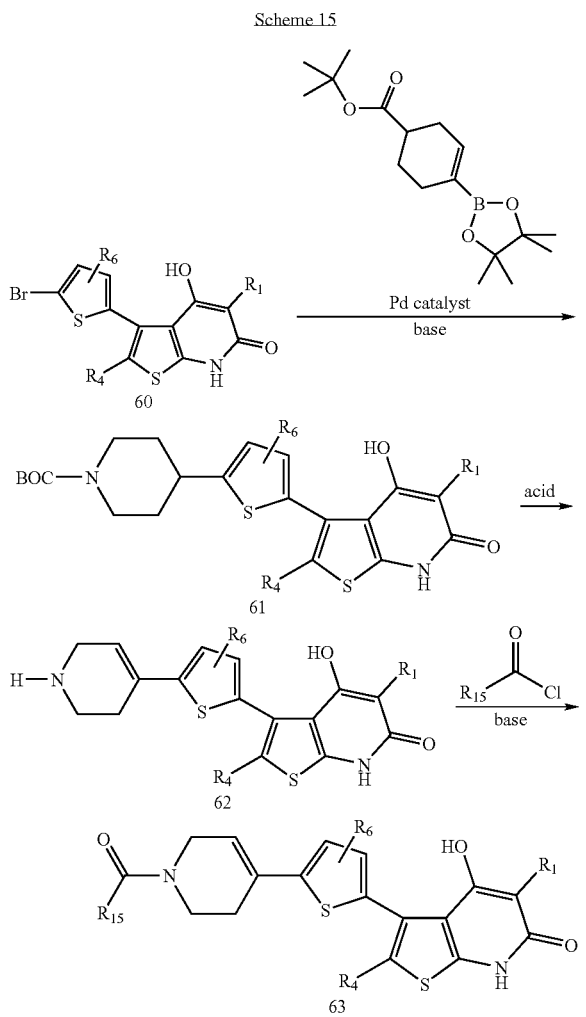

reagent such as but not limited to ethyldimethylazodicarboxylate or dicyclohexylcarbodiimide and the like to provide compounds of general formula 63 which are representative of compounds of the present invention.

Scheme 16

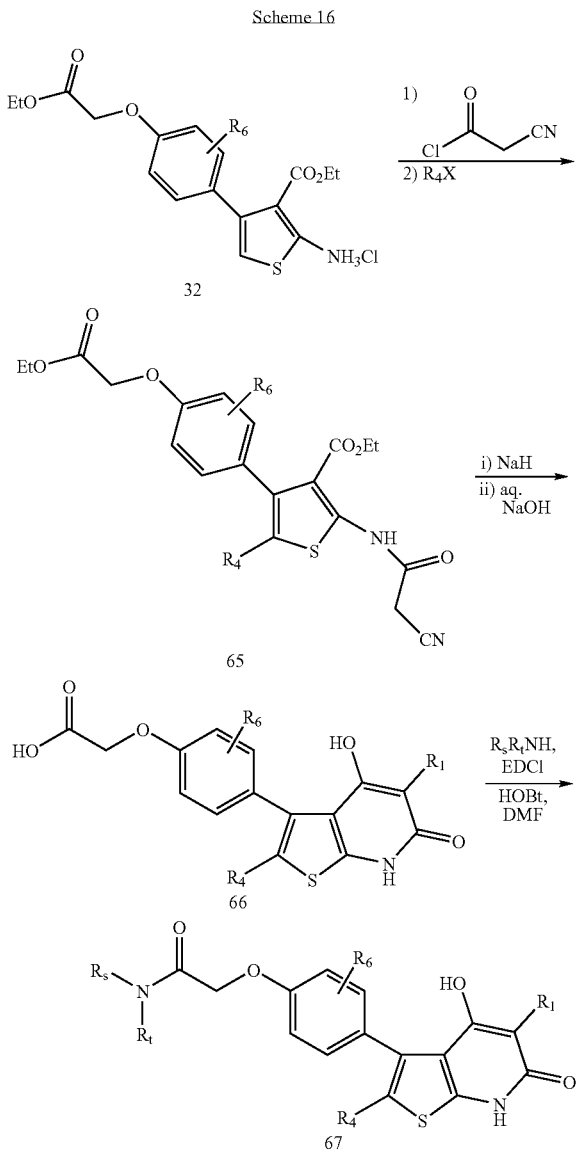

The compounds of general formula 60 shown in Scheme 15 may be obtained through the methodology described in Scheme 19 (wherein the thiophene is substituted with bromine instead of iodine). Compounds of general formula 60 may be treated with (N-tert-butoxycarbonyl)-1,2,3,6-tetrahydropyridine-4-boronic acid pinacol ester (420 mg, 1.36 mmol) (Eastwood et al., *Tetrahedron Lett.*, 2000, 41, 3705–3708) in the presence of a palladium catalyst such as but not limited to tetrakis(triphenylphosphine)palladium (0), and an aqueous base such as but not limited to cesium carbonate to provide compounds of general formula 61. The N-t-butoxycarbonyl protecting group may be removed under conditions known to those skilled in the art to remove a t-butoxycarbonyl group such as but not limited to trifluoroacetic acid in a solvent such as dichloromethane or as outlined in Greene, T. W. and Wuts, G. M. "Protective Groups in Organic Synthesis", third ed. John Wiley & Sons, 1999, to provide compounds of general formula 62. Compounds of general formula 62 may be treated with acid chlorides $R_{15}COCl$ or anhydrides of formula $(R_{15}CO)_2$ wherein $R_{15}$ is alkyl, hydroxyalkyl, alkoxyalkyl, aryl, haloalkyl, aminoalkyl, alkylaminoalkyl, heterocyclealkyl, or heterocycle, in the presence of a base such as but not limited to triethylamine or diisopropylamine in solvents such as dichloromethane or with a carboxylic acid and a coupling As shown in Scheme 16, compounds of general formula 32 when treated with cyanoacetyl chloride using conditions described in Scheme 1 and followed by treatment with electrophilic reagents containing $R_4$ will provide compounds of general formula 65 which are representative of compounds of the present invention where $R_4$ is selected from the group consisting of alkyl, alkylcarbonyl, alkenyl, alkynyl, arylalkyl, heterocyclealkyl, nitro, haloalkyl and halogen, specifically bromine and chlorine. Compounds of general formula 65 when treated with reagents such as but not limited to sodium hydride in solvents such as but not limited to tetrahydrofuran and dioxane and followed by hydrolyisis with bases such as but not limited to NaOH will provide compounds of general formula 66. Compounds of general formula 66 when treated with compounds of formula $R_sR_tNH$, wherein $R_s$ and $R_t$ are hydrogen, alkyl, hydroxyalkyl, alkoxyalkyl, alkynylalkyl, aminoalkyl, amidoalkyl, alkylaminoalkyl, aryl, cycloalkyl, heterocyclealkyl, or heterocycle, a coupling reagent such as but not limited to dicyclohexylcarbodiimide, ethyldimethylazodicarboxylate in the presence of a base such as but not limited to triethylamine or N-methyl morpholine in solvents such as tetrahydrofuran or DMF provide compounds of general formula 67 which are representative of compounds of the present invention.

Compounds of general formula 70 can be treated with reducing agents such iron and ammonnium chloride is aqueous ethanol or treated with hydrogen gas and 10% palladium/carbon to provide compounds of general formula 71. Compounds of general formula 71 can be treated with electrophiles of formula $R_{16}X$, where $R_{16}$ is alkyl, alkoxyalkyl, alkylNHalkyl, alkenylalkyl, alkynylalkyl, arylalkyl, heterocyclealkyl and X is I, Br, Cl, or mesylate in the presence of bases such as but not limited to diisopropyethylamine to form compounds of general formula 72. Compounds of general formula 72 can be cyclized by treatment with a base such as sodium hydride to provide compounds of general formula 73.

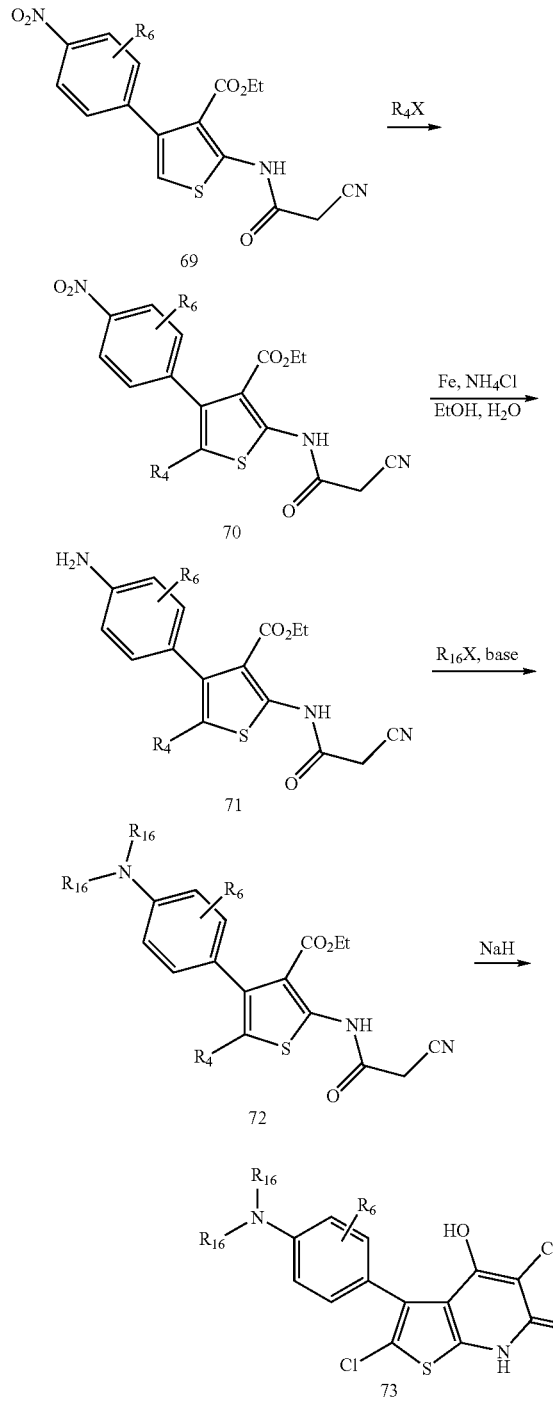

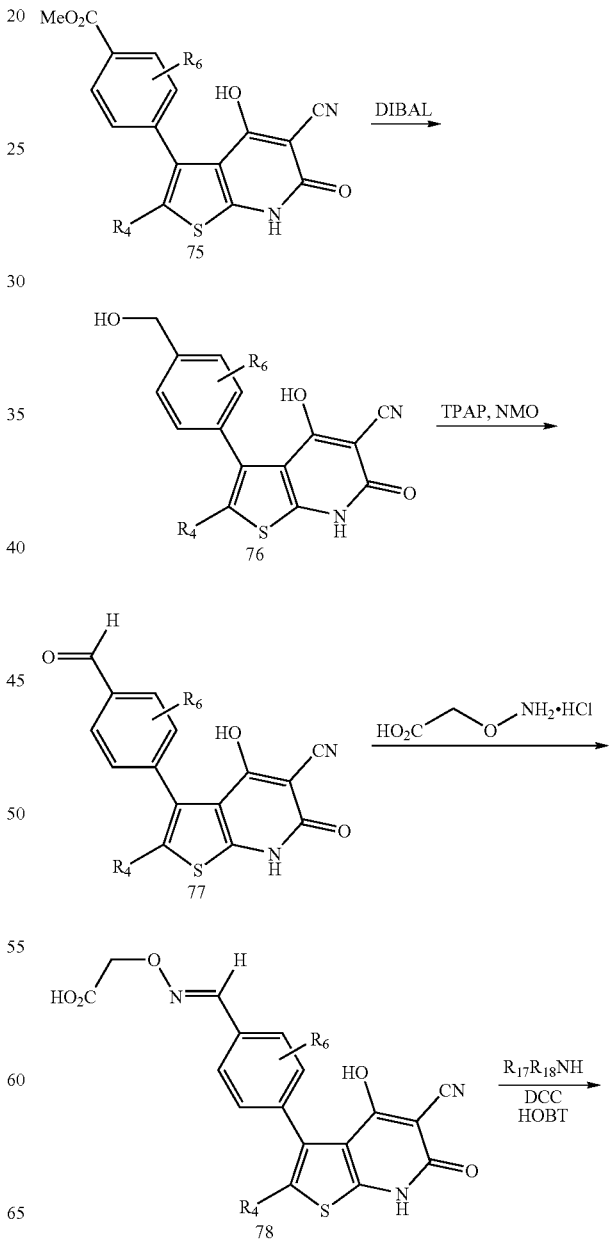

-continued

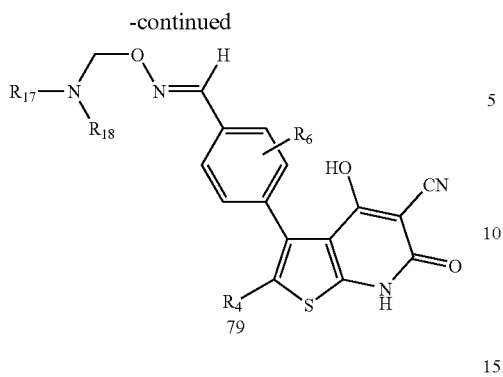
79

As shown in Scheme 18, compounds of general formula 75 when treated with reducing reagents such as but not limited to diisobutyl aluminum hydride in solvents such as but not limited to THF will provide compounds of general formula 76 which are representative of compounds of the present invention. Compounds of general formula 76 when treated with oxidizing reagents such as but not limited to tetrapropylammonium perruthenate in solvents such as but not limited to dichloromethane will provide compounds of general formula 77. Compounds of general formula 77 when condensed with N,O-dimethylhydroxylamine hydrochloride in solvents such as but not limited to aqueous methanol or aqueous dioxane will provide compounds of general formula 78. Compounds of general formula 78 when treated with compounds of formula $R_{17}R_{18}NH$, wherein $R_{17}$ and $R_{18}$ are hydrogen, alkyl, hydroxyalkyl, alkoxyalkyl, aryl, aminoalkyl, amidoalkyl, alkylaminoalkyl, cycloalkyl, heterocyclealkyl, or heterocycle, a coupling reagent such as but not limited to dicyclohexylcarbodiimide, ethyldimethylazodicarboxylate in the presence of a base such as but not limited to triethylamine or N-methyl morpholine in solvents such as tetrahydrofuran or DMF will provide compounds of general formula 79 which are representative of compounds of the present invention.

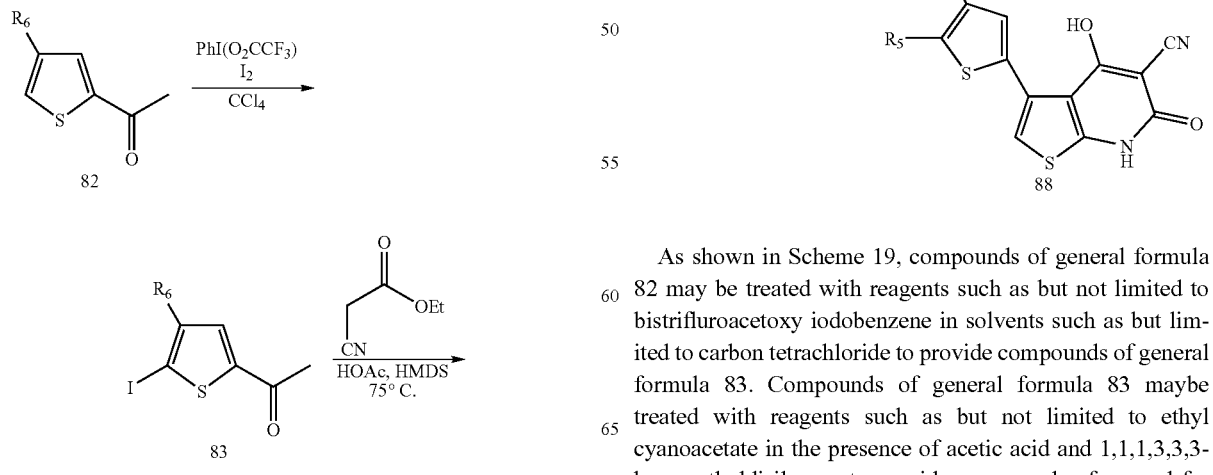

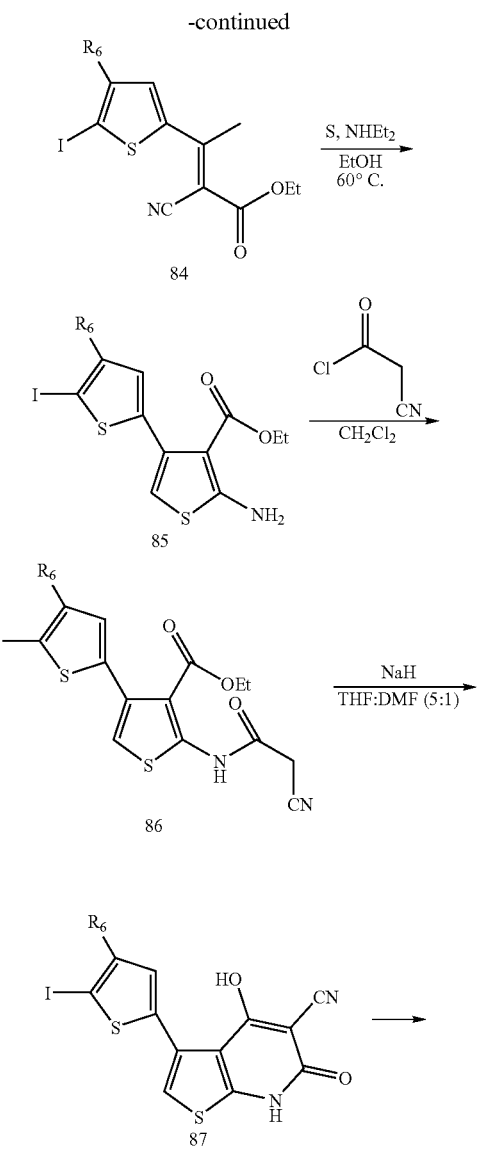

As shown in Scheme 19, compounds of general formula 82 may be treated with reagents such as but not limited to bistrifluroacetoxy iodobenzene in solvents such as but limited to carbon tetrachloride to provide compounds of general formula 83. Compounds of general formula 83 maybe treated with reagents such as but not limited to ethyl cyanoacetate in the presence of acetic acid and 1,1,1,3,3,3-hexamethyldisilazane to provide compounds of general for mula 84. Compounds of general formula 84 when treated with sulfur and morpholine in solvents such as ethanol provide compounds of general formula 85. Compounds of general formula 85 maybe treated with compounds of general formula 4 (after pretreatment of 4 with $PCl_5$, thionyl chloride under heating conditions or oxalyl chloride and catalytic DMF in dichloromethane) to provide compounds of general formula 86. Compounds of general formula 86 may then be cyclized using a base such as but not limited to sodium hydride in solvents such as but not limited to THF or DMF or a combination of the two to provide compounds of general formula 87. Compounds of general formula 87 (when $R_6$=alkyl, such as methyl) can be treated with reagents such as but not limited to Aryl boranes in the presence of Pd catalysts such as $PdCl_2(PPh_3)_2$ and bases such as cesium carbonate in solvents such as dioxane, DMF or a combination of the two to provide compounds of the general formula 88 where $R_5$=Aryl substitution or $R_5$=H. Also, compounds of general formula 87 (when $R_6$=alkyl, such as methyl) can be treated with reagents such as but not limited to alkynes in the presence of Pd catalysts such as $PdCl_2(PPh_3)_2$, CuI and bases such as but not limited to triethyl amine to provide compounds of general formula 88 where $R_5$=alkyne substitution. Compounds of general formula 87 when $R_6$=Br or chlorine may be treated with reagents such as but not limited to Arylboranes, vinylstannanes and alkynes in the presence of Pd catalysts such as $PdCl_2(PPh_3)_2$ or $Pd(PPh_3)_4$ to provide compounds of the general formula 88 where $R_5$ and $R_6$=Aryl substitution, $R_5$=alkyne, $R_6$=alkene, or any combination.

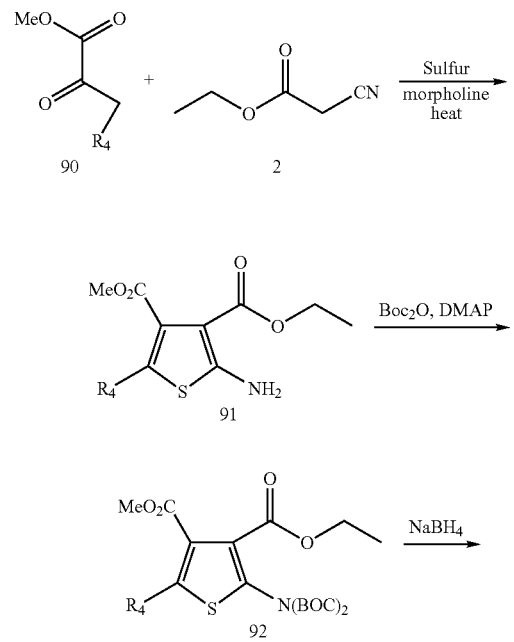

Scheme 20

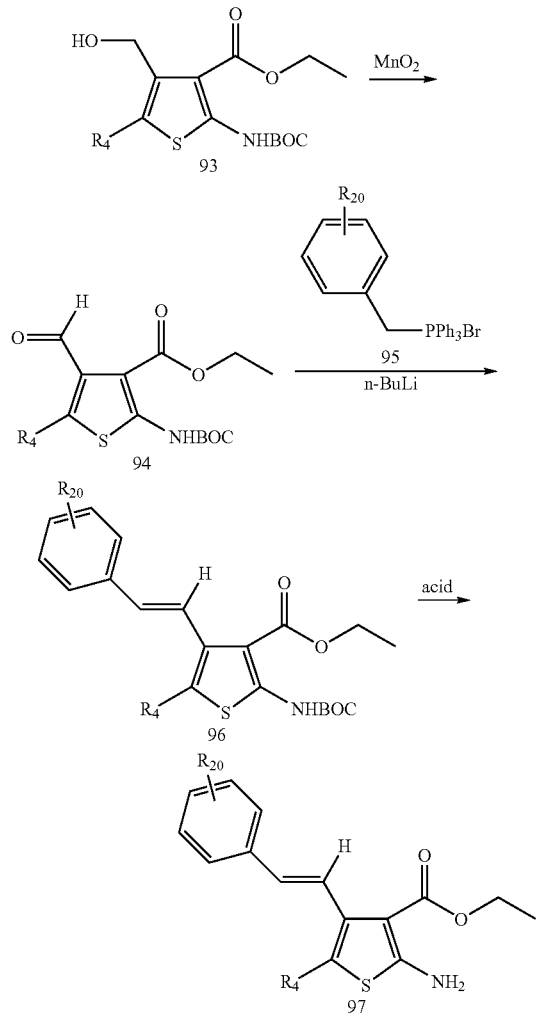

As shown in Scheme 20, compounds of general formula 90 when treated with compounds of general formula 2 in the presence of sulfur and morpholine in solvents such as but not limited to DMF under heated conditions will provide compounds of general formula 91. Compounds of general formula 91 when treated with di-t-butoxydicarbonate and dimethylaminopyridine will provide compounds of the general formula 92. Compounds of general formula 92 can be reduced with reagents such as but not limited to sodium borohydride to provide compounds of the general formula 93. Compounds of general formula 93 can be oxidized with reagents such as but not limited to manganese dioxide to provide compounds of general formula 94. Compounds of general formula 94 can be treated with ylides such as but not limited to 95 containing $R_{20}$ to provide compounds of general formula 96. Compounds of general formula 96 may be treated with reagents known to remove carbamates such as acid or through other methods as described in Greene, T. W. and Wuts, G. M. "Protective Groups in Organic Synthesis", third ed. John Wiley & Sons, 1999 to provide compounds of general formula 97.

Scheme 21

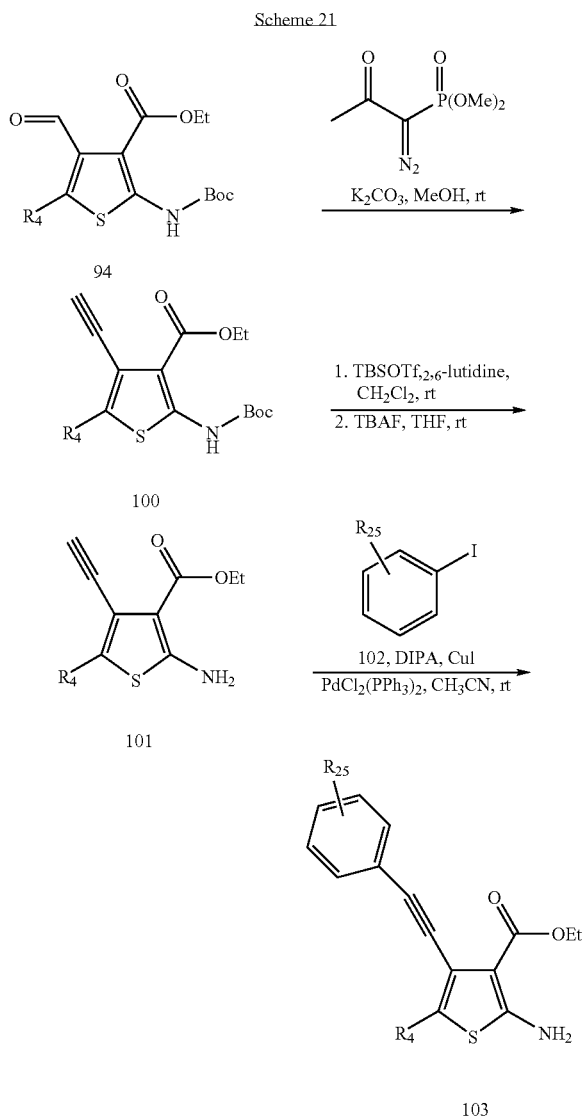

As described in Scheme 21, compounds of general formula 94 when treated with potassium carbonate, followed by (1-diazo-2-oxopropyl)-phosphonic acid dimethyl ester form alkynes of general formula 100, which can be deprotected by treatment with t-butyldimethylsilyltrifluoromethane-sulfonate and 2,6-lutidine, followed by treatment with tetrabutlyammonium fluoride to provide compounds of general formula 101. Compounds of general formula 101 when treated with aryl iodides of general formula 102 where $R_{25}$ is alkyl, alkoxy, aryl, alkenyl, alkynyl, halogen, alkoxyalkyl, hydroxyalkyl, alkylaminoalkyl, trihaloalkyl, heteroaryl, heterocycle and palladium catalysts such as dichlorobis(triphenylphosphine)palladium(II) and copper iodide in the presence of a base such as but not limited to diisopropylamine form compounds of general formula 103.

The present invention will now be described in connection with certain embodiments which are not intended to limit its scope. On the contrary, the present invention covers all alternatives, modifications, and equivalents as can be included within the scope of the claims. Thus, the following examples, which include preferred embodiments, will illustrate the preferred practice of the present invention, it being understood that the examples are for the purposes of illustration of certain preferred embodiments.

Compounds of the invention were named by ACD/ChemSketch version 5.01 (developed by Advanced Chemistry Development, Inc., Toronto, ON, Canada) or were given names which appeared to be consistent with ACD nomenclature.

EXPERIMENTALS

Example 2

3-(3,5-dimethylphenyl)-4-hydroxy-6-oxo-6,7-dihydrothieno[2,3-b]pyridine-5-carbonitrile

Example 2a

2-Amino-4-(3,5-dimethyl-phenyl)-thiophene-3-carboxylic acid ethyl ester

To an ambient solution of 3,5-dimethylacetophenone (1 g, 6.75 mmol) in ethanol (20 mL) was added ethyl cyanoacetate (1.53 mL, 13.5 mmol, neat) dropwise via syringe over 5 minutes. The resultant clear solution was heated at 60° C. for 20 minutes. The solution was then allowed to cool to room temperature and morpholine (2.15 mL) was added in a single portion. The resultant light green solution was heated at 60° C. for an additional 5 minutes and then cooled to room temperature. Elemental sulfur (0.43 g, 13.5 mmol) was then added to the reaction mixture in a single portion and the yellow suspension was heated at 60° C. for 48 hours. The reaction mixture was then cooled to room temperature and ethanol removed under vacuum. The residue was dissolved in $CH_2Cl_2$ and purified on a flash column to provide the title compound. MS (ESI) m/e 274.0 (M−H)+; $^1$H NMR (300 MHz, $CDCl_3$): δ ppm 7.26 (s, 1H), 6.92 (s, 2H), 6.04 (s, 1H), 4.06 (q, 2H, J=7.12), 2.31 (s, 6H), 0.97 (t, 3H, J=7.12).

Example 2b 2-(2-cyano-acetylamino)-4-(3,5-dimethyl-phenyl)-thiophene-3-carboxylic acid ethyl ester To a stirred suspension of $PCl_5$ (0.74 g, 3.5 mmol) in $CH_2Cl_2$ (10 mL) was added a solution of cyanoacetic acid (0.3 g, 3.5 mmol) in $CH_2Cl_2$ (5 mL) and DMF (1 mL) dropwise via syringe at room temperature and the reaction mixture was heated at reflux for 1 hour. The reaction was cooled to room temperature and a solution of 2-Amino-4-(3,5-dimethyl-phenyl)-thiophene-3-carboxylic acid ethyl ester (0.78 g, 2.8 mmol) in $CH_2Cl_2$ (5 mL) was added via canula over 5 minutes. The reaction was then heated at reflux for 2.5 h, cooled to 0° C. and quenched by slow addition of sat. aq. $Na_2CO_3$ (10 mL) until basic (pH 9–10). The mixture was extracted with ethyl acetate (3×30 mL) and the combined organic layers were washed with water (25 mL), brine (15 mL), dried ($Na_2SO_4$), filtered and concentrated under reduced pressure to provide the title compound as a yellow solid. MS (ESI) m/e 341.0 (M−H); $^1$H NMR (300 MHz, $CDCl_3$): δ ppm 12.02 (s, 1H), 7.26 (s, 1H), 6.97 (s, 1H), 6.91 (s, 2H), 6.67 (s, 1H), 4.15 (q, 4H, J=7.12), 3.68 (s, 2H), 2.33 (s, 6H), 0.98 (t, 3H, J=7.12).

Example 2

3-(3,5-dimethylphenyl)-4-hydroxy-6-oxo-6,7-dihydrothieno[2,3-b]pyridine-5-carbonitrile To a suspension of either NaH (60% suspension in mineral oil, pre washed with hexanes, 0.25 g, 6.2 mmol) held at room temperature or Lithium diisopropylamide (LDA, 2M solution in THF, 11.3 mmol, 5.6 mL) held at −78° C. in THF (30 mL) was added a solution of 2-(2-cyano-acetylamino)-4-(3,5-dimethyl-phenyl)-thiophene-3-carboxylic acid ethyl ester (0.968 g, 2.83 mmol) in THF (15 mL) dropwise via syringe over 10 minutes. The mixture was stirred at room temperature for 5 hours (or in the case of LDA, allowed to warm to room temperature over 16 hours), cooled to 0° C. and then quenched by dropwise addition of MeOH (5 mL) followed by 1N HCl to adjust the pH <3. The resultant slurry was filtered and the solid was washed with water (4×4 mL), ether (3×4 mL) and (Na$_2$SO$_4$), filtered and concentrated under reduced pressure to provide the target compound. The filtrate was concentrated and purified on a RP-HPLC system to provide additional compound. MS (ESI) m/e 295 (M−H)$^+$; $^1$H NMR (300 MHz, MeOH-d$_4$): δ ppm 12.53 (br s, 1H), 7.04 (s, 2H), 6.99 (s, 1H), 6.90 (s, 1H), 2.32 (s, 6H).

Example 3

3-(4-fluorophenyl)-4-hydroxy-6-oxo-6,7-dihydrothieno[2,3-b]pyridine-5-carbonitrile Example 3 was prepared using the same procedure as described for Example 2 substituting 4-fluoroacetophenone for 3,5-dimethylacetophenone in Example 2a. MS (ESI) m/e 284.9 (M−H)$^+$; $^1$H NMR (300 MHz, DMSO-d$_6$): δ ppm 12.55 (br s, 1H), 7.45 (m, 2H), 7.19 (m, 2H), 7.03 (s, 1H).

Example 4

3-(4-chlorophenyl)-4-hydroxy-6-oxo-6,7-dihydrothieno[2,3-b]pyridine-5-carbonitrile Example 4 was prepared using the same procedure as described for Example 2 substituting 4-chloroacetophenone for 3,5-dimethylacetophenone in Example 2a. MS (ESI) m/e 300.9 (M−H)$^+$; $^1$H NMR (300 MHz, DMSO-d$_6$): δ ppm 12.40 (br s, 1H), 7.44 (m, 2H), 7.41 (m, 2H), 7.05 (s, 1H).

Example 6

4-hydroxy-6-oxo-3-[4-(trifluoromethyl)phenyl]-6,7-dihydrothieno[2,3-b]pyridine-5-carbonitrile Example 6 was prepared using the same procedure as described for Example 2 substituting 4-trifluoroacetophenone for 3,5-dimethylacetophenone in Example 2a. MS (ESI) m/e 334.9 (M−H)$^+$; $^1$H NMR (300 MHz, DMSO-d$_6$): δ ppm 12.47 (br s, 1H), 7.73 (d, 2H), 7.65 (d, 2H), 7.16 (s, 1H), 5.47 (br s, 1H).

Example 7

2-bromo-3-(4-chlorophenyl)-4-hydroxy-6-oxo-6,7-dihydrothieno[2,3-b]pyridine-5-carbonitrile To a stirred solution of 3-(4-chlorophenyl)-4-hydroxy-6-oxo-6,7-dihydrothieno[2,3-b]pyridine-5-carbonitrile (0.17 g, 0.55 mmol) in AcOH (6 mL) was added pyridine hydrobromide perbromide (0.18 g, 0.6 mmol) in a single portion at room temperature. The reaction was stirred at room temperature for 1 h, diluted with water (25 mL). The resultant solid was filtered and dried to give the title compound. MS (ESI) m/e 380.79 (M−H)+; 1H NMR (300 MHz, DMSO-d6): ppm 7.45 (d, 2H), 7.33 (d, 2H).

Example 8

2-bromo-4-hydroxy-6-oxo-3-[4-(trifluoromethyl)phenyl]-6,7-dihydrothieno[2,3-b]pyridine-5-carbonitrile Example 8 was prepared using the same procedure as described for Example 7 substituting 4-hydroxy-6-oxo-3-[4-(trifluoromethyl)phenyl]-6,7-dihydrothieno[2,3-b]pyridine-5-carbonitrile for 4-hydroxy-6-oxo-3-phenyl-6,7-dihydrothieno[2,3-b]pyridine-5-carbonitrile in Example 7. MS (DCI/NH$_3$) m/e 416 (M+H)$^+$; $^1$H NMR (300 MHz, DMSO-d$_6$): δ ppm 7.77 (d, 2H), 7.55 (d, 2H).

Example 9

3-(4-bromophenyl)-4-hydroxy-6-oxo-6,7-dihydrothieno[2,3-b]pyridine-5-carbonitrile Example 9 was prepared using the same procedures as described for Example 2 substituting 4-bromoacetophenone for 3,5-dimethylacetophenone the step described in Example 2a. MS (DCI/NH$_3$) m/e 348.9 (M+H)$^+$; $^1$H NMR (300 MHz, DMSO-d$_6$): δ ppm 12.37 (br s, 1H), 7.54 (d, 2H), 7.38 (d, 2H), 7.03 (s, 1H).

Example 10

2-bromo-3-(4-fluorophenyl)-4-hydroxy-6-oxo-6,7-dihydrothieno[2,3-b]pyridine-5-carbonitrile Example 10 was prepared using the same procedure as described for Example 7 substituting 4-hydroxy-6-oxo-3-[4-fluorophenyl]-6,7-dihydrothieno[2,3-b]pyridine-5-carbonitrile for 4-hydroxy-6-oxo-3-phenyl-6,7-dihydrothieno[2,3-b]pyridine-5-carbonitrile in Example 7. MS (DCI/NH$_3$) m/e 366.8 (M+H)$^+$; $^1$H NMR (300 MHz, DMSO-d$_6$): δ ppm 7.34 (apparent t, 2H), 7.23 (apparent t, 2H).

Example 12

3-(4'-fluoro-1,1'-biphenyl-4-yl)-4-hydroxy-6-oxo-6,7-dihydrothieno[2,3-b]pyridine-5-carbonitrile To an ambient slurry of 3-(4-bromophenyl)-4-hydroxy-6-oxo-6,7-dihydrothieno[2,3-b]pyridine-5-carbonitrile (0.030 g, 0.086 mmol), 4-fluorophenyl boronic acid (0.024 g, 0.173 mmol) and cesium carbonate (0.084 g, 0.26 mmol) in DME/PhCH$_3$/EtOH/H$_2$O (10/1/6/3 ratio, 2 mL) was added palladium tetrakis(triphenylphosphine) (0.001 g, 0.0009 mmol) in a single portion. The reaction was heated at 60° C. for 16 h, cooled to room temperature, filtered, concentrated and purified by RP-HPLC to afford the title compound. MS (DCI/NH$_3$) m/e 362.2 (M+H)$^+$; $^1$H NMR (300 MHz, DMSO-d$_6$): δ ppm 12.51 (br s, 1H), 7.75 (dd, 2H), 7.64 (d, 2H), 7.52 (d, 2H), 7.31 (apparent t, 2H), 7.07 (s, 1H).

Example 13

4-hydroxy-6-oxo-3-[4'-(trifluoromethyl)-1,1'-biphenyl-4-yl]-6,7-dihydrothieno[2,3-b]pyridine-5-carbonitrile Example 13 was prepared using the same procedure as described for Example 12 substituting 4-(trifluoromethyl) phenyl boronic acid for 4-fluorophenyl boronic acid in Example 12. MS (DCI/NH$_3$) m/e 413.1 (M+H)$^+$; $^1$H NMR (500 MHz, DMSO-d$_6$): δ ppm 12.39 (br s, 1H), 7.94 (d, 2H), 7.83 (d, 2H), 7.73 (d, 2H), 7.57 (d, 2H), 7.07 (s, 1H).

Example 14

3-[4-(1,3-benzodioxol-5-yl)phenyl]-4-hydroxy-6-oxo-6,7-dihydrothieno[2,3-b]pyridine-5-carbonitrile Example 14 was prepared using the same procedure as described for Example 12 substituting 3,4-(methylenedioxy) phenyl boronic acid for 4-fluorophenyl boronic acid in Example 12. MS (DCI/NH$_3$) m/e 388.1 (M+H)$^+$; $^1$H NMR (500 MHz, DMSO-d$_6$): δ ppm 11.93 (br s, 1H), 7.56 (d, 2H), 7.48 (d, 2H), 7.27 (s, 1H), 7.18 (d, 1H), 7.01 (d, 1H), 6.92 (s, 1H), 6.07 (s, 2H).

Example 16

2,5-dibromo-3-(4-chlorophenyl)-4-hydroxythieno[2,3-b]pyridin-6(7H)-one

Example 16a 4-(4-Chlorophenyl)-2-(2-ethoxycarbonyl acetylamino)-thiophene-3-carboxylic acid ethyl ester A solution of 2-Amino-4-(4-chloro-phenyl)-thiophene-3-carboxylic acid ethyl ester (4a) (1.759 g, 6.24 mmol) in diethyl malonate (8.0 g, 50 mmol) was heated at 180° C. for 4 hours. The excess diethyl malonate was removed under reduced pressure to give the title compound. MS (DCI/NH$_3$) m/e 396 (M+H)$^+$; $^1$H NMR (300 MHz, CDCl$_3$): δ ppm 12.21 (s, 1H), 7.33–7.20 (m, 5H), 6.62 (s, 1H), 4.31 (q, J=7.12, 2H), 4.15 (q, J=7.12, 2H), 3.61 (s, 2H), 1.33 (t, J=7.12, 3H), 0.99 (t, J=7.12, 3H).

Example 16b 3-(4-Chloro-phenyl)-4-hydroxy-7H-thieno[2,3-b]pyridine-6-one

To a suspension of NaH (60% suspension in mineral oil, pre washed with hexanes, 0.430 g, 10.73 mmol) in THF (25 mL) was added a solution of 4-(4-chlorophenyl)-2-(2-ethoxycarbonyl acetylamino)-thiophene-3-carboxylic acid ethyl ester (1.9308 g, 4.88 mmol) in THF (25 mL) dropwise via syringe. The reaction mixture was then heated to reflux for 3 hrs, cooled to 0° C. and quenched by dropwise addition of MeOH (5 mL) and H$_2$O (2 mL). The reaction mixture was concentrated to give a crude solid which was then dissolved in MeOH (30 mL) and 40% NaOH (30 mL). The resulting mixture was heated at for 5 hours, cooled to room temperature and acidified with concentrated HCl. The mixture was concentrated under reduced pressure and DMSO/MeOH (1:1) was used to dissolve the residue and filtered. The filtrate was purified on a RP-HPLC system to afford the title compound. MS (ESI) m/e 275.9 (M–H)$^+$; $^1$H NMR (400 MHz, DMSO-d$_6$): δ ppm 11.55 (br s, 1H), 10.92 (s, 1H), 7.47–7.39 (m, 4H), 7.06 (s, 1H), 5.74 (s, 3H).

Example 16

2,5-dibromo-3-(4-chlorophenyl)-4-hydroxythieno[2,3-b]pyridin-6(7H)-one

Example 16 was prepared using the same procedure as described for Example 15 substituting 3-(4-chlorophenyl)-4-hydroxy-7H-thieno[2,3-b]pyridine-6-one for 4-hydroxy-3-phenylthieno[2,3-b]pyridin-6(7H)-6-one in Example 15. MS (DCI/NH$_3$) m/e 437.6 (M+H)$^+$; $^1$H NMR (500 MHz, DMSO-d$_6$): δ ppm 12.36 (br s, 1H), 10.63 (br s, 1H), 7.48 (d, 2H), 7.37 (d, 2H).

Example 17

2,5-dichloro-3-(4-chlorophenyl)-4-hydroxythieno[2,3-b]pyridin-6(7H)-one

To a solution of 3-(4-Chlorophenyl)-4-hydroxy-7H-thieno[2,3-b]pyridine-6-one (16b) (0.072 g, 0.26 mmol) in acetic acid (4 mL) was added N-chlorosuccinimide (0.069 g, 0.52 mmol) and stirred at room temperature for 2 hours The reaction mixture was quenched with water (1 mL), concentrated and purified by RP-HPLC to afford the title compound. MS (DCI/NH$_3$) m/e 347.8 (M+H)$^+$; $^1$H NMR (500 MHz, DMSO-d$_6$): δ ppm 12.36 (br s, 1H), 10.97 (br s, 1H), 7.49 (d, 2H), 7.40 (d, 2H).

Example 23

4-hydroxy-3-(4-nitrophenyl)-6-oxo-6,7-dihydrothieno[2,3-b]pyridine-5-carbonitrile Example 23 was prepared using the same procedure as described for Example 2 substituting 4-nitroacetophenone for 3,5-dimethylacetophenone in Example 2a. MS (DCI/NH$_3$) m/e 313 (M+H)$^+$; $^1$H NMR (300 MHz, DMSO-d$_6$): δ ppm 12.42 (br, 1H), 8.21 (d, 2H), 7.72 (d, 2H), 7.22 (s, 1H).

Example 24

2-bromo-4-hydroxy-3-(4-nitrophenyl)-6-oxo-6,7-dihydrothieno[2,3-b]pyridine-5-carbonitrile Example 24 was prepared using the same procedure as described for Example 7 substituting 4-hydroxy-6-oxo-3-phenyl-6,7-dihydrothieno[2,3-b]pyridine-5-carbonitrile for 4-hydroxy-3-(4-nitrophenyl)-6-oxo-6,7-dihydrothieno[2,3-b]pyridine-5-carbonitrile in Example 7. MS (DCI/NH$_3$) m/e 393 (M+H)$^+$; $^1$H NMR (300 MHz, DMSO-d$_6$): δ ppm 8.25 (d, 2H), 7.62 (d, 2H).

Example 25

3-(1,1'-biphenyl-4-yl)-4-hydroxy-6-oxo-6,7-dihydrothieno[2,3-b]pyridine-5-carbonitrile Example 25 was prepared using the same procedure as described for Example 12 substituting phenyl boronic acid for 4-fluorophenyl boronic acid in Example 12. MS (ESI) m/e 345 (M+H)$^+$.

Example 26

4-hydroxy-3-(2'-methyl-1,1'-biphenyl-4-yl)-6-oxo-6,7-dihydrothieno[2,3-b]pyridine-5-carbonitrile Example 26 was prepared using the same procedure as described for Example 12 substituting 2-methylphenyl boronic acid for 4-fluorophenyl boronic acid in Example 12. MS (ESI) m/e 359 (M+H)$^+$.

Example 27

4-hydroxy-3-(3'-methyl-1,1'-biphenyl-4-yl)-6-oxo-6,7-dihydrothieno[2,3-b]pyridine-5-carbonitrile Example 27 was prepared using the same procedure as described for Example 12 substituting 3-methylphenyl boronic acid for 4-fluorophenyl boronic acid in Example 12. MS (ESI) m/e 359 (M+H)$^+$; $^1$H NMR (500 MHz, DMSO-d$_6$): δ ppm 12.23 (br, 1H), 7.63 (d, 2H), 7.52–7.47 (m, 4H), 7.36 (t, 1H), 7.19 (d, 1H), 7.00 (s, 1H), 2.39 (s, 3H).

Example 28

4-hydroxy-3-(2'-hydroxy-1,1'-biphenyl-4-yl)-6-oxo-6,7-dihydrothieno[2,3-b]pyridine-5-carbonitrile Example 28 was prepared using the same procedure as described for Example 12 substituting 2-(4,4,5,5-tetramethyl-1,3,2-dioxaborolan-2-yl) phenol for 4-fluorophenyl boronic acid in Example 12. MS (ESI) m/e 361 (M+H)$^+$; $^1$H NMR (500 MHz, DMSO-d$_6$): δ ppm 12.44 (br s, 1H), 9.53 (s, 1H), 7.54 (d, 2H), 7.45 (d, 2H), 7.28 (dd, 1H), 7.17 (m, 1H), 7.03 (s, 1H), 6.96 (d, 1H), 6.89 (t, 1H).

Example 29

4-hydroxy-3-(3'-hydroxy-1,1'-biphenyl-4-yl)-6-oxo-6,7-dihydrothieno[2,3-b]pyridine-5-carbonitrile Example 29 was prepared using the same procedure as described for Example 12 substituting 3-(4,4,5,5-tetramethyl-1,3,2-dioxaborolan-2-yl) phenol for 4-fluorophenyl boronic acid in Example 12. MS (ESI) m/e 361 (M+H)$^+$.

Example 30

4-hydroxy-3-(2'-methoxy-1,1'-biphenyl-4-yl)-6-oxo-6,7-dihydrothieno[2,3-b]pyridine-5-carbonitrile Example 30 was prepared using the same procedure as described for Example 12 substituting 2-methoxyphenyl boronic acid for 4-fluorophenyl boronic acid in Example 12. MS (ESI) m/e 375 (M+H)$^+$.

Example 31

4-hydroxy-3-(3'-methoxy-1,1'-biphenyl-4-yl)-6-oxo-6,7-dihydrothieno[2,3-b]pyridine-5-carbonitrile Example 31 was prepared using the same procedure as described for Example 12 substituting 3-methoxyphenyl boronic acid for 4-fluorophenyl boronic acid in Example 12. MS (ESI) m/e 375 (M+H)$^+$.

Example 32

4-hydroxy-3-(4'-methoxy-1,1'-biphenyl-4-yl)-6-oxo-6,7-dihydrothieno[2,3-b]pyridine-5-carbonitrile Example 32 was prepared using the same procedure as described for Example 12 substituting 4-methoxyphenyl boronic acid for 4-fluorophenyl boronic acid in Example 12. MS (ESI) m/e 375 (M+H)$^+$.

Example 33

3-(2'-fluoro-1,1'-biphenyl-4-yl)-4-hydroxy-6-oxo-6,7-dihydrothieno[2,3-b]pyridine-5-carbonitrile Example 33 was prepared using the same procedure as described for Example 12 substituting 2-fluorophenyl boronic acid for 4-fluorophenyl boronic acid in Example 12. MS (ESI) m/e 363 (M+H)$^+$.

Example 34

3-(3'-fluoro-1,1'-biphenyl-4-yl)-4-hydroxy-6-oxo-6,7-dihydrothieno[2,3-b]pyridine-5-carbonitrile Example 34 was prepared using the same procedure as described for Example 12 substituting 3-fluorophenyl boronic acid for 4-fluorophenyl boronic acid in Example 12. MS (ESI) m/e 363 (M+H)$^+$.

Example 35

3-(2'-chloro-1,1'-biphenyl-4-yl)-4-hydroxy-6-oxo-6,7-dihydrothieno[2,3-b]pyridine-5-carbonitrile Example 35 was prepared using the same procedure as described for Example 12 substituting 2-chlorophenyl boronic acid for 4-fluorophenyl boronic acid in Example 12. MS (ESI) m/e 379 (M+H)$^+$.

Example 36

3-(3'-chloro-1,1'-biphenyl-4-yl)-4-hydroxy-6-oxo-6,7-dihydrothieno[2,3-b]pyridine-5-carbonitrile Example 36 was prepared using the same procedure as described for Example 12 substituting 3-chlorophenyl boronic acid for 4-fluorophenyl boronic acid in Example 12. MS (ESI) m/e 379 (M+H)$^+$.

Example 37

3-(4'-chloro-1,1'-biphenyl-4-yl)-4-hydroxy-6-oxo-6,7-dihydrothieno[2,3-b]pyridine-5-carbonitrile Example 37 was prepared using the same procedure as described for Example 12 substituting 4-chlorophenyl boronic acid for 4-fluorophenyl boronic acid in Example 12. MS (ESI) m/e 379 (M+H)$^+$; $^1$H NMR (500 MHz, DMSO-d$_6$): δ ppm 11.97 (br s, 1H), 7.88 (d, 1H), 7.74–7.71 (m, 2H), 7.65–7.63 (m, 2H), 7.54–7.51 (m, 3H), 6.96 (s, 1H).

Example 38

3-(4'-cyano-1,1'-biphenyl-4-yl)-4-hydroxy-6-oxo-6,7-dihydrothieno[2,3-b]pyridine-5-carbonitrile Example 38 was prepared using the same procedure as described for Example 12 substituting 4-cyanophenyl boronic acid for 4-fluorophenyl boronic acid in Example 12. MS (ESI) m/e 370 (M+H)$^+$.

Example 39

3-(3'-acetyl-1,1'-biphenyl-4-yl)-4-hydroxy-6-oxo-6,7-dihydrothieno[2,3-b]pyridine-5-carbonitrile Example 39 was prepared using the same procedure as described for Example 12 substituting 3-acetylphenyl boronic acid for 4-fluorophenyl boronic acid in Example 12. MS (ESI) m/e 387 (M+H)$^+$; $^1$H NMR (500 MHz, DMSO-d$_6$): δ ppm 12.43 (br, 1H), 8.22 (s, 1H), 7.97 (t, 2H), 7.74 (d, 2H), 7.64 (t, 1H), 7.56 (d, 2H), 7.06 (s, 1H), 2.67 (s, 3H).

Example 40

3-[4'-(dimethylamino)-1,1'-biphenyl-4-yl]-4-hydroxy-6-oxo-6,7-dihydrothieno[2,3-b]pyridine-5-carbonitrile Example 40 was prepared using the same procedure as described for Example 12 substituting 4-(dimethylamino)-phenyl boronic acid for 4-fluorophenyl boronic acid in Example 12. MS (ESI) m/e 388 (M+H)$^+$.

Example 41

4-hydroxy-6-oxo-3-(4'-phenoxy-1,1'-biphenyl-4-yl)-6,7-dihydrothieno[2,3-b]pyridine-5-carbonitrile Example 41 was prepared using the same procedure as described for Example 12 substituting 4-phenoxyphenyl boronic acid for 4-fluorophenyl boronic acid in Example 12. MS (ESI) m/e 437 (M+H)$^+$; $^1$H NMR (500 MHz, DMSO-d$_6$): δ ppm 12.17 (br s, 1H), 7.72 (d, 2H), 7.62 (d, 2H), 7.51 (d, 2H), 7.43 (t, 2H), 7.18 (t, 1H), 7.11–7.08 (m, 4H), 6.99 (s, 1H).

Example 42

3-(4'-acetyl-1,1'-biphenyl-4-yl)-4-hydroxy-6-oxo-6,7-dihydrothieno[2,3-b]pyridine-5-carbonitrile Example 42 was prepared using the same procedure as described for Example 12 substituting 4-acetylphenyl boronic acid for 4-fluorophenyl boronic acid in Example 12. MS (ESI) m/e 387 (M+H)$^+$; $^1$H NMR (500 MHz, DMSO-d$_6$): δ ppm 11.98 (br s, 1H), 8.05 (d, 2H), 7.87 (d, 2H), 7.73 (d, 2H), 7.57 (d, 2H), 6.98 (s, 1H), 2.62 (s, 3H).

Example 43

3-(2',3'-dimethyl-1,1'-biphenyl-4-yl)-4-hydroxy-6-oxo-6,7-dihydrothieno[2,3-b]pyridine-5-carbonitrile Example 43 was prepared using the same procedure as described for Example 12 substituting 2,3-dimethylphenyl boronic acid for 4-fluorophenyl boronic acid in Example 12. MS (ESI) m/e 373 (M+H)$^+$; $^1$H NMR (500 MHz, DMSO-d$_6$): δ ppm 12.44 (br s, 1H), 7.59 (d, 2H), 7.28 (d, 2H), 7.19–7.14 (m, 2H), 7.07–7.05 (m, 2H), 2.31 (s, 3H), 2.16 (s, 3H).

Example 44

4-hydroxy-6-oxo-3-[4'-(trifluoromethoxy)-1,1'-biphenyl-4-yl]-6,7-dihydrothieno[2,3-b]pyridine-5-carbonitrile Example 44 was prepared using the same procedure as described for Example 12 substituting 4-trifluoromethylphenyl boronic acid for 4-fluorophenyl boronic acid in Example 12. MS (ESI) m/e 429 (M+H)$^+$; $^1$H NMR (500 MHz, DMSO-d$_6$) δ ppm 12.41 (br s, 1H), 7.83 (d, 2H), 7.68 (d, 2H), 7.54 (d, 2H), 7.45 (d, 2H), 7.06 (s, 1H).

Example 45

3-(3',4'-dimethyl-1,1'-biphenyl-4-yl)-4-hydroxy-6-oxo-6,7-dihydrothieno[2,3-b]pyridine-5-carbonitrile Example 45 was prepared using the same procedure as described for Example 12 substituting 3,4-dimethylphenyl boronic acid for 4-fluorophenyl boronic acid in Example 12. MS (ESI) m/e 373 (M+H)$^+$; $^1$H NMR (500 MHz, DMSO-d$_6$): δ ppm 12.23 (br s, 1H), 7.61 (d, 2H), 7.49 (d, 3H), 7.41 (d, 1H), 7.23 (d, 1H), 6.99 (s, 1H), 2.31 (s, 3H), 2.26 (s, 3H).

Example 46

3-(2',3'-dichloro-1,1'-biphenyl-4-yl)-4-hydroxy-6-oxo-6,7-dihydrothieno[2,3-b]pyridine-5-carbonitrile Example 46 was prepared using the same procedure as described for Example 12 substituting 2,3-dichlorophenyl boronic acid for 4-fluorophenyl boronic acid in Example 12. MS (ESI) m/e 414 (M+H)$^+$.

Example 47

3-(2',4'-dichloro-1,1'-biphenyl-4-yl)-4-hydroxy-6-oxo-6,7-dihydrothieno[2,3-b]pyridine-5-carbonitrile Example 47 was prepared using the same procedure as described for Example 12 substituting 2,4,-dichlorophenyl boronic acid for 4-fluorophenyl boronic acid in Example 12. MS (ESI) m/e 414 (M+H)$^+$; $^1$H NMR (500 MHz, DMSO-d$_6$): δ ppm 12.23 (br s, 1H), 7.75 (d, 1H), 7.55–7.52 (m, 3H), 7.47 (d, 1H), 7.42 (d, 2H), 7.04 (s, 1H).

Example 49

2-bromo-3-(4'-fluoro-1,1'-biphenyl-4-yl)-4-hydroxy-6-oxo-6,7-dihydrothieno[2,3-b]pyridine-5-carbonitrile Example 49 was prepared using the same procedure as described for Example 7 substituting 3-(4'-fluoro-1,1'-biphenyl-4-yl)-4-hydroxy-6-oxo-6,7-dihydrothieno[2,3-b]pyridine-5-carbonitrile for 4-hydroxy-6-oxo-3-phenyl-6,7-dihydrothieno[2,3-b]pyridine-5-carbonitrile in Example 7. MS (ESI) m/e 440.7 (M–H)$^+$; $^1$H NMR (400 MHz, DMSO-d$_6$): δ ppm 7.76 (dd, 2H), 7.68 (d, 2H), 7.38 (d, 2H), 7.30 (t, 2H).

Example 50

3-(4-aminophenyl)-4-hydroxy-6-oxo-6,7-dihydrothieno[2,3-b]pyridine-5-carbonitrile To a stirred suspension of 3-(4-nitrophenyl)-4-hydroxy-6-oxo-6,7-dihydrothieno[2,3-b]pyridine-5-carbonitrile (0.054 g, 0.173 mmol) and ammonium chloride (0.007 g, 0.138 mmol) in ethanol: water mixture (2:1, 24 mL) was added iron powder (0.097 g, 1.73 mmol) in a single portion. The reaction mixture was heated at reflux for 16 hours, cooled to room temperature, filtered and the filtrate concentrated under reduced pressure. The residue was taken up in DMSO/MeOH and purified by RP-HPLC. MS (ESI) m/e 281.7 (M–H)$^+$; $^1$H NMR (400 MHz, DMSO-d$_6$): δ ppm 11.65 (br s, 1H), 7.31 (d, 2H), 6.88 (d, 2H), 6.74 (s, 1H).

Example 52

2-chloro-4-hydroxy-6-oxo-3-[4-(trifluoromethyl) phenyl]-6,7-dihydrothieno[2,3-b]pyridine-5-carbonitrile Example 52 was prepared using the same procedure as described for Example 51 substituting 4-hydroxy-6-oxo-3-[4-(trifluoromethyl)phenyl]-6,7-dihydrothieno[2,3-b]pyridine-5-carbonitrile for 4-hydroxy-6-oxo-3-phenyl-6,7-dihydrothieno[2,3-b]pyridine-5-carbonitrile in Example 51. MS (ESI) m/e 368.9 (M–H)$^+$; $^1$H NMR (300 MHz, DMSO-d$_6$): δ ppm 7.78 (d, 2H), 7.69 (d, 2H).

Example 53

4-hydroxy-3-(4'-hydroxy-1,1'-biphenyl-4-yl)-6-oxo-6,7-dihydrothieno[2,3-b]pyridine-5-carbonitrile Example 53 was prepared using the same procedure as described for Example 12 substituting 4-(4,4,5,5-tetramethyl-1,2,3-dioxaborolan-2-yl) phenol for 4-fluorophenyl boronic acid in Example 12. MS (ESI) m/e 359 (M–H)$^+$; $^1$H NMR (400 MHz, DMSO-d$_6$): δ ppm 12.23 (br s, 1H), 9.50 (s, 1H), 7.56–7.51 (m, 4H), 7.46 (d, 2H), 6.97 (s, 1H), 6.87–6.85 (m, 2H).

Example 57

3-(4'-acetyl-1,1'-biphenyl-4-yl)-2-bromo-4-hydroxy-6-oxo-6,7-dihydrothieno[2,3-b]pyridine-5-carbonitrile Example 57 was prepared using the same procedure as described for Example 7 substituting 3-(4'-acetyl-1,1'-biphenyl-4-yl)-4-hydroxy-6-oxo-6,7-dihydrothieno[2,3-b]pyridine-5-carbonitrile for 4-hydroxy-6-oxo-3-phenyl-6,7-dihydrothieno[2,3-b]pyridine-5-carbonitrile in Example 7. MS (ESI) m/e 464.9 (M–H)$^+$; $^1$H NMR (300 MHz, DMSO-d$_6$): δ ppm 8.06 (d, 2H), 7.90 (d, 2H), 7.79 (d, 2H), 7.44 (d, 2H), 2.63 (s, 3H).

Example 58

2-bromo-4-hydroxy-3-(2'-hydroxy-1,1'-biphenyl-4-yl)-6-oxo-6,7-dihydrothieno[2,3-b]pyridine-5-carbonitrile Example 58 was prepared using the same procedures as described for Example 7 substituting 4-hydroxy-3-(2'-hydroxy-1,1'-biphenyl-4-yl)-6-oxo-6,7-dihydrothieno[2,3-b]pyridine-5-carbonitrile for 4-hydroxy-6-oxo-3-phenyl-6,7-dihydrothieno[2,3-b]pyridine-5-carbonitrile in Example 7. MS (ESI) m/e 438.8 (M–H)$^+$; $^1$H NMR (300 MHz, DMSO-d$_6$): δ ppm 9.58 (br s, 1H), 7.60 (d, 2H), 7.34–7.31 (m, 3H), 7.19–7.16 (m, 1H), 7.97 (dd, 1H), 6.92–6.88 (m, 1H).

Example 59

2-bromo-3-(4'-cyano-1,1'-biphenyl-4-yl)-4-hydroxy-6-oxo-6,7-dihydrothieno[2,3-b]pyridine-5-carbonitrile Example 59 was prepared using the same procedure as described for Example 7 substituting 3-(4'-cyano-1,1'-biphenyl-4-yl)-4-hydroxy-6-oxo-6,7-dihydrothieno[2,3-b]pyridine-5-carbonitrile for 4-hydroxy-6-oxo-3-phenyl-6,7-dihydrothieno[2,3-b]pyridine-5-carbonitrile in Example 7. MS (ESI) m/e 447.8 (M–H)$^+$; $^1$H NMR (300 MHz, DMSO-d$_6$): δ ppm 7.96 (s, 4H), 7.81 (d, 2H), 7.46 (d, 2H).

Example 60

2-chloro-4-hydroxy-3-(2'-hydroxy-1,1'-biphenyl-4-yl)-6-oxo-6,7-dihydrothieno[2,3-b]pyridine-5-carbonitrile

Example 60a

2-amino-4-(4-bromophenyl)-thiophene-3-carboxylic acid ethyl ester

To a warm (60° C.) solution of 4-bromoacetophenone (30 g, 0.151 mol) in ethanol (480 mL) was added ethyl cyanoacetate (68.4 g, 0.605 mol). After 20 min, morpholine (105.2 g, 1.208 mol) and sulphur (19.4 g, 0.604 mol) were sequentially added. After stirring at 65° C. for 24 h, additional morpholine (91 g, 1.04 mol) and ethyl cyanoacetate (28.8 g, 0.25 mol) were added. After stirring for 48 h at 65° C., the reaction was absorbed onto silica gel, placed in a scintered glass funnel, and washed with ethyl acetate (4 L). The filtrate was concentrated under reduced pressure to give a yellow solid. Purification of the residue by flash chromatography on silica gel, eluting with hexane/ethyl acetate (97.5:2.5), gave the titled compound as a yellow solid. MS (APCI) m/e 278 (M—CH$_3$CH$_2$OH)$^+$, NMR (300 MHz, DMSO-d$_6$): δ ppm 7.48 (d, 2H), 7.39 (br s, 2H), 7.19 (d, 2H), 6.21 (s, 1H), 3.96 (q, 2H), and 0.93 (t, 3H).

Example 60b

4-(4-bromophenyl)-5-chloro-2-(2-cyano-acetylamino)-thiophene-3-carboxylic acid ethyl ester To a cold (0° C.) solution of 2-amino-4-(4-bromophenyl)-thiophene-3-carboxylic acid ethyl ester (1.0 g, 3.1 mmol) and triethylamine (0.64 mL, 4.60 mmol) in methylene chloride (6 mL) was added cyanoacetic acid chloride (6.82 mL, 3.41 mmol, 0.5 M in methylene chloride). The cold bath was removed, and the reaction was stirred for 2 h. Saturated aqueous sodium bicarbonate solution (5 mL) was added to the reaction at room temperature. The layers were separated, and the aqueous was extracted with additional methylene chloride (3×5 mL). The combined organic layers were dried with anhydrous sodium sulfate, filtered, and concentrated under reduced pressure to provide the titled compound as a yellow solid. MS (ESI) m/e 393 (M–H)$^-$, NMR (300 MHz, CDCl$_3$): δ ppm 12.0 (br s, 1H), 7.47 d, 2H), 7.16 (d, 2H), 6.68 (s, 1H), 4.16 (q, 2H), 3.69 (s, 2H), and 100 (t, 3H).

Example 60c 4-(4-bromophenyl)-5-chloro-2-(2-cyano-acetylamino)-thiophene-3-carboxylic acid ethyl ester To a cold (0° C.) solution of 4-(4-bromophenyl)-2-(2-cyano-acetylamino)-thiophene-3-carboxylic acid ethyl ester (4.0 g, 10.18 mmol) in methylene chloride (34 mL) was added sulfuryl chloride (0.82 mL, 10.2 mmol). The cold bath was removed, and the reaction was stirred at room temperature for 4 h. Saturated aqueous sodium bicarbonate solution was then added (30 mL) to the reaction. The layers were separated, and the aqueous was extracted with additional methylene chloride (3×15 mL). The combined organic layers were dried with anhydrous sodium sulfate, filtered, and concentrated under reduced pressure to give the titled compound as a solid. MS (DCI/NH$_3$) m/e 446 (M+NH$_3$)$^+$, NMR (300 MHz, CDCl$_3$): δ ppm 12.1 (br s, 1H), 7.53 d, 2H), 7.09 (d, 2H), 4.08 (q, 2H), 3.67 (s, 2H), and 0.91 (t, 3H).

Example 60d 2-chloro-4-hydroxy-3-(4-bromophenyl)-6-oxo-6,7-dihydrothieno[2,3-b]pyridine-5-carbonitrile To a suspension of NaH (1.33 g, 33.2 mmol, 60% dispersion in mineral oil) in tetrahydrofuran (60 mL) at room temperature was added a solution of 4-(4-bromophenyl)-5-chloro-2-(2-cyano-acetylamino)-thiophene-3-carboxylic acid ethyl ester (5.26 g, 12.3 mmol) in tetrahydrofuran (60 mL) over 15 minutes. The reaction was stirred at room temperature for 12 h, and 1 N HCl was added (15 mL). The reaction was then concentrated under reduced pressure, and the resulting solid was triturated with water (15 mL) and diethyl ether (20 mL) to provide the titled compound. MS (APCI) m/e 381 (M–H)$^-$.

Example 60

2-chloro-4-hydroxy-3-(2'-hydroxy-1,1'-biphenyl-4-yl)-6-oxo-6,7-dihydrothieno[2,3-b]pyridine-5-carbonitrile A degassed solution of 2-bromo-4-hydroxy-3-(4-nitrophenyl)-6-oxo-6,7-dihydrothieno[2,3-b]pyridine-5-carbonitrile (6.36 mg, 1.67 mmol), 2-(4,4,5,5-tetramethyl-1,3,2-dioxaborolan-2-yl)phenol (735 mg, 3.34 mmol), cesium carbonate (1.63 g, 5.01 mmol), and tetrakis(triphenylphosphine)palladium (38 mg, 0.034 mmol) in a solvent mixture of 1,2-dimethoxyethane:toluene:ethanol:water (10:1:6:3, 17 mL) was heated to 80° C. for 40 h. The reaction was then cooled to room temperature and diluted with saturated aqueous sodium bicarbonate solution (20 mL) and ethyl acetate (20 mL). The layers were separated, and the aqueous was extracted with additional ethyl acetate (3×20 mL). The combined organic layers were dried with anhydrous sodium sulfate, filtered, and concentrated under reduced pressure. The residue was purified by RP-HPLC to provide the titled compound as a white solid. MS (ESI) m/e 392.9 (M–H)$^+$; $^1$H NMR (400 MHz, DMSO-d$_6$): δ ppm 9.60 (br s, 1H), 7.60 (d, 2H), 7.36 (d, 2H), 7.31 (dd, 1H), 7.20–7.16 (m, 1H), 6.97 (d, 1H), 6.90 (t, 1H).

Example 62

2-bromo-3-(5'-bromo-2'-hydroxy-1,1'-biphenyl-4-yl)-4-hydroxy-6-oxo-6,7-dihydrothieno[2,3-b]pyridine-5-carbonitrile Example 62 was prepared using similar procedures as described for Example 7 substituting 4-hydroxy-3-(2'-hydroxy-1,1'-biphenyl-4-yl)-6-oxo-6,7-dihydrothieno[2,3-b]pyridine-5-carbonitrile for 4-hydroxy-6-oxo-3-phenyl-6,7-dihydrothieno[2,3-b]pyridine-5-carbonitrile and two equivalents of pyridine hydrobromide perbromide instead of one as described in Example 7. MS (ESI) m/e 516.7 (M–H)$^+$; $^1$H NMR (300 MHz, DMSO-d6): δ ppm 9.95 (br s, 1H), 7.60 (d, 2H), 7.42 (d, 2H), 7.35–7.32 (m, 3H), 6.93 (d, 1H).

Example 64

4-hydroxy-3-[2'-(hydroxymethyl)-1,1'-biphenyl-4-yl]-6-oxo-6,7-dihydrothieno[2,3-b]pyridine-5-carbonitrile To a solution of 3-(2'-formyl-1,1'-biphenyl-4-yl)-4-hydroxy-6-oxo-6,7-dihydrothieno[2,3-b]pyridine-5-carbonitrile (0.03 g, 0.08 mmol) in MeOH (2 mL) and dichloromethane (0.5 mL) was added NaBH$_4$ (0.012 g, 0.32 mmol) in a single portion. The reaction was stirred at room temperature for 18 h. It was then cooled to 0° C. in an ice bath, quenched by slow addition of 1N HCl (10 mL) and extracted with dichloromethane (3×10 mL). The organic layers were dried with anhydrous sodium sulfate, concentrated and purified by RP-HPLC to give the title compound as a white solid. MS (ESI) m/e 372.9 (M–H)$^+$; $^1$H NMR (400 MHz, DMSO-d$_6$): δ ppm 12.42 (br s, 1H), 7.60 (dd, 1H), 7.50 (d, 2H), 7.32–7.42 (m, 4H), 7.26 (dd, 1H), 7.07 (s, 1H), 4.46 (s, 2H).

Example 66

4-hydroxy-3-[4-(methoxymethoxy)phenyl]-6-oxo-6,7-dihydrothieno[2,3-b]pyridine-5-carbonitrile Example 66 was prepared using the same procedures as described for Example 2 substituting 1-(4-methoxymethoxy-phenyl)-ethanone for 3,5-dimethylacetophenone in Example 2A. MS (ESI) m/e 326.9 (M–H)$^+$; $^1$H NMR (500 MHz, DMSO-d$_6$): δ ppm 12.42 (br s, 1H), 7.35 (d, 2H), 7.0 (d, 2H), 6.94 (s, 1H), 5.21 (s, 2H), 3.40 (s, 3H).

Example 67

4-hydroxy-6-oxo-3-{2'-[({2-[4-(trifluoromethyl)phenyl]ethyl}amino)methyl]-1,1'-biphenyl-4-yl}-6,7-dihydrothieno[2,3-b]pyridine-5-carbonitrile To a solution of 3-(2'-formyl-1,1'-biphenyl-4-yl)-4-hydroxy-6-oxo-6,7-dihydrothieno[2,3-b]pyridine-5-carbonitrile (0.025 g, 0.067 mmol) in MeOH (1 mL) and dichloromethane (1 mL, with 2% v/v acetic acid) was added 2-(4-trifluoromethyl phenyl)ethyl amine (0.025 g, 0.13 mmol) and shaken at room temperature for 10 min. MP-cyanoborohydride (0.09 g, 0.2 mmol) was then added to the reaction mixture and shaken at room temperature for 24 h. The reaction was filtered, concentrated and purified by RP-HPLC to give the title compound. MS (ESI) m/e 546 (M+H)$^+$; $^1$H NMR (500 MHz, DMSO-d$_6$): δ ppm 11.11 (br s, 1H), 8.97 (br s, 2H), 7.66–7.70 (m, 3H), 7.58 (d, 2H), 7.50–7.54 (m, 2H), 7.46 (d, 2H), 7.37–7.40 (m, 1H), 7.30 (d, 2H), 6.76 (s, 1H), 4.24 (s, 2H), 3.17 (br s, 2H), 2.95 (t, 2H).

Example 68

4-hydroxy-3-[2'-({[2-(4-hydroxy-3,5-dimethoxyphenyl)ethyl]amino}methyl)-1,1'-biphenyl-4-yl]-6-oxo-6,7-dihydrothieno[2,3-b]pyridine-5-carbonitrile Example 68 was prepared using the same procedures as described for Example 67 substituting 4-(2-aminoethyl)-2,6-dimethoxy phenol for 2-(4-trifluoromethyl phenyl)ethyl amine in Example 67. MS (ESI) m/e 554.1 (M+H)$^+$; $^1$H NMR (500 MHz, DMSO-d$_6$): δ ppm 11.7 (br s, 1H), 8.87 (br s, 2H), 7.69–7.71 (m, 1H), 7.58 (d, 2H), 7.50–7.55 (m, 2H), 7.38–7.40 (m, 1H), 7.34 (d, 2H), 6.90 (s, 1H), 6.44 (s, 2H), 4.22 (br s, 2H), 3.97 (s, 1H), 3.71 (s, 6H), 3.10 (br s, 2H), 2.95 (t, 2H).

Example 69

3-[4-(2-formylthien-3-yl)phenyl]-4-hydroxy-6-oxo-6,7-dihydrothieno[2,3-b]pyridine-5-carbonitrile Example 69 was prepared using the same procedure as described for Example 12 substituting 2-formylthiophene-3-boronic acid for 4-fluorophenyl boronic acid in Example 12. MS (ESI) m/e 377 (M–H)$^+$; $^1$H NMR (500 MHz, DMSO-d$_6$): δ ppm 12.14 (br s, 1H), 9.88 (s, 1H), 8.18 (d, 1H), 7.60 (m, 4H), 7.46 (d, 1H), 7.04 (s, 1H).

Example 70

3-(2'-amino-1,1'-biphenyl-4-yl)-4-hydroxy-6-oxo-6,7-dihydrothieno[2,3-b]pyridine-5-carbonitrile Example 70 was prepared using the same procedure as described for Example 12 substituting 2-aminophenyl boronic acid for 4-fluorophenyl boronic acid in Example 12. MS (ESI) m/e 358 (M–H)$^+$; $^1$H NMR (500 MHz, DMSO-d$_6$): δ ppm 12.04 (br s, 1H), 7.54 (d, 2H), 7.40 (d, 2H), 7.10–7.16 (m, 2H), 6.95 (s, 1H), 6.90 (d, 1H), 6.82 (t, 1H).

Example 71

4-hydroxy-3-(4-hydroxyphenyl)-6-oxo-6,7-dihydrothieno[2,3-b]pyridine-5-carbonitrile To a stirred solution of 4-hydroxy-3-[4-(methoxymethoxy)phenyl]-6-oxo-6,7-dihydrothieno[2,3-b]pyridine-5-carbonitrile (0.1 g, 0.305 mmol) in THF (10 mL) was added 1N HCl (20 mL) in a single portion at room temperature and stirred for 16 h at room temperature. The reaction mixture was concentrated and purified by RP-HPLC to afford the title compound. MS (ESI) m/e 282.9 (M–H)$^+$; $^1$H NMR (500 MHz, DMSO-d$_6$): δ ppm 12.56 (br s, 1H), 9.45 (br s, 1H), 7.22 (d, 2H), 6.89 (s, 1H), 6.74 (d, 2H).

Example 72

2-bromo-3-(3-bromo-4-hydroxyphenyl)-4-hydroxy-6-oxo-6,7-dihydrothieno[2,3-b]pyridine-5-carbonitrile Example 72 was prepared using similar procedures as described for Example 7 substituting 4-hydroxy-3-(4-hydroxyphenyl)-6-oxo-6,7-dihydrothieno[2,3-b]pyridine-5-carbonitrile for 4-hydroxy-6-oxo-3-phenyl-6,7-dihydrothieno[2,3-b]pyridine-5-carbonitrile and two equivalents of pyridine hydrobromide perbromide instead of one as described in Example 7. MS (ESI) m/e 440.7 (M–H)$^+$; $^1$H NMR (400 MHz, DMSO-d$_6$): δ ppm 12.28 (br s, 1H), 10.36 (br s, 1H), 7.40 (d, 1H), 7.11 (dd, 1H), 6.97 (d, 1H).

Example 73

2-chloro-3-(2'-chloro-1,1'-biphenyl-4-yl)-4-hydroxy-6-oxo-6,7-dihydrothieno[2,3-b]pyridine-5-carbonitrile The titled compound was prepared by the method described for Example 60, substituting 2-chloro-phenylboronic acid for 2-(4,4,5,5-tetramethyl-1,3,2-dioxaborolan-2-yl)phenol. MS (ESI) m/e 412 (M–H)$^-$; $^1$H NMR (300 MHz, CDCl$_3$): δ ppm 7.59 (dt, 1H), 7.50–7.40 (m, 3H), 7.47 (d, 2H), 7.41 (d, 2H), and 3.75 (br s, 1H).

Example 74

N-[4'-(2-chloro-5-cyano-4-hydroxy-6-oxo-6,7-dihydrothieno[2,3-b]pyridin-3-yl)-1,1'-biphenyl-3-yl]acetamide The titled compound was prepared by the method described for Example 60, substituting 3-acetamido-phenylboronic acid acid for 2-(4,4,5,5-tetramethyl-1,3,2-dioxaborolan-2-yl)phenol. MS (ESI) m/e 434 (M–H)$^-$; $^1$H NMR (300 MHz, CD$_3$OD): δ ppm 7.91 (t, 1H), 7.67 (d, 2H), 7.53 (ddd, 1H), 7.43 (d, 2H), 7.41–7.38 (m, 1H), 7.35–7.32 (m, 1H) and 2.16 (s, 3H).

Example 75

2-chloro-3-(4'-chloro-1,1'-biphenyl-4-yl)-4-hydroxy-6-oxo-6,7-dihydrothieno[2,3-b]pyridine-5-carbonitrile The titled compound was prepared by the method described for Example 60, substituting 4-chloro-phenylboronic acid for 2-(4,4,5,5-tetramethyl-1,3,2-dioxaborolan-2-yl)phenol. MS (ESI) m/e 412 (M–H)$^-$; $^1$H NMR (300 MHz, DMSO-d6): δ ppm 7.76 (d, 2H), 7.69 (d, 2H), 7.54 (d, 2H), 7.41 (d, 2H), and 3.71 (br s, 1H).

Example 76

{[4'-(5-cyano-4-hydroxy-6-oxo-6,7-dihydrothieno[2,3-b]pyridin-3-yl)-1,1'-biphenyl-2-yl]oxy}acetic acid To a stirred solution of 4-hydroxy-3-(2'-hydroxy-1,1'-biphenyl-4-yl)-6-oxo-6,7-dihydrothieno[2,3-b]pyridine-5-carbonitrile (0.090 g, 0.25 mmol) in acetone (20 mL) was added potassium carbonate (0.140 g, 1 mmol) and tetrabutylammonium iodide (0.004 g, 0.0125 mmol) and stirred for 30 min at room temperature. Ethyl bromoacetate (0.083 g, 0.5 mmol) was then added to the reaction mixture and stirred for an additional 16 h at room temperature. The reaction mixture was concentrated and purified by RP-HPLC to afford the title compound. MS (ESI) m/e 416.9 (M–H)$^+$; $^1$H NMR (400 MHz, DMSO-d$_6$): δ ppm 12.44 (br s, 1H), 7.57 (d, 2H), 7.46 (d, 2H), 7.30–7.36 (m, 2H), 7.07 (d, 1H), 7.04 (s, 1H), 6.99 (d, 1H), 4.74 (s, 2H).

Example 77

2-bromo-4-hydroxy-3-(4-hydroxyphenyl)-6-oxo-6,7-dihydrothieno[2,3-b]pyridine-5-carbonitrile Example 77 was prepared using the same procedures as described for Example 7 substituting 4-hydroxy-3-(4-hydroxyphenyl)-6-oxo-6,7-dihydrothieno[2,3-b]pyridine-5-carbonitrile for 4-hydroxy-6-oxo-3-phenyl-6,7-dihydrothieno[2,3-b]pyridine-5-carbonitrile in Example 7. MS (ESI) m/e 362.8 (M–H)$^+$; $^1$H NMR (400 MHz, DMSO-d$_6$): δ ppm 12.39 (br s, 1H), 9.53 (br s, 1H), 7.09 (d, 2H), 6.76 (d, 2H), 4.74 (br s, 1H).

Example 78

2-bromo-3-(3,5-dibromo-4-hydroxyphenyl)-4-hydroxy-6-oxo-6,7-dihydrothieno[2,3-b]pyridine-5-carbonitrile Example 78 was prepared using similar procedures as described for Example 7 substituting 4-hydroxy-3-(4-hydroxyphenyl)-6-oxo-6,7-dihydrothieno[2,3-b]pyridine-5-carbonitrile for 4-hydroxy-6-oxo-3-phenyl-6,7-dihydrothieno[2,3-b]pyridine-5-carbonitrile and three equivalents of pyridine hydrobromide perbromide instead of one as described in Example 7. MS (ESI) m/e 520.6 (M–H)$^+$; $^1$H NMR (400 MHz, MeOH-d$_4$): δ ppm 7.44 (s, 2H).

Example 79

3-(3-bromophenyl)-4-hydroxy-6-oxo-6,7-dihydrothieno[2,3-b]pyridine-5-carbonitrile Example 79 was prepared using the same procedures as described for Example 2 substituting 3-bromoacetophenone for 3,5-dimethylacetophenone the step described in Example 2a. MS (ESI) m/e 346.73 (M–H)$^+$; $^1$H NMR (300 MHz, DMSO-d$_6$): δ ppm 12.48 (br s, 1H), 7.62 (t, 1H), 7.53 (m, 1H), 7.43 (m, 1H), 7.33 (t, 1H), 7.11 (s, 1H).

Example 80

2-chloro-4-hydroxy-3-(2'-methyl-1,1'-biphenyl-4-yl)-6-oxo-6,7-dihydrothieno[2,3-b]pyridine-5-carbonitrile The titled compound was prepared by the method described for Example 60, substituting 2-methyl-phenylboronic acid for 2-(4,4,5,5-tetramethyl-1,3,2-dioxaborolan-2-yl)phenol. MS (ESI) m/e 391 (M–H)$^-$; $^1$H NMR (300 MHz, DMSO-d$_6$): δ ppm 7.40 (d, 2H), 7.35 (d, 2H), 7.32–7.26 (m, 4H), 3.70 (br s, 1H), and 2.30 (s, 3H).

Example 81

2-chloro-4-hydroxy-3-(3'-hydroxy-1,1'-biphenyl-4-yl)-6-oxo-6,7-dihydrothieno[2,3-b]pyridine-5-carbonitrile The titled compoun was prepared by the method described for Example 60, substituting 3-(4,4,5,5-tetramethyl-1,3,2-dioxaborolan-2-yl)phenol for 2-(4,4,5,5-tetramethyl-1,3,2-dioxaborolan-2-yl)phenol. MS (ESI) m/e 393 (M–H)$^-$; $^1$H NMR (300 MHz, DMSO-d$_6$): δ ppm 7.61 (d, 2H), 7.38 (d, 2H), 7.28 (t, 1H), 7.12 (dt, 1H), 7.06 (t, 1H), 6.78 (ddd, 1H), and 3.70 (br s, 1H).

Example 82

3-{4-[bis(3,3-dimethylbutyl)amino]phenyl}-4-hydroxy-6-oxo-6,7-dihydrothieno[2,3-b]pyridine-5-carbonitrile To a solution of 4-hydroxy-3-(4-aminophenyl)-6-oxo-6,7-dihydrothieno[2,3-b]pyridine-5-carbonitrile (35 mg, 0.124 mmol) in methanol containing 2% v/v AcOH (2.5 mL) at room temperature was added 3,3-dimethylbutanal (32 mg, 0.32 mmol). The solution was vigorously shaken for 15 minutes, and MP-cyanoborohydride (138 mg, 0.32 mmol, 2.32 mmol/g loading) was added in one portion. The reaction mixture was shaken vigorously for 18 h, and was then filtered through celite, eluting with methanol. The eluant was concentrated under vacuum, and the crude residue was purified by RPLC to provide the titled compound as a solid. MS (ESI) m/e 390 (M–H)$^-$; $^1$H NMR (300 MHz, DMSO-d$_6$): δ ppm 7.70 (d, 2H), 7.58 (d, 2H), 6.99 (s, 1H), 3.58 (d, 4H), 0.96–0.83 (m, 2H), 0.62 (d, 4H), and 0.33 (br s, 2H).

Example 83

2,5-dichloro-3-(3,5-dichloro-4-hydroxyphenyl)-4-hydroxythieno[2,3-b]pyridin-6(7H)-one

Example 83a 3,5-dichloro-4-hydroxyacetophenone

To a solution of 15.0 g (110 mmol) of 4-hydroxyacetophenone in 150 mL of glacial acetic acid was added 88 mL of water. The solution was cooled with an ice bath, then Cl$_2$ gas was bubbled through the solution. After 1 h, the precipitate was filtered, then Cl$_2$ gas was again bubbled through the filtrate. After 15 min, more precipitate was filtered but kept separate from the first precipitate, then Cl$_2$ gas was bubbled through the filtrate again. The precipitates were checked by TLC (30% ethyl acetate/hexanes) to determine when significant overchlorination began to occur before combining them. The precipitate was collected after another 15 min, and after two more 15 min chlorination/bubbling cycles, the precipitate that formed was no longer the desired product. The combined product lots were dissolved in ethyl acetate, washed with brine, dried over MgSO$_4$, filtered, and concentrated to a solid. This was recrystallized from toluene to give 8.85 g (39%) of titled compound as white crystals. MS (ESI) m/e 202.9, (M–H)$^+$; $^1$H NMR (300 MHz, DMSO-d$_6$) δ 2.54 (s, 3H) 7.92 (s, 2H) 11.16 (s, 1H).

Example 83b 3,5-dichloro-4-benzyloxyacetophenone

To a solution of 8.82 g (43.0 mmol) of 3,5-dichloro-4-hydroxyacetophenone from Example 2a in 45 mL of DMF was added 7.12 g (51.6 mmol) K$_2$CO$_3$, then 5.1 mL (43.0 mmol) of benzyl bromide. The reaction was stirred at ambient temperature for 3.5 h, then poured into 150 mL of water, and extracted with diethyl ether (3×50 mL). The combined ether extracts were back extracted with brine (1×50 mL), dried over MgSO$_4$, filtered, and concentrated to 9.55 g (75%) of the titled compound as a white solid. MS (ESI) m/e 292.8, (M−H)⁻; $^1$H NMR (300 MHz, DMSO-$d_6$) δ 2.60 (s, 3H) 5.12 (s, 2H) 7.43 (m, 3H) 7.54 (m, 2H) 8.03 (s, 2H).

Example 83c

2-Amino-4-(4-benzyloxy-3,5-dichloro-phenyl)-thiophene-3-carboxylic acid ethyl ester To 9.55 g (32.4 mmol) of 3,5-dichloro-4-benzyloxyacetophenone was added 7.32 g (64.7 mmol) of ethyl cyanoacetate, then 50 mL of glacial acetic acid, and 13.5 mL (64.7 mmol) of hexamethyldisilazane. The reaction was stirred at 80° C. for 8 h, then diluted with 200 mL of water and extracted with diethyl ether (3×50 mL). The combined ether layers were back extracted with water (1×50 mL), saturated NaHCO$_{3(aq.)}$ (2×50 mL), and brine (1×50 mL), dried over MgSO$_4$, filtered, and concentrated to an amber oil. This was placed under high vacuum for 20 minutes to remove a volatile byproduct.

The product was taken up in 50 mL of ethanol, then 1.04 g (32.4 mmol) of sulfur and 5.7 mL (64.7 mmol) of morpholine were added. The reaction was stirred at 80° C. for 30 min, then diluted with 200 mL of 0.3 M HCl$_{(aq.)}$ and extracted with diethyl ether (3×50 mL). The combined ether layers were back extracted with water (1×50 mL), and brine (1×50 mL), dried over MgSO$_4$, filtered, and concentrated to a solid. The titled product was purified via silica gel chromatography, eluting with 20% ethyl acetate/hexanes to give 6.0 g (44%) of yellow crystals. MS (ESI) m/e 422, (M+H)⁺, 439, (M+NH4)⁺, 444, (M+Na)⁺; $^1$H NMR (300 MHz, DMSO-$d_6$) δ 0.98 (t, J=7.12 Hz, 3H) 3.32 (s, 3H) 4.00 (q, J=7.12 Hz, 2H) 5.03 (s, 2H) 6.35 (s, 1H) 7.47 (m, 9H).

Example 83d 4-(4-Benzyloxy-3,5-dichloro-phenyl)-2-(2-methoxycarbonyl-acetylamino)-thiophene-3-carboxylic acid ethyl ester To a solution of 2.00 g (4.74 mmol) of 2-amino-4-(4-benzyloxy-3,5-dichloro-phenyl)-thiophene-3-carboxylic acid ethyl ester in 20 mL of CH$_2$Cl$_2$ was added a solution of 789 mg (5.78 mmol) of methyl 3-chlorooxopropionate in 10 mL of CH$_2$Cl$_2$. The reaction was stirred at reflux for 1 h, then cooled and extracted with H$_2$O (1×10 mL), saturated NaHCO$_{3(aq.)}$ (2×10 mL), and brine (1×10 mL). The organic layer was dried over MgSO$_4$, filtered, and concentrated to 1.91 g (77%) of the titled compound as a solid.

Example 83e 3-(3,5-Dichloro-4-benzyloxy-phenyl)-4-hydroxy-7H-thieno[2,3-b]pyridin-6-one To a solution of 1.91 g (3.65 mmol) of 4-(4-benzyloxy-3,5-dichloro-phenyl)-2-(2-methoxycarbonyl-acetylamino)-thiophene-3-carboxylic acid ethyl ester in 20 mL of THF was added 600 mg (15 mmol) of 60% NaH in mineral oil. The reaction was stirred at reflux under N$_2$ for 18 h, then the excess NaH was quenched by the addition of 10 mL of water. The THF was removed in vacuo, then the remaining solution was taken up in 30 mL of 2M NaOH$_{(aq.)}$ and 30 mL of ethanol. This was stirred at 80° C. for 5 h, then concentrated to remove most of the ethanol. The remaining solution was diluted with 100 mL of water, and extracted with diethyl ether (2×30 mL). The ether layers were discarded, along with a small amount of precipitate that formed in the aqueous layer. The stirred aqueous layer was made acidic with 4M HCl to give a precipitate. Diethyl ether was added and the mixture was stirred to suspend the precipitate in the ether layer, then most of the water was decanted. The precipitate was filtered, and washed with water, then diethyl ether to give 1.20 g (79%) of the titled compound as a tan solid. MS (ESI) m/e 417.7, (M+H)⁺; $^1$H NMR (300 MHz, DMSO-$d_6$) δ 5.05 (s, 1H) 5.76 (s, 1H) 7.23 (s, 1H) 7.43 (m, 2H) 7.58 (m, 2H) 11.15 (s, 1H).

Example 83f 3-(4-Hydroxy-3,5-dichloro-phenyl)-2,5-dichloro-4-hydroxy-7H-thieno[2,3-b]pyridin-6-one To a suspension of 200 mg (0.478 mmol) of 3-(3,5-dichloro-4-benzyloxy-phenyl)-4-hydroxy-7H-thieno[2,3-b]pyridin-6-one in 4 mL of CH$_2$Cl$_2$ was added 128 mg (0.959 mmol) of N-chlorosuccinimide. The reaction was stirred for 18 h at ambient temperature, then another 128 mg (0.959 mmol) of N-chlorosuccinimide was added. After an additional 5 h at ambient temperature, the reaction was diluted with 20 mL of CH$_2$Cl$_2$, and extracted with saturated NaHCO$_{3(aq.)}$ solution, and brine (1×5 mL), dried over MgSO$_4$, filtered, and concentrated to 250 mg of a solid.

The solid was taken up in 4 mL of CH$_2$Cl$_2$ and 0.4 mL (2.8 mmol) of iodotrimethylsilane was added. After stirring at ambient temperature for 1.5 h, the reaction was diluted with 20 mL of CH$_2$Cl$_2$. Addition of 10 mL H$_2$O gave an emulsion which was treated with a few drops of 5% NaHSO$_{3(aq.)}$ to discharge the I$_2$ color. The emulsion was filtered to give a precipitate that was washed with water and dried on the filter to give the crude product. This was purified via silica gel chromatography, eluting with 3:1 ethyl acetate: hexanes to give 30 mg (16%, 2 steps) of a solid as the titled compound. MS (ESI) m/e 395.7, (M−H)⁺; $^1$H NMR (300 MHz, DMSO-$d_6$) δ 7.38 (s, 2H) 10.33 (s, 1H) 11.03 (s, 1H) 12.44 (bs, 1H).

Example 84

3-[4-(2,6-dihydroxyphenyl)-phenyl]-4-hydroxy-6-oxo-6,7-dihydro-thieno[2,3b]-pyridine-5-carbonitrile The titled compound was prepared according to the procedures described in Example 3a-b, substituting 2,6-dimethoxyphenylboronic acid for 2,3-dimethoxyphenylboronic acid used in Example 3A (28.0 mg, 74.5%). $^1$H NMR (300 MHz, DMSO-$d_6$) δ 10.80 (s, 1H), 9.07 (s, 2H), 7.41 (d, 2H, J=9 Hz), 7.24 (s, 1H), 7.20 (d, 2H, J=9 Hz), 7.07 (s, 1H), 6.89 (t, 1H, J=9.0 Hz), 6.40 (d, 2H, J=9 Hz). MS (ESI) m/e 377 (M+H)⁺, m/e 375 (M−H)⁻.

Example 85

3-[5-(4-aminophenyl)thien-2-yl]-4-hydroxy-6-oxo-6,7-dihydrothieno[2,3-b]pyridine-5-carbonitrile

Example 85a tert-butyl 4-[5-(5-cyano-4-hydroxy-6-oxo-6,7-dihydrothieno[2,3-b]pyridin-3-yl)thien-2-yl]phenylcarbamate The title compound was prepared according to the procedures described in Example 91 substituting 4-Boc-aminophenyl boronic acid for 4-(Methylsulfonylamino)phenyl boronic acid in Example 91d. $^1$H NMR (300 MHz, METHANOL-D4) δ ppm 1.53 (s, 9H) 7.13 (s, 1H) 7.23 (m, 3H) 7.43 (d, J=8.82 Hz, 1H) 7.55 (m, 2H) MS (ESI) m/z 466.0 (M+H)⁺, 483.1 (M+NH$_4$)⁺, 488.1 (M+Na)⁺

Example 85b

3-[5-(4-aminophenyl)thien-2-yl]-4-hydroxy-6-oxo-6,7-dihydrothieno[2,3-b]pyridine-5-carbonitrile To a suspension of Example 85a (50 mg, 0.11 mmol) in methylene chloride (0.4 mL) was added TFA (0.4 mL). This mixture was stirred for 1.5 hrs, then concentrated and dissolved in DMSO/MeOH (1:1, 2 mL). The resulting solution was purified by RPHPLC on a Waters Symmetry C18 column (25 mm×100 mm, 71 μm particle size) using a gradient of 10% to 100% acetonitrile:0.1% aqueous TFA to provide 21 mg (52%) of Example 85B. $^1$H NMR (300 MHz, DMSO-D6) δ ppm 5.26 (s, 2H) 6.58 (d, J=8.82 Hz, 2H) 6.79 (s, 1H) 7.06 (d, J=4.04 Hz, 1H) 7.31 (d, J=8.46 Hz, 2H) 7.61 (d, J=3.68 Hz, 1H) MS (ESI) m/z 366.0 (M+H)$^+$, 383 (M+NH$_4$)$^+$

Example 86

N-{4-[5-(2-chloro-5-cyano-4-hydroxy-6-oxo-6,7-dihydrothieno[2,3-b]pyridin-3-yl)thieno-2-yl]phenyl}methanesulfonamide The title compound was prepared according to the procedure described in Example 91d substituting Example 97c for Example 91c. $^1$H NMR (300 MHz, METHANOL-D4) δ ppm 2.99 (s, 3H) 3.35 (s, 1H) 7.07 (d, J=3.68 Hz, 1H) 7.29 (d, J=8.82 Hz, 2H) 7.33 (d, J=4.04 Hz, 1H) 7.63 (d, J=8.46 Hz, 2H) MS (ESI) m/z 477 (M+H)$^+$, 495 (M+NH$_4$)$^+$.

Example 86

N-{4-[5-(2-chloro-5-cyano-4-hydroxy-6-oxo-6,7-dihydrothieno[2,3-b]pyridin-3-yl)thieno-2-yl]phenyl}methanesulfonamide

Example 87

2-bromo-3-(3,5-dibromo-4-hydroxyphenyl)-4-hydroxy-6-oxo-6,7-dihydrothieno[2,3-b]pyridine-5-carbonitrile Example 87 was prepared using the same procedure as described for Example 7 substituting 4-hydroxy-3-(4-hydroxyphenyl)-6-oxo-6,7-dihydrothieno[2,3-b]pyridine-5-carbonitrile for 4-hydroxy-6-oxo-3-phenyl-6,7-dihydrothieno[2,3-b]pyridine-5-carbonitrile in Example 7. The title compound was one of three reaction products and purified on a RP-HPLC system. MS (ESI) m/e 520.6 (M−H)$^+$; $^1$H NMR (400 MHz, methanol): δ ppm 7.44 (s, 2H), 2.65 (s, 1H).

Example 88

3-[4-(2,3-dihydroxyphenyl)-phenyl]-4-hydroxy-6-oxo-6,7-dihydro-thieno[2,3b]-pyridine-5-carbonitrile

Example 88a

3-[4-(2,3-dimethoxyphenyl)-phenyl]-4-hydroxy-6-oxo-6,7-dihydro-thieno[2,3b]-pyridine-5-carbonitrile To 4-hydroxy-3-(4-iodo-phenyl)-6-oxo-6,7-dihydro-thieno[2,3-b]pyridine-5-carbonitrile from Example 3a (79 mg, 0.2 mmol), 2,3-dimethoxyphenylboronic acid (0.26 mmol), Cs$_2$CO$_3$ (195 mg, 0.6 mmol) and Pd(Ph$_3$P)$_4$ (12 mg, 0.01 mmol) in a Smith Process Vial™ (2–5 mL) a mixture solvent of DMF, THF and H$_2$O (2.5 mL, 1:1:0.5) was added, following 2,3-dimethoxyphenyl boronic acid (38.2 mg, 0.21 mmol). Under the nitrogen, the vial was sealed and put in microwave reactor. The reaction mixture was heated for 20 minutes at 130° C. Water and ethyl acetate (20 ml, 1:1) were added. The water layer was extracted with ethyl acetate (5 mL) three times. The combined organic layers were dried, concentrated and purified on HPLC to give the title compound (58.6 mg, 72.5%) as white solid. $^1$H NMR (300 MHz, DMSO-d$_6$) 7.51 (d, 2H, J=9 Hz), 7.38 (d, 2H, J=9 Hz), 7.14–6.92 (m, 3H), 6.68 (s, 1H), 3.86 (s, 3H), 3.06 (s, 3H). MS (ESI) positive ion 405 (M+H)$^+$, negative ion 403 (M−H)$^−$.

Example 88b

3-[4-(2,3-dihydroxyphenyl)-phenyl]-4-hydroxy-6-oxo-6,7-dihydro-thieno[2,3b]-pyridine-5-carbonitrile To 3-[4-(2,3-dimethoxyphenyl)-phenyl]-4-hydroxy-6-oxo-6,7-dihydro-thieno[2,3b]-pyridine-5-carbonitrile from Example 3a (40.4 mg, 0.1 mmol) in anhydrous CH$_2$Cl$_2$ (4 ml) was added BBr$_3$ 1M in CH$_2$Cl$_2$ (0.4 ml, 0.4 mmol) dropwise at −10° C. The reaction mixture was stirred at room temperature for 18 h, and then ice-water (10 ml) was added, the mixture was stirred for another 1 h. The precipitated solid was filtered, washed with water and CH$_2$Cl$_2$, and then dried to give pure title compound (28.2 mg, 75%) as a white solid. $^1$H NMR (300 MHz, DMSO-d$_6$) δ 12.7 (s, 1H), 9.53 (s, 1H), 8.32 (s, 1H), 7.52 (d, 2H, J=9 Hz), 7.43 (d, 2H, J=9 Hz), 7.0 (s, 1H), 6.81–6.69 (m, 3H). MS (ESI) positive ion 377 (M+H)$^+$, negative ion 375 (M−H)$^−$.

Example 89

2,5-dibromo-3-(3,5-dibromo-4-hydroxyphenyl)-4-hydroxythieno[2,3-b]pyridin-6(7H)-one

Example 89a 4-benzyloxyacetophenone

To a solution of 13.6 g (100.0 mmol) of 4-hydroxyacetophenone in 100 mL of DMF was added 20 g (144 mmol) of K$_2$CO$_3$, then 12 mL (101 mmol) of benzyl bromide. The reaction was stirred for 1.5 h at ambient temperature, then poured into 300 mL of H$_2$O to give a white precipitate. This was filtered and washed with 50 mL of H$_2$O. The product was taken up in 100 mL of CH$_2$Cl$_2$, and the H$_2$O that separated was drained. The organic layer was extracted with H$_2$O (1×25 mL) and brine (1×25 mL), dried over MgSO$_4$, filtered, and concentrated to 22.1 g (98%) of a white solid as the titled compound. MS (ESI) m/e 226.9, (M+H)$^+$; $^1$H NMR (300 MHz, DMSO-d$_6$) δ 2.50 (m, 3H) 5.21 (s, 2H) 7.11 (m, 2H) 7.41 (m, 5H) 7.92 (m, 2H).

Example 89b

2-Amino-4-(4-benzyloxy-phenyl)-thiophene-3-carboxylic acid ethyl ester

To a mixture of 22.1 g (97.7 mmol) of 4-benzyloxyacetophenone from Example 7a and 22.1 g (195.3 mmol) of ethyl cyanoacetate was added 150 mL of glacial acetic acid. After the ketone had dissolved, 41 mL (197 mmol) of hexamethyldisilazane was added, and the solution was stirred at 80° C. for 17.5 h. The reaction then was poured into 500 mL of water, and extracted with diethyl ether (3×100 mL). The combined ether layers were back extracted with saturated NaHCO$_{3(aq.)}$ (3×100 mL), then brine (1×100 mL), dried over MgSO$_4$, filtered, and concentrated to an oil.

The oil was dissolved in 150 mL of ethanol, then 3.13 g (97.7 mmol) of sulfur, and 17.4 mL (200 mmol) of morpholine were added. The reaction was stirred at reflux for 1.5 5 h, then concentrated in vacuo. The residue was dissolved in 400 mL of diethyl ether, except for 6 g of a solid that was filtered and recrystallized from ethanol to give 4.08 g (11%) of the desired product. The ether layer was then extracted with water (2×50 mL) and brine (1×50 mL), dried over MgSO$_4$, filtered, and concentrated to a solid. This contained product and some 4-benzyloxyacetophenone that was difficult to separate. The crude product was therefore dissolved in 100 mL of warm ethanol and treated with 1 g of NaBH$_4$ to reduce the ketone to the corresponding alcohol. After stirring for 1.5 h, at ambient temperature, the reaction was diluted with 300 mL of H$_2$O and extracted with diethyl ether (2×100 mL), then 1×100 mL of ethyl acetate. The combined ether and ethyl acetate layers were back extracted with 0.2M HCl$_{(aq.)}$ (1×50 mL), then brine (1×30 mL), dried over MgSO$_4$, filtered, and concentrated to a solid. This was purified via silica gel chromatography, eluting with 20% ethyl acetate/hexanes to give 10.67 g (31%) of the titled product. The total yield was 14.75 g (43%). MS (ESI) m/e 354.3, (M+H)$^+$; $^1$H NMR (300 MHz, DMSO-d$_6$) δ 0.91 (t, J=7.12 Hz, 3H) 3.95 (q, J=7.01 Hz, 2H) 5.12 (s, 2H) 6.09 (s, 1H) 6.93 (m, 2H) 7.15 (m, 2H) 7.39 (m, 7H).

Example 89c 4-(4-Benzyloxy-phenyl)-2-(2-ethoxycarbonyl-acetylamino)-thiophene-3-carboxylic acid ethyl ester To 4.08 g (11.5 mmol) of 2-amino-4-(4-benzyloxy-phenyl)-thiophene-3-carboxylic acid ethyl ester from Example 7b in 50 mL of CH$_2$Cl$_2$ was added a solution of 1.9 g (12.6 mmol) of ethyl 3-chlorooxopropionate in 25 mL of CH$_2$Cl$_2$. The solution was stirred at reflux for 40 min, then diluted with another 25 mL of CH$_2$Cl$_2$ and extracted with water (2×25 mL). Some emulsion formed, but this could be broken by filtering through diatomaceous earth. The organic layer was extracted with saturated NaHCO$_{3(aq.)}$ (1×25 mL), and brine (1×25 mL), dried over MgSO$_4$, filtered, and concentrated to an oil. Before crystallization occurred, the oil was taken up in 100 mL of ethanol, and the solution was heated to dissolve some solid that formed too quickly. The titled product crystallized to give 4.41 g (82%) of yellow needles.

Example 89d 3-(4-Benzyloxy-phenyl)-4-hydroxy-7H-thieno[2,3-b]pyridin-6-one

To a solution of 4.42 g (9.45 mmol) of 4-(4-benzyloxy-phenyl)-2-(2-ethoxycarbonyl-acetylamino)-thiophene-3-carboxylic acid ethyl ester from Example 7c in 50 mL of THF was added 1.6 g (40 mmol) of 60% NaH in mineral oil. The mixture was stirred at reflux under N$_2$ for 17 h, then the excess NaH was quenched by the addition of 25 mL H$_2$O. The reaction was concentrated in vacuo to remove most of the THF, then the remaining mixture was taken up in 75 mL of 2M NaOH and 75 mL of ethanol and heated at reflux for 6.5 h. The ethanol was removed in vacuo, and the aqueous solution was diluted with water to a total volume of 150 mL. The solution was extracted with diethyl ether (3×30 mL) to remove the mineral oil, then the aqueous layer was filtered through diatomaceous earth to remove some cloudiness. The solution was made acidic by addition of 80 mL of 4M HCl, and filtered after bubbling had ceased (about 5 min). The precipitate was washed with water, then dried on the filter to give 2.55 g (77%) of a tan solid as the titled compound. MS (ESI) m/e 350, (M+H)$^+$; $^1$H NMR (300 MHz, DMSO-d$_6$) δ 5.13 (s, 2H) 5.70 (s, 1H) 6.92 (s, 1H) 6.98 (m, 2H) 7.40 (m, 7H) 10.82 (s, 1H).

Example 89e 3-(4-Hydroxyphenyl)-4-hydroxy-7H-thieno[2,3-b]pyridin-6-one

To 349 mg (1.00 mmol) of 3-(4-benzyloxy-phenyl)-4-hydroxy-7H-thieno[2,3-b]pyridin-6-one from Example 7d in 10 mL of CH$_2$Cl$_2$ was added 0.7 mL (4.9 mmol) of iodotrimethylsilane. The reaction was stirred at ambient temperature for 48 h, then concentrated in vacuo. The residue was suspended in 10 mL of water, and 5% NaHSO$_3$ (aq.) was added to discharge the I$_2$ color. The insoluble material was filtered, washed with water, then diethyl ether, and dried on the filter to give 183 mg (70%) of a tan solid. MS (ESI) m/e 259.9, (M+H)$^+$; 1H NMR (300 MHz, DMSO-d$_6$) δ 5.69 (s, 1H) 6.72 (m, 2H) 6.85 (s, 1H) 7.24 (m, 2H) 9.39 (s, 1H) 10.79 (s, 1H).

Example 89f 3-(4-Hydroxy-3,5-dibromo-phenyl)-2,5-dibromo-4-hydroxy-7H-thieno[2,3-b]pyridin-6-one To a suspension of 100 mg (0.386 mmol) of 3-(4-hydroxyphenyl)-4-hydroxy-7H-thieno[2,3-b]pyridin-6-one from Example 7e in 5 mL of water was added 20 drops of Br$_2$ via pipette, until a red color persisted. The reaction was stirred at ambient temperature for 3.5 h, then 5% NaHSO$_{3(aq.)}$ was added dropwise to discharge the Br$_2$ color. The insoluble material was filtered, washed with water, and dried on the filter. The product was purified via reverse phase HPLC (0 to 70% CH$_3$CN/0.1% aq. TFA gradient) to give 25 mg (11%) of a solid as the titled compound. MS (ESI) m/e 573.5, (M−H)$^-$; $^1$H NMR (300 MHz, DMSO-d$_6$) δ 7.65 (s, 2H) 10.09 (s, 1H) 10.70 (s, 1H).

Example 90

3-[4-(2,4-dihydroxyphenyl)-phenyl]-4-hydroxy-6-oxo-6,7-dihydro-thieno[2,3b]-pyridine-5-carbonitrile The titled compound was prepared according to the procedures described in Example 3a-b, substituting 2,4-dimethoxyphenylboronic acid for 2,3-dimethoxyphenylboronic acid used in Example 3A (22 mg, 58.5%). $^1$H NMR (300 MHz, DMSO-d$_6$) δ 12.15 (s, 1H), 9.38 (s, 1H), 9.29 (s, 1H), 7.46 (d, 2H, J=9 Hz), 7.39 (d, 2H, J=9 Hz), 7.09 (d, 1H, J=9 Hz), 6.98 (s, 1H), 6.43 (d, 1H, J=3 Hz), 6.32 (dd, 1H, J=6, 3 Hz). MS (ESI) m/e 377 (M+H)$^+$, 375 (M−H)$^-$.

Example 91

N-{4-[5-(5-cyano-4-hydroxy-6-oxo-6,7-dihydrothieno[2,3-b]pyridin-3-yl)thien-2-yl]phenyl}methanesulfonamide Example 91a ethyl 5'-amino-5-bromo-2,3'-bithiophene-4'-carboxylate A mixture of 1-(5-Bromo-thiophen-2-yl)-ethanone (10 g, 48.8 mmol), ethyl cyanoacetate (5.72 mL, 53.6 mmol), ammonium acetate (18.52 mmol, 1.5 g), and acetic acid (4.4 mL, 76.8 mmol) in benzene (40 mL) was azeotroped in an oil bath at 100° C. in a flask fitted with a Dean-Stark Trap and reflux condenser. After 9 h at 100° C., additional ammonium acetate (1.5 g, 18.52 mmol) and acetic acid (4.4 mL, 76.8 mmol) were added and the mixture was azeotroped an additional 9 h. The reaction mixture was concentrated to provide 14 g of condensation product as an orange oil. The residual oil was dissolved in EtOH (36 mL), and treated with diethylamine (6 mL, 57.52 mmol) and sulfur 484.8 mmol, 1.56 g). After heating the reaction mixture at 60° C. for 2 h, the solvent was evaporated. The residue was purified by flash chromatography on silica gel eluting with 50% $CH_2Cl_2$/hexanes to provide 8 g (47%) of Example 91a as a yellow solid.

Example 91b ethyl 5-bromo-5'-[(cyanoacetyl)amino]-2,3'-bithiophene-4'-carboxylate A suspension of $PCl_5$ (7.03 g, 33.75 mmol) in $CH_2Cl_2$ (67 mL) was treated with cyanoacetic acid (2.87 g, 33.75 mmol) dropwise over 5 minutes and the resulting mixture was stirred at ambient temperature until the exotherm subsided and all solids had dissolved. The reaction was then heated at reflux for 30 minutes, cooled to 25° C. and transferred via canula to a solution of Example 91a (7.5 g, 22.5 mmol) in $CH_2Cl_2$ (90 mL). The resulting mixture was heated at reflux 30 minutes and cooled to 25° C. Saturated aqueous $Na_2CO_3$ (150 mL) was added and the mixture was extracted with $CH_2Cl_2$ (2×150 mL). The combined extracts were washed with brine; dried ($Na_2SO_4$); filtered; and evaporated to afford 8.4 g (93%) of Example 91b as a yellow solid.

Example 91c 3-(5-bromothien-2-yl)-4-hydroxy-6-oxo-6,7-dihydrothieno[2,3-b]pyridine-5-carbonitrile To a suspension of sodium hydride (60% in mineral oil, 3.6 g, 90.6 mmol) in THF (120 mL) was added a solution of Example 91b (8 g, 22.6 mmol) in THF (120 mL). The resulting mixture was stirred for 4 h at 25° C. MeOH (2.5 mL) was added and the reaction stirred at 25° C. for 5 minutes. The solvent was evaporated and the concentrate dissolved in water (300 mL). The aqueous layer was washed with ether (200 mL) and ethyl acetate (200 mL) and was allowed to stand at 25° C. for 4 hours. The precipitated solids were collected by filtration to give 6.7 g of Example 91c (84%). $^1$H NMR (300 MHz, DMSO-D6) δ ppm 6.94 (s, 1H) 7.06 (d, J=3.68 Hz, 1H) 7.37 (d, J=4.04 Hz, 1H) MS (ESI) m/z 354.0 $(M+H)^+$, 372 $(M+NH_4)^+$.

Example 91d

N-{4-[5-(5-cyano-4-hydroxy-6-oxo-6,7-dihydrothieno[2,3-b]pyridin-3-yl)thien-2-yl]phenyl}methanesulfonamide A mixture of Example 91c (100 mg, 0.28 mmol), MgO (34 mg, 0.84 mmol) and $Cs_2CO_3$ (277 mg, 0.84 mmol) in dioxane (1.2 mL), DMF (1.2 mL) and $H_2O$ (0.6 mL) was degassed and stirred at 25° C. for 10 minutes. 4-(Methylsulfonylamino)phenyl boronic acid (80 mg, 0.37 mmol) and $Pd(PPh_3)_4$ (13 mg, 0.011 mmol) were added and the reaction mixture was heated at 130° C. for 10 minutes in a microwave reactor. The reaction was cooled to 25° C., diluted with MeOH (10 mL) and filtered. The filtrate was concentrated and purified by RPHPLC on a Waters Symmetry C8 column (25 mm×100 mm, 7 μm particle size) using a gradient of 10% to 100% acetonitrile:0.1% aqueous TFA to provide Example 91D (25 mg, 20%). $^1$H NMR (300 MHz, DMSO-D6) δ ppm 3.04 (m, 3H) 7.17 (s, 1H) 7.25 (d, J=8.82 Hz, 2H) 7.34 (d, J=4.04 Hz, 1H) 7.38 (d, J=4.04 Hz, 1H) 7.63 (d, J=8.46 Hz, 2H) 9.88 (s, 1H). MS (ESI) m/z 444.0 $(M+H)^+$, 461 $(M+NH_4)^+$

Example 92

4-hydroxy-3-[5-(4-hydroxyphenyl)thien-2-yl]-6-oxo-6,7-dihydrothieno[2,3-b]pyridine-5-carbonitrile The title compound was prepared according to the procedures described in Example 91 substituting 4-hydroxyphenyl boronic acid for 4-(Methylsulfonylamino)phenyl boronic acid in Example 91d. $^1$H NMR (300 MHz, METHANOL-D4) δ ppm 6.81 (m, 1H) 7.10 (s, 1H) 7.15 (d, J=3.68 Hz, 1H) 7.22 (d, J=3.68 Hz, 1H) 7.47 (m, 2H) MS (ESI) m/z 3.67 $(M+H)^+$, 484 $(M+NH_4)^+$.

Example 93

2-chloro-3-[4-(2,3-dihydroxypropoxy)phenyl]-4-hydroxy-6-oxo-6,7-dihydrothieno[2,3-b]pyridine-5-carbonitrile To an ambient solution of 3-[4-(allyloxy)phenyl]-2-chloro-4-hydroxy-6-oxo-6,7-dihydrothieno[2,3-b]pyridine-5-carbonitrile (Example 131) (200 mg, 0.52 mmol) and $K_2OsO_4$—$2H_2O$ (10 mg, 0.026 mmol) in acetone (2.6 mL) and $H_2O$ (0.25 mL) was added solid N-methylmorpholine N-oxide (91 mg, 0.78 mmol) in a single portion. The reaction was vigorously stirred for 18 h and was then quenched by the addition of EtOAc (5 mL) and saturated aqueous $Na_2S_2O_3$ (5 mL). The layers were separated, and the aqueous was extracted with additional EtOAc (3×5 mL). The combined organic layers were dried with anhydrous $Na_2SO_4$, filtered, and concentrated under reduced pressure to give a dark oil. The residue was purified by RPLC to give the title compound. MS (ESI) m/e 391 $(M-H)^{31}$; $^1$H NMR (300 MHz, DMSO-$d_6$) δ ppm 3.86 (m, 4H), 4.03 (dd, J=9.83, 4.07 Hz, 1H), 6.92 (d, J=8.82 Hz, 2H), 7.21 (d, J=8.82 Hz, 2H).

Example 94

4-[5-(5-cyano-4-hydroxy-6-oxo-6,7-dihydrothieno[2,3-b]pyridin-3-yl)thien-2-yl]benzenesulfonamide The title compound was prepared according to the procedures described in Example 91 substituting 4-(4,4,5,5-Tetramethyl-[1,3,2]dioxaborolan-2-yl)-benzenesulfonamide for 4-(Methylsulfonylamino)phenyl boronic acid in Example 91d. $^1$H NMR (300 MHz, DMSO-D6) δ ppm 7.26 (s, 1H) 7.38 (d, J=3.68 Hz, 3H) 7.62 (d, J=4.04 Hz, 1H) 7.85 (m, 4H) MS (ESI) m/z 430 $(M+H)^+$, 447 $(M+NH_4)^+$.

Example 95

3-(2'-amino-1,1'-biphenyl-4-yl)-4-hydroxy-6-oxo-6,7-dihydrothieno[2,3-b]pyridine-5-carbonitrile Example 95 was prepared using the same procedure as described for Example 12 substituting 2-aminophenyl boronic acid for 4-fluorophenyl boronic acid in Example 12. MS (ESI) m/e 358 $(M-H)^+$; $^1$H NMR (500 MHz, DMSO-d$_6$): δ ppm 12.04 (br s, 1H), 7.54 (d, J=10, 2H), 7.41 (d, J=10, 2H), 7.10–7.16 (m, 2H), 6.95 (s, 1H), 6.90 (d, J=10, 1H), 6.82 (t, J=10, 1H).

Example 96

4-hydroxy-6-oxo-3-(5-pyridin-4-ylthien-2-yl)-6,7-dihydrothieno[2,3-b]pyridine-5-carbonitrile The title compound was prepared according to the procedures described in Example 151 substituting 4-(tributylstannyl)-pyridine for 2-(tributylstannyl)-pyridine in Example 151C. $^1$H NMR (300 MHz, DMSO-D6) δ ppm 7.11 (s, 1H) 7.71 (d, J=3.68 Hz, 1H) 7.86 (m, 3H) 8.63 (d, J=6.62 Hz, 2H) 11.05 (broad s, 1H); MS (ESI) m/z 351.9 (M+H)$^+$.

Example 97

2-chloro-4-hydroxy-3-[5-(4-hydroxyphenyl)thien-2-yl]-6-oxo-6,7-dihydrothieno[2,3-b]pyridine-5-carbonitrile

Example 97a ethyl 5'-amino-5-bromo-2'-chloro-2,3'-bithiophene-4'-carboxylate To a solution of Example 91a (1.6 g, 4.8 mmol) in methylene chloride (48 mL) was added SO$_2$Cl$_2$ (1M in methylene chloride, 4.8 mL) dropwise over 5 minutes at 0° C. The reaction mixture was stirred for 30 minutes, warmed to 25° C., and stirred for 12 h. Methylene chloride (40 mL) was added and the resulting mixture was washed with saturated Na$_2$CO$_3$ (50 mL) and brine (50 mL). The organic layer was dried (MgSO$_4$), filtered, concentrated and purified by flash column chromatography on silica gel eluting with 15% ethyl acetate/hexanes to provide 1.12 g of Example 97a (63%). $^1$H NMR (300 MHz, DMSO-D6) δ ppm 0.95 (t, J=7.17 Hz, 3H) 3.96 (q, J=7.11 Hz, 2H) 6.81 (d, J=3.68 Hz 1H) 7.18 (d, J=3.68 Hz, 1H) 7.62 (s, 2H).

Example 97b ethyl 5-bromo-2'-chloro-5'-[(cyanoacetyl)amino]-2,3'-bithiophene-4'-carboxylate Example 97b was prepared according to the procedure described in Example 91b substituting Example 97a for Example 91a. $^1$H NMR (300 MHz, DMSO-D6) δ ppm 0.99 (t, J=6.99 Hz, 3H) 4.10 (q, J=7.11 Hz, 2H) 4.31 (s, 2H) 6.90 (d, J=3.68 Hz, 1H) 7.25 (d, J=4.04 Hz, 1H) 11.40 (s, 1H) MS (ESI) m/z 434.7 (M+H)$^+$, 456.7 (M+Na)$^+$.

Example 97c 3-(5-bromothien-2-yl)-2-chloro-4-hydroxy-6-oxo-6,7-dihydrothieno[2,3-b]pyridine-5-carbonitrile Example 97c was prepared according to the procedure described in Example 91c substituting Example 97b for Example 91b. $^1$H NMR (300 MHz, METHANOL-D4) δ ppm 6.88 (d, J=4.04 Hz, 1H) 7.04 (d, J=3.68 Hz, 1H) MS (ESI) m/z 389 (M+H)$^+$, 406 (M+NH$_4$)$^+$.

Example 97d 2-chloro-4-hydroxy-3-[5-(4-hydroxyphenyl)thien-2-yl]-6-oxo-6,7-dihydrothieno[2,3-b]pyridine-5-carbonitrile To Example 97c (100 mg, 0.258 mmol), MgO (31 mg, 0.74 mmol) and Cs$_2$CO$_3$ (241 mg, 0.74 mmol) in dioxane (1.2 mL) and DMF (1.2 mL) was added H$_2$O (0.6 mL). The mixture was degassed and stirred at 25° C. for 10 min. 4-hydroxyphenyl boronic acid (46 mg, 0.33 mmol) and Pd(PPh$_3$)$_4$ (13 mg, 0.011 mmol) were added and the resulting mixture was heated at 130° C. for 10 minutes in a microwave reactor. The reaction was cooled to 25° C., treated with MeOH (10 mL) and filtered. The filtrate was concentrated and purified by RPHPLC on a Waters Symmetry C8 column (25 mm×100 mm, 7 μm particle size) using a gradient of 10% to 100% acetonitrile:0.1% aqueous TFA to provide Example 97d (15 mg, 15%). $^1$H NMR (300 MHz, METHANOL-D4) δ ppm 6.81 (d, J=8.82 Hz, 1H) 7.03 (d, J=3.68 Hz, 1H) 7.20 (d, J=3.68 Hz, 1H) 7.48 (m, 2H) MS (ESI) m/z 400.9 (M+H)$^+$, 418.2 (M+NH$_4$)$^+$.

Example 98

4-hydroxy-3-{5-[4-(hydroxymethyl)phenyl]thien-2-yl}-6-oxo-6,7-dihydrothieno[2,3-b]pyridine-5-carbonitrile The title compound was prepared according to the procedures described in Example 91 substituting 4-hydroxymethylphenyl boronic acid for 4-(Methylsulfonylamino)phenyl boronic acid in Example 91d. $^1$H NMR (300 MHz, DMSO-D6) δ ppm 4.51 (s, 2H) 7.18 (s, 1H) 7.36 (m, 3H) 7.43 (d, J=3.68 Hz, 1H) 7.62 (d, J=8.46 Hz, 2H) MS (ESI) m/z 380.9 (M+H)$^+$, 397.9 (M+NH$_4$)$^+$.

Example 99

2-chloro-4-hydroxy-3-{4-[(1-hydroxycyclopent-3-en-1-yl)methoxy]phenyl}-6-oxo-6,7-dihydrothieno[2,3-b]pyridine-5-carbonitrile

Example 99a 4-acetyl-phenoxyacetic acid ethyl ester

To an ambient slurry of p-hydroxyacetophenone (20 g, 147 mmol) and K$_2$CO$_3$ (30.4 g, 220 mmol) in acetone (150 mL) was added ethyl bromoacetate (17.2 mL, 154 mmol). The slurry was stirred for 18 h and was quenched by the addition of H$_2$O (150 mL) and Et$_2$O (75 mL). The layers were separated, and the aqueous was extracted with additional Et$_2$O (3×75 mL). The combined organic layers were dried with anhydrous Na$_2$SO$_4$, filtered, and concentrated under reduced pressure to give an oil that was used without further purification. MS (ESI) m/e 223 (M+H)$^+$; $^1$H NMR (300 MHz, DMSO-d$_6$) δ ppm 1.22 (t, J=7.12 Hz, 3H), 2.52 (s, 3H), 4.18 (q, J=7.12 Hz, 2H), 4.90 (s, 2H), 7.04 (m, 2H), 7.92 (m, 2H).

Example 99b 2-cyano-3-(4-ethoxycarbonylmethoxy-phenyl)-but-2-enoic acid ethyl ester Hexamethyldisilazane (7.10 mL, 33.75 mmol) was slowly added over 5 minutes to acetic acid (20 mL) at room temperature. 4-Acetyl-phenoxyacetic acid ethyl ester (5.00 g, 22.5 mmol) and ethyl cyanoacetate (4.80 mL, 45.0 mmol) were sequentially added, and the reaction was heated to 70 C for 18 h. The reaction was quenched by the addition of $H_2O$ (100 mL) and EtOAc (150 mL). The layers were separated, and the organic was dried with anhydrous $Na_2SO_4$, filtered, and concentrated under reduced pressure to an oil that was used without further purification. MS (ESI) m/e 318 (M+H)$^+$.

Example 99c 2-amino-4-(4-ethoxycarbonylmethoxy-phenyl)-thiophene-3-carboxylic acid ethyl ester hydrochloride salt A stirred slurry of 2-cyano-3-(4-ethoxycarbonylmethoxy-phenyl)-but-2-enoic acid ethyl ester, (7.1 g, 22.5 mmol), sulfur (720 mg, 22.5 mmol), and morpholine (0.392 mL, 4.5 mmol) in EtOH (75 mL) was heated to 100 C for 6 h and then 60 C for 12 h. The heating bath was removed, and the reaction was filtered and absorbed onto $SiO_2$ gel. The absorbed compound was placed onto a 2 inch bed of $SiO_2$ gel on a scintered-glass funnel and washed with 850 mL of 1:1 Hx:EtOAc. The eluent was concentrated under reduced pressure to an amber oil. To the oil dissolved in 200 mL $Et_2O$ was added 1N HCl in $Et_2O$ (25 mL, 25 mmol). The white solid was filtered and air-dried to give the title compound. MS (ESI) m/e 350 (M—Cl)$^+$; $^1$H NMR (300 MHz, DMSO-d$_6$) δ ppm 0.93 (t, J=7.12 Hz, 3H), 1.22 (t, J=7.12 Hz, 3H), 3.96 (q, J=6.89 Hz, 2H), 4.17 (q, J=7.12 Hz, 2H), 4.77 (s, 2H), 5.50 (brs, 2H), 6.10 (s, 1H), 6.85 (d, J=8.82 Hz, 2H), 7.16 (d, J=8.82 Hz, 2H).

Example 99d

4-[4-(2-allyl-2-hydroxy-pent-4-enyloxy)-phenyl]-2-aminothiophene-3-carboxylic acid ethyl ester To a cold (0 C) solution of 2-amino-4-(4-ethoxycarbonylmethoxy-phenyl)-thiophene-3-carboxylic acid ethyl ester hydrochloride salt (1.5 g, 3.90 mmol) in THF (20 mL) was added allylmagnesium chloride (11.7 mL, 23.4 mmol, 2 M solution in THF). The thick slurry was stirred for 0.5 h and was then quenched by the slow addition of saturated $NH_4Cl$ (20 mL). The layers were separated, and the aqueous was extracted with EtOAc (3×20 mL). The combined organic layers were dried with anhydrous $Na_2SO_4$, filtered, and concentrated under reduced pressure to a dark oil. The residue was purified by MPLC ($SiO_2$ gel, 3:1 to 2:1 Hz EtOAc) to give the title compound. MS (ESI) m/e 388 (M+H)$^+$; $^1$H NMR (300 MHz, DMSO-d$_6$) δ ppm 0.94 (m, 3H), 2.29 (d, J=7.12 Hz, 4H), 3.70 (m, 2H), 3.96 (q, J=7.12 Hz, 2H), 4.78 (s, 1H), 5.03 (m, 4H), 5.88 (m, 2H), 6.09 (1H), 6.84 (m, 2H), 7.14 (m, 2H), 7.33 (s, 2H).

Example 99e

4-[4-(2-allyl-2-hydroxy-pent-4-enyloxy)-phenyl]-2-(2-cyano-acetylamino)-thiophene-3-carboxylic acid ethyl ester The title compound was prepared according to the method described for Example 60b, substituting 2-amino-4-[4-(2-allyl-2-hydroxy-pent-4-enyloxy)-phenyl]-thiophene-3-carboxylic acid ethyl ester for 2-amino-4-(4-bromophenyl)-thiophene-3-carboxylic acid ethyl ester. MS (ESI) m/e 453 (M–H)$^-$.

Example 99f

4-[4-(2-allyl-2-hydroxy-pent-4-enyloxy)-phenyl]-5-chloro-2-(2-cyano-acetylamino)-thiophene-3-carboxylic acid ethyl ester The title compound was prepared according to the method described for Example 60c, substituting 4-[4-(2-allyl-2-hydroxy-pent-4-enyloxy)-phenyl]-2-(2-cyano-acetylamino)-thiophene-3-carboxylic acid ethyl ester for 4-(4-bromophenyl)-2-(2-cyano-acetylamino)-thiophene-3-carboxylic acid ethyl ester. MS (ESI) m/e 487 (M–H)$^-$; $^1$H NMR (300 MHz, DMSO-d$_6$) δ ppm 0.85 (m, 3H), 2.31 (d, J=7.46 Hz, 4H), 3.75 (s, 2H), 4.01 (m, 2H), 4.30 (s, 2H), 4.81 (s, 1H), 5.04 (m, 4H), 5.89 (m, 2H), 6.96 (m, 2H), 7.15 (m, 2H), 11.37 (s, 1H).

Example 99g 5-chloro-2-(2-cyano-acetylamino)-4-[4-(1-hydroxy-cyclopent-3-enylmethoxy)-phenyl]-thiophene-3-carboxylic acid ethyl ester To an ambient solution of 4-[4-(2-allyl-2-hydroxy-pent-4-enyloxy)-phenyl]-5-chloro-2-(2-cyano-acetylamino)-thiophene-3-carboxylic acid ethyl ester (300 mg, 0.613 mmol) in DCM (12.3 mL) was added [1,3-bis-(2,4,6-trimethylphenyl)-2-imidazolidinynlidene)dichloro(phenylmethylene)-(tricyclohexylphoshine)ruthenium] (29 mg, 0.034 mmol) in a single portion. The reaction was stirred overnight and then concentrated under reduced pressure to a dark oil. The residue was purified by MPLC ($SiO_2$ gel, 1:1 Hx:EtOAc) to yield the title compound as an oil. MS (ESI) m/e 459 (M–H)$^-$; $^1$H NMR (300 MHz, DMSO-d$_6$) δ ppm 0.88 (m, 3H), 2.32 (d, J=15.60 Hz, 2H), 2.56 (d, J=15.60 Hz, 2H), 3.91 (s, 2H), 4.01 (m, 2H), 4.31 (m, 2H), 4.90 (s, 1H), 5.67 (s, 2H), 6.98 (m, 2H), 7.14 (m, 2H), 11.37 (s, 1H).

Example 99

2-chloro-4-hydroxy-3-{4-[(1-hydroxycyclopent-3-en-1-yl)methoxy]phenyl}-6-oxo-6,7-dihydrothieno[2,3-b]pyridine-5-carbonitrile The title compound was prepared according to the method described for Example 60d, substituting 5-chloro-2-(2-cyano-acetylamino)-4-[4-(1-hydroxy-cyclopent-3-enylmethoxy)-phenyl)-thiophene-3-carboxylic acid ethyl ester for 4-(4-bromophenyl)-5-chloro-2-(2-cyano-acetylamino)-thiophene-3-carboxylic acid ethyl ester. MS (ESI) m/e 413 (M–H)$^-$, $^1$H NMR (300 MHz, DMSO-d$_6$) δ ppm 2.33 (d, J=15.60 Hz, 2H), 2.57 (d, J=15.60 Hz, 2H), 3.91 (s, 2H), 5.67 (s, 2H), 6.95 (d, J=8.82 Hz, 2H), 7.23 (d, J=8.82 Hz, 2H).

Example 100

2-chloro-4-hydroxy-3-(4-hydroxyphenyl)-6-oxo-6,7-dihydrothieno[2,3-b]pyridine-5-carbonitrile Example 100 was prepared using the same procedure as described for Example 51 substituting 4-hydroxy-3-(4-hydroxyphenyl)-6-oxo-6,7-dihydrothieno[2,3-b]pyridine-5-carbonitrile for 4-hydroxy-6-oxo-3-phenyl-6,7-dihydrothieno[2,3-b]pyridine-5-carbonitrile in Example 51. MS (ESI) m/e 316.9 (M–H)$^+$; $^1$H NMR (500 MHz, DMSO-d$_6$): δ ppm 12.31 (br s, 1H), 9.55 (br s, 1H), 7.12 (d, J=8.54, 2H), 6.79 (d, J=8.55, 2H).

Example 101

4-hydroxy-3-{5-[4-(methylsulfonyl)phenyl]thien-2-yl}-6-oxo-6,7-dihydrothieno[2,3-b]pyridine-5-carbonitrile The title compound was prepared according to the procedures described in Example 91 substituting 4-Methanesulfonyl-phenyl boronic acid for 4-(Methylsulfonylamino)phenyl boronic acid in Example 91d. $^1$H NMR (300 MHz, METHANOL-D4) δ ppm 4.81 (s, 3H) 7.11 (s, 1H) 7.42 (d, J=3.68 Hz, 1H) 7.53 (d, J=3.68 Hz, 1H) 7.97 (m, 2H) 8.09 (m, 2H) MS (ESI) m/z 428.9 (M+H)$^+$, 450.8 (M+Na)$^+$ Anal. Cald for C19H12N2O4S3: C, 53.26; H, 2.82; N, 6.54. Found: C, 52.94; H, 2.54; N, 6.53.

Example 102

N-{4-[5-(5-cyano-4-hydroxy-6-oxo-6,7-dihydrothieno[2,3-b]pyridin-3-yl)thien-2-yl]phenyl}acetamide The title compound was prepared according to the procedures described in Example 91 substituting N-[4-(4,4,5,5-Tetramethyl-[1,3,2]dioxaborolan-2-yl)-phenyl]-acetamide for 4-(Methylsulfonylamino)phenyl boronic acid in Example 91d. $^1$H NMR (300 MHz, DMSO-D6) δ ppm 2.06 (s, 3H) 7.19 (s, 1H) 7.31 (d, J=3.68 Hz, 1H) 7.36 (d, J=4.04 Hz, 1H) 7.61 (m, 4H) 10.05 (s, 1H) MS (ESI) m/z 407.9 (M+H)$^+$, 425.0 (M+NH$_4$)$^+$.

Example 103

4-hydroxy-6-oxo-3-(5-phenylthien-2-yl)-6,7-dihydrothieno[2,3-b]pyridine-5-carbonitrile The title compound was prepared according to the procedures described in Example 91 substituting phenyl boronic acid for 4-(Methylsulfonylamino)phenyl boronic acid in Example 91d. $^1$H NMR (300 MHz, DMSO-D6) δ ppm 7.21 (s, 1H) 7.30 (d, J=7.72 Hz, 1H) 7.35 (d, J=3.68 Hz, 1H) 7.45 (m, 3H) 7.67 (d, J=6.99 Hz, 2H) MS (ESI) m/z 350.9 (M+H)$^+$.

Example 104

3-(2,2'-bithien-5-yl)-4-hydroxy-6-oxo-6,7-dihydrothieno[2,3-b]pyridine-5-carbonitrile The title compound was prepared according to the procedures described in Example 91 substituting 4,4,5,5-Tetramethyl-2-thiophen-2-yl-[1,3,2]dioxaborolane for 4-(Methylsulfonylamino)phenyl boronic acid in Example 91d. $^1$H NMR (300 MHz, DMSO-D6) δ ppm 7.10 (dd, J=5.15, 3.68 Hz, 1H) 7.17 (s, 1H) 7.23 (d, J=4.04 Hz, 1H) 7.31 (d, J=3.68 Hz, 1H) 7.34 (d, J=3.68 Hz, 1H) 7.51 (d, J=4.78 Hz, 1H).

Example 105

3-[4-(3-fluoro-2-hydroxyphenyl)-phenyl]-4-hydroxy-6-oxo-6,7-dihydro-thieno[2,3-b]-pyridine-5-carbonitrile The titled compound was prepared according to the procedures described in Example 3a-b, substituting 3-fluoro-2-methoxyphenylboronic acid for 2,3-dimethoxyphenylboronic acid used in Example 3a (34.0 mg, 90%). $^1$H NMR (300 MHz, DMSO-d$_6$) δ 12.37 (s, 1H), 9.62 (s, 1H), 7.51 (AB, 4H, J=12, 9 Hz), 7.15 (m, 2H), 7.05 (s, 1H), 6.91 (m, 1H). MS (ESI) m/e 379 (M+H)$^+$, m/e 377 (M−H)$^−$.

Example 106

3-[5-(2-aminophenyl)thien-2-yl]-4-hydroxy-6-oxo-6,7-dihydrothieno[2,3-b]pyridine-5-carbonitrile The title compound was prepared according to the procedures described in Example 91 substituting 2-aminophenyl boronic acid for 4-(Methylsulfonylamino)phenyl boronic acid in Example 91d. $^1$H NMR (300 MHz, DMSO-D6) δ ppm 6.64 (t, J=7.35 Hz, 1H) 6.81 (d, J=8.09 Hz, 1H) 6.91 (s, 2H) 7.05 (m, 2H) 7.13 (d, J=3.68 Hz, 1H) 7.25 (s, 1H) 7.62 (d, J=3.68 Hz, 1H) MS (ESI) m/z 366.0 (M+H)$^+$, 383.0 (M+NH$_4$)$^+$

Example 107

3-[5-(4-fluorophenyl)thien-2-yl]-4-hydroxy-6-oxo-6,7-dihydrothieno[2,3-b]pyridine-5-carbonitrile The title compound was prepared according to the procedures described in Example 91 substituting 4-fluorophenyl boronic acid for 4-(Methylsulfonylamino)phenyl boronic acid in Example 91d. $^1$H NMR (300 MHz, METHANOL-D4) δ ppm 7.13 (s, 1H) 7.16 (m, 2H) 7.24 (d, J=4.04 Hz, 1H) 7.29 (d, J=4.04 Hz, 1H) 7.65 (m, 2H) MS (ESI) m/z 369.1 (M+H)$^+$.

Example 108

3-[5-(2,4-difluorophenyl)thien-2-yl]-4-hydroxy-6-oxo-6,7-dihydrothieno[2,3-b]pyridine-5-carbonitrile The title compound was prepared according to the procedures described in Example 91 substituting 2,4-difluorophenyl boronic acid for 4-(Methylsulfonylamino)phenyl boronic acid in Example 91d. $^1$H NMR (300 MHz, METHANOL-D4) δ ppm 7.07 (m, 2H) 7.18 (s, 1H) 7.27 (d, J=4.04 Hz, 1H) 7.40 (d, J=4.04 Hz, 1H) 7.75 (m, 1H) MS (ESI) m/z 386.9 (M+H)$^+$.

Example 109

4-hydroxy-6-oxo-3-(4-thien-3-ylphenyl)-6,7-dihydrothieno[2,3-b]pyridine-5-carbonitrile Example 109 was prepared from 3-(4-Bromo-phenyl)-4-hydroxy-6-oxo-6,7-dihydro-thieno[2,3-b]pyridine-5-carbonitrile (Example 9) using the same procedure as described for Example 189 substituting 3-thiopheneboronic acid for 4-hydroxyphenyl boronic acid. MS (ESI) m/z 350.9 (M+H$^+$); $^1$H NMR (300 MHz, DMSO-d$_6$) δ ppm 7.91 (dd, 1H), 7.71 (d, 2H), 7.65 (dd, 1H), 7.60 (dd, 1H), 7.45 (d, 1H).

Example 110

4-hydroxy-3-[5-(3-methoxyprop-1-ynyl)-4-methylthien-2-yl]-6-oxo-6,7-dihydrothieno[2,3-b]pyridine-5-carbonitrile 4-hydroxy-3-(5-iodo-4-methylthien-2-yl)-6-oxo-6,7-dihydrothieno[2,3-b]pyridine-5-carbonitrile (200 mg, 0.48 mmol, Example 222) was dissolved in DMF (2.4 ml). Et$_3$N 0.133 ml, 0.96 mmol) and methyl propargyl ether (0.202 ml, 2.4 mmol) were added and the mixture was degassed with N$_2$ for 2 min. CuI (9.1 mg, 0.048 mmol) and PdCl$_2$(PPh$_3$)$_2$ (17 mg, 0.024 mmol) were added, the vessel was capped and the reaction was heated at 60° C. with stirring for 2.5 h. The reaction mixture was then cooled and filtered through a plug of silica gel eluting with CH$_2$Cl$_2$→EtOH. The organics were removed by rotary evaporation and the residue was purified by RP-HPLC to give the title compound. MS (ESI) m/z 357.0 (M+H$^+$); $^1$H NMR (300 MHz, DMSO-d$_6$) δ ppm 7.49 (s, 1H), 6.92 (s, 1H), 4.38 (s, 3H), 2.23 (s, 3H).

Example 111

4-hydroxy-3-(4-hydroxyphenyl)-6-oxo-6,7-dihydrothieno[2,3-b]pyridine-5-carbonitrile To solution of 4-hydroxy-3-[4-(methoxymethoxy)phenyl]-6-oxo-6,7-dihydrothieno[2,3-b]pyridine-5-carbonitrile (0.1 g, 0.3 mmol) in THF (10 mL) was added 1N HCl (20 mL) and stirred at room temperature for 24 hours. The reaction mixture was then concentrated and purified on a RP-HPLC system to give the title compound. MS (ESI) m/e 282.9 (M−H)$^+$; $^1$H NMR (500 MHz, DMSO-d$_6$): δ ppm 12.53 (br s, 1H), 9.43 (br s, 1H), 7.21 (d, J=8.73, 2H,), 6.88 (s, 1H), 6.73 (d, J=8.42, 2H).

Example 112

2-bromo-3-(3-bromo-4-hydroxyphenyl)-4-hydroxy-6-oxo-6,7-dihydrothieno[2,3-b]pyridine-5-carbonitrile Example 112 was prepared using the same procedure as described for Example 7 substituting 4-hydroxy-3-(4-hydroxyphenyl)-6-oxo-6,7-dihydrothieno[2,3-b]pyridine-5-carbonitrile for 4-hydroxy-6-oxo-3-phenyl-6,7-dihydrothieno[2,3-b]pyridine-5-carbonitrile in Example 7. The title compound was one of three reaction products and purified on a RP-HPLC system. MS (ESI) m/e 440.7 (M−H)$^+$; $^1$H NMR (400 MHz, DMSO-d$_6$): δ ppm 10.36 (br s, 1H), 7.40 (d, J=2.15, 1H), 7.11 (dd, J=2.15, 8.29, 1H), 6.97 (d, J=8.29, 1H).

Example 113

2,5-dichloro-4-hydroxy-3-(4-hydroxyphenyl)thieno[2,3-b]pyridin-6(7H)-one

To a suspension of 50 mg (0.14 mmol) of 3-(4-benzyloxyphenyl)-4-hydroxy-7H-thieno[2,3-b]pyridin-6-one from Example 7D in 2 mL of CH$_2$Cl$_2$ was added 38 mg (0.28 mmol) of N-chlorosuccinimide. The suspension became a homogeneous solution, and was stirred open to the air while the solvent was allowed to evaporate to dryness over two days. The residue was redissolved in 2 mL of CH$_2$Cl$_2$, and 100 µL (0.72 mmol) of iodotrimethylsilane was added. After 18 h, the reaction was concentrated in vacuo. The residue was dissolved in ethyl acetate (5 mL) and extracted with 5% NaHSO$_{3(aq.)}$ (1×2 mL) to discharge the 12 color, then with brine (1×2 mL), dried over MgSO$_4$, filtered, and concentrated to an oil. This was purified via reverse phase HPLC (0 to 70% CH$_3$CN/0.1% aq. TFA gradient) to give 16 mg (34%) of a solid as the titled compound. MS (ESI) m/e 327.8, (M+H)$^+$; $^1$H NMR (300 MHz, DMSO-d$_6$) δ 6.79 (m, 2H) 7.15 (m, 2H) 9.54 (s, 1H) 10.84 (s, 1H) 12.40 (bs, 1H).

Example 114 methyl 4-[5-(5-cyano-4-hydroxy-6-oxo-6,7-dihydrothieno[2,3-b]pyridin-3-yl)thien-2-yl]phenylcarbamate The title compound was prepared according to the procedures described in Example 91 substituting [4-(4,4,5,5-Tetramethyl-[1,3,2]dioxaborolan-2-yl)-phenyl]-carbamic acid methyl ester for 4-(Methylsulfonylamino)phenyl boronic acid in Example 91d. 1H NMR (300 MHz, METHANOL-D4) δ ppm 3.08 (s, 3H) 7.10 (s, 1H) 7.25 (d, J=4.04 Hz, 1H) 7.44 (d, J=3.68 Hz, 1H) 7.56 (d, J=8.46 Hz, 2H) 7.87 (d, J=8.46 Hz, 2H) MS (ESI) m/z 423.9 (M+H)$^+$.

Example 115

2-chloro-4-hydroxy-3-[4-(2-hydroxy-2-methylpropoxy)phenyl]-6-oxo-6,7-dihydrothieno[2,3-b]pyridine-5-carbonitrile Example 115a 2-amino-4-[4-(2-hydroxy-2-methyl-propoxy)-phenyl]-thiophene-3-carboxylic acid ethyl ester The title compound was prepared according to the method described for Example 99d, substituting methylmagnesium bromide for allylmagnesium chloride. MS (ESI) m/e 336 (M+H)$^+$; $^1$H NMR (300 MHz, DMSO-d$_6$) δ ppm 0.95 (t, J=6.95 Hz, 3H), 1.20 (s, 6H), 3.71 (s, 2H), 3.97 (q, J=7.12 Hz, 2H), 4.61 (s, 1H), 6.08 (s, 1H), 6.86 (d, J=8.48 Hz, 2H), 7.14 (d, J=8.48 Hz, 2H), 7.33 (s, 2H).

Example 115b

4-[4-(2-hydroxy-2-methyl-propoxy)-phenyl]-2-(2-cyano-acetylamino)-thiophene-3-carboxylic acid ethyl ester The title compound was prepared according to the method described for Example 60c, substituting 2-amino-4-[4-(2-hydroxy-2-methyl-propoxy)-phenyl]-thiophene-3-carboxylic acid ethyl ester for 4-(4-bromophenyl)-2-(2-cyano-acetylamino)-thiophene-3-carboxylic acid ethyl ester. MS (ESI) m/e 401 (M−H)$^-$; $^1$H NMR (300 MHz, DMSO-d$_6$) δ ppm 1.00 (m, 3H), 1.21 (s, 6H), 3.73 (s, 2H), 4.10 (m, 2H), 4.26 (s, 2H), 4.62 (s, 1H), 6.93 (m, 3H), 7.20 (d, J=8.48 Hz, 2H), 11.17 (s, 1H).

Example 115c

4-[4-(2-hydroxy-2-methyl-propoxy)-phenyl]-5-chloro-2-(2-cyano-acetylamino)-thiophene-3-carboxylic acid ethyl ester The title compound was prepared according to the method described for Example 60c substituting 4-[4-(2-hydroxy-2-methyl-propoxy)-phenyl]-2-(2-cyano-acetylamino)-thiophene-3-carboxylic acid ethyl ester for 4-(4-bromophenyl)-2-(2-cyano-acetylamino)-thiophene-3-carboxylic acid ethyl ester. MS (ESI) m/e 435 (M−H)$^-$; $^1$H NMR (300 MHz, DMSO-d$_6$) δ ppm 0.87 (m, 3H), 1.21 (s, 6H), 3.74 (s, 2H), 4.01 (m, 2H), 4.30 (s, 2H), 4.63 (s, 1H), 6.96 (m, 2H), 7.14 (m, 2H), 11.37 (s, 1H).

Example 115

2-chloro-4-hydroxy-3-[4-(2-hydroxy-2-methylpropoxy)phenyl]-6-oxo-6,7-dihydrothieno[2,3-b]pyridine-5-carbonitrile The title compound was prepared according to the method described for Example 60d, substituting 4-[4-(2-hydroxy-2-methyl-propoxy)-phenyl]-5-chloro-2-(2-cyano-acetylamino)-thiophene-3-carboxylic acid ethyl ester for 4-(4-bromophenyl)-5-chloro-2-(2-cyano-acetylamino)-thiophene-3-carboxylic acid ethyl ester. MS (ESI) m/e 389 (M−H)−; $^1$H NMR (300 MHz, DMSO-d$_6$) δ ppm 1.22 (s, 6H), 3.72 (s, 2H), 6.95 (d, J=8.48 Hz, 2 H,) 7.23 (d, J=8.48 Hz, 2H).

Example 116

2-chloro-4-hydroxy-3-{4-[(1-hydroxycyclopentyl)methoxy]phenyl}-6-oxo-6,7-dihydrothieno[2,3-b]pyridine-5-carbonitrile To an ambient slurry of 2-chloro-4-hydroxy-3-{4-[(1-hydroxycyclopent-3-en-1-yl)methoxy]phenyl}-6-oxo-6,7-dihydrothieno[2,3-b]pyridine-5-carbonitrile (60 mg, 0.15 mmol) and potassium diazodicarboxylate (88 mg, 0.45 mmol) in a mixture of DMSO (1.0 mL) and MeOH (1.3 mL) was slowly added a solution of AcOH (0.051 mL, 0.90 mmol) in MeOH (0.30 mL). After 10 minutes, the reaction was quenched by the addition of 1N HCl (10 mL) and EtOAc (5 mL). The layers were separated, and the aqueous was extracted with additional EtOAc (2×5 mL). The combined organic layers were dried with anhydrous Na$_2$SO$_4$, filtered, and concentrated under reduced pressure. The residue was purified by RPLC to give the titled compound as a white solid. MS (ESI) m/e 415 (M−H)−; $^1$H NMR (300 MHz, DMSO-d$_6$) δ ppm 1.67 (m, 8H), 3.88 (s, 2H), 6.94 (d, J=8.82 Hz, 2H), 7.22 (d, J=8.82 Hz, 2H).

Example 117

2-bromo-4-hydroxy-3-(4-hydroxyphenyl)-6-oxo-6,7-dihydrothieno[2,3-b]pyridine-5-carbonitrile Example 117 was prepared using the same procedure as described for Example 7 substituting 4-hydroxy-3-(4-hydroxyphenyl)-6-oxo-6,7-dihydrothieno[2,3-b]pyridine-5-carbonitrile for 4-hydroxy-6-oxo-3-phenyl-6,7-dihydrothieno[2,3-b]pyridine-5-carbonitrile in Example 7. The title compound was one of three reaction products and purified on a RP-HPLC system. MS (ESI) m/e 362.8 (M−H)+; $^1$H NMR (400 MHz, DMSO-d$_6$): δ ppm 9.51 (br s, 1H), 7.09 (d, J=8.59, 2H), 6.76 (d, J=8.59, 2H).

Example 118

2-chloro-4-hydroxy-3-[4-(hydroxymethyl)phenyl]-6-oxo-6,7-dihydrothieno[2,3-b]pyridine-5-carbonitrile 1M DIBAL-H (10 mL, 10 mmol) was slowly added to a solution of methyl 4-(2-chloro-5-cyano-4-hydroxy-6-oxo-6,7-dihydrothieno[2,3-b]pyridin-3-yl)benzoate (0.3 g, 0.832 mmol) in anhydrous THF (80 mL) held at −78° C. The solution was then allowed to warm to rt and stirred overnight. The reaction was quenched with MeOH (2 mL) and 1N HCl (5 mL), filtered through silica gel, concentrated and purified on a RP-HPLC system. MS (ESI) m/e 330.9 (M−H)+; $^1$H NMR (400 MHz, DMSO-d$_6$): δ ppm 7.35 (d, J=8.28, 2H), 7.29 (d, J=7.98, 2H), 4.60 (br s, 1H), 4.55 (s, 2H).

Example 119

4-hydroxy-3-[5-(4-methoxyphenyl)thien-2-yl]-6-oxo-6,7-dihydrothieno[2,3-b]pyridine-5-carbonitrile The title compound was prepared according to the procedures described in Example 91 substituting 4-methoxyphenyl boronic acid for 4-(Methylsulfonylamino)phenyl boronic acid in Example 91d. $^1$H NMR (300 MHz, METHANOL-D4) δ ppm 3.82 (s, 3H) 6.95 (d, J=8.82 Hz, 2H) 7.05 (s, 1H) 7.19 (d, J=3.68 Hz, 1H) 7.29 (d, J=3.68 Hz, 1H) 7.57 (d, J=8.82 Hz, 2H) MS (ESI) m/z 380.9 (M+H)+.

Example 120

4-hydroxy-2-methyl-6-oxo-3-(phenylethynyl)-6,7-dihydrothieno[2,3-b]pyridine-5-carbonitrile

Example 120a

2-Amino-5-methyl-thiophene-3-carboxylic acid ethyl ester

To propionaldehyde (2.9 g, 50 mmol) and ethyl cyanoacetate (11.3 g, 100 mmol) in acetic acid (50 mL) HMDS (1,1,1,3,3,3-hexamethyldisilazane) (16.15 g, 100 mmol) was added dropwise. The reaction mixture was stirred at 75° C. for 12 h and then evaporated in vacuo to remove solvent. Ethyl acetate and water (100 mL, 1:1) was added, the water layer was extracted with ethyl acetate twice (100 mL). The combined organic layers were washed with sat. aq. HaHCO$_3$ and water. After the solvent was removed, the residue was 2-cyano-pent-2-enoic acid ethyl acetate, which was dissolved in EtOH (100 mL). Sulfur (3.12 g, 100 mmol) and morpholine (8.75 g, 100 mmol) were added. The reaction mixture was refluxed for 2 h and cooled to room temperature, and then filtered to remove the excess sulfur. The filtrate was concentrated and residue was purified by chromatography on silica gel column to give title compound (4.5 g, 48.6%) as an oil. $^1$H NMR (300 MHz, DMSO-d$_6$) δ 7.08 (s, 2H), 6.49 (d, 1H, J=3.0 Hz), 4.14 (q, 2H, J=6.0 Hz), 2.18 (d, 3H, J=1.0 Hz). 1.23 (t, 3H, J=6.0 Hz), MS (ESI) m/e 186 (M+H)+, 184 (M−H)−.

Example 120b 2-(2-Cyano-acetylamino)-5-methyl-thiophene-3-carboxylic acid ethyl ester To phosphorus pentachloride (5.0 g, 24 mmol) in CH$_2$Cl$_2$ (50 mL) cyanoacetic acid (2.0 g, 24 mmol) was added. The reaction mixture was refluxed for 0.5 h and cooled to give a colorless clear solution. 2-Amino-5-methyl-thiophene-3-carboxylic acid ethyl eater (4.2 g, 22.7 mmol) in CH$_2$Cl$_2$ (20 mL) was added dropwise. The reaction mixture was refluxed and checked by TLC until starting material disappeared after about 1 h. Aq. sat. Na$_2$CO$_3$ solution was added until pH=7. The organic layer was washed with brine, dried and evaporated under vacuum to give the title product (5.7 g, 100%). $^1$H NMR (300 MHz, DMSO-d$_6$) δ 11.0 (s, 1H), 6.91 (d, 1H, J=3.0 Hz), 4.29 (q, 2H, J=9.0 Hz), 4.27 (s, 2H), 2.36 (d, 3H, J=1.0 Hz). 1.30 (t, 3H, J=9.0 Hz), MS (ESI) m/e 253 (M+H)+, 251 (M−H)−.

Example 120c 2-(2-Cyano-acetylamino)-4-iodo-5-methyl-thiophene-3-carboxylic acid ethyl ester To $I_2$ (2.8 g, 11 mmol) and[bis(trifluoroacetoxy0-iodo] benzene (4.73 g, 11 mmol) in $CCl_4$ (100 mL) 2-(2-cyano-acetylamino)-5-methyl-thiophene-3-carboxylic acid ethyl ester (2.5 g, 10 mmol) in $CH_2Cl_2$ (5 mL) was added. The reaction mixture was stirred at 55° C. for 18 h and evaporated to remove the solvent. The residue was purified on a preparative HPLC to give the titled compound (650 mg, 17%). $^1$H NMR (300 MHz, DMSO-d$_6$) δ 10.8 (s, 1H), 4.35 (q, 2H, J=7.5 Hz), 4.21 (s, 2H), 2.12 (s, 3H), 1.33 (t, 3H, J=7.5 Hz), MS (ESI) m/e 379 (M+H)$^+$, 377 (M−H)$^−$.

Example 120d

4-Hydroxy-2methyl-6-oxo-3-phenylethyny-6,7-dihydro-thieno[2,3-b]pyridine-5-cabonitrile 2-(2-Cyano-acetylamino)-4-iodo-5-methyl-thiophene-3-carboxylic acid ethyl ester (189 mg, 0.5 mmol) was cyclized by NaH in THF at room temperature for 12 h as described in Example 29D. After reaction was finished, methanol (2 mL) was added and the mixture was evaporated. The residue was purified on HPLC to give 4-hydroxy-3-iodo-2methyl-6-oxo-6,7-dihydro-thieno[2,3-b]pyridine-5-cabonitrile (38 mg, 22.9%). This compound (33 mg, 0.1 mmol) was taken up in a Smith Process Vial (2–5 mL), CuI (7.6 mg, 0.04 mmol), Pd(PPh$_3$)$_2$Cl$_2$ (14 mg, 0.02 mmol), DMF (2 ml), diisopro pylamine (1 mL) and phenylacetylene (20.4 mg, 0.2 mmol) were then added sequentially. After degassed, the vial was sealed and stirred at 70° C. for 2 h. The resulting mixture was filtered and the solid was washed with methanol (5 mL×2). The combined organic layers were concentrated under vacuum and purification on HPLC to give title compound (20 mg, 65%) as a white solid. $^1$H NMR (300 MHz, DMSO-d$_6$) δ 11.0 (s, 1H), 7.52–7.38 (m, 5H), 2.44 (s, 3H, MS (ESI) m/e 307 (M+H)$^+$, 305 (M−H)$^−$.

Example 121

2-chloro-3-{4-[(1-ethyl-4-hydroxypiperidin-4-yl)methoxy]phenyl}-4-hydroxy-6-oxo-6,7-dihydrothieno[2,3-b]pyridine-5-carbonitrile A mixture of 2-chloro-4-hydroxy-3-{4-[(4-hydroxypiperidin-4-yl)methoxy]phenyl}-6-oxo-6,7-dihydrothieno[2,3-b]pyridine-5-carbonitrile TFA salt (40 mg, 0.073 mmol), acetaldehyde (0.006 mL, 0.110 mmol), and MS-CNBH$_3$ (88 mg, 0.110 mmol, 1.25 mmol/g loading) in a 1:1 mixture of DMSO/MeOH (1 mL) containing 2% v/v AcOH was shaken in a 1 dram vial at rt for 18 h. The mixture was then filtered and purified by RP-HPLC to give the title compound. MS (ESI) m/e 460 (M+H)$^+$; $^1$H NMR (300 MHz, DMSO-d$_6$) δ ppm 1.24 (t, J=7.29 Hz, 3H), 1.83 (m, 2H), 1.98 (m, 2H), 3.15 (m, 4H), 3.32 (d, J=7.29 Hz, 2H), 3.87 (s, 2H), 5.22 (s, 1H), 6.92 (d, J=8.82 Hz, 2H), 7.20 (d, J=8.82 Hz, 2H), 8.91 (s, 1H), 10.77 (s, 1H).

Example 122

4-hydroxy-3-[5-(3-methoxyprop-1-ynyl)thien-2-yl]-6-oxo-6,7-dihydrothieno[2,3-b]pyridine-5-carbonitrile A solution of Example 91c (100 mg, 0.283 mmol), 3-Methoxy-propyne (40.4 μL, 0.453 mmol), and Et$_3$N (197 μL, 1.42 mmol) in DMF (2.5 mL) was degassed and treated with Pd(PPh$_3$)$_2$Cl$_2$ (10 mg, 0.014 mmol) and CuI (1.7 mg, 0.0085 mmol). The reaction was heated under nitrogen at 80° C. for 12 h. The reaction was concentrated and the concentrate was purified by RPHPLC on a Waters Symmetry C18 column (25 mm×100 mm, 7 μm particle size) using a gradient of 10% to 100% acetonitrile:0.1% aqueous TFA to provide 28 mg (29%) of the title compound. $^1$H NMR (300 MHz, DMSO-D6) δ ppm 4.23 (s, 2H) 4.37 (s, 3H) 7.23 (s, 1H) 7.27 (d, J=3.68, 1H), 7.34 (d, J=3.68, 1H) MS (ESI) m/z 342.9 (M+H)$^+$.

Example 123

4-hydroxy-3-[5-(5-hydroxypent-1-ynyl)thien-2-yl]-6-oxo-6,7-dihydrothieno[2,3-b]pyridine-5-carbonitrile The title compound was prepared according to the procedure described in Example 122 substituting Pent-4-yn-1-ol for 3-Methoxy-propyne in Example 122. $^1$H NMR (300 MHz, DMSO-D6) δ ppm 1.69 (m, 2H) 2.61 (t, J=6.25 Hz, 2H) 3.50 (t, J=6.25 Hz, 2H) 7.12 (d, J=3.68 Hz, 1H) 7.17 (s, 1H) 7.24 (d, J=3.68 Hz, 1H) MS (ESI) m/z 356.9 (M+H)$^+$.

Example 124

3-{4-[(1-acetyl-4-hydroxypiperidin-4-yl)methoxy]phenyl}-2-chloro-4-hydroxy-6-oxo-6,7-dihydrothieno[2,3-b]pyridine-5-carbonitrile An ambient solution of 2-chloro-4-hydroxy-3-{4-[(4-hydroxypiperidin-4-yl)methoxy]phenyl}-6-oxo-6,7-dihydrothieno[2,3-b]pyridine-5-carbonitrile TFA salt (40 mg, 0.073 mmol), Et$_3$N (0.015 mL, 0.11 mmol), and Ac$_2$O (0.007 mL, 0.073 mmol) in DCM (0.5 mL) was stirred for 18 h. The reaction was then quenched by the addition of saturated NaHCO$_3$ (1 mL) and EtOAc (1 mL). The layers were separated, and the aqueous was extracted with additional EtOAc (2×1 mL). The combined organic layers were dried with anhydrous Na$_2$SO$_4$, filtered, and concentrated under reduced pressure. The residue was purified by RPLC to give the title compound. MS (ESI) m/e 474 (M+H)$^+$; $^1$H NMR (300 MHz, DMSO-d$_6$) δ ppm 1.61 (m, 4H), 2.01 (s, 3H), 2.94 (m, 2H), 3.4 (m, 2H), 3.81 (s, 2H), 6.95 (d, J=8.81 Hz, 2H), 7.22 (d, J=8.48 Hz, 2H).

Example 125

2-Bromo-4-hydroxy-3-[4-(4-hydroxy-but-1-ynyl)-phenyl]-6-oxo-6,7-dihydro-thieno[2,3-b]pyridine-5-carbonitrile The title compound was prepared according to the bromination procedure described in Example 10, substituting 4-hydroxy-3-[4-(4-hydroxy-but-1-ynyl)-phenyl]-6-oxo-6,7-dihydro-thieno[2,3-b]pyridine-5-carbonitrile for 4-hydroxy-3-[4-(5-hydroxy-pent-1-ynyl)-phenyl]-6-oxo-6,7-dihydro-thieno[2,3-b]pyridine-5-carbonitrile used in Example 10. MS (ESI) m/e 414 (M−H)$^+$; $^1$H NMR (300 MHz, DMSO-d$_6$) δ 2.57 (t, J=6.12 Hz, 2H), 3.60 (t, J=6.15 Hz, 2H), 7.18 (d, J=8.48 Hz, 2H), 7.33 (d, J=8.48 Hz, 2H).

Example 126

4-hydroxy-3-[5-(3-hydroxyprop-1-ynyl)thien-2-yl]-6-oxo-6,7-dihydrothieno[2,3-b]pyridine-5-carbonitrile The title compound was prepared according to the procedure described in Example 122 substituting prop-2-yn-1-ol for 3-Methoxy-propyne in Example 122. $^1$H NMR (300 MHz, DMSO-D6) δ ppm 4.33 (s, 2H) 7.21 (d, J=4.04 Hz, 2H) 7.28 (d, J=4.04 Hz, 1H) MS (ESI) m/z 328.9 (M+H)$^+$.

Example 127

2-chloro-4-hydroxy-3-{4-[(4-hydroxy-1-isobutylpiperidin-4-yl)methoxy]phenyl}-6-oxo-6,7-dihydrothieno[2,3-b]pyridine-5-carbonitrile The title compound was prepared according to the method described for Example 121, substituting isobutyraldehyde for acetaldehyde. MS (ESI) m/e 488 (M+H)$^+$; $^1$H NMR (300 MHz, DMSO-d$_6$) δ ppm 0.96 (d, J=6.45 Hz, 3H), 1.75 (m, 2H), 2.10 (m, 3H), 2.95 (t, J=6.44 Hz, 2H), 3.15 (m, 2H), 3.40 (m, 2H), 3.87 (s, 2H), 5.22 (s, 1H), 6.92 (d, J=8.82 Hz, 2H), 7.20 (d, J=8.82 Hz, 2H), 8.91 (s, 1H), 10.77 (s, 1H).

Example 128

4-Hydroxy-3-[4-(4-hydroxy-but-1-enyl)-phenyl]-6-oxo-6,7-dihydro-thieno[2,3-b]pyridine-5-carbonitrile To a stirred suspension of 3-(4-iodo-phenyl)-4-hydroxy-6-oxo-6,7-dihydro-thieno[2,3-b]pyridine-5-carbonitrile (60 mg, 0.15 mmol), triethylamine (0.1 mL), Pd(OAc)$_2$ (3 mg), P(o-Tol)$_3$ (9 mg), and MgO (18 mg, 0.45 mmol) was added 0.1 mL of but-3-en-1-ol in a single portion. The resulting mixture was heated to 150° C. using microwave reactor for 20 min, then filtered, concentrated and purified by reverse phase HPLC to give the titled compound. MS (ESI) m/e 399 (M+H)$^+$; $^1$H NMR (500 MHz, DMSO-d$_6$): δ 2.35 (q, J=5 Hz, 2H), 3.53 (t, J=5 Hz, 2H), 6.28 (dt, J=15.91, 7.02 Hz, 1H), 6.45 (d, J=15.91 Hz, 1H), 6.60 (s, 1H), 7.27 (d, J=8.42 Hz, 2H), 7.39 (d, J=8.11 Hz, 2H).

Example 129

4-hydroxy-6-oxo-3-[5-(1,2,3,6-tetrahydropyridin-4-yl)thien-2-yl]-6,7-dihydrothieno[2,3-b]pyridine-5-carbonitrile

Example 129a tert-butyl 4-[5-(5-cyano-4-hydroxy-6-oxo-6,7-dihydrothieno[2,3-b]pyridin-3-yl)thien-2-yl]-3,6-dihydropyridine-1(2H)-carboxylate A mixture of Example 91c (400 mg, 1.13 mmol), (N-tert-butoxycarbonyl)-1,2,3,6-tetrahydropyridine-4-boronic acid pinacol ester (420 mg, 1.36 mmol) (Eastwood et al., Tetrahedron Lett., 2000, 41, 3705–3708.), and MgO (100 mg, 2.5 mmol) in 1,4-dioxane (4.4 mL), DMF (3.5 mL) and water (2.3 mL) was degassed and treated with Cs$_2$CO$_3$ (921 mg, 2.83 mmol) and Pd(Ph$_3$P)$_4$ (39 mg, 0.034 mmol). The resulting mixture was heated at 80° C. under a nitrogen atmosphere for 16 h. After cooling to 25° C., the reaction mixture was filtered and the solvent was evaporated from the filtrate. The residual dark oil was treated with water (50 mL) and the resulting mixture was stirred at 25° C. for 0.5 h. The solids were filtered, dried in a vacuum oven at 50° C., triturated with EtOAc (2×2 mL), and dried to afford 340 mg (66%) of Example 129a as a tan solid. $^1$H NMR (300 MHz, DMSO-D6) δ ppm 1.43 (s, 9H) 2.50 (m, 2H) 3.53 (m, 2H) 4.00 (m, 2H) 6.05 (br s, 1H) 6.91 (s, 1H) 6.97 (d, J=3.68 Hz, 1H) 7.46 (d, J=3.68 Hz, 1H) 11.34 (br s, 1H); MS (ESI) 478 m/z (M+Na)$^+$.

Example 129

4-hydroxy-6-oxo-3-[5-(1,2,3,6-tetrahydropyridin-4-yl)thien-2-yl]-6,7-dihydrothieno[2,3-b]pyridine-5-carbonitrile A mixture of Example 129a (100 mg, 0.22 mmol) in CH$_2$Cl$_2$ (6 mL), cooled to 0° C. in an ice bath, was treated with TFA (322 μL, 4.18 mmol) and the resulting solution was stirred at 0° C. for 1 h and at 25° C. for 2 h. The reaction was cooled to 0° C. and was treated with saturated aqueous Na$_2$CO$_3$ (7 mL) under continuous stirring. The resulting mixture was filtered and the solids collected were washed with water (1 mL) and dried to afford 65 mg (83%) of Example 129 as a tan solid. $^1$H NMR (300 MHz, DMSO-d$_6$) δ ppm 2.45 (m, 2H) 3.05 (m, 2H) 3.47 (m, 2H) 6.08 (m, 1H) 6.82 (s, 1H) 6.95 (d, J=3.68 Hz, 1H) 7.57 (d, J=3.68 Hz, 1H) 10.81 (br s, 1H); MS (ESI) 355.9 m/z (M+H)$^+$.

Example 131

3-[4-(allyloxy)phenyl]-2-chloro-4-hydroxy-6-oxo-6,7-dihydrothieno[2,3-b]pyridine-5-carbonitrile

Example 131a 1-(4-allyloxyphenyl)ethanone

The title compound was prepared according to the method described for Example 99a, substituting allyl bromide for ethyl bromoacetate. MS (ESI) m/e 178 (M+H)$^+$.

Example 131b 2-amino-4-(4-allyloxy-phenyl)-thiophene-3-carboxylic acid ethyl ester The title compound was prepared according to the method described for Example 2a, substituting 1-(4-allyloxyphenyl)ethanone for 3,5-dimethylacetophenone. MS (ESI) m/e 304 (M+H)$^+$; $^1$H NMR (300 MHz, DMSO-d$_6$) δ ppm 0.94 (t, J=7.12 Hz, 3H), 3.96 (q, J=7.12 Hz, 2H), 4.57 (m, 2H), 5.25 (dd, J=10.51, 1.70 Hz, 1H), 5.39 (m, 1H), 6.04 (m, 2H), 6.87 (m, 2H), 7.14 (m, 2H), 7.33 (s, 2H).

Example 131c 4-(4-allyloxy-phenyl)-2-(2-cyano-acetylamino)-thiophene-3-carboxylic acid ethyl ester The title compound was prepared according to the method described for Example 60b, substituting 2-amino-4-(4-allyloxy-phenyl)-thiophene-3-carboxylic acid ethyl ester for 2-amino-4-(4-bromophenyl)-thiophene-3-carboxylic acid ethyl ester. MS (ESI) m/e 369 (M−H)$^-$.

Example 131d

4-(4-allyloxy-phenyl)-5-chloro-2-(2-cyano-acetylamino)-thiophene-3-carboxylic acid ethyl ester

The title compound was prepared according to the method described for Example 60c, substituting 4-(4-allyloxy-phenyl)-2-(2-cyano-acetylamino)-thiophene-3-carboxylic acid ethyl ester for 4-(4-bromophenyl)-2-(2-cyano-acetylamino)-thiophene-3-carboxylic acid ethyl ester. $^1$H NMR (300 MHz, CDCl$_3$) δ ppm 0.90 (m, 3H), 3.67 (s, 2H), 4.07 (q, J=7.12 Hz, 2H), 4.59 (m, 2H), 5.31 (dd, J=10.51, 1.36 Hz, 1H), 5.45 (m, 1H), 6.08 (m, 1H), 6.94 (m, 2H), 7.14 (m, 2H), 12.11 (s, 1H).

Example 131

3-[4-(allyloxy)phenyl]-2-chloro-4-hydroxy-6-oxo-6,7-dihydrothieno[2,3-b]pyridine-5-carbonitrile

The title compound was prepared according to the method described for Example 60d, substituting 4-(4-allyloxy-phenyl)-5-chloro-2-(2-cyano-acetylamino)-thiophene-3-carboxylic acid ethyl ester for 4-(4-bromophenyl)-5-chloro-2-(2-cyano-acetylamino)-thiophene-3-carboxylic acid ethyl ester. MS (ESI) m/e 357 (M−H)$^−$; $^1$H NMR (300 MHz, DMSO-d$_6$) δ ppm 4.61 (m, 2H), 5.29 (m, 1H), 5.43 (dd, J=17.29, 1.70 Hz, 1H), 6.08 (m, 1H), 6.94 (d, J=8.81 Hz, 2H), 7.21 (d, J=8.81 Hz, 2H).

Example 132

7-[4-(5-Cyano-4-hydroxy-6-oxo-6,7-dihydro-thieno[2,3-b]pyridin-3-yl)-phenyl]-hept-6-ynoic acid diethylamide

To a solution of 7-[4-(5-cyano-4-hydroxy-6-oxo-6,7-dihydro-thieno[2,3-b]pyridin-3-yl)-phenyl]-hept-6-ynoic acid (24 mg, 0.06 mmol) in 0.5 mL DMF was added HOBT (trace) followed by TBTU (23 mg, 0.07 mmol). The pH of the reaction mixture was adjusted to pH>6 using Et$_3$N, then stirred at rt overnight. Solvent was removed in vacuo, the resulting slurry was redissolved in MeOH and purified using reverse phase HPLC to afford the titled compound. MS (ESI) m/e 448 (M+H)$^+$; $^1$H NMR (400 MHz, DMSO-d$_6$): δ 1.00 (t, J=8.1 Hz, 3H), 1.10 (t, J=8.1 Hz, 3H), 1.58–1.68 (m, 4H), 2.33 (t, J=6.90 Hz, 2H), 2.45 (t, J=6.90 Hz, 2H), 3.23–3.33 (m, 4H), 6.65 (s, 1H), 7.26 (d, J=8.59 Hz, 2H), 7.42 (d, J=8.59 Hz, 2H).

Example 133

4-hydroxy-6-oxo-3-[5-(2-oxo-2,3-dihydro-1H-indol-5-yl)thien-2-yl]-6,7-dihydrothieno[2,3-b]pyridine-5-carbonitrile

Example 133a

5-(4,4,5,5-tetramethyl-1,3,2-dioxaborolan-2-yl)-1,3-dihydro-2H-indol-2-one

To a solution of 5-Bromo-1,3-dihydro-indol-2-one (318 mg, 1.5 mmol) and Bis(pinacolato)diboron (420 mg, 1,65 mmol) in dioxane (15 mL) was added KOAc (516 mg, 5.25 mmol). The resulting mixture was degassed, treated with [1,1'-Bis(diphenylphosphino)ferrocene]dichloropalladium methylene choloride complex (62 mg, 0.075 mmol), heated at 90° C. for 12 h and concentrated. The residue was dissolved in CH$_2$Cl$_2$ (100 mL), washed with water (100 mL) and brine (100 mL), dried (MgSO$_4$), filtered and concentrated. The concentrate was purified by flash chromatography on silica gel eluting with 30% ethyl acetate/hexanes to afford 320 mg of Example 133a (82%). $^1$H NMR (300 MHz, DMSO-D6) δ ppm 1.27 (s, 12H) 3.46 (s, 2H) 6.81 (d, J=7.72 Hz, 1H) 7.49 (m, 2H) 10.51 (s, 1H)) MS (ESI) m/z 260.2 (M+H)$^+$, 276.8 (M+NH$_4$)$^+$.

Example 133b

4-hydroxy-6-oxo-3-[5-(2-oxo-2,3-dihydro-1H-indol-5-yl)thien-2-yl]-6,7-dihydrothieno[2,3-b]pyridine-5-carbonitrile

The title compound was prepared according to the procedures described in Example 91 substituting Example 133a for 4-(Methylsulfonylamino)phenyl boronic acid in Example 91d. $^1$H NMR (300 MHz, DMSO-D6) δ ppm 3.53 (s, 2H) 6.85 (d, J=8.09 Hz, 1H) 7.14 (s, 1H) 7.32 (q, J=3.68 Hz, 2H) 7.48 (m, 2H) 10.47 (s, 1H) MS (ESI) m/z 406.1 (M+H)$^+$.

Example 134

3-[5-(4-cyanophenyl)thien-2-yl]-4-hydroxy-6-oxo-6,7-dihydrothieno[2,3-b]pyridine-5-carbonitrile

The title compound was prepared according to the procedures described in Example 91 substituting 4-cyanophenyl boronic acid for 4-(Methylsulfonylamino)phenyl boronic acid in Example 91d. $^1$H NMR (300 MHz, METHANOL-D4) δ ppm 7.13 (s, 1H) 7.39 (d, J=4.04 Hz, 1H) 7.52 (d, J=3.68 Hz, 1H) 7.73 (d, J=8.46 Hz, 2H) 7.83 (d, J=8.46 Hz), 2H) MS (ESI) m/z 376.0 (M+H)$^+$, 392.9 (M+NH$_4$)$^+$.

Example 135

2-chloro-3-{4-[(1-cyclopropyl-4-hydroxypiperidin-4-yl)methoxy]phenyl}-4-hydroxy-6-oxo-6,7-dihydrothieno[2,3-b]pyridine-5-carbonitrile

A mixture of 2-chloro-4-hydroxy-3-{4-[(4-hydroxy-piperidin-4-yl)methoxy]phenyl}-6-oxo-6,7-dihydrothieno[2,3-b]pyridine-5-carbonitrile TFA salt (70 mg, 0.128 mmol),[(1-ethoxycyclopropyl)oxy]trimethylsilane (0.103 mL, 0.513 mmol), 3A molecular sieves (30 mg), and NaCNBH$_3$ (32 mg, 0.513 mmol) in MeOH (1 mL) was heated to reflux for 12 h. The reaction was then quenched by the addition of H$_2$O (1 mL) and EtOAc (1 mL). The layers were separated, and the aqueous was extracted with additional EtOAc (2×1 mL). The combined organic layers were dried with anhydrous Na$_2$SO$_4$, filtered, and concentrated under reduced pressure. The residue was purified by RP-HPLC to give the title compound. MS (ESI) m/e 472 (M+H)$^+$; $^1$H NMR (300 MHz, DMSO-d$_6$) δ ppm 0.84 (m, 2H), 0.94 (m, 2H), 1.80 (d, J=12.0 Hz, 2H), 1.94 (m, 2H), 2.97, (m, 1H), 3.40 (m, 4H), 3.86 (s, 2H), 5.22 (s, 1H), 6.92 (d, J=8.82 Hz, 2H), 7.22 (d, J=8.82 Hz, 2H), 8.81 (s, 1H), 10.77 (s, 1H).

Example 136

3-[4-(4-fluro-2-hydroxyphenyl)-phenyl]-4-hydroxy-6-oxo-6,7-dihydro-thieno[2,3b]-pyridine-5-carbonitrile

The titled compound was prepared according to the procedures described in Example 3a-b, substituting 4-fluoro-2-methoxyphenylboronic acid for 2,3-dimethoxyphenylboronic acid used in Example 3a (32.0 mg, 84.6%). $^1$H NMR (300 MHz, DMSO-d$_6$) δ 12.42 (s, 1H), 10.11 (s, 1H), 7.48 (AB, 4H, J=9.0 Hz), 7.31 (t, 1H, J=9.0 Hz), 7.02 (s, 1H), 6.73 (m, 2H). MS (ESI) m/e 379 (M+H)$^+$, 377 (M−H)$^-$.

Example 137

4-hydroxy-3-[4-(methoxymethoxy)phenyl]-6-oxo-6,7-dihydrothieno[2,3-b]pyridine-5-carbonitrile

Example 137a 1-(4-Methoxymethoxy-phenyl)-ethanone

Chloromethyl methyl ether (19.2 mL, 252 mmol) was added dropwise to a 0° C. solution of 4-hydroxyacetophenone (6.855 g, 50.35 mmol) and triethylamine (8.4 mL, 60.42 mmol) in dichloromethane (100 mL). The solution was then allowed to warm to rt overnight, quenched with MeOH (40 mL), filtered and the filtrate concentrated and purified by flash chromatography to give the title compound which was used as is in the next step.

Example 137

4-hydroxy-3-[4-(methoxymethoxy)phenyl]-6-oxo-6,7-dihydrothieno[2,3-b]pyridine-5-carbonitrile Example 137 was prepared using the same procedure as described for Example 2 substituting 1-(4-Methoxymethoxy-phenyl)-ethanone for 3,5-dimethylacetophenone in Example 2a. MS (ESI) m/e 326.9 (M−H)$^+$; $^1$H NMR (400 MHz, DMSO-d$_6$): δ ppm 7.35 (d, J=8.59, 2H), 7.00 (d, J=8.90, 2H), 5.21 (s, 2H), 3.43 (s, 3H).

Example 138

4-[5-(5-cyano-4-hydroxy-6-oxo-6,7-dihydrothieno[2,3-b]pyridin-3-yl)thien-2-yl]benzoic acid The title compound was prepared according to the procedures described in Example 91 substituting 4-methylcarboxylatephenyl boronic acid for 4-(Methylsulfonylamino)phenyl boronic acid in Example 91d. $^1$H NMR (300 MHz, METHANOL-D4) δ ppm 7.10 (s, 1H) 7.39 (d, J=4.04 Hz, 1H) 7.47 (d, J=3.68 Hz, 1H) 7.76 (d, J=8.46 Hz, 2H) 8.03 (d, J=8.46 Hz, 2H) MS (ESI) m/z 395.0 (M+H)$^+$, 411.9 (M+NH$_4$)$^+$

Example 139

3-[5-(3-aminophenyl)thien-2-yl]-4-hydroxy-6-oxo-6,7-dihydrothieno[2,3-b]pyridine-5-carbonitrile The title compound was prepared according to the procedures described in Example 91 substituting 3-aminophenyl boronic acid for 4-(Methylsulfonylamino)phenyl boronic acid in Example 91d. $^1$H NMR (300 MHz, METHANOL-D4) δ ppm 6.63 (dd, J=7.35, 1.84 Hz, 1H) 6.90 (s, 1H) 7.00 (m, 2H) 7.09 (t, J=7.72 Hz, 1H) 7.22 (d, J=3.68 Hz, 1H) 7.43 (d, J=4.04 Hz, 1H) MS (ESI) m/z 366.0 (M+H)$^+$, 383.0 (M+NH$_4$)$_+$.

Example 140

4-hydroxy-3-(2'-hydroxy-1,1'-biphenyl-4-yl)thieno[2,3-b]pyridin-6(7H)-one 4-hydroxy-3-(2'-hydroxy-1,1'-biphenyl-4-yl)-6-oxo-6,7-dihydrothieno[2,3-b]pyridine-5-carbonitrile (0.040 g) in 40% H$_2$SO$_4$ (20 mL) was heated at reflux for 16 hours, cooled to room temperature and quenched with 50% NaOH (till pH=2). It was then extracted with ethyl acetate (3×70 mL), organic extracts washed with water (25 mL), brine (15 mL), concentrated and purified on a RP-HPLC system to afford the title compound. MS (ESI) m/e 334.0 (M−H)$^+$; $^1$H NMR (400 MHz, DMSO-d$_6$): δ ppm 10.96 (s, 1H), 9.52 (s, 1H), 7.53 (d, J=8.59, 2H), 7.47 (d, J=7.98, 2H), 7.29 (dd, J=7.67, 1.84, 1H), 7.16 (m, 1H), 7.04 (s, 1H), 6.96 (d, J=7.97, 1H), 6.89 (m, 1H), 5.76 (s, 1H).

Example 141

Methyl 4-(2-chloro-5-cyano-4-hydroxy-6-oxo-6,7-dihydrothieno[2,3-b]pyridin-3-yl)benzoate Example 141 was prepared using the same procedure as described for Example 60d substituting 4-acetyl-benzoic acid methyl for 4-bromoacetophenone in Example 60d. MS (ESI) m/e 358.9 (M−H)$^+$; $^1$H NMR (300 MHz, DMSO-d$_6$): δ ppm 7.98 (d, J=8.47, 2H), 7.50 (d, J=8.47, 2H), 3.89 (s, 3H).

Example 142

2-Chloro-4-hydroxy-6-oxo-3-(2-phenyl-cyclopropyl)-6,7-dihydro-thieno[2,3-b]pyridine-5-carbonitrile

Example 142a 1-(2-Phenyl-cyclopropyl)-ethanone

To Me$_3$SOI (2.2 g, 10 mmol) in DMSO (20 mL) was added NaH (50%, 480 mg, 10 mmol). 4-Phenyl-but-3-en-2-one (1.13 g, 7.7 mmol) was added after 10 min. The reaction mixture was quenched after 30 min with water, extracted with EtOAc, and washed with water (3×30 mL). The organic extract was dried over MgSO$_4$ and concentrated to give 1-(2-Phenyl-cyclopropyl)-ethanone (1.5 g, 97%).

Example 142b

2-Amino-4-(2-phenyl-cyclopropyl)-thiophene-3-carboxylic acid ethyl ester 1-(2-Phenyl-cyclopropyl)-ethanone from Example 22b was dissolved in a mixture of HOAc (5 mL) and HMDS (2.4 g, 15 mmol) followed by addition of CNCH$_2$CO$_2$Et. The mixture was then heated at 80° C. for 2 h and then concentrated and flashed (10:1 hexanes/ethyl acetate) to give 2-cyano-3-(2-phenyl-cyclopropyl)-but-2-enoic acid ethyl ester (1.8 g, contaminated with CNCH$_2$CO$_2$Et). This material was then dissolved in EtOH (20 mL) followed by addition of sulfur (450 mg, 14 mmol) and Et$_3$N (1.5 g, 15 mmol). The mixture was heated at 80° C. for 16 h, concentrated, and purified by column chromatography to give 2-amino-4-(2-phenyl-cyclopropyl)-thiophene-3-carboxylic acid ethyl ester (450 mg, 21% over 2 steps).

Example 142c 2-chloro-4-hydroxy-6-oxo-3-(2-phenyl-cyclopropyl)-6,7-dihydro-thieno[2,3-b]pyridine-5-carbonitrile The amino ester from Example 22b was added to a freshly made ClCOCH$_2$CN (3 mmol) in CH$_2$Cl$_2$ (4.5 mL). The reaction mixture was quenched with aqueous NaHCO$_3$ and extracted with CH$_2$Cl$_2$. The organic extract was dried over MgSO$_4$ and concentrated to give 2-(2-cyano-acetylamino)-4-(2-phenyl-cyclopropyl)-thiophene-3-carboxylic acid ethyl ester (550 mg, 99%). A portion of this material (354 mg, 1 mmol) was dissolved in CHCl$_3$ (3 mL) followed by addition of of NCS (160 mg, 1.2 mmol). The mixture was purified by flash column after 3 h to give 5-chloro-2-(2-cyano-acetylamino)-4-(2-phenyl-cyclopropyl)-thiophene-3-carboxylic acid ethyl ester (350 mg, 91%). This material was dissolved in THF (3 mL) followed by addition of NaH (50%, 170 mg, 3.5 mmol). The reaction mixture was quenched after 16 h and extracted with EtOAc. The crude was purified by reversed phase HPLC to give 2-chloro-4-hydroxy-6-oxo-3-(2-phenyl-cyclopropyl)-6,7-dihydro-thieno[2,3-b]pyridine-5-carbonitrile (50 mg, 16%). MS (ESI) m/e 344.9, 342.9 (M+H)$^+$; 1H NMR (400 MHz, DMSO-d$_6$): δ 7.27 (m, 2H), 7.16 (m, 3H), 3.09 (ddd, J=5.2, 6.4, and 9.6 Hz, 1H), 2.69 (ddd, J=5.6, 5.6, and 8.4 Hz, 1H), 1.84 (ddd, J=4.4, 6.4, and 8.8 Hz, 1H), and 1.25 (ddd, 4.4, 6.4, and 9.2 Hz, 1H).

Example 143

3-[5-(4-acetylphenyl)thien-2-yl]-4-hydroxy-6-oxo-6,7-dihydrothieno[2,3-b]pyridine-5-carbonitrile The title compound was prepared according to the procedures described in Example 91 substituting 4-acetylphenyl boronic acid for 4-(Methylsulfonylamino)phenyl boronic acid in Example 91d. $^1$H NMR (300 MHz, methanol-D4) δ ppm 2.62 (s, 3H) 7.20 (s, 1H) 7.32 (d, J=4.04 Hz, 1H) 7.52 (d, J=4.04 Hz, 1H) 7.79 (d, J=8.82 Hz, 2H) 8.03 (d, J=8.82 Hz, 2H) MS (ESI) m/z 393.0 (M+H)$^+$.

Example 144

4-hydroxy-6-oxo-3-(4-vinylphenyl)-6,7-dihydrothieno[2,3-b]pyridine-5-carbonitrile

Example 144a 1-(4-Vinyl-phenyl)-ethanone

To a stirred mixture of 4-iodoacetophenone (1.0 g, 4.1 mmol), Pd$_2$(dba)$_3$ (186 mg, 0.2 mmol), P(2-furyl)$_3$ (94 mg, 0.4 mmol), and CuI (77 mg, 0.4 mmol) in 20 mL of anhydrous DMF under N$_2$ atmosphere was added vinyltributyltin (1.43 mL, 4.9 mmol) via syringe. An exothermic reaction was observed. After stirred for over night at r.t., the reaction mixture was poured into EtOAc (20 mL), washed with sat. aq. CsF solution, and brine. The organic layer was dried over Na$_2$SO$_4$, evaporated. The titled compound (610 mg, 100%) was isolated after silica gel MPLC eluting with 0–15% EtOAC in hexanes.

Example 144b

4-Hydroxy-6-oxo-3-(4-vinyl-phenyl)-6,7-dihydrothieno[2,3-b]pyridine-5-carbonitrile The titled compound was prepared according to the procedures described in Example 29b-d, substituting 1-(4-vinyl-phenyl)-ethanone from Example 26a for 1-(4-allyloxy-phenyl)-propan-1-one from 29a. MS (ESI) m/e 295 (M+H)$^+$; 1H NMR (300 MHz, DMSO-d$_6$): δ 12.45 (s, 1H), 7.46 (d, J=8.5 Hz, 2H), 7.40 (d, J=8.5 Hz, 2H), 7.01 (s, 1H), 6.77 (dd, J=17.8, 11.0 Hz, 1H), 5.86 (dd, J=18.7, 1.0 Hz, 1H), 5.28 (dd, J=11.2, 1.0 Hz, 1H).

Example 145

3-[5-(2,4-dihydroxyphenyl)thien-2-yl]-4-hydroxy-6-oxo-6,7-dihydrothieno[2,3-b]pyridine-5-carbonitrile

Example 145a 4-(4,4,5,5-tetramethyl-1,3,2-dioxaborolan-2-yl)benzene-1,3-diol Example 145a was prepared according to the procedure described in Example 133a substituting 4-Bromo-benzene-1,3-diol for 5-Bromo-1,3-dihydro-indol-2-one. $^1$H NMR (300 MHz, DMSO-D6) δ ppm 1.26 (s, 12H) 6.22 (m, 2H) 7.28 (d, J=8.09 Hz, 1H) 8.38 (s, 1H) 9.67 (s, 1H).

Example 145B

3-[5-(2,4-dihydroxyphenyl)thien-2-yl]-4-hydroxy-6-oxo-6,7-dihydrothieno[2,3-b]pyridine-5-carbonitrile The title compound was prepared according to the procedures described in Example 91 substituting 145a for 4-(Methylsulfonylamino)phenyl boronic acid in Example 91d. $^1$H NMR (300 MHz, METHANOL-D4) δ ppm 6.35 (m, 2H) 7.04 (s, 1H) 7.22 (d, J=3.68 Hz, 1H) 7.33 (d, J=3.68 Hz, 1H) 7.40 (d, J=8.46 Hz, 1H) MS (ESI) m/z 382.9 (M+H)$^+$.

Example 146

3-[3-(allyloxy)phenyl]-2-bromo-4-hydroxy-6-oxo-6,7-dihydrothieno[2,3-b]pyridine-5-carbonitrile

Example 146a 1-(3-Allyloxy-phenyl)-ethanone

To solution of 3-hydroxyacetophenone (2.140 g, 15.72 mmol) in acetone (100 mL) was added potassium carbonate (4.344 g, 31.43 mmol), and 3-bromo-propene (2.282 g, 18.86 mmol) and the reaction was stirred at room temperature for 16 h. The solvent was removed in vacuo and water (25 mL) was added to the reaction mixture and then extracted with ethyl acetate (3×60 mL). The organic extracts were washed with brine (15 mL), dried (Na$_2$SO$_4$) and concentrated to give the title compound which was used as is in the next step.

Example 146b

3-[3-(Allyloxy)phenyl]-4-hydroxy-6-oxo-6,7-dihydrothieno[2,3-b]pyridine-5-carbonitrile Example 146a was prepared using the same procedure as described for Example 2 substituting 1-(3-Allyloxy-phenyl)-ethanone for 3,5-dimethylacetophenone in Example 2a. MS (ESI) m/e 322.9 (M−H)$^+$; $^1$H NMR (400 MHz, DMSO-d$_6$): δ ppm 12.47 (br s, 1H), 7.25 (m, 1H), 7.01–6.97 (m, 3H), 6.92–6.90 (m, 1H), 6.10–6.00 (m, 1H), 5.42–5.37 (m, 1H), 5.27–5.24 (m, 1H), 4.58–4.56 (m, 2H).

Example 146

3-[3-(allyloxy)phenyl]-2-bromo-4-hydroxy-6-oxo-6,7-dihydrothieno[2,3-b]pyridine-5-carbonitrile Example 146 was prepared using the same procedure as described for Example 7 substituting 3-[3-(allyloxy)phenyl]-4-hydroxy-6-oxo-6,7-dihydrothieno[2,3-b]pyridine-5-carbonitrile for 4-hydroxy-6-oxo-3-phenyl-6,7-dihydrothieno[2,3-b]pyridine-5-carbonitrile in Example 7. MS (ESI) m/e 402.8 (M−H)$^+$; $^1$H NMR (400 MHz, DMSO-d$_6$): δ ppm 12.25 (br s, 1H), 7.29 (m, 1H), 6.96–6.94 (m, 1H), 6.86–6.84 (m, 2H), 6.10–6.00 (m, 1H), 5.42–5.38 (m, 1H), 5.27–5.24 (m, 1H), 4.57–4.55 (m, 2H).

Example 147

3-{5-[3-(dimethylamino)prop-1-ynyl]thien-2-yl}-4-hydroxy-6-oxo-6,7-dihydrothieno[2,3-b]pyridine-5-carbonitrile A solution of Example 91c (80 mg, 0.23 mmol), N,N-dimethylpropargyl amine (24.5 mg, 0.295 mmol), and Et$_3$N (157.6 µL, 1.13 mmol) in DMF (2.2 mL) was degassed and treated with Pd(PPh$_3$)$_2$Cl$_2$ (7.9 mg, 0.01 mmol) and CuI (1.3 mg, 0.007 mmol). The reaction was heated under nitrogen at 80° C. for 12 h. The solvent was evaporated and the concentrate was purified by RPHPLC on a Waters Symmetry C8 column (25 mm×100 mm, 7 µm particle size) using a gradient of 10% to 100% acetonitrile:0.1% aqueous TFA to provide 15 mg of the title compound as a TFA salt. $^1$H NMR (300 MHz, DMSO-D6) δ ppm 2.88 (s, 6H) 4.38 (s, 2H) 7.04 (s, 1H) 7.31 (d, J=4.04 Hz, 1H) 7.51 (d, J=3.68 Hz, 1H) 10.05 (br. s, 1H) 10.95 (br. s, 1H); MS (ESI) m/z 356.1 (M+H)$^+$.

Example 149

3-(4-bromophenyl)-2-chloro-4-hydroxy-6-oxo-6,7-dihydrothieno[2,3-b]pyridine-5-carbonitrile N-chlorosuccinamide (1.56 mmol, 0.2 g) was added to a solution of 3-(4-bromophenyl)-4-hydroxy-6-oxo-6,7-dihydrothieno[2,3-b]pyridine-5-carbonitrile (1 mmol, 0.350 g) in acetic acid (5 mL) at room temperature. The reaction was heated at 90° C. for 5 h, cooled and quenched with water (30 mL). The aqueous mixture was extracted with ethyl acetate (3×30 mL), dried (Na$_2$SO$_4$), concentrated and purified on RP-HPLC to afford the title compound. MS (ESI) m/e 381 (M−H)$^+$; 1H NMR (500 MHz, DMSO-d$_6$): δ ppm 11.93 (br s, 1H), 7.59 (d, J=10, 2H), 7.28 (d, J=10, 2H).

Example 150

4-hydroxy-3-[4-(4-hydroxybut-1-ynyl)phenyl]-6-oxo-6,7-dihydrothieno[2,3-b]pyridine-5-carbonitrile To an ambient slurry of 3-(4-bromophenyl)-4-hydroxy-6-oxo-6,7-dihydrothieno[2,3-b]pyridine-5-carbonitrile (0.050 g, 0.14 mmol), but-3-yn-1-ol (0.030 g, 0.42 mmol), copper (I) iodide (0.005 g), triphenylphosphine (0.009 g, 0.03 mmol) and diethyl amine (0.15 mL, 1.4 mmol) in DMF (1.5 mL) was added dichlorobis(triphenylphosphine)palladium (II) (0.002 g, 0.003 mmol) in a single portion. The reaction was heated at 120° C. for 20 min in a microwave, cooled to room temperature, filtered, concentrated and purified by RP-HPLC to afford the title compound. MS (ESI) m/e 334.9 (M−H)$^+$; $^1$H NMR (300 MHz, DMSO-d$_6$): δ ppm 12.02 (br s, 1H), 7.39 (d, J=9, 2H), 7.35 (d, J=9, 2H), 6.94 (s, 1H), 3.59 (t, J=9, 2H), 2.57 (t, J=9, 2H).

Example 151

4-hydroxy-6-oxo-3-(5-pyridin-2-ylthien-2-yl)-6,7-dihydrothieno[2,3-b]pyridine-5-carbonitrile

Example 151 a ethyl 5'-amino-5-bromo-2,3'-bithiophene-4'-carboxylate

A mixture of 1-(5-Bromo-thiophen-2-yl)-ethanone (5 g, 24.4 mmol), ethyl cyanoacetate (2.86 mL, 26.8 mmol), ammonium acetate (9.76 mmol, 751.5 mg), and acetic acid (2.2 mL, 38.4 mmol) in benzene (20 mL) was azeotroped in an oil bath at 100° C. in a flask fitted with a Dean-Stark Trap and reflux condenser. After 9 h at 100° C., additional ammonium acetate (751.5 mg, 9.76 mmol) and acetic acid (2.2 mL, 38.4 mmol) were added and the mixture was azeotroped an additional 9 h. The reaction mixture was concentrated to provide 6.9 g of condensation product as an orange oil. The residual oil was dissolved in EtOH (18 mL), and treated with diethylamine (3 mL, 28.76 mmol) and sulfur 24.4 mmol, 780 mg). After heating the reaction mixture at 60° C. for 2 h, the solvent was evaporated. The residue was purified by flash chromatography on silica gel eluting with 50% CH$_2$Cl$_2$/hexanes to provide 4 g (47%) of Example 151a as a yellow solid. 1H NMR (300 MHz, chloroform-d$^3$) δ ppm 1.14 (t, J=7.17 Hz, 3H) 4.16 (q, J=6.99 Hz, 2H) 6.10 (br.s, 2H) 6.21 (s, 1H) 6.75 (d, J=3.68 Hz, 1H) 6.93 (d, J=3.68 Hz, 1H).

Example 151b ethyl 5-bromo-5'-[(cyanoacetyl)amino]-2,3'-bithiophene-4'-carboxylate A stirred suspension of PCl$_5$ (2.35 g, 11.3 mmol) in CH$_2$Cl$_2$ (22.6 mL) was treated with cyanoacetic acid (0.96 g, 11.3 mmol) dropwise over 5 minutes and the resulting mixture was stirred at ambient temperature until the exotherm subsided and all solids had dissolved. The reaction was heated at reflux for 30 minutes, cooled to 25° C., and transferred via canula to a solution of Example 151a (2.5 g, 7.53 mmol) in CH$_2$Cl$_2$ (30 mL). The resulting mixture was heated at reflux 30 minutes and cooled to 25° C. Saturated aqueous Na$_2$CO$_3$ (50 mL) was added and the mixture was extracted with CH$_2$Cl$_2$ (2×75 mL). The combined extracts were washed with brine; dried (Na$_2$SO$_4$); filtered; and evaporated to afford 2.8 g (93%) of Example 151b as a yellow solid. $^1$H NMR (300 MHz, chloroform-D) δ ppm 1.16 (t, J=7.17 Hz, 3H) 3.68 (s, 2H) 4.26 (q, J=7.11 Hz, 2H) 6.77 (d, J=3.68 Hz, 1H) 6.84 (s, 1H) 6.97 (d, J=3.68 Hz, 1H) 12.03 (s, 1H); MS (ESI) m/z 400 (M+H)$^+$.

Example 151c

5'-(2-Cyano-acetylamino)-5-pyridin-2-yl-[2,3'] bithiophenyl-4'-carboxylic acid ethyl ester A solution of Example 151b (100 mg, 0.25 mmol) and 2-(tributylstannyl)pyridine (184 mg, 0.5 mmol) in DME (2 mL) was degassed and treated with Pd(PPh$_3$)$_2$Cl$_2$ (17.5 mg, 0.025 mmol). The reaction was heated under nitrogen at 105° C. for 16 h. The solvent was evaporated and the crude concentrate was purified by flash chromatography on silica gel eluting with 10% EtOAc/hexanes to provide 26 mg (26%) of Example 151c as a yellow solid. $^1$H NMR (300 MHz, DMSO-D6) δ ppm 1.11 (t, J=7.17 Hz, 3H) 4.21 (q, J=7.11 Hz, 2H) 4.27 (s, 2H) 7.12 (d, J=3.68 Hz, 1H) 7.27 (m, 2H) 7.74 (d, J=4.04 Hz, 1H) 7.85 (m, J=7.54, 1.65 Hz, 1H) 7.93 (m, 1H) 8.52 (d, J=4.41 Hz, 1H) 11.20 (s, 1H); MS (ESI) m/z 398 (M+H)$^+$.

Example 151d 4-hydroxy-6-oxo-3-(5-pyridin-2-ylthien-2-yl)-6,7-dihydrothieno[2,3-b]pyridine-5-carbonitrile To a suspension of sodium hydride (60% in mineral oil, 10 mg, 0.25 mmol) in THF (0.5 mL) and DMF (0.5 mL) was added a solution of Example 2d (25 mg, 0.063 mmol) in THF (0.5 mL). The resulting mixture was stirred for 2 h at 25° C. and cooled to 0° C. MeOH (0.25 mL) was added and the reaction was stirred at 25° C. for 5 minutes. The solvent was evaporated and the concentrate was purified by RPHPLC on a Waters Symmetry C8 column (25 mm×100 mm, 7 μm particle size) using a gradient of 10% to 100% acetonitrile:0.1% aqueous NH$_4$OAc to provide 7 mg (32%) of the title compound as a tan solid. $^1$H NMR (300 MHz, DMSO-D$_6$ w/CF$_3$COOD) δ ppm 7.40 (s, 1H) 7.42 (d, J=3.68 Hz, 1H) 7.55 (m, 1H) 7.93 (d, J=4.04 Hz, 1H) 8.15 (m, 2H) 8.67 (d, J=5.52 Hz, 1H); MS (ESI) m/z 351.9 (M+H)$^+$.

Example 152

4-hydroxy-3-(2'-hydroxy-1,1'-biphenyl-4-yl)-6-oxo-6,7-dihydrothieno[2,3-b]pyridine-5-carbaldehyde oxime Example 152a 3-[4-(2-hydroxyphenyl)-phenyl]-4-hydroxy-5-iminomethyl-6-oxo-7H-thieno[2,3b]-pyridine-6-one To 3-[4-(2-hydroxyphenyl)-phenyl]-4-hydroxy-6-oxo-6,7-dihydro-thieno[2,3b]-pyridine-5-carbonitrile (721 mg, 2 mmol) in formic acid (12 mL) nickel aluminide (1.4 g, 10 mmol) was added. The reaction mixture was refluxed 24 h, and then was cooled and filtered. The solid was washed with methanol (10 mL) twice. The combined organic layers were concentrated under vacuum and the residue was purified on HPLC. The title compound was obtained (188.5 mg, 26%) as a white solid. $^1$H NMR (300 MHz, DMSO-d$_6$) δ 11.48, 11.43 (2s, 1H), 10.72, 10.05 (2 m, 1H), 9.54 (s, 1H), 9.31 (s, 1H), 8.25 (m, 1H), 7.48 (AB, 4H, J=6.0 Hz), 7.28 (d, 1H, J=6.0 Hz), 7.16 (t, 1H, J=6.0 Hz),), 6.97–6.84 (m, 2H), 6.81 (s, 1H). MS (ESI) m/e 363 (M+H)$^+$, 361 (M−H)$^−$.

Example 152b

3-[4-(2-Hydroxyphenyl)-phenyl]-4-hydroxy-6-oxo-6,7-dihydro-thieno[2,3b]-pyridine-5-carbaldehyde oxime To 3-[4-(2-hydroxyphenyl)-phenyl]-4-hydroxy-5-iminomethyl-6-oxo-7H-thieno[2,3 b]-pyridine-6-one from Example 21A (26 mg, 0.072 mmol) in ethanol (2 mL) hydroxylamine hydrochloride (7 mg, 0.1 mmol) was added, followed by pyridine (7.9 mg, 0.1 mmol). The reaction mixture was refluxed for 1 h. The mixture was then cooled and concentrated under vacuum. The residue was purified on preparative HPLC. The title compound was obtained (20 mg, 75.6%) as a white solid. $^1$H NMR (300 MHz, DMSO-d$_6$) δ 11.46 (s, 1H), 9.56 (s, 1H), 8.36 (s, 1H), 7.3 (AB, 4H, J=9.0 Hz), 7.46 (m, 1H), 7.31 (d, 1H, J=6.0 Hz), 7.16 (t, 1H, J=6.0 Hz), 7.07 (s, 1H), 6.97–6.87 (m, 2H), MS (ESI) m/e 379 (M+H)$^+$, 377 (M−H)$^−$.

Example 153

3-[3-(allyloxy)phenyl]-2-chloro-4-hydroxy-6-oxo-6,7-dihydrothieno[2,3-b]pyridine-5-carbonitrile Example 153 was prepared using the same procedure as described for Example 51 substituting 3-[3-(allyloxy)phenyl]-4-hydroxy-6-oxo-6,7-dihydrothieno[2,3-b]pyridine-5-carbonitrile for 4-hydroxy-6-oxo-3-phenyl-6,7-dihydrothieno[2,3-b]pyridine-5-carbonitrile in Example 51. MS (ESI) m/e 356.9 (M−H)$^+$; $^1$H NMR (500 MHz, DMSO-d$_6$): δ ppm 12.29 (br s, 1H), 7.26 (m, 1H), 6.93–6.91 (m, 1H), 6.85–6.84 (m, 2H), 6.03–5.97 (m, 1H), 5.38–5.34 (m, 1H), 5.22–5.20 (m, 1H), 4.53–4.52 (m, 2H).

Example 154

3-[4-(5-Bromo-2,4-dihydroxyphenyl)-phenyl]-4-hydroxy-6-oxo-6,7-dihydro-thieno[2,3b]-pyridine-5-carbonitrile The titled compound was obtained from the same reaction mixture of Example 4 as a by-product (18.0 mg, 39.5%). $^1$H NMR (300 MHz, DMSO-d$_6$) δ 12.41 (s, 1H), 10.16 (s, 1H), 9.75 (s, 1H), 7.45 (AB, 4H, J=20, 9 Hz), 7.32 (s, 1H), 7.0 (s, 1H), 6.66 (s, 1H). MS (ESI) m/e 457 (M+H)$^+$, 455 (M−H)$^−$.

Example 155

3-[4-(4,6-dimethyl-2-hydroxyphenyl)-phenyl]-4-hydroxy-6-oxo-6,7-dihydro-thieno[2,3b]-pyridine-5-carbonitrile The titled compound was prepared according to the procedures described in Example 3a-b, substituting 4,6-dimethyl-2-methoxyphenylboronic acid for 2,3-dimethoxyphenylboronic acid used in Example 3a was obtained (33.0 mg, 85%). $^1$H NMR (300 MHz, DMSO-d$_6$) δ 12.43 (s, 1H), 9.0 (s, 1H), 7.44 (d, 2H, J=9.0 Hz), 7.15 (d, 2H, J=9.0 Hz), 7.05 (s, 1H), 6.58 (s, 1H), 6.56 (s, 1H). MS (ESI) m/e 389 (M+H)$^+$, 387 (M−H)$^−$.

Example 156

N-{4-[5-(5-cyano-4-hydroxy-6-oxo-6,7-dihydrothieno[2,3-b]pyridin-3-yl)thien-2-yl]-2-fluorophenyl}acetamide

Example 156a

N-[3-fluoro-4-(4,4,5,5-tetramethyl-1,3,2-dioxaborolan-2-yl)phenyl]acetamide

Example 156a was prepared according to the procedure described in Example 133a substituting N-(4-Bromo-3-fluoro-phenyl)-acetamide for 5-Bromo-1,3-dihydro-indol-2-one. $^1$H NMR (300 MHz, DMSO-D6) δ ppm 1.29 (s, 12H) 2.11 (s, 3H) 7.40 (m, 2H) 8.05 (t, J=7.91 Hz, 1H) 9.81 (s, 1H) MS (ESI) m/z 280.0 (M+H)$^+$.

Example 156b

N-{4-[5-(5-cyano-4-hydroxy-6-oxo-6,7-dihydrothieno[2,3-b]pyridin-3-yl)thien-2-yl]-3-fluorophenyl}acetamide The title compound was prepared according to the procedures described in Example 91 substituting 156a for 4-(Methylsulfonylamino)phenyl boronic acid in Example 91d. $^1$H NMR (300 MHz, METHANOL-D4) δ ppm 2.18 (s, 3H) 7.10 (s, 1H) 7.32 (d, J=3.31 Hz, 1H) 7.43 (dd, J=4.41, 2.57 Hz, 2H) 7.47 (d, J=1.84 Hz, 1H) 8.00 (m, 1H) MS (ESI) m/z 425.9 (M+H)$^+$.

Example 158

2-[({(1E)-[4-(5-cyano-4-hydroxy-6-oxo-6,7-dihydrothieno[2,3-b]pyridin-3-yl)phenyl]methylene}amino)oxy]-N-(pyridin-2-ylmethyl)acetamide

Example 158a

4-Hydroxy-3-(4-hydroxymethyl-phenyl)-6-oxo-3a,6,7,7a-tetrahydro-thieno[2,3-b]pyridine-5-carbonitrile Example 158a was prepared using the same procedures as described for Example 2 substituting 1-[4-(tert-butyl-diphenyl-silanyloxymethyl)-phenyl]-ethanone for 3,5-dimethylacetophenone in Example 2a. A tetrabutylammonium fluoride deprotection step was incorporated into this procedure prior to the last, base-induced cyclization step. MS (ESI) m/e 299 (M+H)$^+$; $^1$H NMR (300 MHz, DMSO-d$_6$): δ ppm 12.44 (br s, 1H), 7.37 (d, J=9, 2H), 7.29 (d, J=9, 2H), 6.96 (s, 1H), 4.52 (s, 2H).

Example 158b 3-(4-Formyl-phenyl)-4-hydroxy-6-oxo-3 a,6,7,7a-tetrahydro-thieno[2,3-b]pyridine-5-carbonitrile Tetrapropylammonium perruthenate (0.16 g, 0.46 mmol) was added to a solution of 4-Hydroxy-3-(4-hydroxymethyl-phenyl)-6-oxo-3a,6,7,7a-tetrahydro-thieno[2,3-b]pyridine-5-carbonitrile (0.55 g, 1.84 mmol) and 4-methylmorpholine N-oxide (0.65 g, 5.52 mmol) in 2:1 mixture of dichloromethane/N,N-dimethylacetamide (33 mL) at room temperature. The reaction was stirred till complete consumption of the starting alcohol, filtered over celite, filtrate washed with 1N HCl, dried (MgSO$_4$) and concentrated to a brown solid. MS (ESI) m/e 294.9 (M−H)$^+$; $^1$H NMR (300 MHz, DMSO-d$_6$): δ ppm 12.01 (br s, 1H), 10.04 (s, 1H), 7.87 (d, J=9, 2H), 7.66 (d, J=9, 2H), 7.07 (s, 1H).

Example 158c

[4-(5-Cyano-4-hydroxy-6-oxo-3a,6,7,7a-tetrahydrothieno[2,3-b]pyridin-3-yl)-benzylideneaminooxy]-acetic acid N,O-Dimethylhydroxylamine hydrochloride (0.067 g, 0.3 mmol) was added to a room temperature solution of 3-(4-Formyl-phenyl)-4-hydroxy-6-oxo-3a,6,7,7a-tetrahydro-thieno[2,3-b]pyridine-5-carbonitrile (0.1 g, 0.29 mmol) and sodium acetate (0.025 g, 0.3 mmol) in 1:1:1 mixture of methanol/dioxane/water (6 mL). The reaction mixture was quenched with 3N HCl after complete reaction, extracted with ethyl acetate (3×20 mL), organic extracts washed with brine, dried (MgSO$_4$) and concentrated to a brown solid. MS (ESI) m/e 369.5 (M+H)$^+$; $^1$H NMR (300 MHz, DMSO-d$_6$): δ ppm 12.30 (br s, 1H), 8.36 (s, 1H), 7.59 (d, J=9, 2H), 7.47 (d, J=9, 2H), 7.03 (s, 1H), 4.66 (s, 2H).

Example 158

2-[({(1E)-[4-(5-cyano-4-hydroxy-6-oxo-6,7-dihydrothieno[2,3-b]pyridin-3-yl)phenyl]methylene}amino)oxy]-N-(pyridin-2-ylmethyl)acetamide

[4-(5-Cyano-4-hydroxy-6-oxo-3a,6,7,7a-tetrahydrothieno[2,3-b]pyridin-3-yl)-benzylideneaminooxy]-acetic acid (0.035 g, 0.1 mmol) and C-pyridin-2-yl-methylamine (0.013 g, 0.12 mmol) were added to a suspension of resin bound 1,3-dicyclohexyl carbodiimide (0.166 g, 1.2 mmol/g, 0.2 mmol) and 1-hydroxybenzotriazole hydrate (0.013 g, 0.1 mmol) in 1:1 dichloromethane/N,N-dimethylacetamide (4 mL) at room temperature. After complete reaction, resin bound trisamine (4.7 mmol/g, 0.053 g, 0.25 mmol) was added to the reaction mixture, shaken at room temperature for 1 hour, filtered, concentrated and purified by RP-HPLC to afford the title compound. MS (ESI) m/e 457.8 (M−H)$^+$; $^1$H NMR (500 MHz, DMSO-d$_6$): δ ppm 12.15 (br s, 1H), 8.52–8.56 (m, 2H), 8.42 (s, 1H), 7.88 (dt, J=10.5, 1H), 7.61 (d, J=10, 2H), 7.51 (d, J=10, 2H), 7.38–7.43 (m 2H), 7.01 (s, 1H), 4.65 (s, 2H), 4.50 (d, J=5, 1H).

Example 159

2-chloro-4-hydroxy-3-(5-methyl-2-furyl)-6-oxo-6,7-dihydrothieno[2,3-b]pyridine-5-carbonitrile The titled compound was prepared using similar procedures as described for Example 22, substituting 1-(5-methylfuran-2-yl)-ethanone for 1-(2-phenyl-cyclopropyl)-ethanone. MS (ESI) m/e 306.9 (M+H)$^+$; $^1$H NMR (300 MHz, DMSO-d$_6$): δ ppm 6.54 (d, 3.1 Hz, 2H), 6.16 (d, 3.1 Hz, 2H), 2.29 (s, 1H).

Example 160

4-hydroxy-3-(3-hydroxyphenyl)-6-oxo-6,7-dihydrothieno[2,3-b]pyridine-5-carbonitrile Boron trichloride (1M in dichloromethane, 5 mL, 5 mmol) was added to a solution of 3-[3-(allyloxy)phenyl]-4-hydroxy-6-oxo-6,7-dihydrothieno[2,3-b]pyridine-5-carbonitrile (146B) (0.54 g, 1.65 mmol) in dichloromethane (30 mL) and the reaction was stirred at room temperature for 16 h. It was quenched with water (20 mL), filtered, concentrated and purified on a RP-HPLC system. The title compound was one of the three reaction products that were purified. MS (ESI) m/e 283.0 (M−H)+; $^1$H NMR (500 MHz, DMSO-$d_6$): δ ppm 12.46 (br s, 1H), 9.36 (br s, 1H), 7.14 (t, 1H), 6.96 (s, 1H), 6.83–6.80 (m, 2H), 6.7–6.72 (m, 1H).

Example 161

2-chloro-3-{4-[(1-cyclopentyl-4-hydroxypiperidin-4-yl)methoxy]phenyl}-4-hydroxy-6-oxo-6,7-dihydrothieno[2,3-b]pyridine-5-carbonitrile The title compound was prepared according to the method described for Example 121, substituting cyclopentanone for acetaldehyde. MS (ESI) m/e 500 (M+H)+; $^1$H NMR (300 MHz, DMSO-$d_6$) δ ppm 1.65 (m, 6H), 1.80 (m, 2H), 2.03 (m, 4H), 3.16 (m, 4H), 3.51 (m, 1H), 3.86 (s, 2H), 5.22 (s, 1H), 6.92 (d, J=8.82 Hz, 2H), 7.22 (d, J=8.82 Hz, 2H), 9.00 (s, 1H), 10.77 (s, 1H).

Example 162

3-[4-(2,5-dihydroxyphenyl)-phenyl]-4-hydroxy-6-oxo-6,7-dihydro-thieno[2,3b]-pyridine-5-carbonitrile The titled compound was prepared according to the procedures described in Example 3A-B, substituting 2,5-dimethoxyphenylboronic acid for 2,3-dimethoxyphenylboronic acid used in Example 3a (31.0 mg, 80%). $^1$H NMR (300 MHz, DMSO-$d_6$) δ 12.7 (s, 1H), 9.53 (s, 1H), 8.8 (s, 2H), 7.46 (AB, 4H, J=9 Hz), 6.96 (s, 1H), 6.77–6.56 (m, 3H). MS (ESI) m/e 377 (M+H)+, m/e 375 (M−H)−.

Example 164

3-[4-(2,3-Dihydroxy-propoxy)-4-hydroxy]-2-methyl-6-oxo-6,7-dihydro-thieno[2,3-b]pyridine-5-carbonitrile To the solution of 5-(4-Allyloxy-phenyl)-4-hydroxy-2-methyl-6-oxo-6,7-dihydro-thieno[2,3-b]pyridine-5-carbonitrile from Example 29D (340 mg, 1 mmol) in acetone (6 mL) and water (1 mL) 4-methyl-morpholine (351 mg, 3 mmol) was added, followed by catalyst amount of OsO$_4$ (12 mg). The reaction mixture was stirred at room temperature for 2 h and quenched with saturated Na$_2$S$_2$O$_3$ aqueous. After removed the solvents under vacuo, the residue was purified on Gilson preparative HPLC to give the titled compound as a white solid (190 mg, 51% yield). $^1$H NMR (300 MHz, DMSO-$d_6$) δ 10.57 (s, 1H), 7.08 (d, 2H, J=9.0 Hz), 6.84 (d, 2H, J=9.0 Hz), 4.95 (d, 1H, J=6.0 Hz), 4.66 (t, 1H, J=6.0 Hz), 4.01 (2d, 1H, J=6.0 Hz), 3.85 (m, 2H), 3.46 (t, 2H, J=6.0 Hz), 2.09 (s, 3H). MS (ESI) m/e 373 (M+H)+, 371 (M−H)−.

Example 165

3-[4-(allyloxy)phenyl]-2-bromo-4-hydroxy-6-oxo-6,7-dihydrothieno[2,3-b]pyridine-5-carbonitrile To an ambient solution of 3-[4-(allyloxy)phenyl]-4-hydroxy-6-oxo-6,7-dihydrothieno[2,3-b]pyridine-5-carbonitrile (Example 215) (100 mg, 0.309 mmol) in AcOH (1 mL) was added pyridinium perbromide (99 mg, 0.309 mmol). The reaction was stirred for 1 h and then diluted with H$_2$O (2 mL). The solid was filtered, air-dried, and purified by RPLC to give the title compound. MS (ESI) m/e 401 (M−H)−; $^1$H NMR (300 MHz, DMSO-$d_6$) δ ppm 4.60 (m, 2H), 5.28 (dd, J=12.04, 1.53 Hz, 1H), 5.44 (dd, J=17.29, 1.70 Hz, 1H), 6.07 (m, 1H), 6.92 (d, J=8.82 Hz, 2H), 7.17 (d, J=8.48 Hz, 2H).

Example 166

3-[5-(1-acetyl-1,2,3,6-tetrahydropyridin-4-yl)thien-2-yl]-4-hydroxy-6-oxo-6,7-dihydrothieno[2,3-b]pyridine-5-carbonitrile A mixture of Example 129 (40 mg, 0.113 mmol) in CH$_2$Cl$_2$ (3 mL), cooled to 0° C. in an ice bath, was treated with Et$_3$N (86.5 μL, 0.62 mmol) and acetyl chloride (24.2 μL, 0.34 mmol). The resulting mixture was stirred at 25° C. for 5 h and the solvent was evaporated. The residue was triturated with EtOAc (2 mL) and the solids filtered. The solids were suspended in water (1.5 mL) under continuous stirring and 1 N NaOH was added until the aqueous layer reached pH 9–10. After stirring at 25° C. for 25 minutes solids had dissolved and the solution was acidified to pH 2 with 1 N HCl. The precipitated solids were filtered, washed with water (0.5 mL), and dried to afford 33 mg (74%) of Example 166 as a tan solid. $^1$H NMR (500 MHz, DMSO-$d_6$, 80° C.) δ ppm 2.05 (s, 3H) 3.38 (m, 2H) 3.65 (m, 2H) 4.10 (br s, 2H) 6.08 (m, 1H) 6.99 (d, J=3.91 Hz, 1H) 7.01 (s, 1H) 7.34 (d, J=3.91 Hz, 1H); MS (ESI) 397.9 m/z (M+H)+.

Example 167

3-{5-[4-(allyloxy)phenyl]thien-2-yl}-4-hydroxy-6-oxo-6,7-dihydrothieno[2,3-b]pyridine-5-carbonitrile

Example 167a

1-[5-(4-hydroxyphenyl)thien-2-yl]ethanone

To a degassed suspension of 2-acetyl-5-bromothiophene (5 g, 24.4 mmol), 4-hydroxyphenylboronic acid (4.04 g, 29.3 mmol) and Na$_2$CO$_3$ (6.5 g, 61 mmol) in DMF (30 mL), 1,4-dioxane (150 mL) and H$_2$O (30 mL) was added tetrakis (triphenylphosphine)palladium (1.12 g, 0.9 mmol). The resulting mixture was heated at 80° C. for 5 h, cooled to 25° C., and filtered. The filtrate was concentrated in vacuo to a volume of 50 ml. The concentrate was treated with ethyl acetate (250 mL) and washed with 0.5NHCl (200 mL) and brine (200 mL). The organic layer was dried (MgSO$_4$) and concentrated to afford 4.2 g of Example 167a (78%). $^1$H NMR (300 MHz, DMSO-D6) δ ppm 2.74 (s, 3H) 6.85 (d, J=8.82 Hz, 2H) 7.44 (d, J=4.04 Hz, 1H) 7.60 (d, J=8.82 Hz, 2H) 7.88 (d, J=4.04 Hz, 1H) 9.91 (s, 1H) MS (DCI) m/z 218.9 (M+H)+.

Example 167b

1-{5-[4-(allyloxy)phenyl]thien-2-yl}ethanone

To a suspension of Example 167A (4.2 g, 19.2 mmol) and $K_2CO_3$ (8 g, 57.5 mmol) in DMF (100 mL) was added allyl bromide (1.95 mL, 24 mmol) dropwise over 5 minutes. The resulting mixture was stirred 12 h at 25° C., diluted with ether (300 mL) and washed with 1N HCl (400 mL) and brine (200 mL). The organic layer was dried ($MgSO_4$), filtered, and concentrated. The concentrate was purified by flash chromatography on silica gel to afford 4.56 g of Example 167b (92%). $^1$H NMR (300 MHz, chloroform-D) δ ppm 2.56 (m, 3H) 4.58 (m, 2H) 5.38 (m, 2H) 6.06 (m, 1H) 6.95 (d, J=8.82 Hz, 2H) 7.21 (d, J=4.04 Hz, 1H) 7.58 (d, J=8.82 Hz, 2H) 7.63 (d, J=4.04 Hz, 1H) MS (DCI) m/z 259.0 (M+H)$^+$.

Example 167c ethyl 5-[4-(allyloxy)phenyl]-5'-amino-2,3'-bithiophene-4'-carboxylate Example 167c was prepared according to the procedure described in Example 91a substituting Example 167b for 2-acetyl-5-bromothiophene. $^1$H NMR (300 MHz, DMSO-D6) δ ppm 1.08 (t, J=7.17 Hz, 3H) 4.08 (q, J=6.99 Hz, 2H) 4.60 (d, J=5.15 Hz, 2H) 5.33 (m, 2H) 6.05 (m, 1H) 6.38 (s, 1H) 6.98 (m, 3H) 7.25 (d, J=3.68 Hz, 1H) 7.42 (s, 2H) 7.55 (d, J=8.82 Hz, 2H) MS (ESI) m/z 386.0 (M+H)$^+$.

Example 167d ethyl 5-[4-(allyloxy)phenyl]-5'-[(cyanoacetyl)amino]-2,3'-bithiophene-4'-carboxylate Example 167d was prepared according to the procedure described in Example 91b substituting Example 167c for Example 91a. $^1$H NMR (300 MHz, DMSO-D6) δ ppm 1.08 (t, J=7.17 Hz, 3H) 4.08 (q, J=6.99 Hz, 2H) 4.16 (s, 2H) 4.60 (d, J=5.15 Hz, 2H) 5.33 (m, 2H) 6.05 (m, 1H) 6.38 (s, 1H) 6.98 (m, 3H) 7.25 (d, J=3.68 Hz, 1H) 7.42 (s, 2H) 7.55 (d, J=8.82 Hz, 2H) MS (ESI) m/z 453.0 (M+H)$^+$

Example 167e

3-{5-[4-(allyloxy)phenyl]thien-2-yl}-4-hydroxy-6-oxo-6,7-dihydrothieno[2,3-b]pyridine-5-carbonitrile The title compound was prepared according to the procedure described in Example 91c substituting Example 167d for Example 91b $^1$H NMR (300 MHz, DMSO-D6) δ ppm 4.61 (d, J=5.15 Hz, 2H) 5.28 (d, J=10.66 Hz, 1H) 5.42 (dd, J=17.28, 1.47 Hz, 1H) 6.06 (m, 1H) 7.01 (d, J=8.82 Hz, 2H) 7.18 (s, 1H) 7.31 (m, 2H) 7.58 (d, J=8.46 Hz, 2H) MS (DCI) m/z 406.9 (M+H)$^+$, 424 (M+NH$_4$)$^+$.

Example 168

7-[3-(5-Cyano-4-hydroxy-6-oxo-6,7-dihydro-thieno[2,3-b]pyridin-3-yl)-phenyl]-hept-6-ynoic acid To a solution of 3-(3-bromo-phenyl)-4-hydroxy-6-oxo-6,7-dihydro-thieno[2,3-b]pyridine-5-carbonitrile (50 mg, 0.15 mmol) in 1.5 mL DMF was added diethylamine (0.16 mL, 1.5 mmol), followed by copper(I) iodide (trace), Pd(PPh$_3$)Cl$_2$ (3.5 mg, 0.005 mmol), and triphenylphosphine (12 mg, 0.04 mmol). The resulting mixture was stirred at rt for 5 min, after which hept-6-ynoic acid (63 μL, 0.5 mmol) was added. The reaction was then heated to 120° C. using microwave reactor for 25 min, filtered, concentrated and purified by reverse phase HPLC to give the titled compound. MS (ESI) m/e 391 (M−H)$^+$; $^1$H NMR (300 MHz, DMSO-d$_6$): δ 1.54 (m, 4H), 2.22 (m, 4H), 6.68 (s, 1H), 7.21–7.26 (m, 2H), 7.37–7.44 (m, 2H).

Example 169

4-hydroxy-3-[5-(3-methoxyprop-1-ynyl)-4-vinylthien-2-yl]-6-oxo-6,7-dihydrothieno[2,3-b]pyridine-5-carbonitrile 3-[4-Bromo-5-(3-methoxy-prop-1-ynyl)-thiophen-2-yl]-4-hydroxy-6-oxo-6,7-dihydro-thieno[2,3-b]pyridine-5-carbonitrile (75 mg, 0.18 mmol, Example 183) was dissolved in 2 mL of 1:1 DMF:DME and at rt, vinyl tributyltin (0.2 mmol) was added. The reaction vessel was flushed with N$_2$, capped and heated to 100° C. for 2 h. The reaction mixture was filtered and filtered again through a plug of silica gel. The residue was taken up in 1:1 MeOH : DMSO, filtered and purified by RP-HPLC to provide the title compound. MS (ESI) m/z 367.0 (M−H$^+$); $^1$H NMR (300 MHz, DMSO-d$_6$) δ ppm 7.67 (s, 1H), 7.44 (s, 1H), 7.04 (s, 1H), 6.98 (s, 1H), 6.83 (dd, 1H), 5.83 (d, 1H), 5.30 (d, 1H), 4.38 (d, 2H), 4.38 (app d, 2H), 3.43 (app d, 3H).

Example 169a 3-(4-Bromo-5-iodo-thiophen-2-yl)-4-hydroxy-6-oxo-6,7-dihydro-thieno[2,3-b]pyridine-5-carbonitrile Example 169a was prepared in the same manner as Example 222 except substituting 1-(4-Bromo-thiophen-2-yl)-ethanone for 1-(4-Methyl-thiophen-2-yl)-ethanone. MS (ESI) m/z 480.0 (M+H)$^+$; $^1$H NMR (300 MHz, DMSO-d$_6$) δ ppm 7.29 (s, 1H), 7.26 (s, 1H).

Example 169b

3-[4-Bromo-5-(3-methoxy-prop-1-ynyl)-thiophen-2-yl]-4-hydroxy-6-oxo-6,7-dihydro-thieno[2,3-b]pyridine-5-carbonitrile Prepared in the same manner as Example 110 substituting 3-(4-Bromo-5-iodo-thiophen-2-yl)-4-hydroxy-6-oxo-6,7-dihydro-thieno[2,3-b]pyridine-5-carbonitrile for Example 222. MS (ESI) m/z 421.0 (M+H)$^+$; $^1$H NMR (300 MHz, DMSO-d$_6$) δ ppm 7.48 (s, 1H), 7.32 (s, 1H), 4.41 (s, 2H), 3.35 (s, 3H).

Example 170

3-[4-(6-chloro-2-hydroxyphenyl)-phenyl]-4-hydroxy-6-oxo-6,7-dihydro-thieno[2,3b]-pyridine-5-carbonitrile The titled compound was prepared according to the procedures described in Example 3a-b, substituting 6-chloro-2-methoxyphenylboronic acid for 2,3-dimethoxyphenylboronic acid used in Example 3a was obtained (31.0 mg, 78.5%). $^1$H NMR (300 MHz, DMSO-d$_6$) δ 9.8 (s, 1H), 7.49 (d, 2H, J=9.0 Hz), 7.23 (d, 2H, J =9.0 Hz), 7.18 (t, 1H, J=9.0 Hz), 7.04 (s, 1H), 7.0–6.9 (m, 2H). MS (ESI) m/e 395 (M+H)$^+$, m/e 393 (M−H)$^−$.

Example 171

2-chloro-4-hydroxy-3-(3'-hydroxy-1,1'-biphenyl-4-yl)-6-oxo-6,7-dihydrothieno[2,3-b]pyridine-5-carbonitrile The title compound was prepared according to the method described for Example 60, substituting 3-(4,4,5,5-tetramethyl-1,3,2-dioxaborolan-2-yl)phenol for 2-(4,4,5,5-tetramethyl-1,3,2-dioxaborolan-2-yl)phenol. MS (ESI) m/e 393 (M−H)$^-$; $^1$H NMR (300 MHz, DMSO-$d_6$) δ ppm 6.78 (dd, J=7.12, 2.37 Hz, 1H), 7.06 (m, 1H), 7.12 (d, J=7.80 Hz, 1H), 7.25 (m, 1H), 7.38 (d, J=8.48 Hz, 2H), 7.61 (d, J=8.48 Hz, 2H).

Example 172

2-chloro-3-{4-[(1-cyclobutyl-4-hydroxypiperidin-4-yl)methoxy]phenyl}-4-hydroxy-6-oxo-6,7-dihydrothieno[2,3-b]pyridine-5-carbonitrile The title compound was prepared according to the method described for Example 121, substituting cyclobutanone for acetaldehyde. MS (ESI) m/e 486 (M+H)$^+$; $^1$H NMR (300 MHz, DMSO-$d_6$) δ ppm 1.78 (m, 4H), 1.95 (m, 2H), 2.20 (m, 4H), 2.98 (m, 2H), 3.30 (m, 2H), 3.70 (m, 1H), 3.86 (s, 2H), 5.22 (s, 1H), 6.92 (d, J=8.82 Hz, 2H), 7.22 (d, J=8.82 Hz, 2H), 9.00 (s, 1H), 10.77 (s, 1H).

Example 173

7-[4-(5-cyano-4-hydroxy-6-oxo-6,7-dihydrothieno[2,3-b]pyridin-3-yl)phenyl]hept-6-ynoic acid Example 173 was prepared using the same procedure as described for Example 150 substituting hept-6-ynoic acid for but-3-yn-1-ol in Example 150. MS (ESI) m/e 391 (M−H)$^+$; $^1$H NMR (300 MHz, DMSO-$d_6$): δ ppm 12.4 (br s, 1H), 7.39 (m, 4H), 7.03 (s, 1H), 2.45 (t, J=9, 2H), 2.28 (t, J=9, 2H), 1.54–1.69 (m, 4H).

Example 174

3-(3,5-dichloro-4-hydroxyphenyl)-4-hydroxy-6-oxo-6,7-dihydrothieno[2,3-b]pyridine-5-carbonitrile

Example 174a 4-(4-benzyloxy-3,5-dichloro-phenyl)-2-(2-cyano-acetylamino)-thiophene-3-carboxylic acid ethyl ester To a solution of PCl$_5$ (387 mg, 1.86 mmol) in CH$_2$Cl$_2$ (4 mL) was added cyanoacetic acid (158 mg, 1.86 mmol). The reaction was heated to reflux for 30 minutes. Upon cooling to room temperature, 2-amino-4-(4-benzyolxy-3,5-dichloro-phenyl)-thiophene-3-carboxylic acid ethyl ester (630 mg, 1.49 mmol) in CH$_2$Cl$_2$ (4 mL) was added and the reaction mix was heated to reflux for an additional 30 minutes. Upon cooling to room temperature the reaction was diluted with EtOAc (8 mL) and washed with saturated NaHCO$_3$ soln (8 mL). The aqueous layer was back-extracted with EtOAC (8 mL) and the combined organic layers were washed with brine (8 mL), dried over MgSO$_4$ and concentrated in vacuo to give 610 mg of a pale yellow solid (1.2 mmol, 83% yield).

Example 174b 3-(4-benxyloxy-3,5-dichloro-phenyl)-4-hydroxy-6-oxo-6,7-dihydro-thieno[2,3-b]pyridine-5-carbonitrile To a suspension of NaH (108 mg, 2.7 mmol) in THF (20 mL) was added 4-(4-benzyloxy-3,5-dichloro-phenyl)-2-(2-cyano-acetylamino)-thiophene-3-carboxylic acid ethyl ester (600 mg, 1.2 mmol) in THF (20 mL). The reaction stirred at room temperature for 6 h. It was acidified with 1M HCl and concentrated in vacuo. The resulting orange solid was taken up in H$_2$O and filtered, rinsing with H$_2$O (2×10 mL) and CH$_2$Cl$_2$ (3×10 mL). A green-yellow solid resulted (250 mg, 0.56 mmol, 46% yield).

Example 174

3-(3,5-dichloro-4-hydroxy-phenyl)-4-hydroxy-6-oxo-6,7-dihydro-thieno[2,3-b]pyridine-5-carbonitrile The 3-(4-benzyloxy-3,5-dichloro-phenyl)-4-hydroxy-6-oxo-6,7-dihydro-thieno[2,3-b]pyridine-5-carbonitrile (125 mg, 0.281 mmol) was dissolved in 30% HBr/AcOH (1.3 mL) and sealed in a reaction tube with stirring for 40 minutes at 70° C. The reaction is cooled to room temperature and concentrated in vacuo. The resulting solid is washed with Et$_2$O and filtered, then placed under high vacuum for 2 hours. The solid is taken up in NH$_4$OH (2 mL) and stirred at room temperature for 1 hour. The reaction mix is concentrated and taken up in 1M HCl. The resulting solid is filtered and rinsed with water to give 66 mg of a white solid (0.18 mmol, 66% yield). $^1$H NMR (300 MHz, DMSO-D$_6$) δ 12.45 (bs, 1H), 10.18 (bs, 1H), 7.42 (s, 2H), 7.08 (s, 1H), 4.60 (bs, 1H). MS (ESI APCI) positive ion 353 (M+H)$^+$; negative ion 351 (M−H)$^-$.

Example 175

2-[({(1E)-[4-(5-cyano-4-hydroxy-6-oxo-6,7-dihydrothieno[2,3-b]pyridin-3-yl)phenyl]methylene}amino)oxy]-N-[(2S)-2,3-dihydroxypropyl]acetamide Example 175 was prepared using the same procedure as described for Example 158 substituting (2S)-3-amino-propane-1,2-diol for C-pyridin-2-yl-methylamine in Example 158. MS (ESI) m/e 440.9 (M−H)$^+$; $^1$H NMR (500 MHz, DMSO-$d_6$): δ ppm 12.3 (br s, 1H), 8.39 (s, 1H), 7.66 (t, J=5, 1H), 7.60 (d, J=10, 2H), 7.49 (d, J=10, 2H), 7.03 (s, 1H), 4.55 (s, 2H), 3.50 (m, 2H), 3.30 (m, 2H), 3.04 (m, 1H).

Example 176

4-Hydroxy-6-oxo-3-[4-(1H-pyrazol-3-yl)-phenyl]-6,7-dihydro-thieno[2,3-b]pyridine-5-carbonitrile To a suspension of 3-(4-iodo-phenyl)-4-hydroxy-6-oxo-6,7-dihydro-thieno[2,3-b]pyridine-5-carbonitrile (60 mg, 0.15 mmol) and MgO (18 mg, 0.45 mmol) in 2 mL DMF and 2 mL dioxane, was added Cs$_2$CO$_3$ (0.45 mL, 1M solution in H$_2$O), followed by 3-(4,4,5,5-tetramethyl-[1,3,2]dioxaborolan-2-yl)-1H-pyrazole (38 mg, 0.2 mmol), and Pd(PPh$_3$)$_4$ (10 mg, 0.008 mmol). The reaction was heated to 130° C. using microwave reactor for 15 min, filtered, concentrated and purified by reverse phase HPLC to give the titled compound. MS (ESI) m/e 335 (M+H)$^+$; $^1$H NMR (500 MHz, DMSO-d$_6$): δ 6.61 (s, 1H), 7.00 (s, 1H), 7.43 (d, J=8.42 Hz, 2H), 7.49 (d, J=8.42 Hz, 2H), 8.04 (s, 1H).

Example 177

3-{5-[4-(2,3-dihydroxypropoxy)phenyl]thien-2-yl}-4-hydroxy-6-oxo-6,7-dihydrothieno[2,3-b]pyridine-5-carbonitrile To a suspension of Example 167e (50 mg, 0.12 mmol) in THF (1.5 mL) and water (0.1 mL) was added N-methyl-morpholine-N-oxide (94 mg, 0.8 mmol), followed by osmium tetroxide (2.5% in t-BuOH, 125 mg, 0.012 mmol). The reaction mixture was stirred at 25° C. for 16 h, and was quenched by adding saturated aqueous Na$_2$SO$_3$ (0.5 mL). The resulting mixture was concentrated and purified by RPHPLC on a Waters Symmetry C8 column (25 mm×100 mm, 7 µm particle size) using a gradient of 10% to 100% acetonitrile:0.1% aqueous TFA to provide 12 mg (22%) of Example 177. $^1$H NMR (300 MHz, METHANOL-D4) δ ppm 3.68 (t, J=5.70 Hz, 2H) 4.00 (m, 2H) 4.08 (dd, J=6.99, 5.15 Hz 1H) 6.89 (s, 1H) 6.97 (d, J=8.82 Hz, 2H) 7.16 (d, J=3.68 Hz, 1H) 7.43 (d, J=3.68 Hz, 1H) 7.56 (d, J=8.82 Hz, 2H) MS (ESI) m/z 441.0 (M+H)$^+$.

Example 178

2-Bromo-4-hydroxy-3-[4-(5-hydroxy-pent-1-ynyl)-phenyl]-6-oxo-6,7-dihydro-thieno[2,3-b]pyridine-5-carbonitrile To a stirred solution of 4-hydroxy-3-[4-(5-hydroxy-pent-1-ynyl)-phenyl]-6-oxo-6,7-dihydro-thieno[2,3-b]pyridine-5-carbonitrile (35 mg, 0.1 mmol) in acetic acid (1 mL) was added N-bromosuccinamide (18 mg, 0.1 mmol) in a single portion at room temperature, and stirred at rt overnight. The reaction mixture was concentrated and purified by reverse phase HPLC to afford the titled compound. MS (ESI) m/e 428 (M−H)$^+$; $^1$H NMR (300 MHz, DMSO-d$_6$): δ 1.68–1.75 (m, 2H), 3.51–3.57 (m, 2H), 4.54 (t, J=5.26 Hz, 2H), 7.19 (d, J=8.48 Hz, 2H), 7.31 (d, J=8.48 Hz, 2H).

Example 179

4-hydroxy-6-oxo-3-(5,6,7,8-tetrahydronaphthalen-2-yl)-6,7-dihydrothieno[2,3-b]pyridine-5-carbonitrile The titled compound was prepared according to the procedures as described in Example 29b-d, substituting 1-(5,6,7,8-tetrahydro-naphthalen-2-yl)-ethanone for 1-(4-allyloxy-phenyl)-propan-1-one from 29a. MS (ESI) m/e 323 (M+H)$^+$; $^1$H NMR (300 MHz, DMSO-d$_6$): δ 12.49 (s, 1H), 7.28 (m, 1H), 7.13 (d, J=7.5 Hz, 1H), 7.01 (d, J=7.5 Hz, 1H), 6.92 (s, 1H), 2.73 (br s, 4H), 1.75 (br s, 4H).

Example 180

2-[({(1E)-[4-(5-cyano-4-hydroxy-6-oxo-6,7-dihydrothieno[2,3-b]pyridin-3-yl)phenyl]methylene}amino)oxy]-N-[2-(4-methylpiperazin-1-yl)ethyl]acetamide Example 180 was prepared using the same procedure as described for Example 158 substituting 2-(4-methyl-piperazin-1-yl)-ethylamine for C-pyridin-2-yl-methylamine in Example 158. MS (ESI) m/e 493.1 (M−H)$^+$; $^1$H NMR (500 MHz, DMSO-d$_6$): δ ppm 11.8 (br s, 1H), 8.39 (s, 1H), 7.89 (s, 1H), 7.57 (d, J=10, 2H), 7.48 (d, J=10, 2H), 6.92 (s, 1H), 4.54 (s, 2H), 3.37 (m 2H), 2.76–3.13 (m, 10H), 2.73 (s, 3H).

Example 181

N-{3-chloro-4-[5-(5-cyano-4-hydroxy-6-oxo-6,7-dihydrothieno[2,3-b]pyridin-3-yl)thien-2-yl]phenyl}acetamide

Example 181a

N-[3-chloro-4-(4,4,5,5-tetramethyl-1,3,2-dioxaborolan-2-yl)phenyl]acetamide

Example 181a was prepared according to the procedure described in Example 133a substituting N-(4-Bromo-3-chloro-phenyl)-acetamide for 5-Bromo-1,3-dihydro-indol-2-one. $^1$H NMR (300 MHz, DMSO-D6) δ ppm 1.29 (s, 12H) 2.06 (s, 3H) 7.43 (m, 2H) 7.58 (d, J=8.09 Hz, 1H) 10.19 (s, 1H).

Example 181b

N-{3-chloro-4-[5-(5-cyano-4-hydroxy-6-oxo-6,7-dihydrothieno[2,3-b]pyridin-3-yl)thien-2-yl]phenyl}acetamide The title compound was prepared according to the procedures described in Example 91 substituting Example 181a for 4-(Methylsulfonylamino)phenyl boronic acid in Example 91d. $^1$H NMR (300 MHz, methanol-D4) δ ppm 2.15 (s, 3H) 7.15 (s, 1H) 7.19 (d, J=8.46 Hz, 1H) 7.28 (m, 1H) 7.47 (m, 1H) 7.55 (m, 1H) 7.86 (m, 1H) MS (ESI) m/z 441.8.0 (M+H)$^+$.

Example 182

4-hydroxy-3-[4-(5-hydroxypent-1-ynyl)phenyl]-6-oxo-6,7-dihydrothieno[2,3-b]pyridine-5-carbonitrile Example 182 was prepared using the same procedure as described for Example 150 substituting pent-4-yn-1-ol for but-3-yn-1-ol in Example 150. MS (ESI) m/e 349 (M−H)$^+$; $^1$H NMR (300 MHz, DMSO-d$_6$): δ ppm 12.2 (br s, 1H), 7.39 (d, J=9, 2H), 7.33 (d, J=9, 2H), 6.98 (s, 1H), 3.53 (t, J=9, 2H), 2.45 (t, J=9, 2H), 1.70 (quintet, J=9, 2H).

Example 183

3-[4-bromo-5-(3-methoxyprop-1-ynyl)thien-2-yl]-4-hydroxy-6-oxo-6,7-dihydrothieno[2,3-b]pyridine-5-carbonitrile Example 183 was prepared in the same manner as Example 110 substituting 3-(4-Bromo-5-iodo-thiophen-2-yl)-4-hydroxy-6-oxo-6,7-dihydro-thieno[2,3-b]pyridine-5-carbonitrile (Example 183a) for 4-hydroxy-3-(5-iodo-4-methylthien-2-yl)-6-oxo-6,7-dihydrothieno[2,3-b]pyridine-5- carbonitrile (Example 222). MS (ESI) m/z 421.0 (M+H)$^+$; $^1$H NMR (300 MHz, DMSO-d$_6$) δ ppm 7.48 (s, 1H), 7.32 (s, 1H), 4.41 (s, 2H), 3.35 (s, 3H).

Example 183a 3-(4-Bromo-5-iodo-thiophen-2-yl)-4-hydroxy-6-oxo-6,7-dihydro-thieno[2,3-b]pyridine-5-carbonitrile Example 183a was prepared in the same manner as Example 222 except substituting 1-(4-Bromo-thiophen-2-yl)-ethanone for 1-(4-Methyl-thiophen-2-yl)-ethanone. MS (ESI) m/z 480.0 (M+H)$^+$; $^1$H NMR (300 MHz, DMSO-d$_6$) δ ppm 7.29 (s, 1H), 7.26 (s, 1H).

Example 184

2-[4-(2-chloro-5-cyano-4-hydroxy-6-oxo-6,7-dihydrothieno[2,3-b]pyridin-3-yl)phenoxy]-N-(3-hydroxypropyl)acetamide Example 184a 2-[4-(2-chloro-5-cyano-4-hydroxy-6-oxo-6,7-dihydrothieno[2,3-b]pyridin-3-yl)phenoxy]acetic acid To an ambient suspension of NaH (235 mg, 5.89 mmol, 60% dispersion in mineral oil, washed with dry hexane) in dry THF (6 mL) was added 2-amino-4-(4-ethoxycarbonylmethoxy-phenyl)-5-chloro-thiophene-3-carboxylic acid ethyl ester (1.06 g, 2.36 mmol) as a solution in THF (6 mL). The reaction was stirred overnight at room temperature and was then diluted with 1N NaOH (10 mL) and MeOH (10 mL). After stirring an additional 1.5 h at room temperature, the reaction was concentrated under reduced pressure to ~20 mL. The solution was acidified to pH ~1 with 1N HCl and extracted with EtOAc (3×30 mL). The combined organic layers were dried with anhydrous Na$_2$SO$_4$, filtered, and concentrated under reduced pressure to a beije solid that was used without further purification. MS (ESI) m/e 375 (M−H)$^−$; $^1$H NMR (300 MHz, BENZENE-d$_6$) δ ppm 4.72 (s, 2H), 6.94 (d, J=8.48 Hz, 2H), 7.26 (d, J=8.48 Hz, 2H).

Example 184

2-[4-(2-chloro-5-cyano-4-hydroxy-6-oxo-6,7-dihydrothieno[2,3-b]pyridin-3-yl)phenoxy]-N-(3-hydroxypropyl)acetamide A suspension of 2-[4-(2-chloro-5-cyano-4-hydroxy-6-oxo-6,7-dihydrothieno[2,3-b]pyridin-3-yl)phenoxy]acetic acid (35 mg, 0.093 mmol), HOBt (13 mg, 0.093 mmol), PS-DCC (88 m, 0.121 mmol, 1.37 mmol/g loading), and 3-amino-propan-1-ol (7 mg, 0.0098 mmol) were shaken in a vial at 50 C for 18 h. The reaction was then filtered through celite, eluting with MeOH, and the eluent was concentrated under reduced pressure. The residue was purified by RP-HPLC to give the title compound. MS (ESI) m/e 432 (M−H)$^−$; $^1$H NMR (300 MHz, DMSO-d$_6$) δ ppm 1.60 (m, 2H), 3.21 (m, 2H), 3.42 (t, J=6.27 Hz, 2H), 4.49 (s, 2H), 6.95 (d, J=8.81 Hz, 2H), 7.23 (d, J=8.81 Hz, 2H), 8.11 (m, 1H).

Example 185

2-chloro-3-[4-(cyanomethoxy)phenyl]-4-hydroxy-6-oxo-6,7-dihydrothieno[2,3-b]pyridine-5-carbonitrile Example 185a 4-(4-acetyl-phenoxy)-acetonitrile The title compound was prepared according to the method described for Example 99a, substituting bromoacetonitrile for ethyl bromoacetate. MS (ESI) m/e 174 (M−H)$^−$.

Example 185b 2-cyano-3-(4-cyanomethoxy-phenyl)-but-2-enoic acid ethyl ester

The title compound was prepared according to the method described for Example 99b, substituting 4-(4-acetyl-phenoxy)-acetonitrile for 4-acetyl-phenoxyxacetic acid ethyl ester. MS (ESI) m/e 269 (M−H)$^−$.

Example 185c 2-amino-4-(4-cyanomethoxy-phenyl)-thiophene-3-carboxylic acid ethyl ester A stirred slurry of 2-cyano-3-(4-cyanomethoxy-phenyl)-but-2-enoic acid ethyl ester, (7.9 g, 29 mmol), sulfur (1.03 g, 32 mmol), and morpholine (0.513 mL, 5.9 mmol) in EtOH (100 mL) was heated to 100 C for 6 h and then 60 C for 12 h. The heating bath was removed, and the reaction was filtered and absorbed onto SiO$_2$ gel. The absorbed compound was placed onto a 2 inch bed of SiO$_2$ gel on a scintered-glass funnel, and washed with 850 mL of 1:1 Hx:EtOAc. The eluent was concentrated under reduced pressure to an amber oil that was purified by MPLC (SiO$_2$ gel, 9:1 Hx:EtOAc to 1:1 Hx:EtOAc) to give the title compound. MS (ESI) m/e 301 (M−H)$^−$; $^1$H NMR (300 MHz, DMSO-d$_6$) δ ppm 0.93 (t, J=7.12 Hz, 3H), 3.95 (q, J=7.12 Hz, 2H), 5.17 (s, 2H), 6.15 (s, 1H), 7.00 (m, 2H), 7.23 (d, J=8.82 Hz, 2H), 7.36 (s, 2H).

Example 185d 2-(2-cyano-acetylamino)-4-(4-cyanomethoxy-phenyl)-thiophene-3-carboxylic acid ethyl ester The title compound was prepared according to the method described for Example 60b, substituting 2-amino-4-(4-cyanomethoxy-phenyl)-thiophene-3-carboxylic acid ethyl ester for 2-amino-4-(4-bromophenyl)-thiophene-3-carboxylic acid ethyl ester. MS (ESI) m/e 368 (M−H)$^−$.

Example 185e 2-(2-cyano-acetylamino)-4-(4-cyanomethoxy-phenyl)-5-chloro-thiophene-3-carboxylic acid ethyl ester The title compound was prepared according to the method described for Example 60c substituting 2-(2-cyano-acetylamino)-4-(4-cyanomethoxy-phenyl)-thiophene-3-carboxylic acid ethyl ester for 4-(4-bromophenyl)-2-(2-cyano-acetylamino)-thiophene-3-carboxylic acid ethyl ester. MS (ESI) m/e 402 (M−H)$^−$; $^1$H NMR (300 MHz, DMSO-d$_6$) δ ppm 0.85 (t, J=7.12 Hz, 3H), 4.01 (m, 2H), 4.31 (s, 2H), 5.22 (s, 2H), 7.11 (d, J=8.82 Hz, 2H), 7.25 (m, 2H), 11.40 (s, 1H).

Example 185

2-chloro-3-[4-(cyanomethoxy)phenyl]-4-hydroxy-6-oxo-6,7-dihydrothieno[2,3-b]pyridine-5-carbonitrile The title compound was prepared according to the method described for Example 60d, substituting 2-(2-cyano-acetylamino)-4-(4-cyanomethoxy-phenyl)-5-chloro-thiophene-3-carboxylic acid ethyl ester for 4-(4-bromophenyl)-5-chloro-2-(2-cyano-acetylamino)-thiophene-3-carboxylic acid ethyl ester. MS (ESI) m/e 356 (M−H)−; $^1$H NMR (300 MHz, DMSO-d$_6$) δ ppm 5.22 (s, 2H), 7.08 (d, J=8.82 Hz, 2H), 7.33 (d, J=8.48 Hz, 2H), 12.12 (s, 1H).

Example 186

4-hydroxy-3-[4-(3-methoxyprop-1-ynyl)phenyl]-6-oxo-6,7-dihydrothieno[2,3-b]pyridine-5-carbonitrile The title compound was prepared according to the procedure described in example 193 substituting 3-methoxypropyne for hex-5-ynenitrile. MS (ESI) m/e 335 (M−H)+; $^1$H NMR (400 MHz, DMSO-d$_6$): δ ppm 1.90 (s, 3H), 4.34 (s, 2H), 6.68 (s, 1H), 7.35 (d, J=8.29 Hz, 2H), 7.46 (d, J=8.29, 2H).

Example 187

4-Hydroxy-6-oxo-3-[4-(4-pyrrolidin-1-yl-but-1-enyl)-phenyl]-6,7-dihydro-thieno[2,3-b]pyridine-5-carbonitrile

Example 187a

1-But-3-enyl-pyrrolidine

4-Bromo-but-1-ene (81 mg, 0.6 mmol) was added dropwise to a stirred suspension of pyrrolidine (50 μL, 0.6 mmol) and Cs$_2$CO$_3$ (196 mg, 0.6 mmol) in 1 mL DMF. The mixture was heated to 120° C. using microwave for 20 min, then filtered and used for the next step directly without purification.

Example 187b

4-Hydroxy-6-oxo-3-[4-(4-pyrrolidin-1-yl-but-1-enyl)-phenyl]-6,7-dihydro-thieno[2,3-b]pyridine-5-carbonitrile The titled compound was then prepared following the standard Heck reaction procedure described in Example 8, substituting 1-but-3-enyl-pyrrolidine from Example 19a for but-3-en-1-ol used in Example 8. MS (ESI) m/e 392 (M+H)+; $^1$H NMR (500 MHz, DMSO-d$_6$): δ 1.89–1.94 (m, 4H), 2.51–2.56 (m, 2H), 2.86–2.96 (m, 2H), 3.24–3.25 (m, 4H), 6.20 (dt, J=15.83, 6.90 Hz, 1H), 6.55 (d, J=15.91 Hz, 1H), 6.63 (s, 1H), 7.32 (d, J=8.11 Hz, 2H), 7.42 (d, J=8.11 Hz, 2H).

Example 188 tert-butyl 4-[5-(5-cyano-4-hydroxy-6-oxo-6,7-dihydrothieno[2,3-b]pyridin-3-yl)thien-2-yl]phenylcarbamate The title compound was prepared according to the procedures described in Example 91 substituting [4-(4,4,5,5-Tetramethyl-[1,3,2]dioxaborolan-2-yl)-phenyl]-carbamic acid tert-butyl ester for 4-(Methylsulfonylamino)phenyl boronic acid in Example 91d. $^1$H NMR (300 MHz, METHANOL-D4) δ ppm 1.53 (s, 9H) 7.13 (s, 1H) 7.23 (m, 3H) 7.43 (d, J=8.82 Hz, 1H) 7.55 (m, 2H) MS (ESI) m/z 466.0 (M+H)+, 483.1 (M+NH$_4$)+.

Example 189

4-hydroxy-3-[5-(4-hydroxyphenyl)-4-methylthien-2-yl]-6-oxo-6,7-dihydrothieno[2,3-b]pyridine-5-carbonitrile To 4-hydroxy-3-(5-iodo-4-methylthien-2-yl)-6-oxo-6,7-dihydrothieno[2,3-b]pyridine-5-carbonitrile (200 mg, 0.48 mmol, Example 222) and MgO (58.0 mg, 1.44 mmol) in dioxane (1.25 ml) and DMF (1.25 ml) was added H$_2$O (0.530 ml) and the mixture was stirred for 10 min and then degassed with N$_2$ for 2 min. 4-hydroxyphenylboronic acid (86 mg, 0.62 mmol), Cs$_2$CO$_3$ (344 mg, 1.06 mmol) and Pd(PPh$_3$)$_4$ (28.0 mg, 0.024 mm were added, the vessel flushed with N$_2$, and then stirred at 80° C. for 2 h. The reaction was cooled to rt and overwhelmed with MeOH, filtered and the filtrate was concentrated to give a brown oil. The residue was taken up in DMSO: MeOH (1:1) and purified by reverse phase HPLC to give the title compound (98 mg, 0.26 mmol, 53%) as a light yellow solid MS (ESI) m/z 381.0 (M+H+); $^1$H NMR (300 MHz, DMSO-d$_6$) δ ppm 7.51 (s, 3H), 7.28 (d, 1H), 6.83 (d, 1H), 6.79 (s, 1H), 4.09 (m, 1H), 2.22 (s, 1H) and 4-hydroxy-3-(4-methylthien-2-yl)-6-oxo-6,7-dihydrothieno[2,3-b]pyridine-5-carbonitrile (Example 217) as a solid.

Example 190

2-chloro-3-4-(diallylamino)phenyl]-4-hydroxy-6-oxo-6,7-dihydrothieno[2,3-b]pyridine-5-carbonitrile

Example 190a 2-(2-Cyano-acetylamino)-4-(4-nitrophenyl)-thiophene-3-carboxylic acid ethyl ester The titled compound was prepared according to the method described for Example 2b, substituting 4-nitroacetophenone for 3,5-dimethylacetophenone in Example 2a. MS (ESI) m/e 358 (M−H)−.

Example 190b 2-(2-Cyano-acetylamino)-4-(4-nitrophenyl)-5-chloro-thiophene-3-carboxylic acid ethyl ester The title compound was prepared according to the method described for Example 60c, substituting 2-(2-cyano-acetylamino)-4-(4-nitrophenyl)-thiophene-3-carboxylic acid ethyl ester for 4-(4-bromophenyl)-2-(2-cyano-acetylamino)-thiophene-3-carboxylic acid ethyl ester. MS (ESI) m/e 392 (M−H)−.

Example 190c

2-(2-Cyano-acetylamino)-4-(4-aminophenyl)-5-chloro-thiophene-3-carboxylic acid ethyl ester

A mixture of 2-(2-cyano-acetylamino)-4-(4-nitrophenyl)-5-chloro-thiophene-3-carboxylic acid ethyl ester (1.00 g, 2.54 mmol), Fe (432 mg, 7.71 mmol), and $NH_4Cl$ (110 mg, 2.03 mmol) in EtOH (20 mL) and $H_2O$ (10 mL) was heated to 85 C for 2 h. The reaction was cooled to room temperature and filtered through a plug of celite, eluting with hot MeOH. The eluent was concentrated under reduced pressure to give a solid that was used in the next step without further purification. MS (ESI) m/e 362 $(M-H)^-$.

Example 190d

2-(2-Cyano-acetylamino)-4-(4-diallylaminophenyl)-5-chloro-thiophene-3-carboxylic acid ethyl ester

An ambient mixture of 2-(2-cyano-acetylamino)-4-(4-aminophenyl)-5-chloro-thiophene-3-carboxylic acid ethyl ester (365 mg, 1.00 mmol), $NaHCO_3$ (210 mg, 2.50 mmol), and allyl bromide (0.173 mL, 2.00 mmol) in DMF (3.5 mL) was stirred for 18 h. The reaction was then diluted with $H_2O$ (5 mL) and $Et_2O$ (5 mL). The layers were separated, and the aqueous was extracted with additional $Et_2O$ (2×5 mL). The combined organic layers were dried with anhydrous $Na_2SO_4$, filtered, and concentrated under reduced pressure to an oil that was used without further purification. MS (ESI) m/e 442 $(M-H)^-$.

Example 190

2-chloro-3-[4-(diallylamino)phenyl]-4-hydroxy-6-oxo-6,7-dihydrothieno[2,3-b]pyridine-5-carbonitrile

The title compound was prepared according to the method described for Example 60d, substituting 2-(2-cyano-acetylamino)-4-(4-diallylaminophenyl)-5-chloro-thiophene-3-carboxylic acid ethyl ester for 4-(4-bromophenyl)-5-chloro-2-(2-cyano-acetylamino)-thiophene-3-carboxylic acid ethyl ester. MS (ESI) m/e 396 $(M-H)^-$; $^1H$ NMR (300 MHz, DMSO-$d_6$) δ ppm 3.96 (d, J=4.75 Hz, 4H), 5.19 (m, 4H), 5.88 (m, 2H), 6.67 (d, J=8.82 Hz, 2H), 7.10 (d, J=8.82 Hz, 2H).

Example 191

4-hydroxy-3-[5-(1H-indol-5-yl)thien-2-yl]-6-oxo-6,7-dihydrothieno[2,3-b]pyridine-5-carbonitrile

The title compound was prepared according to the procedures described in Example 91 substituting 5-(boronic acid)-1H-indole for 4-(Methylsulfonylamino)phenyl boronic acid in Example 91d. $^1H$ NMR (300 MHz, DMSO-D6) δ ppm 6.47 (m, 1H) 7.17 (s, 1H) 7.32 (m, 2H) 7.38 (m, 1H) 7.42 (m, 2H) 7.83 (s, 1H) 11.18 (s, 1H) MS (ESI) m/z 389.9 $(M+H)^+$.

Example 192

2-bromo-3-(5'-bromo-2'-hydroxy-1,1'-biphenyl-4-yl)-4-hydroxy-6-oxo-6,7-dihydrothieno[2,3-b]pyridine-5-carbonitrile

Example 192 was prepared using the same procedure as described for Example 7 substituting 4-hydroxy-3-(2'-hydroxy-1,1'-biphenyl-4-yl)-6-oxo-6,7-dihydrothieno[2,3-b]pyridine-5-carbonitrile for 4-hydroxy-6-oxo-3-phenyl-6,7-dihydrothieno[2,3-b]pyridine-5-carbonitrile in Example 7. The title compound was one of the two reaction products that were purified on a RP-HPLC system. MS (ESI) m/e 516.7 $(M-H)^+$; $^1H$ NMR (400 MHz, DMSO-$d_6$): δ ppm 12.31 (br s, 1H), 9.95 (s, 1H), 7.60 (d, J=7.98, 2H), 7.43 (d, J=2.45, 1H), 7.35–7.32 (m, 3H), 6.93 (d, J=8.60, 1H).

Example 193

3-[4-(5-cyanopent-1-ynyl)phenyl]-4-hydroxy-6-oxo-6,7-dihydrothieno[2,3-b]pyridine-5-carbonitrile

To a solution of 3-(4-iodo-phenyl)-4-hydroxy-6-oxo-6,7-dihydro-thieno[2,3-b]pyridine-5-carbonitrile (60 mg, 0.15 mmol) in 1.5 mL DMF was added diethylamine (0.16 mL, 1.5 mmol), followed by copper(I) iodide (trace), Pd(PPh$_3$)Cl$_2$ (3.5 mg, 0.005 mmol), and triphenylphosphine (12 mg, 0.04 mmol). The resulting mixture was stirred at rt for 5 min, after which hex-5-ynenitrile (50 μL, 0.5 mmol) was added. The reaction was then heated to 90° C. using microwave reactor for 20 min, filtered, concentrated and purified by reverse phase HPLC to give the titled compound. MS (ESI) m/e 358 $(M-H)^+$; $^1H$ NMR (300 MHz, DMSO-$d_6$): δ 1.82–1.91 (m, 2H), 2.56 (t, J=7.12 Hz, 2H), 2.65 (t, J=7.12 Hz, 2H), 6.67 (s, 1H), 7.31 (d, J=8.48 Hz, 2H) 7.43 (d, J=8.48, 2H), 10.80 (s, 1H).

Example 194

2-[4-(2-chloro-5-cyano-4-hydroxy-6-oxo-6,7-dihydrothieno[2,3-b]pyridin-3-yl)phenoxy]acetamide

Example 194a

2-amino-4-(4-ethoxycarbonylmethoxy-phenyl)-thiophene-3-carboxylic acid ethyl ester

The title compound was prepared according to the method described for Example 60b, substituting 2-amino-4-(4-ethoxycarbonylmethoxy-phenyl)-thiophene-3-carboxylic acid ethyl ester hydrochloride salt for 2-amino-4-(4-bromophenyl)-thiophene-3-carboxylic acid ethyl ester. MS (ESI) m/e 415 $(M-H)^-$.

Example 194b

2-amino-4-(4-ethoxycarbonylmethoxy-phenyl)-5-chloro-thiophene-3-carboxylic acid ethyl ester

The title compound was prepared according to the method described for Example 60c, substituting 2-amino-4-(4-ethoxycarbonylmethoxy-phenyl)-thiophene-3-carboxylic acid ethyl ester for 4-(4-bromophenyl)-2-(2-cyano-acetylamino)-thiophene-3-carboxylic acid ethyl ester. MS (ESI) m/e 449 $(M-H)^-$; $^1H$ NMR (300 MHz, DMSO-$d_6$) δ ppm 0.86 (t, J=7.12 Hz, 3H), 1.20 (t, J=7.12 Hz, 3H), 4.01 (q, J=7.12 Hz, 2H), 4.18 (q, J=7.12 Hz, 2H), 4.30 (s, 2H), 4.81 (s, 2H), 6.96 (m, 2H), 7.16 (m, 2H), 11.38 (s, 1H).

Example 194

2-[4-(2-chloro-5-cyano-4-hydroxy-6-oxo-6,7-dihydrothieno[2,3-b]pyridin-3-yl)phenoxy]acetamide To an ambient suspension of NaH (1.56 g, 39.0 mmol, 60% dispersion in mineral oil, washed with dry hexane) in dry THF (40 mL) was added 2-amino-4-(4-ethoxycarbonylmethoxy-phenyl)-5-chloro-thiophene-3-carboxylic acid ethyl ester (7.0 g, 15.6 mmol) as a solution in THF (40 mL). The reaction was stirred overnight at room temperature and was then diluted with 7N $NH_3$ in MeOH (150 mL). After stirring an additional 1 h at room temperature, the reaction was concentrated under reduced pressure to a solid. The residue was dissolved in $H_2O$ (50 mL) and acidified to pH ~1 with 1N HCl. The solid was filtered, air-dried, and purified by RP-HPLC to give the title compound as a white solid. MS (ESI) m/e (M–H)$^-$; $^1$H NMR (300 MHz, ACETONE-$d_6$) δ ppm 4.44 (s, 2H), 6.90 (d, J=8.81 Hz, 2H), 7.00 (brs, 2H), 7.18 (d, J=8.81 Hz, 2H).

Example 195

2-[({(1E)-[4-(5-cyano-4-hydroxy-6-oxo-6,7-dihydrothieno[2,3-b]pyridin-3-yl)phenyl]methylene}amino)oxy]-N-(2-pyridin-2-ylethyl)acetamide Example 195 was prepared using the same procedure as described for Example 158 substituting 2-pyridin-2-yl-ethylamine for C-pyridin-2-yl-methylamine in Example 158. MS (ESI) m/e 471.9 (M–H)$^+$; $^1$H NMR (500 MHz, DMSO-$d_6$): δ ppm 12.0 (br s, 1H), 8.67 (d, J=5, 1H), 8.31 (s, 1H), 8.11 (t, J=5, 1H), 8.00 (t, J=5, 1H), 7.62–7.68 (m, 2H), 7.58 (m, 4H), 6.99 (s, 1H), 4.48 (s, 2H), 3.56 (m, 2H), 3.09 (m, 2H).

Example 196

2-chloro-4-hydroxy-3-{4-[(4-hydroxypiperidin-4-yl)methoxy]phenyl}-6-oxo-6,7-dihydrothieno[2,3-b]pyridine-5-carbonitrile

Example 196a 1-oxa-3-aza-spiro-[2.5]octane-6-caboxylic acid tert-butyl ester NaH (1.33 g, 33.17 mmol, 60% dispersion in mineral oil) was washed with dry hexane (2×10 mL) and was then suspended in DMSO (33 mL). To the suspension was added solid trimethylsulfoxonium iodide (7.30 g, 33.17 mmol) in 5 portions over 30 minutes. After stirring the reaction at 40 C for 1 h, a solution of 4-oxo-piperidine-1-carboxylic acid tert-butyl ester (6.0 g, 30.2 mmol) in DMSO (5 mL) was slowly added. The reaction was heated to 50 C for 12 h and was then quenched by the addition of EtOAc (50 mL) and saturated aqueous $NH_4Cl$ (20 mL). The layers were separated, and the aqueous was extracted with additional EtOAc (2×20 mL). The combined organic layers were washed with brine (2×20 mL), dried with anhydrous $Na_2SO_4$, filtered, and concentrated under reduced pressure to give the title compound, which was used without further purification. $^1$H NMR (300 MHz, DMSO-$d_6$) δ ppm 1.38 (m, 11H), 1.64 (m, 2H), 2.65 (s, 2H), 3.36 (m, 2H), 3.50 (m, 2H).

Example 196b 4-(4-acetyl-phenoxymethyl)-4-hydroxy-piperidine-1-carboxylic acid tert-butyl ester A solution of 4-hydroxyacetophenone (2.11 g, 15.49 mmol), 1-oxa-3-aza-spiro-[2.5]octane-6-caboxylic acid tert-butyl ester (3.0 g, 14.1 mmol), and KOH (15.5 mL, 15.5 mmol, 1N in $H_2O$) in isopropanol (47 mL) was heated to reflux overnight. The reaction was then quenched by the addition of $H_2O$ (20 mL) and EtOAc (30 mL). The layers were separated, and the aqueous was extracted with additional EtOAc (2×30 mL). The combined organic layers were washed with brine (2×20 mL), dried with anhydrous $Na_2SO_4$, filtered, and concentrated under reduced pressure. The residue was purified by MPLC ($SiO_2$ gel, 3:1 Hx:EtOAc to 100% EtOAc) to give the title compound. MS (ESI) m/e 250 (M—$CO_2C(CH_3)_3$)$^+$; $^1$H NMR (300 MHz, DMSO-$d_6$) δ ppm 1.40 (s, 9H), 1.55 (m, 4H), 2.50 (s, 3H), 3.08 (s, 2H), 3.74 (d, J=12.54 Hz, 2H), 3.86 (s, 2H), 4.79 (s, 1H), 7.04 (m, 2H), 7.91 (m, 2H).

Example 196c

4-[4-(2-cyano-2-ethoxycarbonyl-1-methyl-vinyl)-phenoxymethyl]-4-hydroxy-piperidine-1-carboxylic acid tert-butyl ester The title compound was prepared according to the method described for Example 99b, substituting 4-(4-acetyl-phenoxymethyl)-4-hydroxy-piperidine-1-carboxylic acid tert-butyl ester for 4-Acetyl-phenoxyxacetic acid ethyl ester. MS (ESI) m/e 443 (M–H)$^-$.

Example 196d

4-[4-(5-amino-4-ethoxycarbonyl-thiophene-3-yl)-phenoxymethyl]-4-hydroxy-piperidine-1-carboxylic acid tert-butyl ester The title compound was prepared according to the method described for Example 99c, substituting 4-[4-(2-cyano-2-ethoxycarbonyl-1-methyl-vinyl)-phenoxymethyl]-4-hydroxy-piperidine-1-carboxylic acid tert-butyl ester for 2-cyano-3-(4-ethoxycarbonylmethoxy-phenyl)-but-2-enoic acid ethyl ester. MS (ESI) m/e 475 (M–H)$^-$; $^1$H NMR (300 MHz, DMSO-$d_6$) δ ppm 0.95 (t, J=7.12 Hz, 3H), 1.40 (s, 9H), 1.56 (m, 4H), 3.05 (br s, 2H), 3.73 (m, 4H), 3.97 (m, 2H), 4.73 (s, 1H), 6.08 (s, 1H), 6.86 (m, 2H), 7.15 (m, 2H), 7.33 (s, 2H).

Example 196

2-chloro-4-hydroxy-3-{4-[(4-hydroxypiperidin-4-yl)methoxy]phenyl}-6-oxo-6,7-dihydrothieno[2,3-b]pyridine-5-carbonitrile To an ambient solution of 4-[4-(5-amino-4-ethoxycarbonyl-thiophene-3-yl)-phenoxymethyl]-4-hydroxy-piperidine-1-carboxylic acid tert-butyl ester (900 mg 1.66 mmol) in DCM (6 mL) was added $SO_2Cl_2$. The reaction was stirred at room temperature for 0.5 h and was quenched by the addition of saturated aqueous $NaHCO_3$ (10 mL) and EtOAc (15 mL). The layers were separated, and the aqueous was extracted with additional EtOAc (2×20 mL). The combined organic layers were washed with brine (2×20 mL), dried with anhydrous $Na_2SO_4$, filtered, and concentrated under reduced pressure to a brown residue.

The residue was dissolved in THF (4 mL) and slowly added to a suspension of NaH (160 mg, 4.0 mmol, 60% dispersion in mineral oil) in THF (4.0 mL) over 5 minutes. The reaction was stirred overnight and was quenched by the addition of 1N HCl (10 ml) and EtOAc (15 mL). The combined organic layers were dried with anhydrous $Na_2SO_4$, filtered, and concentrated under reduced pressure to a brown residue. The residue was immediately dissolved in DCM (4 mL) and TFA (4 mL) was added in a single portion. The reaction was stirred for 2 h and was then concentrated under reduced pressure. The residue was purified by RP-HPLC to give the title compound as a solid. $^1$H NMR (300 MHz, DMSO-d6) δ ppm 1.76 (m, 2H), 1.89 (m, 2H), 3.27 (m, 4H), 3.86 (s, 2H), 5.16 (br s, 1H), 6.91 (d, J=8.82 Hz, 2H), 7.21 (d, J=8.82 Hz, 2H), 8.23 (br s, 1H).

Example 197

3-(2'-amino-1,1'-biphenyl-4-yl)-2-chloro-4-hydroxy-6-oxo-6,7-dihydrothieno[2,3-b]pyridine-5-carbonitrile Example 197 was prepared using the same procedure as described for Example 60 substituting 2-aminophenyl boronic acid for 2-(4,4,5,5-tetramethyl-1,3,2-dioxaborolan-2-yl)phenol in Example 60. MS (ESI) m/e 391.7 (M–H)$^+$; $^1$H NMR (500 MHz, DMSO-d$_6$): δ ppm 10.7 (br s, 1H), 7.36 (m, 4H), 7.06 (br s, 2H), 6.79 (br s, 1H), 6.67 (s, 1H), 4.78 (br s, 2H).

Example 198

4-hydroxy-6-oxo-3-(1,2,3,4-tetrahydronaphthalen-2-yl)-6,7-dihydrothieno[2,3-b]pyridine-5-carbonitrile The titled compound was prepared using the same procedure as described for Example 42, substituting 1,2,3,4-tetrahydro-naphthalene-2-carboxylic acid for indan-2-carboxylic acid in the synthesis described in Example 42a. MS (ESI) m/e 345 (M+Na)$^+$, 340 (M+NH$_4$)$^+$, 323 (M+H)$^+$; 321 (M–H)$^-$. $^1$H NMR (300 MHz, DMSO-d$_6$) δ 1.73 (m, 1H), 2.09 (m, 1H), 2.67 (dd, J=15.94, 11.53 Hz, 1H), 2.82 (m, 2H), 3.12 (dd, J=16.28, 3.39 Hz, 1H), 3.79 (m, 1H), 6.39, (s, 1H), 7.07, (m, 4H).

Example 199

3-(5-bromothien-2-yl)-4-hydroxy-6-oxo-6,7-dihydrothieno[2,3-b]pyridine-5-carbonitrile The title compound was prepared according to the procedure describe in Example 91c. $^1$H NMR (300 MHz, DMSO-D6) δ ppm 6.94 (s, 1H) 7.06 (d, J=3.68 Hz, 1H) 7.37 (d, J=4.04 Hz, 1H) MS (ESI) m/z 354.0 (M+H)$^+$, 372 (M+NH$_4$)$^+$.

Example 200

4-hydroxy-3-[5-(4-nitrophenyl)thien-2-yl]-6-oxo-6,7-dihydrothieno[2,3-b]pyridine-5-carbonitrile The title compound was prepared according to the procedures described in Example 91 substituting 4-nitrophenyl boronic acid for 4-(Methylsulfonylamino)phenyl boronic acid in Example 91d. $^1$H NMR (300 MHz, DMSO-D6) δ ppm 7.26 (s, 1H) 7.48 (d, J=4.04 Hz, 1H) 7.75 (d, J=3.68 Hz, 1H) 7.94 (m, 2H) 8.26 (d, J=8.82 Hz, 2H) MS (ESI-Q1) m/z 393.7 (M+H)$^+$.

Example 201

6-[4-(5-cyano-4-hydroxy-6-oxo-6,7-dihydrothieno[2,3-b]pyridin-3-yl)phenyl]hex-5-ynoic acid The title compound was prepared according to the procedure described in Example 32, substituting hex-5-ynoic acid for hex-5-ynenitrile used in Example 32. MS (ESI) m/e 377 (M–H)$^+$; $^1$H NMR (300 MHz, DMSO-d$_6$): δ 1.62–1.79 (m, 2H), 2.06–2.38 (m, 4H), 6.66 (s, 1H), 7.28 (d, J=8.48 Hz, 2H), 7.42 (d, J=8.48 Hz, 2H).

Example 202

3-[4-(4-cyanobut-1-ynyl)phenyl]-4-hydroxy-6-oxo-6,7-dihydrothieno[2,3-b]pyridine-5-carbonitrile Example 202 was prepared using the same procedure as described for Example 150 substituting pent-4-ynenitrile for but-3-yn-1-ol in Example 150. MS (ESI) m/e 344 (M–H)$^+$; $^1$H NMR (300 MHz, DMSO-d$_6$): δ ppm 12.37 (br s, 1H), 7.42 (d, J=9, 2H), 7.37 (d, J=9, 2H), 7.02 (s, 1H), 2.81–2.83 (m, 4H).

Example 203

2-[({(1E)-[4-(5-cyano-4-hydroxy-6-oxo-6,7-dihydrothieno[2,3-b]pyridin-3-yl)phenyl]methylene}amino)oxy]-N-(pyridin-3-ylmethyl)acetamide Example 203 was prepared using the same procedure as described for Example 158 substituting C-pyridin-3-yl-methylamine for C-pyridin-2-yl-methylamine in Example 158. MS (ESI) m/e 458.1 (M–H)$^+$; $^1$H NMR (500 MHz, DMSO-d$_6$): δ ppm 12.00 (br s, 1H), 8.54 (dd, J=10.5, 2H), 8.55 (t, J=5, 1H), 8.39 (s, 1H), 8.06 (d, J=5, 1H), 7.67 (m, 1H), 7.57 (d, J=10, 2H), 7.50 (d, J=10, 2H), 6.99 (s, 1H), 4.61 (s, 2H), 4.46 (d, J=5, 1H).

Example 204

3-(2,3-dihydro-1,4-benzodioxin-6-yl)-4-hydroxy-6-oxo-6,7-dihydrothieno[2,3-b]pyridine-5-carbonitrile The titled compound was prepared according to the procedures as described in Example 2, substituting 1-(2,3-Dihydro-benzo[1,4]dioxin-6-yl)-ethanone for 3,5-dimethylacetophenone from Example 2a. MS (ESI) m/e 327 (M+H)$^+$; $^1$H NMR (300 MHz, DMSO-d$_6$): δ 12.46 (s, 1H), 6.93 (s, 1H), 6.91 (d, J=1.7 Hz, 1H), 6.86 (d, J=2.03 Hz, 1H), 6.83 (s, 1H), 4.25 (s, 4H).

Example 205

N-{4-[5-(5-cyano-4-hydroxy-6-oxo-6,7-dihydrothieno[2,3-b]pyridin-3-yl)-2-phenylthien-3-yl]phenyl}methanesulfonamide To 3-[4-Bromo-5-(3-methoxy-prop-1-ynyl)-thiophen-2-yl]-4-hydroxy-6-oxo-6,7-dihydro-thieno[2,3-b]pyridine-5-carbonitrile (150 mg, 0.31 mmol, Example 183a) and MgO (43.0 mg, 1.07 mmol) in dioxane (1.25 ml) in DMF (1.25 ml) was added H₂O (0.351 ml) and the mixture was stirred for 10 min and then degassed with N₂ for 2 min. Phenylboronic acid (42.0 mg, 0.31 mmol), Cs₂CO₃ (226 mg, 0.70 mmol) and Pd(PPh₃)₄ (20.0 mg, 0.017 mmol) were added, the vessel flushed with N₂, and then stirred at 70° C. for 2 h. Then p-methanesulfonylamide boronic acid (135 mg, 0.62 mmol) was added and the temperature was adjusted to 95° C. and the reaction was stirred for an additional 5 h. The reaction was cooled to rt and overwhelmed with MeOH, filtered and the filtrate was concentrated to give a brown oil. The residue was taken up in DMSO:MeOH (1:1) and purified by RP-HPLC to give the title compound. MS (ESI) m/z 520.0 (M+H⁺); ¹H NMR (300 MHz, DMSO-d₆) δ ppm 9.82 (s, 1H), 7.45–7.10 (m, 11H), 3.02 (s, 3H).

Example 206

4-hydroxy-6-oxo-3-(5-vinylthien-2-yl)-6,7-dihydrothieno[2,3-b]pyridine-5-carbonitrile To a degassed suspension of Example 91c (100 mg, 0.383 mmol), MgO (46 mg, 1.15 mmol) and tributyl vinyl stannane (182 mg, 0.575 mmol) in DME (2.5 mL) and DMF (0.6 mL) was added dicholorobis(triphenylphosphine)palladium (14 mg, 0.02 mmol). The reaction mixture was heated at 100° C. for 10 minutes in a microwave reactor and then centrifuged. The supernatant was purified by RPHPLC on a Waters Symmetry C8 column (25 mm×100 mm, 7 μm particle size) using a gradient of 10% to 100% acetonitrile: 0.1% aqueous TFA to provide 22 mg (19%) of the title compound. ¹H NMR (300 MHz, METHANOL-D4) δ ppm 5.13 (d, J=15.77 Hz 1H) 5.54 (d, J=11.22 Hz, 1H) 6.82 (dd, J=17.65, 10.66 Hz, 1H) 6.95 (d, J=3.68 Hz, 1H) 7.05 (s, 1H) 7.13 (d, J=3.68 Hz, 1H) MS (ESI) m/z 300.9 (M+H)⁺, 317.9 (M+NH₄)⁺.

Example 207

4-hydroxy-6-oxo-3-(5-pyrazin-2-ylthien-2-yl)-6,7-dihydrothieno[2,3-b]pyridine-5-carbonitrile The title compound was prepared according to the procedures described in Example 151 substituting tributylstannyl-pyrazine for 2-(tributylstannyl)-pyridine in Example 151c. ¹H NMR (300 MHz, DMSO-D6) δ ppm 7.01 (s, 1H) 7.74 (d, J=4.04 Hz, 1H) 7.86 (d, J=4.04 Hz, 1H) 8.46 (d, J=2.57 Hz, 1H) 8.55 (dd, J=2.57, 1.47 Hz, 1H) 9.21 (d, J=1.84 Hz, 1H); MS (ESI) m/z 353.0 (M+H)⁺.

Example 208

2-[({(1E)-[4-(5-cyano-4-hydroxy-6-oxo-6,7-dihydrothieno[2,3-b]pyridin-3-yl)phenyl]methylene}amino)oxy]-N-[(1R)-1-(hydroxymethyl)-3-methylbutyl]acetamide Example 208 was prepared using the same procedure as described for Example 158 substituting (2R)-2-Amino-4-methyl-pentan-1-ol for C-pyridin-2-yl-methylamine in Example 158. MS (ESI) m/e 467.1 (M–H)⁺; ¹H NMR (500 MHz, DMSO-d₆): δ ppm 12.40 (br s, 1H), 8.39 (s, 1H), 7.59 (d, J=10, 2H), 7.48 (d, J=10, 2H), 7.37 (d, J=10, 2H), 7.06 (s, 1H), 4.50 (s, 2H), 3.86 (m, 1H), 3.25–3.37 (m, 2H), 1.61 (m 1H), 1.31 (m, 2H), 0.82 (d, J=10, 6H).

Example 210

4-hydroxy-3-{4-[(E)-({2-[(2R)-2-(hydroxymethyl)pyrrolidin-1-yl]-2-oxoethoxy}imino)methyl]phenyl}-6-oxo-6,7-dihydrothieno[2,3-b]pyridine-5-carbonitrile Example 210 was prepared using the same procedure as described for Example 158 substituting D-prolinol for C-pyridin-2-yl-methylamine in Example 158. MS (ESI) m/e 451 (M–H)⁺; ¹H NMR (500 MHz, DMSO-d₆): δ ppm 12.23 (br s, 1H), 8.35 (s, 1H), 7.58 (d, J=10, 2H), 7.48 (d, J=10, 2H), 7.02 (s, 1H), 4.76 (s, 2H), 3.97 (m, 2H), 3.28–3.33 (m, 3H), 1.76–1.90 (m, 4H).

Example 211

3-(2,3-dihydro-1H-inden-5-yl)-4-hydroxy-6-oxo-6,7-dihydrothieno[2,3-b]pyridine-5-carbonitrile The titled compound was prepared according to the procedures as described in Example 29b-d, substituting 1-indan-5-yl-ethanone for 1-(4-allyloxy-phenyl)-propan-1-one from 29a. MS (ESI) m/e 309 (M+H)⁺; ¹H NMR (300 MHz, DMSO-d₆): δ 12.52 (s, 1H), 7.25 (s, 1H), 7.20 (d, J=7.8 Hz, 1H), 7.15 (dd, J=7.8, 1.7 Hz, 1H), 6.95 (s, 1H), 2.87 (t, J=7.5 Hz, 4H), 2.04 (p, J=7.5 Hz, 2H).

Example 212

4-hydroxy-3-[5-(4-hydroxybut-1-ynyl)thien-2-yl]-6-oxo-6,7-dihydrothieno[2,3-b]pyridine-5-carbonitrile The title compound was prepared according to the procedure described in Example 122 substituting But-3-yn-1-ol for 3-Methoxy-propyne. ¹H NMR (300 MHz, DMSO-D6) δ ppm 2.60 (t, J=6.80 Hz, 2H) 3.58 (t, J=6.80 Hz, 2H) 7.13 (d, J=3.68 Hz, 1H) 7.16 (s, 1H) 7.25 (d, J=3.68 Hz, 1H) MS (ESI) m/z 342.8 (M+H)⁺.

Example 213

2-[({(1E)-[4-(5-cyano-4-hydroxy-6-oxo-6,7-dihydrothieno[2,3-b]pyridin-3-yl)phenyl]methylene}amino)oxy]-N-[3-(dimethylamino)propyl]acetamide Example 213 was prepared using the same procedure as described for Example 158 substituting V,N-dimethyl-propane-1,3-diamine for C-pyridin-2-yl-methylamine in Example 158. MS (ESI) m/e 452.1 (M–H)⁺; ¹H NMR (500 MHz, DMSO-d₆): δ ppm 11.67 (br s, 1H), 9.22 (s, 1H), 8.38 (s, 1H), 8.00 (m, 1H), 7.58 (d, J=10, 2H), 7.49 (d, J=10, 2H), 6.90 (s, 1H), 4.54 (s, 2H), 3.20 (m, 2H), 2.99 (m, 3H), 2.69 (s, 6H), 1.76 (m, 2H).

Example 214

2-[4-(2-chloro-5-cyano-4-hydroxy-6-oxo-6,7-dihydrothieno[2,3-b]pyridin-3-yl)phenoxy]-N-methylacetamide To a stirred solution of [4-(2-chloro-5-cyano-4-hydroxy-6-oxo-6,7-dihydro-thieno[2,3-b]pyridin-3-yl)-phenoxy]-acetic acid (20 mg, 0.053 mmol, Example 184A)), EDCI (10.2 mg, 0.053 mmol), HOBT (7.2 mg, 0.053 mmol), and NMM (0.0146 mL, 0.133 mmol), in DMF (0.4 mL) was added methylamine (0.0265 mL, 0.053 mmol, 2M in THF). The solution was stirred at room temperature overnight. The solution was diluted with dichloromethane, washed with water, concentrated to dryness and purified by RP-HPLC to give the title compound. MS (ESI) m/e 387.9 (M–H)$^+$; $^1$H NMR (300 MHz, MeOD-d$_4$) δ 2.9 (s, 3H), 4.55 (s, 2H), 4.8 (m, 2H), 6.95 (d, 2H), 7.30 (d, 2H).

Example 215

3-[4-(allyloxy)phenyl]-4-hydroxy-6-oxo-6,7-dihydrothieno[2,3-b]pyridine-5-carbonitrile The title compound was prepared according to the method described for Example 60d, substituting 4-(4-allyloxy-phenyl)-2-(2-cyano-acetylamino)-thiophene-3-carboxylic acid ethyl ester for 4-(4-bromophenyl)-5-chloro-2-(2-cyano-acetylamino)-thiophene-3-carboxylic acid ethyl ester. MS (ESI) m/e 323 (M–H)$^-$; $^1$H NMR (300 MHz, DMSO-d$_6$) δ ppm 4.59 (m, 2H), 5.27 (m, 1H), 5.42 (m, 1H), 6.06 (m, 1H), 6.93 (m, 3H), 7.34 (m, 2H).

Example 216

{[4'-(5-cyano-4-hydroxy-6-oxo-6,7-dihydrothieno[2,3-b]pyridin-3-yl)-1,1'-biphenyl-2-yl]oxy}acetic acid To solution of 4-hydroxy-3-(2'-hydroxy-1,1'-biphenyl-4-yl)-6-oxo-6,7-dihydrothieno[2,3-b]pyridine-5-carbonitrile (0.090 g, 0.25 mmol) in acetone (20 mL) was added potassium carbonate (0.14 g, 1 mmol) and tetrabutyl-ammonium iodide (0.005 g, 0.5 mmol) at room temperature. After stirring for 30 min, bromo-acetic acid ethyl ester (0.083 g, 0.5 mmol) was then added into the reaction mixture and stirred for 16 h. The solvent was removed in vacuo, diluted with water (15 mL), extracted with ethyl acetate (3×30 mL), organics extracts washed with brine (15 mL), dried (Na$_2$SO$_4$), concentrated and purified on a RP-HPLC system. The title compound was one of the three reaction products that were purified. MS (ESI) m/e 416.9 (M–H)$^+$; $^1$H NMR (400 MHz, DMSO-d$_6$): δ ppm 12.44 (br s, 1H), 7.57 (d, J=7.98, 2H), 7.46 (d, J=8.29, 2H), 7.36–7.30 (m, 2H), 7.08–6.98 (m, 3H), 4.74 (s, 2H).

Example 217

4-Hydroxy-3-(4-methylthien-2-yl)-6-oxo-6,7-dihydrothieno[2,3-b]pyridine-5-carbonitrile By-product from synthesis of (Example 189) recovered by HPLC. MS (ESI) m/z 289.0 (M+H$^+$), $^1$H NMR (300 MHz, DMSO-d$_6$) δ ppm 7.49 (d, 1H), 6.94 (s, 1H), 6.76 (s, 1H) 2.19 (s, 3H).

Example 218

N-{4-5-(5-cyano-4-hydroxy-6-oxo-6,7-dihydrothieno[2,3-b]pyridin-3-yl)-3-methylthien-2-yl]phenyl}methanesulfonamide Example 218 was prepared using the same procedure as Example 189 substituting p-methanesulfonylamide boronic acid for 4-hydroxyphenylboronic acid. MS (ESI) m/z 458.0 (M+H$^+$); $^1$H NMR (300 MHz, DMSO-d$_6$) δ ppm 7.53 (s, 1H), 7.45 (d, 2H), 7.28 (d, 2H), 6.83 (s, 1H), 3.04 (s, 3H), 2.26 (s, 3H).

Example 219

4-hydroxy-3-[4-(3-hydroxy-3-methylbut-1-ynyl)phenyl]-6-oxo-6,7-dihydrothieno[2,3-b]pyridine-5-carbonitrile Example 219 was prepared using the same procedure as described for Example 150 substituting 2-methyl-but-3-yn-2-ol for but-3-yn-1-ol in Example 150. MS (ESI) m/e 349 (M–H)$^+$; $^1$H NMR (300 MHz, DMSO-d$_6$): δ ppm 12.38 (br s, 1H), 7.41 (d, J=9, 2H), 7.33 (d, J=9, 2H), 7.02 (s, 1H), 1.48 (s, 6H).

Example 220

N-[2-(acetylamino)ethyl]-2-[({(1E)-[4-(5-cyano-4-hydroxy-6-oxo-6,7-dihydrothieno[2,3-b]pyridin-3-yl)phenyl]methylene}amino)oxy]acetamide Example 220 was prepared using the same procedure as described for Example 158 substituting N-(2-amino-ethyl)-acetamide for C-pyridin-2-yl-methylamine in Example 158. MS (ESI) m/e 451.9 (M–H)$^+$; $^1$H NMR (500 MHz, DMSO-d$_6$): δ ppm 11.75 (br s, 1H), 8.37 (s, 1H), 7.87 (m, 2H), 7.57 (d, J=10, 2H), 7.49 (d, J=10, 2H), 6.90 (s, 1H), 4.52 (s, 2H), 3.08–3.20 (m, 4H), 1.76 (s, 3H).

Example 221

2-[({(1E)-[4-(5-cyano-4-hydroxy-6-oxo-6,7-dihydrothieno[2,3-b]pyridin-3-yl)phenyl]methylene}amino)oxy]-N-(pyrimidin-4-ylmethyl)acetamide Example 221 was prepared using the same procedure as described for Example 158 substituting C-pyrimidin-4-yl-methylamine for C-pyridin-2-yl-methylamine in Example 158. MS (ESI) m/e 458.7 (M–H)$^+$; $^1$H NMR (500 MHz, DMSO-d$_6$): δ ppm 12.00 (br s, 1H), 9.08 (s, 1H), 8.67 (m, 1H), 8.57 (m, 1H), 8.41 (s, 1H), 7.59 (d, J=10, 2H), 7.53 (d, J=10, 2H), 7.38 (d, J=5, 1H), 6.66 (s, 1H), 4.66 (s, 2H), 4.43 (d, J=5, 2H).

Example 222

4-hydroxy-3-(5-iodo-4-methylthien-2-yl)-6-oxo-6,7-dihydrothieno[2,3-b]pyridine-5-carbonitrile To 5'-(2-Cyano-acetylamino)-5-iodo-4-methyl-[2,3']bithiophenyl-4'-carboxylic acid ethyl ester (1.7 g, 3.7 mmol, Example 222 d) in THF : DMF (1:1, 18.5 ml) under N$_2$ at 0° C. was added NaH (95%, 442 mg, 18.5 mmol). The suspension was allowed to warm to rt with stirring overnight. The reaction was quenched with H$_2$O. The mixture was placed in a separatory funnel, overwhelmed with H$_2$O and extracted with EtOAc. Most of the color is removed with this washing step. The aqueous layer was acidified with 6 M HCl and a solid ppt out which was collected by filtration to give 4-hydroxy-3-(5-iodo-4-methylthien-2-yl)-6-oxo-6,7-dihydrothieno[2,3-b]pyridine-5-carbonitrile (880 mg, 2.1 mmol, 58%); MS (ESI) m/z 415.0 (M+H$^+$); $^1$H NMR (300 MHz, DMSO-d$_6$) δ ppm 7.32 (s, 1H), 7.04 (s, 1H), 6.86 (s, 1H), 2.13 (s, 3H).

Example 222a 1-(5-Iodo-4-methyl-thiophen-2-yl)-ethanone.

Commercially available 1-(4-Methyl-thiophen-2-yl)-ethanone (2.0 g, 14.2 mmol) was combined with bis(trifluoroacetoxy)iodobenzene (6.3 g, 14.2 mmol) and iodine (3.6 g, 14.2 mmol) in $CCl_4$ (30 ml). The purple suspension was stirred for 2 h upon which time the reaction was judged to be complete by HPLC. The reaction was diluted with $CH_2Cl_2$ and washed with $Na_2S_2O_3$ (aq, sat.) until the purple color dissipated. The organics were washed with $H_2O$ and brine. The aqueous layers were extracted once with $CH_2Cl_2$ and the combined organics were dried ($Na_2SO_4$), filtered and concentrated by rotary evaporation to give a yellow residue which was purified by flash column chromatography (hexanes:ethyl acetate gradient 2–50% ethyl acetate) to give 1-(5-Iodo-4-methyl-thiophen-2-yl)-ethanone (2.5 g, 66%) as a solid; MS (ESI) m/z 266.9 (M+H$^+$); $^1$H NMR (300 MHz, DMSO-$d_6$) δ 7.65 (s, 1H), 2.47 (s, 3H), 2.19 (s, 3H).

Example 222b

2-Cyano-3-(5-iodo-4-methyl-thiophen-2-yl)-but-2-enoic acid ethyl ester.

Acetic acid (9.4 ml) was placed in a flask at rt and HMDS (3.0 ml, 14.1 mmol) was added dropwise. After the exotherm subsided, 1-(5-Iodo-4-methyl-thiophen-2-yl)-ethanone (2.5 g, 9.4 mmol) was added as a solid followed by ethyl cyanoacetate (2.0 ml, 18.8 mmol). The reaction was stirred at 80° C. for 8 h, cooled to rt and concentrated by rotary evaporation to give a brown residue. The residue was taken up in EtOAc, washed with NaHCO$_3$ (aq, sat.) and then with H$_2$O. The organics were dried (NaSO$_4$), filtered and concentrated to give a brown solid. The solid was triturated with EtOH and filtered to give 2-Cyano-3-(5-iodo-4-methyl-thiophen-2-yl)-but-2-enoic acid ethyl ester (2.0 g, 5.5 mmol, 58%) as a light yellow solid. MS (ESI) m/z 362.0 (M+H$^+$); $^1$H NMR (300 MHz, DMSO-$d_6$) δ ppm 1.27 (t, 1H) 2.21 (s, 1H) 2.66 (s, 1H) 4.26 (q, 1H) 7.67 (s, 4H).

Example 222c

5'-Amino-5-iodo-4-methyl-[2,3']bithiophenyl-4'-carboxylic acid ethyl ester.

2-Cyano-3-(5-iodo-4-methyl-thiophen-2-yl)-but-2-enoic acid ethyl ester (2.0 g, 5.5 mmol) was dissolved in EtOH (5.5 ml) and treated with diethyl amine (0.57 ml, 5.5 mmol) and sulfur (176 mg, 5.5 mg). The reaction was stirred at 60° C. for 2 h and cooled to rt. The dark mixture was concentrated by rotary evaporation, loaded onto silica gel and filtered through a fritted funnel, eluting with 5:1 hexanes:ethyl acetate to give a yellow residue. The residue was purified by flash column chromatography (Horizon, hexanes: ethyl acetate, 5–50% ethyl acetate) to give 5'-Amino-5-iodo-4-methyl-[2,3']bithiophenyl-4'-carboxylic acid ethyl ester (2.0 g, 5.1 mmol, 93%). MS (ESI) m/z 394.0 (M+H$^+$); $^1$H NMR (300 MHz, DMSO-$d_6$) δ ppm 7.41 (s, 2H), 6.76 (s, 1H), 6.34 (s, 1H), 4.07 (q, 2H), 2.13 (s, 3H), 1.08 (t, 3H).

Example 222d

5'-(2-Cyano-acetylamino)-5-iodo-4-methyl-[2,3']bithiophenyl-4'-carboxylic acid ethyl ester.

Cyanoacetic acid (1.2 g, 14.0 mmol) and CH$_2$Cl$_2$ (14 ml) were combined at rt under N$_2$. The solids do not dissolve. PCl$_5$ (2.9 g, 14.0 mmol) was added as a solid portion wise (bubbles vigorously). The suspension was heated at reflux for 30 min and all solids dissolve to give a clear, light yellow solution. The acyl chloride solution was cooled and added directly to 5'-Amino-5-iodo-4-methyl-[2,3']bithiophenyl-4'-carboxylic acid ethyl ester (2.0 g, 5.1 mmol) in CH$_2$Cl$_2$. The solution was stirred at rt for 2.5 h. The reaction was poured into NaHCO$_3$ (aq, sat.) and washed a second time with NaHCO$_3$ (aq, sat.). The organics were washed with brine and dried (Na$_2$SO$_4$), filtered and concentrated by rotary evaporation to give a light yellow solid which was then triturated with CH$_3$CN and filtered to give 5'-(2-Cyano-acetylamino)-5-iodo-4-methyl-[2,3']bithiophenyl-4'-carboxylic acid ethyl ester (1.7 g, 3.7 mmol) as a white solid. This material was taken to the next step without further purification.

Example 223

5-(5-cyano-4-hydroxy-6-oxo-6,7-dihydrothieno[2,3-b]pyridin-3-yl)-N-[2-(dimethylamino)ethyl]thiophene-2-carboxamide

Example 223a tert-butyl 5-acetylthiophene-2-carboxylate

A solution of 5-acetylthiophene-2-carboxylic acid (7 g, 41 mmol) in DMA (100 mL) was treated with 2-methyl-2-propanol (54 mL, 576 mmol), DMAP (3 g, 25 mmol), and EDCI (9.9 g, 51.5 mmol). The resulting mixture was stirred at 25° C. for 16 h. Water (200 mL) was added and the mixture was extracted with ethyl ether (350 mL). The organic phase was washed with 1 N HCl (100 mL), water (3×100 mL), saturated aqueous NaHCO$_3$ (100 mL), and brine (100 mL); dried (Na$_2$SO$_4$); filtered; and evaporated to afford 6.7 g (72%) of the title compound as a tan solid. $^1$H NMR (300 MHz, DMSO-D6) δ ppm 1.53 (s, 9H) 2.58 (s, 3H) 7.75 (d, J=3.68 Hz, 1H) 7.92 (d, J=3.68 Hz, 1H); MS (DCI) 227 m/z (M+H)$^+$.

Example 223b

5'-tert-butyl 4-ethyl 5-amino-2,2'-bithiophene-4,5'-dicarboxylate

The title compound was prepared according to the procedure described in Example 238b substituting Example 223a for Example 238a. The crude product was purified by flash chromatography on silica gel eluting with 3:1 CH$_2$Cl$_2$/hexanes to provide Example 223b. $^1$H NMR (300 MHz, DMSO-D6) δ ppm 1.06 (t, J=7.17 Hz, 3H) 1.52 (s, 9H) 4.07 (q, J=7.23 Hz, 2H) 6.49 (s, 1H) 7.04 (d, J=3.68 Hz, 1H) 7.46 (s, 2H) 7.57 (d, H); MS (ESI) 354 m/z (M+H)$^+$.

Example 223c

5'-[(cyanoacetyl)amino]-4'-(ethoxycarbonyl)-2,2'-bithiophene-5-carboxylic acid

The title compound was prepared according to the procedure described in Example 151b substituting Example 223b for Example 151a. The crude product was purified by flash chromatography on silica gel eluting with 94:5:1 CHCl$_3$/MeOH/AcOH to provide Example 223c. $^1$H NMR (300 MHz, DMSO-D6) δ ppm 1.09 (t, J=7.17 Hz, 3H) 4.19 (q, J=7.11 Hz, 2H) 4.27 (s, 2H) 7.14 (d, J=3.68 Hz, 1H) 7.31 (s, 1H) 7.65 (d, J=3.68 Hz, 1H) 11.20 S, 1H) 13.05 (br s, 1H); MS (ESI) 365 m/z (M+H)$^+$.

Example 223d ethyl 5-[(cyanoacetyl)amino]-5'-({[2-(dimethylamino)ethyl]amino}carbonyl)-2,2'-bithiophene-4-carboxylate Example 223c (45 mg, 0.12 mmol) in DMA (0.75 mL) was treated with EDCI (29.7 mg, 0.16 mol), HOBt (16.7 mg, 0.124 mmol), N,N-dimethylenediamine (0.017 mL, 0.15 mmol) and 4-methylmorpholine (0.054 mL, 0.49 mmol) and the mixture was stirred at 25° C. for 16 h. Water (2 mL) was added and the resulting mixture was stirred at 25° C. for 15 minutes. The precipitated solids were filtered, dissolved in CHCl$_3$, and purified by flash chromatography on silica gel eluting with 8% MeOH/CHCl$_3$ to provide 33 mg (62%) of Example 223d as a tan solid. MS (APCI) 435 m/z (M+H)$^+$.

Example 223

5-(5-cyano-4-hydroxy-6-oxo-6,7-dihydrothieno[2,3-b]pyridin-2-yl)-N-[2-(dimethylamino)ethyl]thiophene-2-carboxamide The title compound was prepared according to the procedure described in Example 238e substituting Example 223d for Example 238d. The crude product was purified by reverse-phase HPLC on a Waters Symmetry C8 column (40 mm×100 mm) using a gradient of 10% to 100% acetonitrile: 0.1% aqueous TFA to provide the desired product as a mono TFA salt. $^1$H NMR (300 MHz, DMSO-D6) δ ppm 2.85 (d, J=4.78 Hz, 6H) 3.25 (m, 2H) 3.58 (m, 2H) 7.04 (s, 1H) 7.58 (abq, J=3.5 Hz, 2H) 8.60 (t, J=5.70 Hz, 1H), 9.28 (br s, 1H) 11.15 (br s, 1H); MS (ESI) 389 m/z (M+H)$^+$.

Example 224

4-hydroxy-3-{4-[3-(methylamino)prop-1-ynyl]phenyl}-6-oxo-6,7-dihydrothieno[2,3-b]pyridine-5-carbonitrile Example 224 was prepared using the same procedure as described for Example 150 substituting methyl-prop-2-ynyl-amine for but-3-yn-1-ol in Example 150. MS (ESI) m/e 333.9 (M−H)$^+$; $^1$H NMR (300 MHz, DMSO-d$_6$): δ ppm 11.8 (br s, 1H), 8.97 (broad m, 1H), 7.50 (d, J=9, 2H), 7.44 (d, J=9, 2H), 6.93 (s, 1H), 4.17 (m, 2H), 2.68 (m, 3H).

Example 225

2-[({(1E)-[4-(5-cyano-4-hydroxy-6-oxo-6,7-dihydrothieno[2,3-b]pyridin-3-yl)phenyl]methylene}amino)oxy]-N-[3-(1H-imidazol-1-yl)propyl]acetamide Example 225 was prepared using the same procedure as described for Example 158 substituting 3-Imidazol-1-yl-propylamine for C-pyridin-2-yl-methylamine in Example 158. MS (ESI) m/e 475 (M−H)$^+$; $^1$H NMR (500 MHz, DMSO-d$_6$): δ ppm 11.78 (br s, 1H), 8.79 (s, 1H), 8.38 (s, 1H), 7.99 (m, 1H), 7.73 (s, 1H), 7.59 (m, 3H), 7.49 (d, J=10, 2H), 6.91 (s, 1H), 4.54 (s, 2H), 4.15 (m, 2H), 3.17 (m, 2H), 1.96 (m, 2H).

Example 226

3-{5-[(1E)-N-ethoxyethanimidoyl]thien-2-yl}-4-hydroxy-6-oxo-6,7-dihydrothieno[2,3-b]pyridine-5-carbonitrile The title compound was prepared according to the procedures described in Example 238 substituting O-ethylhydroxylamine hydrochloride for hydroxylamine hydrochloride in Example 238f to afford the desired product as an E or Z isomer. 1H NMR (300 MHz, DMSO-D6) δ ppm 1.29 (t, J=6.99 Hz, 3H) 2.28 (s, 3H) 4.20 (q, J=6.99 Hz, 2H) 7.16 (s, 1H) 7.35 (d, J=4.04 Hz, 1H) 7.48 (d, J=4.04 Hz, 1H) 12.28 (br s, 1H); MS (ESI) 360 m/z (M+H)$^+$.

Example 227

4-hydroxy-6-oxo-3-(5-pyridin-3-ylthien-2-yl)-6,7-dihydrothieno[2,3-b]pyridine-5-carbonitrile The title compound was prepared according to the procedures described in Example 151 substituting 3-(tributylstannyl)-pyridine for 2-(tributylstannyl)-pyridine in Example 151c. $^1$H NMR (300 MHz, DMSO-D6) δ ppm 7.43 (dd, J=8.09, 4.78 Hz, 1H) 7.53 (d, J=3.68 Hz, 1H) 7.68 (d, J=3.68 Hz, 1H) 8.03 (m, 1H) 8.47 (dd, J=4.78, 1.84 Hz, 1H) 8.89 (d, J=1.84 Hz, 1H); MS (ESI) m/z 351.9 (M+H)$^+$.

Example 228

7-(5-cyano-4-hydroxy-6-oxo-3-phenyl-6,7-dihydrothieno[2,3-b]pyridin-2-yl)hept-6-ynoic acid To a solution of 2-Bromo-4-hydroxy-6-oxo-3-phenyl-6,7-dihydro-thieno[2,3-b]pyridine-5-carbonitrile (150 mg, 0.45 mmol) in 4.5 mL DMF was added diethylamine (0.48 mL, 4.5 mmol), followed by copper(I) iodide (trace), Pd(PPh$_3$)Cl$_2$ (10 mg, 0.015 mmol), and triphenylphosphine (36 mg, 0.12 mmol). The resulting mixture was stirred at rt for 5 min, after which hept-6-ynoic acid (0.19 mL, 1.5 mmol) was added. The reaction was then heated to 120° C. using microwave for 25 min, filtered, concentrated and purified by reverse phase HPLC. MS (ESI) m/e 393 (M+H)$^+$; $^1$H NMR (400 MHz, DMSO-d$_6$): δ ppm 1.28–1.56 (m, 4H), 2.12–2.30 (m, 4H), 7.20–7.35 (m, 5H).

Example 229

3-[4-(allyloxy)phenyl]-4-hydroxy-2-methyl-6-oxo-6,7-dihydrothieno[2,3-b]pyridine-5-carbonitrile Example 229A 1-(4-Allyloxy-phenyl)-propan-1-one To 1-(4-hydroxy-phenyl)-propan-1-one (4.6 g, 30 mmol) and K$_2$CO$_3$ (5 g, 36 mmol) in DMF (10 mL) was added allylbromide (7.26 g, 60 mmol) dropwise with violent stirring. The reaction mixture was stirred at room temperature for 12 h and filtered to remove salt. The filtrate was concentrated to yield the titled compound (5.5 g, 97%) as a colorless oil. $^1$H NMR (300 MHz, DMSO-d$_6$) δ 7.94 (d, 2H, J=9.0 Hz), 7.05 (d, 2H, J=9.0 Hz), 6.05 (m, 1H), 5.44, 5.38, 5.30, 5.26 (4d, 2H, J=3.0 Hz), 4.66 (d, 2H, J=6.0 Hz), 2.98 (q, 2H, J=7.5 Hz), 1.07 (t, 3H, J=7.5 Hz). MS (ESI) m/e 191 (M+H)$^+$; 189 (M−H)$^-$.

Example 229b 4-(4-Allyloxyphenyl)-2-amino-5-methyl-thiophene-3-carboxylic acid ethyl ester To 1-(4-Allyloxy-phenyl)-propan-1-one from Example 29A (5.5 g, 29 mmol) in 20 mL acetic acid were added ethyl cyanoacetate (6.56 g, 58 mmol) and HMDS (7.02 g, 43.5 mmol). The mixture was heated at 75° C. for 4 h, and then cooled to room temperature. After solvent was removed by evaporator under vacuo, water and ethyl acetate (100 mL, 1:1) were added. The organic layer was washed with saturated aq. NaHCO$_3$ and brine, dried over MgSO$_4$ and concentrated to give a colorless oil which was dissolved in ethanol (40 ml). To this solution sulfur (1.86 g, 58 mmol) and morpholine (5.1 g, 58 mmol) were added. The mixture was refluxed for 2 h and checked by TLC. The mixture was filtered to remove excess sulfur. The filtrate was evaporated in vacuo and the residue was purified by column chromatography on silica gel to afford 6.76 g (73.5%) of the titled compound. $^1$H NMR (300 MHz, DMSO-d$_6$) δ 7.22 (s, 2H), 7.01 (d, 2H, J=9.0 Hz), 6.90 (d, 2H, J=9.0 Hz), 6.05 (m, 1H), 5.43, 5.37, 5.27, 5.24 (4d, 2H, J=3.0 Hz), 4.57 (d, 2H, J=6.0 Hz), 3.83 (q, 2H, J=6.0 Hz), 1.94 (s, 3H), 0.80 (t, 3H, J=6.0 Hz). MS (ESI) m/e 318 (M+H)$^+$, 316 (M−H)$^-$.

Example 229c 4-(4-Allyloxy-phenyl)-2-(2-cyano-acetylamino)-5-methyl-thiophene-3-carboxylic acid ethyl ester To PCl$_{15}$ (854 g, 4.1 mol) in 10 mL anhydrous CH$_2$Cl$_2$ was added cyanoacetic acid (348 g, 4.1 mmol). The reaction mixture was refluxed for 0.5 h, and then 4-(4-Allyloxyphenyl)-2-amino-5-methyl-thiophene-3-carboxylic acid ethyl ester from Example 29B (1.0 g, 3.1 mmol) in 5 ml anhydrous CH$_2$Cl$_2$ was added dropwise at room temperature. The reaction mixture was refluxed for 1 h and cooled to room temperature, and then saturated aq. Na$_2$CO$_3$ was added until pH=7. The organic layer was washed with brine, dried over MgSO$_4$, concentrated in vacuo to give the titled compound (1.2 g, 100% yield) as a pale yellow oil which was pure enough to used in next step. $^1$H NMR (300 MHz, DMSO-d$_6$) δ 11.15 (s, 1H), 7.07 (d, 2H, J=9.0 Hz), 6.97 (d, 2H, J=9.0 Hz), 6.05 (m, 1H), 5.44, 5.38, 5.28, 5.25 (4d, 2H, J=3.0 Hz), 4.60 (d, 2H, J=6.0 Hz), 4.25 (s, 2H), 3.97 (q, 2H, J=6.0 Hz), 2.12 (s, 3H), 0.84 (t, 3H, J=6.0 Hz). MS (ESI) m/e 385 (M+H)$^+$, 383 (M−H)$^-$.

Example 229d 5-(4-Allyloxy-phenyl)-4-hydroxy-2-methyl-6-oxo-6,7-dihydro-thieno[2,3-b]pyridine-5-carbonitrile To a suspension of NaH (248 mg, 6.2 mmol) in anhydrous THF (8 mL) 4-(4-Allyloxy-phenyl)-2-(2-cyano-acetylamino)-5-methyl-thiophene-3-carboxylic acid ethyl ester (1.2 g, 3.1 mmol) in THF (2 mL) was added. The reaction mixture was stirred at room temperature for 8 h and MeOH (2 mL) was added. After removed the solvent in vacuum, water and ethyl acetate were added (20 mL, 1:1) to give a red clear solution. The resulting solution was acidified by addition of 1N HCl aqueous until pH=2. The precipitated solid was washed with water and ethyl acetate and dried to give the titled compound (1.0 g, 95% yield). $^1$H NMR (300 MHz, DMSO-d$_6$) δ 10.57 (s, 1H), 7.08 (d, 2H, J=9.0 Hz), 6.86 (d, 2H, J=9.0 Hz), 6.07 (m, 1H), 5.64, 5.40, 5.29, 5.26 (4d, 2H, J=3.0 Hz), 4.58 (d, 2H, J=6.0 Hz), 2.09 (s, 3H). MS (ESI) m/e 339 (M+H)$^+$, 337 (M−H)$^-$.

Example 230

2-[4-(2-chloro-5-cyano-4-hydroxy-6-oxo-6,7-dihydrothieno[2,3-b]pyridin-3-yl)phenoxy]-N-[3-(2-oxopyrrolidin-1-yl)propyl]acetamide The titled compound was prepared according to the procedure described in Example 184, substituting 1-(3-amino-propyl)-pyrrolidine-2-one for 3-amino-propan-1-ol. MS (ESI) m/e 499 (M−H)$^-$; $^1$H NMR (300 MHz, DMSO-d$_6$) δ ppm 1.62 (m, 2H), 1.91 (m, 2H), 2.22 (t, J=7.97 Hz, 2H), 3.14 (m, 4H), 3.32 (m, 2H), 4.50 (s, 2H), 6.98 (d, J=8.81 Hz, 2H), 7.25 (d, J=8.81 Hz, 2H), 8.15 (m, 1H).

Example 231

4-hydroxy-3-[4-(4-hydroxyphenyl)-5-phenylthien-2-yl]-6-oxo-6,7-dihydrothieno[2,3-b]pyridine-5-carbonitrile Example 231 was prepared using the same procedure as Example 205 substituting 4-hydroxyphenylboronic acid for p-methanesulfonylamide boronic acid. MS (ESI) m/z 444.0 (M+H)$^+$; $^1$H NMR (300 MHz, DMSO-d$_6$) δ ppm 7.71 (s, 1H), 7.32–7.26 (m, 5H), 7.08 (d, 2H), 6.94 (s, 1H), 6.70 (d, 2H).

Example 232

3-(3,5-dibromo-4-hydroxyphenyl)-4-hydroxy-6-oxo-6,7-dihydrothieno[2,3-b]pyridine-5-carbonitrile

Example 232a 3,5-Dibromo-4-hydroxyacetophenone

To a solution of 4-hydroxyacetophenone (15 g, 95.4 mmol) in 2M NaOH (30 mL) was added 1M H$_2$SO$_4$ until the pH=7. The solution was diluted by addition of H$_2$O (20 mL) and the resulting suspension was heated to 70° C. Bromine (11.3 mL, 0.19 mol) was added through an addition funnel. The reaction was cooled to room temperature and the resulting solid was filtered and rinsed with water. It was recrystallized from toluene (500 mL) to give clean 3,5-dibromo-4-hydroxyacetophenone (15 g, 51.2 mmol, 54% yield).

Example 232b 1-(4-Benzyloxy-3,5-dibromo-phenyl)-ethanone

To a solution of 3,5-dibromo-4-hydroxyacetophenone from Example 45A (15 g, 51.2 mmol) in DMF (51 mL) was added K$_2$CO$_3$ (10.2 g, 74.1 mmol) and benzyl bromide (6.0 mL, 50.7 mmol). The reaction stirred at room temperature for 45 minutes. It was diluted with water (200 mL) and extracted with EtOAc (3×75 mL). The combined organic layers were washed with 2M NaOH solution (2×75 mL), water (75 mL), and brine (75 mL) and then dried over MgSO$_4$ and concentrated in vacuo to give 1-(4-benzyloxy-3,5-dibromo-phenyl)-ethanone as an off white solid (14.3 g, 37.2 mmol, 73% yield).

Example 232c

2-Amino-4-(4-benzyloxy-3,5-dibromo-phenyl)-thiophene-3-carboxylic acid ethyl ester To a solution of 1-(4-benzyloxy-3,5-dibromo-phenyl)-ethanone from Example 36B (14.3 g, 37.2 mmol) in absolute ethanol (100 mL) ethyl cyanoacetate (7.6 mL, 74.5 mmol) was added. The reaction was heated to 50° C. and the morpholine (13 mL, 0.15 mol) was added. The reaction was further heated to 60° C. and the sulfur (2.4 g, 74.5 mmol) was added. The reaction stirred at 60° C. for 18 h and was then cooled to room temperature and filtered to remove sulfur. Upon concentration in vacuo, the residue was taken up in H$_2$O (100 mL) and washed with EtOAC (3×100 mL). The combined organic layers were washed with brine (100 mL), dried over MgSO$_4$ and concentrated in vacuo. The resulting crude compound was purified via column chromatography eluting with 10% EtOAc/hexanes. The resulting solid was recrystallized from EtOH (100 mL) to give the titled product as an off white solid (2.9 g, 5.7 mmol, 15% yield).

Example 232d 4-(4-Benzyloxy-3,5-dibromo-phenyl)-2-(2-cyano-acetylamino)-thiophene-3-carboxylic acid ethyl ester To a solution of PCl$_5$ (0.9 g, 4.32 mmol) in CH$_2$Cl$_2$ (15 mL) was added cyanoacetic acid (374 mg, 4.32 mmol). The reaction was heated to reflux for 30 minutes. Upon cooling to room temperature, 2-amino-4-(4-benzyolxy-3,5-dibromo-phenyl)-thiophene-3-carboxylic acid ethyl ester from Example 36c (1.8 g, 3.52 mmol) in CH$_2$Cl$_2$ (15 mL) was added and the reaction mix was heated to reflux for an additional 30 minutes. Upon cooling to room temperature the reaction was diluted with EtOAc (50 mL) and washed with saturated NaHCO$_3$ soln (40 mL). The aqueous layer was back-extracted with EtOAC (40 mL) and the combined organic layers were dried over MgSO$_4$ and concentrated in vacuo to give 1.8 g of the titled product (3.1 mmol, 88% yield).

Example 232e 3-(4-Benzyloxy-3,5-dibromo-phenyl)-4-hydroxy-6-oxo-6,7-dihydro-thieno[2,3-b]pyridine-5-carbonitrile To a suspension of NaH (275 mg, 6.87 mmol) in THF (50 mL) was added 4-(4-benzyloxy-3,5-dibromo-phenyl)-2-(2-cyano-acetylamino)-thiophene-3-carboxylic acid ethyl ester from Example 36D (1.8 g, 3.12 mmol) in THF (50 mL). The reaction stirred at room temperature for 18 h. It was acidified with 1M HCl and concentrated in vacuo. The resulting orange solid was taken up in H$_2$O and filtered, rinsing with H$_2$O (2×20 mL) and CH$_2$Cl$_2$ (3×20 mL). The titled compound was isolated as a yellow solid (940 mg, 1.76 mmol, 56% yield).

Example 232f 3-(3,5-Dibromo-4-hydroxy-phenyl)-4-hydroxy-6-oxo-6,7-dihydro-thieno[2,3-b]pyridine-5-carbonitrile The 3-(4-benzyloxy-3,5-dibromo-phenyl)-4-hydroxy-6-oxo-6,7-dihydro-thieno[2,3-b]pyridine-5-carbonitrile from Example 36e (150 mg, 0.281 mmol) was dissolved in 30% HBr/AcOH (2 mL) and sealed in a reaction tube with stirring for 30 min at 70° C. The reaction is cooled to room temperature and concentrated in vacuo. The resulting solid is washed with Et$_2$O and filtered, then placed under high vacuum to remove remaining acid. The solid is then taken up in NH$_4$OH (2 mL) and stirred at room temperature for 20 minutes. The reaction mix is concentrated and taken up in 1M HCl. The resulting solid is filtered and rinsed with water to give 75 mg of a green solid as the titled compound (0.169 mmol, 60% yield). $^1$H NMR (300 MHz, DMSO-d$_6$) δ 12.54 (bs, 1H), 9.98 (bs, 1H), 7.59 (s, 2H), 7.09 (s, 1H), 4.13 (bs, 1H). MS (ESI APCI) m/e 442 (M+H)$^+$; 440 (M−H)$^−$.

Example 233

2-[({(1E)-[4-(5-cyano-4-hydroxy-6-oxo-6,7-dihydrothieno[2,3-b]pyridin-3-yl)phenyl]methylene}amino)oxy]-N-[2-(1-methylpyrrolidin-2-yl)ethyl]acetamide Example 233 was prepared using the same procedure as described for Example 158 substituting 2-(1-methyl-pyrrolidin-2-yl)-ethylamine for C-pyridin-2-yl-methylamine in Example 158. MS (ESI) m/e 478.1 (M−H)$^+$; $^1$H NMR (500 MHz, DMSO-d$_6$): δ ppm 11.8 (br s, 1H), 9.38 (s, 1H), 8.39 (s, 1H), 7.99 (m, 1H), 7.57 (d, J=10, 2H), 7.49 (d, J=10, 2H), 6.92 (s, 1H), 4.53 (s, 2H), 3.49 (m, 1H), 3.23 (m, 2H), 3.10 (m, 1H), 2.94 (m, 1H), 2.73 (s, 3H), 2.26 (m, 1H), 2.05 (m, 1H), 1.79–1.89 (m, 2H), 1.60 (m, 2H).

Example 234

4-hydroxy-6-oxo-3-{4-[3-(tetrahydrofuran-3-yloxy)prop-1-ynyl]phenyl}-6,7-dihydrothieno[2,3-b]pyridine-5-carbonitrile Example 234 was prepared using the same procedure as described for Example 150 substituting 3-prop-2-ynyloxy-tetrahydrofuran for but-3-yn-1-ol in Example 150. MS (ESI) m/e 391.1 (M−H)$^+$; $^1$H NMR (300 MHz, DMSO-d$_6$): δ ppm 12.3 (br s, 1H), 7.44 (apparent s, 4H), 7.03 (s, 1H), 4.41 (s, 2H), 4.33–4.38 (m, 1H), 3.65–3.78 (m, 4H), 1.94–2.02 (m, 2H).

Example 235

2-[4-(2-chloro-5-cyano-4-hydroxy-6-oxo-6,7-dihydrothieno[2,3-b]pyridin-3-yl)phenoxy]-N-[3-(1H-imidazol-1-yl)propyl]acetamide The titled compound was prepared according to the procedure described in Example 184, substituting 3-imidazol-1-yl-propylamine for 3-amino-propan-1-ol. MS (ESI) m/e 482 (M−H)$^1$; $^1$H NMR (300 MHz, DMSO-d$_6$) δ ppm 2.01 (m, 2H), 3.15 (m, 2H), 4.17 (t, J=6.78 Hz, 2H), 4.54 (s, 2H), 6.95 (d, J=8.81 Hz, 2H), 7.24 (d, J=8.81 Hz, 2H), 7.63 (s, 1H) 7.77 (s, 1H) 8.20 (m, 1H), 8.98 (s, 1H).

Example 236

3-(1,3-benzodioxol-5-yl)-4-hydroxy-6-oxo-6,7-dihydrothieno[2,3-b]pyridine-5-carbonitrile The titled compound was prepared according to the procedures as described in Example 29b-d, substituting 1-benzo[1,3]dioxol-5-yl-ethanone for 1-(4-allyloxy-phenyl)-propan-1-one from 29a. MS (ESI) m/e 313 (M+H)$^+$; $^1$H NMR (300 MHz, DMSO-d$_6$): δ 12.55 (s, 1H), 6.99 (br s, 1H), 6.96 (s, 1H), 6.89 (s, 1H), 6.89 (overlapping s, 1H), 6.04 (s, 2H).

Example 237

5-ethanimidoyl-4-hydroxy-3-(2'-hydroxy-1,1'-biphenyl-4-yl)thieno[2,3-b]pyridin-6(7H)-one MeMgBr (1.4 M in ether, 15 mL, 21 mmol) was slowly added to a solution of 4-hydroxy-3-(2'-hydroxy-1,1'-biphenyl-4-yl)-6-oxo-6,7-dihydrothieno[2,3-b]pyridine-5-carbonitrile (1.5 g, 4.18 mmol) in anhydrous THF (90 mL) at 0° C. The reaction mixture was slowly warmed to room temperature over 4 hours and quenched with 1N HCl. It was then filtered, concentrated, and purified on a RP-HPLC system to give the title compound. MS (ESI) m/e 375.0 (M−H)$^+$; $^1$H NMR (400 MHz, DMSO-d$_6$): δ ppm 12.37 (br s, 1H), 11.33 (s, 1H), 9.51 (s, 1H), 9.32 (s, 1H), 7.49 (d, J=8.59, 2H), 7.42 (d, J=8.59, 2H), 7.29 (dd, J=7.68, 1.85, 1H), 7.18–7.14 (m, 1H), 6.96 (dd, J=8.29, 1.23, 1H), 6.91–6.84 (m, 1H), 6.75 (s, 1H), 2.55 (s, 3H).

Example 238

4-Hydroxy-3-{5-[(1E)-N-hydroxyethanimidoyl]thien-2-yl}-6-oxo-6,7-dihydrothieno[2,3-b]pyridine-5-carbonitrile

Example 238a

5-Acetyl-N-methoxy-N-methylthiophene-2-carboxamide

A solution of 5-acetylthiophene-2-carboxylic acid (5 g, 0.0294 mol) in DMA (80 mL) was treated with EDCI (8.47 g, 0.044 mol), HOBt (3.97 g, 0.044 mol), N,O-dimethylhydroxylamine hydrochloride (5.7 g, 0.059 mol) and 4-methylmorpholine (16.14 mL, 0.147 mol). The resulting thick mixture was stirred at 25° C. for 16 h. Water (250 mL) was added and the mixture was extracted with 1:1 EtOAc/ether (2×200 mL). The combined extracts were washed with 1N HCl (150 mL), water (3×200 mL), saturated NaHCO$_3$ (150 mL), and brine (150 mL); dried (Na$_2$SO$_4$); filtered; and evaporated to afford 5.4 g (86%) of the desired product. $^1$H NMR (300 MHz, DMSO-D6) δ ppm 2.58 (s, 3H) 3.31 (s, 3H) 3.78 (s, 3H) 7.85 (d, J=4.04 Hz, 1H) 7.92 (d, J=4.04 Hz, 1H); MS (DCI) 214 m/z (M+H)$^+$.

Example 238b

Ethyl 5-amino-5'-{[methoxy(methyl)amino]carbonyl}-2,2'-bithiophene-4-carboxylate Acetic acid (11 mL) was treated with 1,1,1,3,3,3-hexamethyldisilazane (4.13 mL, 19.7 mmol) dropwise over 4 minutes. A strong exotherm accompanied the addition. Example 238a (2.8 g, 13.14 mmol) and ethyl cyanoacetate (2.8 mL, 26.3 mmol) were added and the resulting mixture was heated at 70° C. for 20 h. The solvent was evaporated and saturated aqueous NaHCO$_3$ (100 mL) was added to the residue. The mixture was extracted with EtOAc (100 mL). The organic layer was washed with saturated NaHCO$_3$ (100 mL) and brine, dried (Na$_2$SO$_4$), filtered, and evaporated to afford an orange oil. The residual oil was dissolved in EtOH (11 mL), and treated with diethylamine (1.62 mL, 15.76 mmol) and sulfur 13.14 mmol, 420 mg). The reaction mixture was heated at 60° C. for 2 h and cooled to 0° C. Solids formed were filtered, washed with cold EtOH (5 mL) and air dried on the filter to provide 2.36 g (53%) of the desired product. $^1$H NMR (300 MHz, DMSO-D6) δ ppm 1.04 (t, J=6.99 Hz, 3H) 3.27 (s, 3H) 3.76 (s, 3H) 4.05 (q, J=7.23 Hz, 2H) 6.46 (s, 1H) 7.05 (d, J=4.04 Hz, 1H) 7.45 (s, 2H) 7.71 (d, J=4.04 Hz, 1H) MS (ESI) 341 m/z (M+H)$^+$.

Example 238c

Ethyl 5'-acetyl-5-amino-2,2'-bithiophene-4-carboxylate

A 0° C. solution of Example 238b (690 mg, 2.03 mmol) in THF (70 ml) was treated with MeMgBr (3M in ether, 6.09 mL, 18.26 mmol) dropwise over 8 minutes. After stirring at 0° C. for 40 minutes, the reaction was quenched by addition of 1N HCl (20 mL). The reaction mixture was stirred 5 minutes and saturated aqueous NaHCO$_3$ was added until the aqueous phase was neutralized (pH 7–8). The resulting mixture was extracted with CH$_2$Cl$_2$ (150 mL). The organic layer was washed with brine, dried (Na$_2$SO$_4$), filtered, and evaporated. The residue was purified by flash chromatography on silica gel eluting with 20% EtOAc/hexanes to provide 450 mg (75%) of Example 238c as a yellow solid. $^1$H NMR (300 MHz, chloroform-D) δ ppm 1.11 (t, J=7.17 Hz, 3H) 2.55 (s, 3H) 4.16 (q, J=6.99 Hz, 2H) 6.13 (br s, 2H) 6.29 (s, 1H) 7.02 (d, J=4.04 Hz, 1H) 7.58 (d, J=3.68 Hz, 1H).

Example 238d

Ehyl 5'-acetyl-5-[(cyanoacetyl)amino]-2,2'-bithiophene-4-carboxylate

Example 23 8d was prepared according to the procedure described in Example 151b substituting Example 238c for Example 151a. $^1$H NMR (300 MHz, chloroform-D) δ ppm 1.13 (t, J=7.17 Hz, 3H) 2.5 7 (s, 3H) 3.69 (s, 2H) 4.2 5 (q, J=6.99 Hz, 2H) 6.90 (s, 1H) 7.04 (d, J=4.04 Hz, 1H) 7.61 (d, J=4.04 Hz, 1H) 12.01 (s, 1H).

Example 238e

2-(5-acetylthien-2-yl)-4-hydroxy-6-oxo-6,7-dihydrothieno[2,3-b]pyridine-5-carbonitrile To a mixture of NaH (95%, 9.0 mg, 0.358 mmol) in THF (0.6 mL) and DMF (0.4 mL) was added a solution of Example 238d (37 mg, 0.102 mmol) in THF (0.4 mL). After stirring at 25° C. for 2.5 h, the reaction was cooled to 0° C. and treated with MeOH (0.050 mL). The solvent was evaporated by passing a stream of warm nitrogen over the surface of the quenched reaction solution. The concentrate was dissolved in water (1.5 mL) and extracted with EtOAc (1 mL). The aqueous phase was acidified to pH 2 by addition of 0.5 N HCl and the precipitated solids were filtered and dried to provide 24 mg (75%) of the desired product. $^1$H NMR (300 MHz, methanol-D4) δ ppm 2.57 (s, 3H) 7.27 (s, 1H) 7.34 (d, J=4.04 Hz, 1H) 7.80 (d, J=3.68 Hz, 1H); MS (ESI) 317 m/z (M+H)$^+$.

Example 238

4-hydroxy-2-{5-[(1E)-N-hydroxyethanimidoyl]thien-2-yl}-6-oxo-6,7-dihydrothieno[2,3-b]pyridine-5-carbonitrile Example 238e (60 mg, 0.19 mmol) in MeOH (3.5 mL) was treated with hydroxylamine hydrochloride (26.4 mg, 0.379 mmol). The resulting mixture was heated in an oil bath at 70° C. for 8 h. The solvent was evaporated and the concentrate was purified by RPHPLC on a Waters Symmetry C8 column (25 mm×100 mm, 7 µm particle size) using a gradient of 10% to 100% acetonitrile:0.1% aqueous NH$_4$OAc to provide 35 mg (32%) of the title compound as a 1:1 mixture of E and Z isomers as a tan solid. (1:1 E, Z) 1H NMR (300 MHz, DMSO-D6) δ ppm 2.16, 2.26 (s, 3H) 7.13, 7.15 (s, 1H) 7.26, 7.36 (d, J=3.68 Hz, d, J=4.04 Hz, 1H) 7.31, 7.41 (d, J=3.68 Hz, d, J=4.04 Hz, 1H) 11.15, 11.62 (br s, 1H); MS (ESI) 329.8 m/z (M–H$^+$).

Example 240

4-hydroxy-6-oxo-3-[(E)-2-phenylvinyl]-6,7-dihydrothieno[2,3-b]pyridine-5-carbonitrile

Example 240a 2-amino-thiophene-3,4-dicarboxylic acid 3-ethyl ester 4-methyl ester.

Methyl pyruvate (8.82 mL, 95.67 mmol), ethyl cyanoacetate (10.0 mL, 93.70 mmol) and sulfur (3.01 g, 93.79 mmol) were dissolved in anhydrous DMF (60 mL). This was treated with triethylamine (13.07 mL, 93.79 mmol) by slowly adding it over 10 min. The reaction was then heated to 50° C. for 2 hr. The reaction was poured into a H$_2$O (300 mL) brine (30 mL) mixture. This was extracted with Et$_2$O (3×100 mL). The extracts were then washed with H$_2$O (2×100 mL) followed by brine (1×100 mL). They were dried (Na$_2$SO$_4$), filtered and the solvent removed in vacuo. The crude product was purified by flash chromatography (SiO$_2$, 1 EtOAc/1 hexanes) to afford the title compound (11.19 g, 51%). $^1$H NMR (300 MHz, CDCl$_3$): δ ppm 1.31 (t, 3H), 3.83 (s, 3H), 4.26 (q, 2H), 5.98 (s, 2H), 6.61 (s, 1H).

Example 240b 2-bis-t-butoxycarbonylamino-thiophene-3,4-dicarboxylic acid-3-ethyl ester-4-methyl ester 2-Amino-thiophene-3,4-dicarboxylic acid 3-ethyl ester 4-methyl ester (4.0 g, 17.47 mmol) was dissolved in anhydrous CH$_2$Cl$_2$ (110 mL). This was treated with triethylamine (5.36 mL, 38.43 mmol) followed by 4-(dimethylamino)pyridine (0.427 g, 3.46 mmol) and di-t-butyldicarbonate (8.39 g, 38.43 mmol). The reaction was heated to reflux for 4 hr. The reaction was cooled to room temperature then it was diluted with CH$_2$Cl$_2$ (100 mL). This was washed with 1N HCl (1×150 mL), H$_2$O (1×150 mL), and brine (1×150 mL). The CH$_2$Cl$_2$ layer was then dried (Na$_2$SO$_4$), filtered, and the solvent removed in vacuo. The crude product was purified by flash chromatography (SiO$_2$, 1 EtOAc/3 hexanes) to afford the title compound (7.10 g, 95%). MS (CI) m/e 330.0 (M+H)$^+$; $^1$H NMR (300 MHz, CDCl$_3$): δ ppm 1.33 (t, 3H), 1.42 (s, 18H), 3.85 (s, 3H), 4.32 (q, 2H), 7.86 (s, 1H).

Example 240c 2-t-butoxycarbonylamino-4-hydroxymethyl-thiophene-3-carboxylic acid ethyl ester 2-Bis-t-butoxycarbonylamino-thiophene-3,4-dicarboxylic acid-3-ethyl ester-4-methyl ester (7.10 g, 16.55 mmol) was dissolved in THF (75 mL). This was treated with a solution of calcium chloride (3.67 g, 33.10 mmol) dissolved in EtOH (75 mL). The solution was cooled to 0° C. and then treated with sodium borohydride (2.50 g, 66.20 mmol). Once the addition was complete the reaction was stirred at room temperature for 7 hr. Three additional additions of calcium chloride (3.67 g, 33.10 mmol) and sodium borohydride (2.50 g, 66.20 mmol) were made at 8–16 hr intervals. The reaction was then diluted with EtOAc (250 mL) and then quenched by the careful addition of 1N HCl (250 mL). The layers were separated and the aqueous layer was extracted with EtOAc (2×250 mL). The combined organic layers were washed with sat. NaHCO$_3$ (1×100 mL), H$_2$O (1×100 mL), and brine (1×100 mL). They were dried (Na$_2$SO$_4$), filtered and the solvent removed in vacuo. The crude product was purified by flash chromatography (SiO$_2$, 1 EtOAc/3 hexanes) to afford the title compound (2.83 g, 57%). MS (CI) m/e 301.1 (M+NH$_4$-H$_2$O); $^1$H NMR (300 MHz, CDCl$_3$) δ ppm 1.43 (t, 3H), 1.54 (s, 9H), 2.66 (s, 1H), 4.40 (q, 2H), 4.68 (s, 2H), 6.65 (s, 1H), 10.14 (s, 1H).

Example 240d 2-t-butoxycarbonylamino-4-formyl-thiophene-3-carboxylic acid ethyl ester 2-t-Butoxycarbonylamino-4-hydroxymethyl-thiophene-3-carboxylic acid ethyl ester (2.83 g, 9.44 mmol) was dissolved in anhydrous CH$_2$Cl$_2$ (165 mL) and treated with manganese dioxide (16.41 g, 188.70 mmol). It was stirred at room temperature for 5 hr then it was filtered through a pad of Celite. The Celite was washed with copious amounts of acetone. The filtrate was concentrated in vacuo to give title compound (2.69 g, 95%). MS m/e (CI) 300.0 (M+H)$^+$; $^1$H NMR (300 MHz, CDCl3): δ ppm 1.42 (t, 3H), 1.55 (s, 9H), 4.43 (q, 2H), 7.59 (s, 1H), 10.30 (s, 1H), 10.34 (s, 1H).

Example 240e 2-t-butoxycarbonylamino-4-styryl-thiophene-3-carboxylic acid ethyl ester Benzyltriphenylphosphonium bromide (1.30 g, 3.01 mmol) was suspended in anhydrous THF (6 mL) and cooled to 0° C. This was treated with n-butyllithium (1.20 mL, 3.01 mmol, 2.5M in hexanes) by slow addition. It was then stirred at 0° C. for 1.5 hr. Next it was treated with a solution of 2-t-butoxycarbonylamino-4-formyl-thiophene-3-carboxylic acid ethyl ester (0.300 g, 1.00 mmol) dissolved in anhydrous THF (6 mL) by slow addition. The reaction was allowed to stir at room temperature for 1 hr. It was then quenched with sat. NH$_4$Cl (12 mL). This was extracted with CH$_2$Cl$_2$ (3×25 mL). The combined extracts were washed with H$_2$O (1×25 mL) and brine (1×25 mL). The extracts were dried (Na$_2$SO$_4$), filtered, and the solvent removed in vacuo. The crude product was purified by flash chromatography (SiO$_2$, 1 EtOAc/3 hexanes) to afford the title compound (0.3432 g, 92%). MS m/e (CI) 374.1 (M+H)$^+$; $^1$H NMR (300 MHz, CDCl$_3$): δ ppm 1.26 (m, 1H), 1.36 (t, 1H), 1.44 (m, 1H), 1.54

(s, 9H), 4.35 (m, 1H), 6.34 (s, 1H), 6.59 (m, 1H), 6.93 (d, 1H), 6.89 (s, 1H), 7.17 (s, 1H), 7.35 (t, 1H), 7.47 (d, 1H), 7.59 (d, 1H), 10.40 (s, 1H).

Example 240f 2-amino-4-styryl-thiophene-3-carboxylic acid ethyl ester 2-t-Butoxycarbonylamino-4-styryl-thiophene-3-carboxylic acid ethyl ester (0.335 g, 0.848 mmol) was dissolved in anhydrous $CH_2Cl_2$ (8 mL). This was treated with trifluoroacetic acid (0.346 mL, 4.49 mmol) and stirred at room temperature for 6 hr. More trifluoroacetic acid (0.346 mL, 4.49 mmol) was added and stirring at room temperature was continued for 30 min. The reaction was neutralized with sat. $NaHCO_3$ (25 mL) and then extracted with $CH_2Cl_2$ (2×25 mL). The combined organic layers were washed with $H_2O$ (1×25 mL) and brine (1×25 mL). The organic layer was then dried ($Na_2SO_4$), filtered and the solvent removed in vacuo. The crude product was purified by flash chromatography ($SiO_2$, 15 EtOAc/85 hexanes) to afford the title compound (0.1298 g, 56%) as an inseparable mixture. MS m/e (CI) 274.0 (M+H)$^+$; 1H NMR (300 MHz, CDCl$_3$): δ ppm 0.85 (d, 1H), 1.32 (m, 4H), 4.26 (m, 1H), 6.75 (s, 1H), 7.18 (m, 4H), 7.35 (d, 1H), 7.52 (d, 1H), 7.66 (d, 1H), 7.78 (s, 1H).

Example 240g 2-(2-cyano-acetylamino)-4-styryl-thiophene-3-carboxylic acid ethyl ester 2-Amino-4-styryl-thiophene-3-carboxylic acid ethyl ester (0.1298 g, 0.475 mmol) S was dissolved in anhydrous $CH_2Cl_2$ (2.0 mL). This was treated with cyanoacetyl chloride (0.713 mL, 0.713 mmol, 1 M in $CH_2Cl_2$) and stirred at room temperature for 1 hr. More cyanoacetyl chloride (0.238 mL, 0.238 mmol) was added and stirring was continued at room temperature for 1 hr then refluxed for 30 min. The reaction was diluted with EtOAc (25 mL). This was washed with sat. $NaHCO_3$ (1×25 mL), $H_2O$ (1×25 mL), and brine (1×25 mL). The organic layer was dried ($Na_2SO_4$), filtered and the solvent removed in vacuo to give 0.0803 g (50%) of crude 7 which was carried on to the next step.

Example 240

4-hydroxy-6-oxo-3-styryl-6,7-dihydro-thiophene[2,3-b]pyridine-5-carbonitrile 2-(2-Cyano-acetylamino)-4-styryl-thiophene-3-carboxylic acid ethyl ester (0.0803 g, 0.236 mmol) was dissolved in anhydrous THF/DMF mixture (3.0 mL, 5:1, v:v). This was treated with sodium hydride (0.023 g, 0.945 mmol) and stirred at room temperature for 1 hr. MeOH (2.0 mL) was added to the reaction and it was concentrated in vacuo. Purification by reverse phase HPLC gave 0.0045 g (6.5%) of pure title compound. MS m/e (CI) 294.9 (M+H), 312.1 (M+NH$_4$), 316.9 (M+Na); $^1$H NMR (300 MHz, MeOH-d$_4$): δ ppm 7.04 (m, 1H), 7.09 (s, 1H), 7.22 (s, 1H), 7.25 (m, 1H), 7.33 (s, 1H), 7.51 (d, 1H), 7.89 (s, 1H), 7.94 (m, 1H)

Example 241

4-hydroxy-6-oxo-3-(phenylethynyl)-6,7-dihydrothieno[2,3-b]pyridine-5-carbonitrile Example 241a 2-t-butoxycarbonylamino-4-ethynyl-thiophene-3-carboxylic acid ethyl ester 2-t-Butoxycarbonylamino-4-formyl-thiophene-3-carboxylic acid ethyl ester (6.35 g, 21.31 mmol) from example 240d was dissolved in absolute EtOH (325 mL). This was treated with potassium carbonate (%.89 g, 42.62 mmol) followed by (1-diazo-2-oxopropyl)-phosphonic acid dimethyl ester (4.91 g, 25.57 mmol). The reaction was stirred at room temperature for 14 hr. The reaction was concentrated to 12 volume then poured into sat. $NaHCO_3$ (250 mL) and then extracted with EtOAc (3×250 mL). The combined extracts were washed with brine (2×250 mL). They were dried ($Na_2SO_4$), filtered and the solvent removed in vacuo. The crude product was purified by flash chromatography (SiO2, 1 EtOAc/9 hexanes) to afford the title compound (5.86 g, 93%). MS m/e (CI) 296.0 (M+H), 313.1 (M+NH$_4$); $^1$H NMR (300 MHz, CDCl$_3$): δ ppm 1.41 (t, 3H), 1.53 (s, 9H), 3.11 (s, 1H), 4.37 (q, 2H), 6.98 (s, 1H), 10.30 (s, 1H).

Example 241b 2-amino-4-ethynyl-thiophene-3-carboxylic acid ethyl ester 2-t-Butoxycarbonylamino-4-ethynyl-thiophene-3-carboxylic acid ethyl ester (5.86 g, 19.85 mmol) was dissolved in anhydrous $CH_2Cl_2$ (125 mL). This was treated with 2,6-lutidine (4.62 mL, 39.70 mmol) followed by dropwise addition of t-butyldimethylsilyl trifluoromethanesulfonate (6.84 mL, 29.77 mmol). This was stirred at room temperature for 2 hr. Next it was poured into sat. $NH_4Cl$ (100 mL) and then extracted with EtOAc (3×100 mL). The combined extracts were washed with $H_2O$ (1×100 mL), and brine (1×100 mL). The organic layer was dried ($Na_2SO_4$), filtered and the solvent removed in vacuo. The residue was dissolved in anhydrous THF (85 mL) and treated with tetrabutylammonium fluoride (19.85 mL, 19.85 mmol, 1 M in THF). The reaction was then stirred at room temperature for 1 hr. The reaction was poured into sat. $NH_4Cl$ (100 mL) and then extracted with EtOAc (3×100 mL). The combined extracts were washed with $H_2O$ (1×100 mL), and brine (1×100 mL). The extracts were dried ($Na_2SO_4$), filtered and the solvent removed in vacuo. The crude product was purified by flash chromatography ($SiO_2$, 1 EtOAc/9 hexanes) to afford the title compound (3.0 g, 77%). MS m/e (CI) 196.0 (M+H)$^+$; $^1$H NMR (300 MHz, CDCl$_3$): δ ppm 1.38 (t, 2H), 3.07 (s, 1H), 4.32 (q, 2H), 6.04 (s, 2H), 6.54 (s, 1H), 7.26 (s, 1H); MS m/e (CI) 196.0 (M+H)$^+$.

Example 241c 2-amino-4-phenylethynyl-thiophene-3-carboxylic acid ethyl ester

2-Amino-4-ethynyl-thiophene-3-carboxylic acid ethyl ester (0.075 g, 0.385 mmol) was dissolved in anhydrous $CH_3CN$ (2.0 mL). This was treated with iodobenzene (0.129 mL, 1.15 mmol) followed by diisopropylamine (0.272 mL, 1.92 mmol). The solution was then degassed and treated with copper iodide (0.0018 g, 0.010 mmol) and dichlorobis(triphenylphosphine)palladium(II) (0.014 g, 0.019 mmol). The reaction was then stirred at room temperature for 30 min. The reaction was concentrated in vacuo. The crude product was purified by flash chromatography (SiO$_2$, 15 EtOAc/85 hexanes) to afford the title compound (0.081 g, 78%). MS m/e (CI) 272.0 (M+H)$^+$.

Example 241d 2-(2-cyano-acetylamino)-4-phenylethynyl-thiophene-3-carboxylic acid ethyl ester Example 241D was prepared using the same procedure as described for Example 240G substituting 2-amino-4-phenylethynyl-thiophene-3-carboxylic acid ethyl ester (0.081 g, 0.298 mmol) for 2-(2-cyano-acetylamino)-4-styryl-thiophene-3-carboxylic acid ethyl ester in Example 240G to give the title compound (0.087, 86%). MS m/e (CI) 356.1 (M+NH$_4$); $^1$H NMR (300 MHz, CDCl$_3$): δ ppm 1.42 (t, 3H), 3.68 (s, 2H), 4.46 (q, 2H), 7.13 (s, 1H), 7.51 (m, 2H), 12.03 (s, 1H).

Example 241

4-hydroxy-6-oxo-3-(phenylethynyl)-6,7-dihydrothieno[2,3-b]pyridine-5-carbonitrile Example 241 was prepared using the same procedure as described for Example 240 substituting 2-(2-cyano-acetylamino)-4-phenylethynyl-thiophene-3-carboxylic acid ethyl ester (0.087 g, 0.256 mmol) for 2-(2-Cyano-acetylamino)-4-styryl-thiophene-3-carboxylic acid ethyl ester in Example 240 to give the title compound (0.0043 g, 5.8%). MS m/e (CI) 292.8 (M+H)$^+$ 314.8 (M+Na); $^1$H NMR (300 MHz, MeOH-d$_4$) δ ppm 7.09 (s, 1H), 7.33 (m, 3H), 7.58 (m, 2H).

Example 242

N-{3-[4-(5-Cyano-4-hydroxy-6-oxo-6,7-dihydrothieno[2,3-b]pyridin-3-yl)phenyl]prop-2-ynyl}methanesulfonamide The title compound was prepared according to procedure described in Example 32, substituting N-prop-2-ynyl-methanesulfonamide (J. Med. Chem. 1988, 31, 577) for hex-5-ynenitrile used in Example 32. MS (ESI) m/e 398 (M–H)$^+$; $^1$H NMR (500 MHz, DMSO-d$_6$) δ 3.04 (s, 3H), 4.08 (s, 2H), 6.69 (s, 1H), 7.34 (d, J=8.42 Hz, 2H), 7.46 (d, J=8.42 Hz, 2H).

Example 243

4-Hydroxy-3-[4-(4-hydroxybutyl)phenyl]-6-oxo-6,7-dihydrothieno[2,3-b]pyridine-5-carbonitrile The title compound was prepared according to the hydrogenation procedure described in Example 35, substituting 4-hydroxy-3-[4-(4-hydroxy-but-1-ynyl)-phenyl]-6-oxo-6,7-dihydro-thieno[2,3-b]pyridine-5-carbonitrile for 4-hydroxy-3-[4-(5-hydroxy-pent-1-ynyl)-phenyl]-6-oxo-6,7-dihydro-thieno[2,3-b]pyridine-5-carbonitrile. MS (ESI) m/e 341 (M+H)$^+$; $^1$H NMR (500 MHz, DMSO-d$_6$): δ 1.44–1.48 (m, 2H), 1.58–1.64 (m, 2H), 2.06 (t, J=7.64 Hz, 2H), 2.59 (t, J=7.64 Hz, 2H), 6.96 (s, 1H), 7.16 (d, J=8.11 Hz, 2H), 7.32 (d, J=8.11 Hz, 2H), 12.47 (s, 1H).

Example 244

3-[4-(4-Azidobut-1-ynyl)phenyl]-4-hydroxy-6-oxo-6,7-dihydrothieno[2,3-b]pyridine-5-carbonitrile To a solution of 4-hydroxy-3-[4-(4-hydroxy-but-1-ynyl)-phenyl]-6-oxo-6,7-dihydro-thieno[2,3-b]pyridine-5-carbonitrile (0.23 g, 0.7 mmol) in 5 mL DMF was added triethylamine (0.28 mL, 2 mmol), followed by MsCl (85 µL, 1 mmol). The mixture was stirred at rt for 2 hr, after which NaN$_3$ (0.36 g, 5.6 mmol) was added, and heated to 90° C. overnight. Solvent was removed in vacuo and purified via reverse phase HPLC to afford the titled compound. MS (ESI) m/e 360 (M–H)$^+$; $^1$H NMR (300 MHz, DMSO-d$_6$): δ 2.76 (t, J=6.61 Hz, 2H), 3.52 (t, J=6.44 Hz, 2H), 6.67 (s, 1H), 7.29 (d, J=8.48 Hz, 2H), 7.44 (d, J=8.48 Hz, 2H).

Example 245

4-Hydroxy-3-[4-(5-hydroxypentyl)phenyl]-6-oxo-6,7-dihydrothieno[2,3-b]pyridine-5-carbonitrile To a suspension of Pd (BaSO$_4$) (15 mg) in toluene (2 mL) and methanol (1 mL), was added 4-hydroxy-3-[4-(5-hydroxy-pent-1-ynyl)-phenyl]-6-oxo-6,7-dihydro-thieno[2,3-b]pyridine-5-carbonitrile (50 mg) in a single portion. The reaction was purged with hydrogen, and stirred under atmosphere hydrogen at rt for 24 h. The mixture was filtered through celite, and rinsed with methanol. The filtrate was concentrated and purified via reverse phase HPLC to afford the titled compound. MS (ESI) m/e 353 (M–H)$^+$; $^1$H NMR (500 MHz, DMSO-d$_6$): δ 1.31–1.47 (m, 4H), 1.55–1.61 (m, 2H), 1.94 (t, J=7.64 Hz, 2H), 2.58 (t, J=7.64 Hz, 2H), 6.91 (s, 1H), 7.15 (d, J=8.11 Hz, 2H), 7.31 (d, J=8.11 Hz, 2H).

Example 246

Ethyl 4-hydroxy-3-(2'-hydroxy-1,1'-biphenyl-4-yl)-6-oxo-6,7-dihydrothieno[2,3-b]pyridine-5-carboxylate

Example 246a

2-Amino-4-(4-bromophenyl)-thiophene-3-carboxylic acid ethyl ester

The titled compound was synthesized according the procedure described in Example 29b, substituting 4-bromoacetophenone for 1-(4-allyloxy-phenyl)-propan-1-one used in Example 29b.

Example 246b 4-(4-Bromo-phenyl)-2-(2-ethoxycarbonyl-acetylamino)-thiophene-3-carboxylic acid ethyl ester To a solution of 2-amino-4-(4-bromophenyl)-thiophene-3-carboxylic acid ethyl ester (4.00 g, 11.5 mmol) in CH$_2$Cl$_2$ (40 mL) was added ethyl chloromalonate (2.15 g, 14.2 mmol) slowly. The mixture was then heated to reflux for 30 min. The mixture was concentrated under reduced pressure and separated by flash chromatography on silica gel (5–30% ethyl acetate in hexanes) giving the titled compound (4.98 g, 98.5%).

Example 246c 3-(4-Bromo-phenyl)-4-hydroxy-6-oxo-6,7-dihydro-thieno[2,3-b]pyridine-5-carboxylic acid ethyl ester To a solution of 4-(4-bromo-phenyl)-2-(2-ethoxycarbonyl-acetylamino)-thiophene-3-carboxylic acid ethyl ester (4.98 g, 11.3 mmol) in DMF (30 mL) at 0° C. was added a dispersion of sodium hydride in mineral oil (60%, 2.73 g, 68.2 mmol). After warming to ambient temperature the reaction was stirred overnight. Aqueous HCl (1.2 M, 100 mL) was added while cooling the mixture to 0° C. After stirring 1 h. the mixture was filtered and washed with $H_2O$ and hexanes giving the titled compound (2.85 g, 64%) as a gray solid.

Example 246d

4-Hydroxy-3-(2'-hydroxy-biphenyl-4-yl)-6-oxo-6,7-dihydro-thieno[2,3-b]pyridine-5-carboxylic acid ethyl ester To a mixture of 3-(4-bromo-phenyl)-4-hydroxy-6-oxo-6,7-dihydro-thieno[2,3-b]pyridine-5-carboxylic acid ethyl ester (100 mg, 0.25 mmol), 2-hydroxyphenylboronic acid (53 mg, 0.38 mmol), $K_3PO_4$ (169 mg, 0.63 mmol), P(o-tolyl)$_3$ (7.7 mg, $2.5 \times 10^{-5}$ mol), and Pd(OAc)$_2$ (2.8 mg, $1.3 \times 10-5$ mol) was added THF (1.5 mL) and $H_2O$ (0.5 mL). The mixture was purged with nitrogen for 15 min., capped, and heated to 80° C. for 1.5 h. The reaction mixture was concentrated under reduced pressure and purified by reverse phase HPLC (0–70% $CH_3CN$ in $NH_4OAc$ aq.) to give the titled compound. MS (ESI) m/e 430 $(M+Na)^+$, 408 $(M+H)^+$; 406 $(M-H)^-$. $^1H$ NMR (300 MHz, DMSO-$d_6$) δ 1.28 (t, J=7.12 Hz, 3H), 4.29 (q, J=7.01 Hz, 2H), 6.89 (td, J=7.46, 1.35 Hz, 1H), 6.96 (dd, J=8.14, 1.02 Hz, 1H), 6.99 (s, 1H), 7.17 (m, 1H), 7.30 (dd, J=7.46, 1.70 Hz, 1H), 7.46 (m, 2H), 7.54 (m, 2H), 9.56 (s, 1H), 12.21 (br s, 1H).

Example 247

3-(2'-fluoro-6'-hydroxy-1,1'-biphenyl-4-yl)-4-hydroxy-6-oxo-6,7-dihydrothieno[2,3-b]pyridine-5-carbonitrile The titled compound was prepared according to the procedures described in Example 3a-b, substituting 6-fluoro-2-methoxyphenylboronic acid for 2,3-dimethoxyphenylboronic acid used in Example 3a (30.5.0 mg, 80.6%). $^1H$ NMR (300 MHz, DMSO-$d_6$) δ 12.44 (s, 1H), 9.92 (s, 1H), 7.48 (d, 2H, J=9 Hz), 7.37 (d, 2H, J=9 Hz), 7.19 (q, 1H, J=9.0 Hz), 7.06 (s, 1H), 6.82–6.70 (m, 2H). MS (ESI) m/e 379 $(M+H)^+$, 377 $(M-H)^-$.

Determination of Biological Activity In vitro
AMPK Assay

Using a modification of a protocol described by Davies et. al. (Zhou, M. et.al. UCP-3 expression in skeletal muscle: effects of exercise, hypoxia, and AMP-activated protein kinase. Am. J. Physiol. Endocrinol. Metab. 279: E622 (2000)), in a 20 μl reaction volume $^{33}$P-ATP (PerkinElmer, Boston, Mass.), 600 μM ATP, 20 μM SAMS peptide (HMR-SAMSGLHLVKRR), AMPK and AMP or compounds at the indicated concentrations were incubated for 15 minutes at 30° C. in buffer containing 40 mM HEPES, 80 mM NaCl, 2 mM MgCl$_2$, 0.8 mM EDTA, 8% glycerol, 0.18% Triton-X-100 and 1 mM DTT. The reaction was stopped with 10 μl per well of 7.5 M Guanidine HCl, the plates were shaken briefly and 15 μl of reaction mix was transferred to SAM filter plates (Promega, Madison, Wis.). 100 μl 2 M NaCl was added per well and the plates incubated at room termerature for 1–2 minutes. Wells were then washed 8 times with 2 M NaCl, 12 times with 2 M NaCl with 1% phosphoric acid, 4 times with water and 1 time with EtOH before air drying, adding scintillant and measuring CPM, in a Topcount (Perkin Elmer). Percent activation was determined as compared to the maximal activation achieved by AMP under these assay conditions. AMPK used in the assays described above was partially purified (Blazquez, C. et.al. The AMP-activated protein kinase is involved in the regulation of ketone body production by astrocytes. J. Neurochem. 73: 1674 (1999)) from HEKs (a human embryonic kidney cell line) and unless otherwise specified, chemicals used in the above assay were supplied by Sigma.

Representative compounds of the present invention activate AMPK at a dose range of 1–100 μM. Represenetive compounds of the present invention activate AMPK greater than 50% compared to AMP at a dose of 100 μM. In a preferred range, representative compounds of the present invention activate AMPK greater than 50% compared to AMP at a dose of 30 μM. In a more preferred range, representative compounds of the present invention activate AMPK greater than 50% compared to AMP at a dose of 10 μM. And in a most prefered range, representative compounds of the present invention activate AMPK greater than 50% compared to AMP at a dose of 1 μM.

IN VIVO ASSAY

Representative compounds of the present invention were evaluated for their effects on plasma glucose and triglyceride levels after 5 days of dosing in ob/ob mice according to the following procedure. On day 1, 6–7 week old male mice were culled into treatments groups based on plasma glucose and body weights. A post-prandial glucose level of 250–400 mg/dl was deemed acceptable for study entry. The compounds were dosed into the intraperitoneal cavity (IP), and glucose readings were measured at 1 and 3 hr. IP-dosing of animals continued twice a day (bid) for 5 days. On day 5, 16 hr after the previous dose, at 8AM, plasma glucose and body weight were determined. In addition, plasma was collected 1 hour after the final dose on day 5 for plasma glucose and triglyceride evaluation, and then the animals were sacrificed via CO2 and cardiac puncture. Representative compounds of the present invention were evaluated and found to decrease plasma glucose >25% and decrease plasma triglyceride levels >50% relative to control animals.

The total daily dose of the present compounds in single or divided doses can be in amounts, for example, from 0.01 to 50 mg/kg body weight or more usually from 0.1 to 25 mg/kg body weight. In general, treatment regimens comprise administration to a patient in need of such treatment from about 10 mg to about 1000 mg of the compounds per day in single or multiple doses.

Therapeutic compositions of the present compounds comprise an effective amount of the same formulated with one or more therapeutically suitable excipients. The term "therapeutically suitable excipient," as used herein, represents a non-toxic, solid, semi-solid or liquid filler, diluent, encapsulating material, or formulation auxiliary of any type. Examples of therapeutically suitable excipients include sugars; cellulose and derivatives thereof; oils; glycols; solutions; buffering, coloring, releasing, coating, sweetening, flavoring, and perfuming agents; and the like. These therapeutic compositions can be administered parenterally, intracisternally, orally, rectally, or intraperitoneally.

Liquid dosage forms for oral administration of the present compounds comprise formulations of the same as emulsions, microemulsions, solutions, suspensions, syrups, and elixirs. In addition to the compounds, the liquid dosage forms can contain diluents and/or solubilizing or emulsifying agents. Besides inert diluents, the oral compositions can include wetting, emulsifying, sweetening, flavoring, and perfuming agents.

Injectable preparations of the present compounds comprise sterile, injectable, aqueous and oleaginous solutions, suspensions or emulsions, any of which can be optionally formulated with parenterally suitable diluents, dispersing, wetting, or suspending agents. These injectable preparations can be sterilized by filtration through a bacterial-retaining filter or formulated with sterilizing agents which dissolve or disperse in the injectable media.

Regulating of the effects of AMP-activated protein kinase through administration of the compounds of the present invention can be delayed by using a liquid suspension of crystalline or amorphous material with poor water solubility. The rate of absorption of the compounds depends upon their rate of dissolution which, in turn, depends on their crystallinity. Delayed absorption of a parenterally administered compound can be accomplished by dissolving or suspending the compound in oil. Injectable depot forms of the compounds can also be prepared by microencapsulating the same in biodegradable polymers. Depending upon the ratio of compound to polymer and the nature of the polymer employed, the rate of release can be controlled. Depot injectable formulations are also prepared by entrapping the compounds in liposomes or microemulsions which are compatible with body tissues.

Solid dosage forms for oral administration of the present compounds include capsules, tablets, pills, powders, and granules. In such forms, the compound is mixed with at least one inert, therapeutically suitable excipient such as a carrier, filler, extender, disintegrating agent, solution retarding agent, wetting agent, absorbent, or lubricant. With capsules, tablets, and pills, the excipient can also contain buffering agents. Suppositories for rectal administration can be prepared by mixing the compounds with a suitable non-irritating excipient which is solid at ordinary temperature but fluid in the rectum.

The present compounds can be micro-encapsulated with one or more of the excipients discussed previously. The solid dosage forms of tablets, dragees, capsules, pills, and granules can be prepared with coatings and shells such as enteric and release-controlling. In these forms, the compounds can be mixed with at least one inert diluent and can optionally comprise tableting lubricants and aids. Capsules can also optionally contain opacifying agents which delay release of the compounds in a desired part of the intestinal tract.

Transdermal patches have the added advantage of providing controlled delivery of the present compounds to the body. Such dosage forms are prepared by dissolving or dispensing the compounds in the proper medium. Absorption enhancers can also be used to increase the flux of the compounds across the skin, and the rate of absorption can be controlled by providing a rate controlling membrane or by dispersing the compounds in a polymer matrix or gel.

Disorders that may be regulated by activation of AMPK are treated or prevented in a patient by administering to the patient, a therapeutically effective amount of compound of the present invention in such an amount and for such time as is necessary to achieve the desired result. The term "therapeutically effective amount," refers to a sufficient amount of a compound to effectively emeliorate disorders reglulated by ghrelin at a reasonable benefit/risk ratio applicable to any medical treatment. The specific therapeutically effective dose level for any particular patient will depend upon a variety of factors including the disorder being treated and the severity of the disorder; the activity of the compound employed; the specific composition employed; the age, body weight, general health, sex, and diet of the patient; the time of administration, route of administration, rate of excretion; the duration of the treatment; and drugs used in combination or coincidental therapy.

It is understood that the foregoing detailed description and accompanying examples are merely illustrative and are not to be taken as limitations upon the scope of the invention, which is defined solely by the appended claims and their equivalents. Various changes and modifications to the disclosed aspects will be apparent to those skilled in the art. Such changes and modifications, including without limitation those relating to the chemical structures, substituents, derivatives, intermediates, syntheses, formulations and/or methods of use of the invention, may be made without departing from the spirit and scope thereof.

What is claimed is:

1. A compound of formula (I):

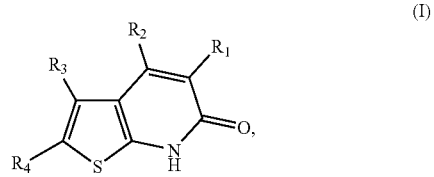

or a therapeutically suitable salt, ester or prodrug thereof, wherein $R_1$ is selected from the group consisting of hydrogen, alkoxy, alkoxycarbonyl, alkyl, alkenyl, alkynyl, carboxy, carboxyalkyl, cyano, cyanoalkyl, halogen, haloalkyl, trihaloalkyl, heterocycle, hydroxyalkyl, $R_aR_bN—$, $R_aR_b$Nalkyl, and $R_cR_dNC(O)—$, wherein alkyl may be optionally substituted with $O=$ and $R_f—N=$;

$R_2$ is selected from the group consisting of $R_fO—$, $HO—$, $R_fS—$, and $HS—$;

$R_3$ is selected from the group consisting of alkoxycarbonyl, substituted aryl, arylalkyl, arylalkenyl, arylalkynyl, cycloalkyl, carboxy, carboxyalkyl, halogen, heteroaryl, heterocycle, heterocyclealkyl, $R_gR_jN—$, and $R_gR_j$Nalkyl, wherein cycloalkyl may be fused to an aryl ring as defined herein;

$R_4$ is selected from the group consisting of hydrogen, alkyl, alkenyl, alkynyl, aryl, arylalkyl, arylcarbonyl, aryloxycarbonyl, carboxy, carboxyalkyl, carboxyalkynyl, halogen, haloalkyl, heteroaryl, heterocycle, heterocyclealkyl, heterocyclecarbonyl, heterocycleoxycarbonyl, hydroxyalkyl, $HO—N=CH—(CH_2)_u—$, and $R_mR_nN—$;

u is 0, 1 or 2;

$R_a$ and $R_b$ are each individually selected from the group consisting of hydrogen, alkyl, alkylcarbonyl, alkoxylcarbonyl, aryl, arylalkyl, arylcarbonyl, arylalkyloxycarbonyl, heteroaryl, heterocycle, heterocyclealkyl, heterocyclecarbonyl, and heterocycleoxycarbonyl;

$R_c$ and $R_d$ are each independently selected from the group consisting of hydrogen, alkyl, aryl, arylalkyl, haloalkyl, hydroxyalkyl, and heterocycle;

$R_f$ is selected from the group consisting of alkyl, cycloalkyl, cycloalkylalkyl, alkoxyalkyl, alkylthioalkyl, and haloalkyl;

$R_g$ and $R_j$ are each independently selected from the group consisting of hydrogen, alkyl, alkoxycarbonyl, aryl, arylalkyl, arylcarbonyl, aryloxycarbonyl, heteroaryl, heterocycle, heterocyclealkyl, heterocyclecarbonyl, heterocycleoxycarbonyl, and haloalkyl;

$R_m$ and $R_n$ are each independently selected from the group consisting of hydrogen, alkyl, alkoxycarbonyl, aryl, arylalkyl, heteroaryl, heterocycle, heterocyclealkyl, and haloalkyl; and $R_t$ is selected from the group consisting of hydrogen, alkyl and HO—.

2. The compound of claim 1, wherein $R_1$ is selected from the group consisting of hydrogen, alkoxy, alkoxycarbonyl, alkyl, alkenyl, alkynyl, carboxy, carboxyalkyl, cyano, cyanoalkyl, halogen, haloalkyl, trihaloalkyl, heterocycle, hydroxyalkyl, $R_aR_bN$—, $R_aR_b$Nalkyl, and $R_cR_dNC(O)$—, wherein alkyl may be optionally substituted with O= and $R_t$—N=;

$R_2$ is selected from the group consisting of $R_fO$—, and HO—;

$R_3$ is selected from the group consisting of alkoxycarbonyl, substituted aryl, arylalkyl, arylalkenyl, arylalkynyl, cycloalkyl, carboxy, carboxylalkyl, halogen, heteroaryl, heterocycle, heterocyclealkyl, $R_gR_jN$—, and $R_gR_j$Nalkyl, wherein cycloalkyl may be fused to an aryl ring as defined herein;

$R_4$ is selected from the group consisting of hydrogen, alkyl, alkenyl, alkynyl, aryl, arylalkyl, arylcarbonyl, aryloxycarbonyl, carboxy, carboxyalkyl, carboxyalkynyl, halogen, haloalkyl, heteroaryl, heterocycle, heterocyclealkyl, heterocyclecarbonyl, heterocycleoxycarbonyl, hydroxyalkyl, HO—N=CH—$(CH_2)_u$—, and $R_mR_nN$—;

u is 0, 1 or 2;

$R_a$ and $R_b$ are each individually selected from the group consisting of hydrogen, alkyl, alkylcarbonyl, alkoxylcarbonyl, aryl, arylalkyl, arylcarbonyl, arylalkyloxycarbonyl, heteroaryl, heterocycle, heterocyclealkyl, heterocyclecarbonyl, and heterocycleoxycarbonyl;

$R_c$ and $R_d$ are each independently selected from the group consisting of hydrogen, alkyl, aryl, arylalkyl, haloalkyl, hydroxyalkyl, and heterocycle;

$R_f$ is selected from the group consisting of alkyl, cycloalkyl, cycloalkylalkyl, alkoxyalkyl, alkylthioalkyl, and haloalkyl;

$R_g$ and $R_j$ are each independently selected from the group consisting of hydrogen, alkyl, alkoxycarbonyl, aryl, arylalkyl, arylcarbonyl, aryloxycarbonyl, heteroaryl, heterocycle, heterocyclealkyl, heterocyclecarbonyl, heterocycleoxycarbonyl, and haloalkyl;

$R_m$ and $R_n$ are each independently selected from the group consisting of hydrogen, alkyl, alkoxycarbonyl, aryl, arylalkyl, heteroaryl, heterocycle, heterocyclealkyl, and haloalkyl; and $R_t$ is selected from the group consisting of hydrogen, alkyl and HO—.

3. The compound of claim 1, wherein $R_1$ is selected from the group consisting of hydrogen, alkoxy, alkoxycarbonyl, alkyl, alkynyl, carboxy, cyano, halogen, heterocycle, and hydroxyalkyl, wherein alkyl may be optionally substituted with O= and $R_t$—N=;

$R_2$ is selected from the group consisting of $R_fO$—, and HO—;

$R_3$ is selected from the group consisting of alkoxycarbonyl, substituted aryl, arylalkyl, arylalkenyl, arylalkynyl, cycloalkyl, carboxy, carboxylalkyl, halogen, heteroaryl, heterocycle, heterocyclealkyl, $R_gR_jN$—, and $R_gR_j$Nalkyl, wherein cycloalkyl may be fused to an aryl ring as defined herein;

$R_4$ is selected from the group consisting of hydrogen, alkyl, carboxyalkynyl, halogen, haloalkyl, heteroaryl, heterocycle, heterocyclealkyl, and HO—N=CH—$(CH_2)_u$—;

u is 0, 1 or 2;

$R_f$ is selected from the group consisting of alkyl, cycloalkyl, cycloalkylalkyl, alkoxyalkyl, alkylthioalkyl, and haloalkyl;

$R_g$ and $R_j$ are each independently selected from the group consisting of hydrogen, alkyl, alkoxycarbonyl, aryl, arylalkyl, arylcarbonyl, aryloxycarbonyl, heteroaryl, heterocycle, heterocyclealkyl, heterocyclecarbonyl, heterocycleoxycarbonyl, and haloalkyl; and $R_t$ is selected from the group consisting of hydrogen, alkyl and HO—.

4. The compound of claim 1, wherein $R_1$ is selected from the group consisting of hydrogen, alkoxy, alkoxycarbonyl, alkyl, alkynyl, carboxy, cyano, halogen, heterocycle, and hydroxyalkyl, wherein alkyl may be optionally substituted with O= and $R_t$—N=;

$R_2$ is selected from the group consisting of $R_fO$—, and HO—;

$R_3$ is selected from the group consisting of alkoxycarbonyl, arylalkyl, arylalkenyl, arylalkynyl, cycloalkyl, carboxy, carboxylalkyl, halogen, heterocyclealkyl, $R_gR_jN$—, and $R_gR_j$Nalkyl, wherein cycloalkyl may be fused to an aryl ring as defined herein;

$R_4$ is selected from the group consisting of hydrogen, alkyl, carboxyalkynyl, halogen, haloalkyl, heteroaryl, heterocycle, heterocyclealkyl, and HO—N=CH—$(CH_2)_u$—;

u is 0, 1 or 2;

$R_f$ is selected from the group consisting of alkyl, cycloalkyl, cycloalkylalkyl, alkoxyalkyl, alkylthioalkyl, and haloalkyl; and $R_t$ is selected from the group consisting of hydrogen, alkyl and HO—.

5. The compound of claim 1, wherein $R_1$ is selected from the group consisting of hydrogen, alkoxy, alkoxycarbonyl, alkyl, alkynyl, carboxy, cyano, halogen, heterocycle, and hydroxyalkyl, wherein alkyl may be optionally substituted with O= and $R_t$—N=;

$R_2$ is selected from the group consisting of $R_fO$—, and HO—;

$R_3$ is selected from the group consisting of heteroaryl and heterocycle;

$R_4$ is selected from the group consisting of hydrogen, alkyl, carboxyalkynyl, halogen, haloalkyl, heteroaryl, heterocycle, heterocyclealkyl, and HO—N=CH—$(CH_2)_u$—;

u is 0, 1 or 2;

$R_f$ is selected from the group consisting of alkyl, cycloalkyl, cycloalkylalkyl, alkoxyalkyl, alkylthioalkyl, and haloalkyl;

$R_g$ and $R_j$ are each independently selected from the group consisting of hydrogen, alkyl, alkoxycarbonyl, aryl, arylalkyl, arylcarbonyl, aryloxycarbonyl, heteroaryl, heterocycle, heterocyclealkyl, heterocyclecarbonyl, heterocycleoxycarbonyl, and haloalkyl; and $R_t$ is selected from the group consisting of hydrogen, alkyl and HO—.

6. A compound of formula (II)

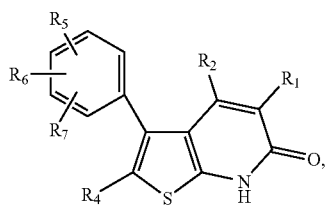

or a therapeutically suitable salt, ester or prodrug thereof, wherein $R_1$ is selected from the group consisting of hydrogen, alkyl, alkoxy, alkoxycarbonyl, alkynyl, carboxy, cyano, halogen, heterocycle, and hydroxyalkyl, wherein alkyl may be optionally substituted with O= and $R_t$—N=;

$R_2$ is selected from the group consisting of $R_fO$—, and HO—;

$R_4$ is selected from the group consisting of hydrogen, alkyl, carboxyalkynyl, halogen, haloalkyl, heteroaryl, heterocycle, heterocyclealkyl, and HO—N=CH—$(CH_2)_u$—;

$R_5$ is selected from the group consisting of alkenyl, alkenyloxy, alkoxy, alkoxyalkoxy, alkoxycarbonyl, alkyl, alkylcarbonyl, alkoxycarbonylalkoxy, alkynyl, aryl, aryloxy, carboxy, carboxyalkyl, carboxyalkoxy, cyano, cycloalkylalkoxy, formyl, halo, haloalkyl, trihaloalkyl, trihaloalkoxy, heteroaryl, heterocycle, hydroxy, hydroxyalkyl, hydroxyalkoxy, dihydroxyalkoxy, nitro, $R_pR_qN$—, $R_rR_sNC(O)$alkoxy, and $R_rR_sNSO_2$alkoxy;

$R_6$ and $R_7$ are each individually selected from the group consisting of hydrogen, alkenyl, alkenyloxy, alkoxy, alkoxyalkoxy, alkoxycarbonyl, alkoxyalkynyl, alkyl, alkylcarbonyl, alkoxycarbonylalkoxy, alkynyl, aryl, aryloxy, carboxy, carboxyalkyl, carboxyalkoxy, carboxyalkynyl, cyano, cyanoalkoxy, cyanoalkynyl, cycloalkenylalkoxy, formyl, halo, haloalkyl, trihaloalkyl, trihaloalkoxy, heteroaryl, heterocycle, heterocyclealkenyl, heterocyclealkoxy, heterocycleoxyalkynyl, hydroxy, hydroxyalkenyl, hydroxyalkyl, hydroxyalkoxy, hydroxyalkynyl, dihydroxyalkoxy, nitro, $R_pR_qN$—, $R_rR_sNC(O)$alkoxy, $R_rR_sNC(O)$alkynyl, and $R_rR_sNSO_2$alkoxy, $R_w$—O—N=CH—, and $R_xR_yN$-alkynyl or $R_6$ and $R_7$ together with the atoms to which they are attached form a ring selected from the group consisting of cycloalkyl and heterocycle;

u is 0, 1 or 2;

$R_f$ is selected from the group consisting of alkyl, cycloalkyl, cycloalkylalkyl, alkoxyalkyl, alkylthioalkyl, and haloalkyl;

$R_p$ is selected from the group consisting of hydrogen, alkenyl, alkenylcarbonyl, alkoxycarbonyl, alkoxycarbonylalkyl, alkoxycarbonylalkylcarbonyl, alkyl, alkylcarbonyl, alkynyl, aryl, arylalkenyl, arylalkyl, arylcarbonyl, haloalkyl, haloalkylcarbonyl, heteroaryl, heterocycle, heterocyclealkenyl, heterocyclealkyl, heterocyclealkylcarbonyl, heterocyclecarbonyl, trihaloalkyl, trihaloalkylcarbonyl, hydroxyalkyl, and hydroxyalkylcarbonyl;

$R_q$ are each independently selected from the group consisting of hydrogen, alkyl, alkenyl;

$R_r$ and $R_s$ are each independently selected from the group consisting of hydrogen, alkyl, arylalkyl, hydroxyalkyl, heterocyclealkyl;

$R_t$ is selected from the group consisting of hydrogen, alkyl and HO—;

$R_w$ is selected from the group consisting of hydrogen, alkylcarbonyl-NH-alkyl-NHC(O)-alkyl, alkyl, alkyl (alkyl)N-alkyl-NHC(O)-alkyl, hydroxyalkyl-NHC(O)-alkyl, heterocyclealkyl-NHC(O)-alkyl, heterocycle-NHC(O)-alkyl, heteroarylalkyl-NHC(O)-alkyl; and $R_x$ and $R_y$ are each individually selected fro the group consisting of hydrogen, alkyl and alkylsulfonyl.

7. The compound of claim 6, wherein $R_1$ is selected from the group consisting of hydrogen, alkyl, alkoxy, alkoxycarbonyl, carboxy, cyano, halogen, hydroxyalkyl, and heterocycle, wherein alkyl may be optionally substituted with O= and $R_t$—N=;

$R_2$ is selected from the group consisting of $R_fO$—, and HO—;

$R_4$ is selected from the group consisting of hydrogen, alkyl, carboxyalkynyl, halogen, haloalkyl, and HO—N=CH—$(CH_2)_u$—;

$R_5$ is selected from the group consisting of alkenyl, alkenyloxy, alkoxy, alkoxyalkoxy, alkoxycarbonyl, alkyl, alkylcarbonyl, alkoxycarbonylalkoxy, alkynyl, aryl, aryloxy, carboxy, carboxyalkyl, carboxyalkoxy, cyano, cycloalkylalkoxy, formyl, halo, haloalkyl, trihaloalkyl, trihaloalkoxy, heteroaryl, heterocycle, hydroxy, hydroxyalkyl, hydroxyalkoxy, dihydroxyalkoxy, nitro, $R_pR_qN$—, $R_rR_sNC(O)$alkoxy, and $R_rR_sNSO_2$alkoxy;

$R_6$ and $R_7$ are each individually selected from the group consisting of hydrogen, alkenyl, alkenyloxy, alkoxy, alkoxyalkoxy, alkoxycarbonyl, alkoxyalkynyl, alkyl, alkylcarbonyl, alkoxycarbonylalkoxy, alkynyl, aryl, aryloxy, carboxy, carboxyalkyl, carboxyalkoxy, carboxyalkynyl, cyano, cyanoalkoxy, cyanoalkynyl, cycloalkenylalkoxy, formyl, halo, haloalkyl, trihaloalkyl, trihaloalkoxy, heteroaryl, heterocycle, heterocyclealkenyl, heterocyclealkoxy, heterocycleoxyalkynyl, hydroxy, hydroxyalkenyl, hydroxyalkyl, hydroxyalkoxy, hydroxyalkynyl, dihydroxyalkoxy, nitro, $R_pR_qN$—, $R_rR_sNC(O)$alkoxy, $R_rR_sNC(O)$alkynyl, and $R_rR_sNSO_2$alkoxy, $R_w$—O—N=CH—, and $R_xR_yN$-alkynyl or $R_6$ and $R_7$ together with the atoms to which they are attached form a ring selected from the group consisting of cycloalkyl and heterocycle;

u is 0, 1 or 2;

$R_f$ is selected from the group consisting of alkyl, cycloalkyl, cycloalkylalkyl, alkoxyalkyl, alkylthioalkyl, and haloalkyl $R_p$ is selected from the group consisting of hydrogen, alkenyl, alkenylcarbonyl, alkoxycarbonyl, alkoxycarbonylalkyl, alkoxycarbonylalkylcarbonyl, alkyl, alkylcarbonyl, alkynyl, aryl, arylalkenyl, arylalkyl, arylcarbonyl, haloalkyl, haloalkylcarbonyl, heteroaryl, heterocycle, heterocyclealkenyl, heterocyclealkyl, heterocyclealkylcarbonyl, heterocyclecarbonyl, trihaloalkyl, trihaloalkylcarbonyl, hydroxyalkyl, and hydroxyalkylcarbonyl;

$R_q$ are each independently selected from the group consisting of hydrogen, alkyl, alkenyl;

$R_r$ and $R_s$ are each independently selected from the group consisting of hydrogen, alkyl, arylalkyl, hydroxyalkyl, heterocyclealkyl;

R$_t$ is selected from the group consisting of hydrogen, alkyl and HO—;

R$_w$ is selected from the group consisting of hydrogen, alkylcarbonyl-NH-alkyl-NHC(O)-alkyl, alkyl, alkyl (alkyl)N-alkyl-NHC(O)-alkyl, hydroxyalkyl-NHC(O)-alkyl, heterocyclealkyl-NHC(O)-alkyl, heterocycle-NHC(O)-alkyl, heteroarylalkyl-NHC(O)-alkyl; and R$_x$ and R$_y$ are each individually selected fro the group consisting of hydrogen, alkyl and alkylsulfonyl.

8. The compound of claim 6, wherein

R$_1$ is selected from the group consisting of hydrogen, alkyl, alkoxy, alkoxycarbonyl, alkynyl, carboxy, cyano, halogen, heterocycle, and hydroxyalkyl, wherein alkyl may be optionally substituted with O= and R$_f$—N=;

R$_2$ is selected from the group consisting of R$_f$O—, and HO—;

R$_4$ is selected from the group consisting of hydrogen, alkyl, carboxyalkynyl, halogen, haloalkyl, and HO—N=CH—(CH$_2$)$_u$—;

R$_5$ is selected from the group consisting of aryl, aryloxy, and heterocycle;

R$_6$ and R$_7$ are each individually selected from the group consisting of hydrogen, alkenyl, alkenyloxy, alkoxy, alkoxyalkoxy, alkoxycarbonyl, alkoxyalkynyl, alkyl, alkylcarbonyl, alkoxycarbonylalkoxy, alkynyl, aryl, aryloxy, carboxy, carboxyalkyl, carboxyalkoxy, carboxyalkynyl, cyano, cyanoalkoxy, cyanoalkynyl, cycloalkenylalkoxy, formyl, halo, haloalkyl, trihaloalkyl, trihaloalkoxy, heteroaryl, heterocycle, heterocyclealkenyl, heterocyclealkoxy, heterocycleoxyalkynyl, hydroxy, hydroxyalkenyl, hydroxyalkyl, hydroxyalkoxy, hydroxyalkynyl, dihydroxyalkoxy, nitro, R$_p$R$_q$N—, R$_r$R$_s$NC(O)alkoxy, R$_r$R$_s$NC(O)alkynyl, and R$_r$R$_s$NSO$_2$alkoxy, R$_w$—O—N=CH—, and R$_x$R$_y$N-alkynyl or R$_6$ and R$_7$ together with the atoms to which they are attached form a ring selected from the group consisting of cycloalkyl and heterocycle;

u is 0, 1 or 2;

R$_f$ is selected from the group consisting of alkyl, cycloalkyl, cycloalkylalkyl, alkoxyalkyl, alkylthioalkyl, and haloalkyl;

R$_p$ is selected from the group consisting of hydrogen, alkenyl, alkenylcarbonyl, alkoxycarbonyl, alkoxycarbonylalkyl, alkoxycarbonylalkylcarbonyl, alkyl, alkylcarbonyl, alkynyl, aryl, arylalkenyl, arylalkyl, arylcarbonyl, haloalkyl, haloalkylcarbonyl, heteroaryl, heterocycle, heterocyclealkenyl, heterocyclealkyl, heterocyclealkylcarbonyl, heterocyclecarbonyl, trihaloalkyl, trihaloalkylcarbonyl, hydroxyalkyl, and hydroxyalkylcarbonyl;

R$_q$ are each independently selected from the group consisting of hydrogen, alkyl, alkenyl;

R$_r$ and R$_s$ are each independently selected from the group consisting of hydrogen, alkyl, arylalkyl, hydroxyalkyl, heterocyclealkyl;

R$_t$ is selected from the group consisting of hydrogen, alkyl and HO—;

R$_w$ is selected from the group consisting of hydrogen, alkylcarbonyl-NH-alkyl-NHC(O)-alkyl, alkyl, alkyl (alkyl)N-alkyl-NHC(O)-alkyl, hydroxyalkyl-NHC(O)-alkyl, heterocyclealkyl-NHC(O)-alkyl, heterocycle-NHC(O)-alkyl, heteroarylalkyl-NHC(O)-alkyl; and R$_x$ and R$_y$ are each individually selected fro the group consisting of hydrogen, alkyl and alkylsulfonyl.

9. A compound of formula (III)

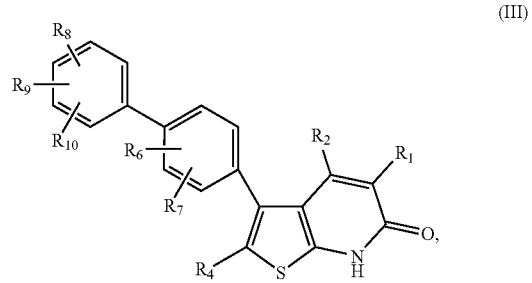

(III)

or a therapeutically suitable salt, ester or prodrug thereof, wherein

R$_1$ is selected from the group consisting of hydrogen, alkyl, alkoxy, alkoxycarbonyl, alkynyl, carboxy, cyano, halogen, heterocycle, and hydroxyalkyl, wherein alkyl may be optionally substituted with O= and R$_f$—N=;

R$_2$ is selected from the group consisting of R$_f$O—, and HO—;

R$_4$ is selected from the group consisting of hydrogen, alkyl, carboxyalkynyl, halogen, haloalkyl, heteroaryl, heterocycle, heterocyclealkyl, and HO—N=CH—(CH$_2$)$_u$—;

R$_6$ and R$_7$ are each individually selected from the group consisting of hydrogen, alkenyl, alkenyloxy, alkoxy, alkoxyalkoxy, alkoxycarbonyl, alkoxyalkynyl, alkyl, alkylcarbonyl, alkoxycarbonylalkoxy, alkynyl, aryl, aryloxy, carboxy, carboxyalkyl, carboxyalkoxy, carboxyalkynyl, cyano, cyanoalkoxy, cyanoalkynyl, cycloalkenylalkoxy, formyl, halo, haloalkyl, trihaloalkyl, trihaloalkoxy, heteroaryl, heterocycle, heterocyclealkenyl, heterocyclealkoxy, heterocycleoxyalkynyl, hydroxy, hydroxyalkenyl, hydroxyalkyl, hydroxyalkoxy, hydroxyalkynyl, dihydroxyalkoxy, nitro, R$_p$R$_q$N—, R$_r$R$_s$NC(O)alkoxy, R$_r$R$_s$NC(O)alkynyl, and R$_r$R$_s$NSO$_2$alkoxy, R$_w$—O—N=CH—, and R$_x$R$_y$NH-alkynyl or R$_6$ and R$_7$ together with the atoms to which they are attached form a ring selected from the group consisting of cycloalkyl and heterocycle;

R$_8$, R$_9$ and R$_{10}$ are each individually selected from the group consisting of hydrogen, alkenyl, alkenyloxy, alkoxy, alkoxyalkoxy, alkoxycarbonyl, alkoxyalkynyl, alkyl, alkylcarbonyl, alkylSO$_2$—, alkoxycarbonylalkoxy, alkynyl, arylalkynyl, aryloxy, carboxy, carboxyalkyl, carboxyalkynyl, carboxyalkoxy, cyano, formyl, halo, haloalkyl, heterocyclealkoxy, heterocycleoxyalkynyl, trihaloalkyl, trihaloalkoxy, hydroxy, hydroxyalkyl, hydroxyalkenyl, hydroxyalkynyl, hydroxyalkoxy, dihydroxyalkoxy, nitro, R$_u$R$_v$N—, R$_u$R$_v$Nalkyl-, R$_u$R$_v$N—C(O)-alkyl-, R$_u$R$_v$Nalkynyl-, R$_u$R$_v$N-C(O)alkynyl-, R$_r$R$_s$NSO$_2$—, or R$_8$ and R$_9$ taken together with the atoms to which they are attached form a 1,3-dioxolyl ring;

u is 0, 1 or 2;

R$_f$ is selected from the group consisting of alkyl, cycloalkyl, cycloalkylalkyl, alkoxyalkyl, alkylthioalkyl, and haloalkyl;

R$_p$ is selected from the group consisting of hydrogen, alkenyl, alkenylcarbonyl, alkoxycarbonyl, alkoxycarbonylalkyl, alkoxycarbonylalkylcarbonyl, alkyl, alkylcarbonyl, alkynyl, aryl, arylalkenyl, arylalkyl, arylcarbonyl, haloalkyl, haloalkylcarbonyl, heteroaryl, heterocycle, heterocyclealkenyl, heterocyclealkyl, heterocyclealkylcarbonyl, heterocyclecarbonyl, trihaloalkyl, trihaloalkylcarbonyl, hydroxyalkyl, and hydroxyalkylcarbonyl;

$R_q$ are each independently selected from the group consisting of hydrogen, alkyl;

$R_r$ and $R_s$ are each independently selected from the group consisting of hydrogen, alkyl, arylalkyl, hydroxyalkyl, heterocyclealkyl;

$R_t$ is selected from the group consisting of hydrogen, alkyl and HO—;

$R_u$ and $R_v$ are each individually selected from the group consisting of hydrogen, alkylcarbonyl, alkyl, alkylSO$_2$—, alkenyl, arylalkyl, $R_w$ is selected from the group consisting of hydrogen, alkylcarbonyl-NH-alkyl-NHC(O)-alkyl, alkyl, alkyl(alkyl)N-alkyl-NHC(O)-alkyl, hydroxyalkyl-NHC(O)-alkyl, heterocyclealkyl-NHC(O)-alkyl, heterocycle-NHC(O)-alkyl, heteroarylalkyl-NHC(O)-alkyl; and $R_x$ and $R_y$ are each individually selected fro the group consisting of hydrogen, alkyl and alkylsulfonyl.

10. The compound that is selected from the group consisting of 3-(3,5-dimethylphenyl)-4-hydroxy-6-oxo-6,7-dihydrothieno[2,3-b]pyridine-5-carbonitrile;
3-(4-fluorophenyl)-4-hydroxy-6-oxo-6,7-dihydrothieno[2,3-b]pyridine-5-carbonitrile;
3-(4-chlorophenyl)-4-hydroxy-6-oxo-6,7-dihydrothieno[2,3-b]pyridine-5-carbonitrile;
4-hydroxy-6-oxo-3-[4-(trifluoromethyl)phenyl]-6,7-dihydrothieno[2,3-b]pyridine-5-carbonitrile;
2-bromo-3-(4-chlorophenyl)-4-hydroxy-6-oxo-6,7-dihydrothieno[2,3-b]pyridine-5-carbonitrile;
2-bromo-4-hydroxy-6-oxo-3-[4-(trifluoromethyl)phenyl]-6,7-dihydrothieno[2,3-b]pyridine-5-carbonitrile;
3-(4-bromophenyl)-4-hydroxy-6-oxo-6,7-dihydrothieno[2,3-b]pyridine-5-carbonitrile;
2-bromo-3-(4-fluorophenyl)-4-hydroxy-6-oxo-6,7-dihydrothieno[2,3-b]pyridine-5-carbonitrile;
3-(4'-fluoro-1,1'-biphenyl-4-yl)-4-hydroxy-6-oxo-6,7-dihydrothieno[2,3-b]pyridine-5-carbonitrile;
4-hydroxy-6-oxo-3-[4'-(trifluoromethyl)-1,1'-biphenyl-4-yl]-6,7-dihydrothieno[2,3-b]pyridine-5-carbonitrile;
3-[4-(1,3-benzodioxol-5-yl)phenyl]-4-hydroxy-6-oxo-6,7-dihydrothieno[2,3-b]pyridine-5-carbonitrile;
2,5-dibromo-3-(4-chlorophenyl)-4-hydroxythieno[2,3-b]pyridin-6(7H)-one;
2,5-dichloro-3-(4-chlorophenyl)-4-hydroxythieno[2,3-b]pyridin-6(7H)-one;
4-hydroxy-3-(4-nitrophenyl)-6-oxo-6,7-dihydrothieno[2,3-b]pyridine-5-carbonitrile;
2-bromo-4-hydroxy-3-(4-nitrophenyl)-6-oxo-6,7-dihydrothieno[2,3-b]pyridine-5-carbonitrile;
3-(1,1'-biphenyl-4-yl)-4-hydroxy-6-oxo-6,7-dihydrothieno[2,3-b]pyridine-5-carbonitrile;
4-hydroxy-3-(2'-methyl-1,1'-biphenyl-4-yl)-6-oxo-6,7-dihydrothieno[2,3-b]pyridine-5-carbonitrile;
4-hydroxy-3-(3'-methyl-1,1'-biphenyl-4-yl)-6-oxo-6,7-dihydrothieno[2,3-b]pyridine-5-carbonitrile;
4-hydroxy-3-(2'-hydroxy-1,1'-biphenyl-4-yl)-6-oxo-6,7-dihydrothieno[2,3-b]pyridine-5-carbonitrile;
4-hydroxy-3-(3'-hydroxy-1,1'-biphenyl-4-yl)-6-oxo-6,7-dihydrothieno[2,3-b]pyridine-5-carbonitrile;
4-hydroxy-3-(2'-methoxy-1,1'-biphenyl-4-yl)-6-oxo-6,7-dihydrothieno[2,3-b]pyridine-5-carbonitrile;
4-hydroxy-3-(3'-methoxy-1,1'-biphenyl-4-yl)-6-oxo-6,7-dihydrothieno[2,3-b]pyridine-5-carbonitrile;
4-hydroxy-3-(4'-methoxy-1,1'-biphenyl-4-yl)-6-oxo-6,7-dihydrothieno[2,3-b]pyridine-5-carbonitrile;
3-(2'-fluoro-1,1'-biphenyl-4-yl)-4-hydroxy-6-oxo-6,7-dihydrothieno[2,3-b]pyridine-5-carbonitrile;
3-(3'-fluoro-1,1'-biphenyl-4-yl)-4-hydroxy-6-oxo-6,7-dihydrothieno[2,3-b]pyridine-5-carbonitrile;
3-(2'-chloro-1,1'-biphenyl-4-yl)-4-hydroxy-6-oxo-6,7-dihydrothieno[2,3-b]pyridine-5-carbonitrile;
3-(3'-chloro-1,1'-biphenyl-4-yl)-4-hydroxy-6-oxo-6,7-dihydrothieno[2,3-b]pyridine-5-carbonitrile;
3-(4'-chloro-1,1'-biphenyl-4-yl)-4-hydroxy-6-oxo-6,7-dihydrothieno[2,3-b]pyridine-5-carbonitrile;
3-(4'-cyano-1,1'-biphenyl-4-yl)-4-hydroxy-6-oxo-6,7-dihydrothieno[2,3-b]pyridine-5-carbonitrile;
3-(3'-acetyl-1,1'-biphenyl-4-yl)-4-hydroxy-6-oxo-6,7-dihydrothieno[2,3-b]pyridine-5-carbonitrile;
3-[4'-(dimethylamino)-1,1'-biphenyl-4-yl]-4-hydroxy-6-oxo-6,7-dihydrothieno[2,3-b]pyridine-5-carbonitrile;
4-hydroxy-6-oxo-3-(4'-phenoxy-1,1'-biphenyl-4-yl)-6,7-dihydrothieno[2,3-b]pyridine-5-carbonitrile;
3-(4'-acetyl-1,1'-biphenyl-4-yl)-4-hydroxy-6-oxo-6,7-dihydrothieno[2,3-b]pyridine-5-carbonitrile;
3-(2',3'-dimethyl-1,1'-biphenyl-4-yl)-4-hydroxy-6-oxo-6,7-dihydrothieno[2,3-b]pyridine-5-carbonitrile;
4-hydroxy-6-oxo-3-[4'-(trifluoromethoxy)-1,1'-biphenyl-4-yl]-6,7-dihydrothieno[2,3-b]pyridine-5-carbonitrile;
3-(3',4'-dimethyl-1,1'-biphenyl-4-yl)-4-hydroxy-6-oxo-6,7-dihydrothieno[2,3-b]pyridine-5-carbonitrile;
3-(2',3'-dichloro-1,1'-biphenyl-4-yl)-4-hydroxy-6-oxo-6,7-dihydrothieno[2,3-b]pyridine-5-carbonitrile;
3-(2',4'-dichloro-1,1'-biphenyl-4-yl)-4-hydroxy-6-oxo-6,7-dihydrothieno[2,3-b]pyridine-5-carbonitrile;
2-bromo-3-(4'-fluoro-1,1'-biphenyl-4-yl)-4-hydroxy-6-oxo-6,7-dihydrothieno[2,3-b]pyridine-5-carbonitrile;
3-(4-aminophenyl)-4-hydroxy-6-oxo-6,7-dihydrothieno[2,3-b]pyridine-5-carbonitrile;
2-chloro-4-hydroxy-6-oxo-3-[4-(trifluoromethyl)phenyl]-6,7-dihydrothieno[2,3-b]pyridine-5-carbonitrile;
4-hydroxy-3-(4'-hydroxy-1,1'-biphenyl-4-yl)-6-oxo-6,7-dihydrothieno[2,3-b]pyridine-5-carbonitrile;
3-(4'-acetyl-1,1'-biphenyl-4-yl)-2-bromo-4-hydroxy-6-oxo-6,7-dihydrothieno[2,3-b]pyridine-5-carbonitrile;
2-bromo-4-hydroxy-3-(2'-hydroxy-1,1'-biphenyl-4-yl)-6-oxo-6,7-dihydrothieno[2,3-b]pyridine-5-carbonitrile;
2-bromo-3-(4'-cyano-1,1'-biphenyl-4-yl)-4-hydroxy-6-oxo-6,7-dihydrothieno[2,3-b]pyridine-5-carbonitrile;
2-chloro-4-hydroxy-3-(2'-hydroxy-1,1'-biphenyl-4-yl)-6-oxo-6,7-dihydrothieno[2,3-b]pyridine-5-carbonitrile;
2-bromo-3-(5'-bromo-2'-hydroxy-1,1'-biphenyl-4-yl)-4-hydroxy-6-oxo-6,7-dihydrothieno[2,3-b]pyridine-5-carbonitrile;
4-hydroxy-3-[2'-(hydroxymethyl)-1,1'-biphenyl-4-yl]-6-oxo-6,7-dihydrothieno[2,3-b]pyridine-5-carbonitrile;
4-hydroxy-3-[4-(methoxymethoxy)phenyl]-6-oxo-6,7-dihydrothieno[2,3-b]pyridine-5-carbonitrile;
4-hydroxy-6-oxo-3-{2'-[({2-[4-(trifluoromethyl)phenyl]ethyl}amino)methyl]-1,1'-biphenyl-4-yl}-6,7-dihydrothieno[2,3-b]pyridine-5-carbonitrile;
4-hydroxy-3-[2'-({[2-(4-hydroxy-3,5-dimethoxyphenyl)ethyl]amino}methyl)-1,1'-biphenyl-4-yl]-6-oxo-6,7-dihydrothieno[2,3-b]pyridine-5-carbonitrile;
3-[4-(2-formylthien-3-yl)phenyl]-4-hydroxy-6-oxo-6,7-dihydrothieno[2,3-b]pyridine-5-carbonitrile;
3-(2'-amino-1,1'-biphenyl-4-yl)-4-hydroxy-6-oxo-6,7-dihydrothieno[2,3-b]pyridine-5-carbonitrile;
4-hydroxy-3-(4-hydroxyphenyl)-6-oxo-6,7-dihydrothieno[2,3-b]pyridine-5-carbonitrile;

2-bromo-3-(3-bromo-4-hydroxyphenyl)-4-hydroxy-6-oxo-6,7-dihydrothieno[2,3-b]pyridine-5-carbonitrile;
2-chloro-3-(2'-chloro-1,1'-biphenyl-4-yl)-4-hydroxy-6-oxo-6,7-dihydrothieno[2,3-b]pyridine-5-carbonitrile;
N-[4'-(2-chloro-5-cyano-4-hydroxy-6-oxo-6,7-dihydrothieno[2,3-b]pyridin-3-yl)-1,1'-biphenyl-3-yl]acetamide;
2-chloro-3-(4'-chloro-1,1'-biphenyl-4-yl)-4-hydroxy-6-oxo-6,7-dihydrothieno[2,3-b]pyridine-5-carbonitrile;
{[4'-(5-cyano-4-hydroxy-6-oxo-6,7-dihydrothieno[2,3-b]pyridin-3-yl)-1,1'-biphenyl-2-yl]oxy}acetic acid;
2-bromo-4-hydroxy-3-(4-hydroxyphenyl)-6-oxo-6,7-dihydrothieno[2,3-b]pyridine-5-carbonitrile;
2-bromo-3-(3,5-dibromo-4-hydroxyphenyl)-4-hydroxy-6-oxo-6,7-dihydrothieno[2,3-b]pyridine-5-carbonitrile;
3-(3-bromophenyl)-4-hydroxy-6-oxo-6,7-dihydrothieno[2,3-b]pyridine-5-carbonitrile;
2-chloro-4-hydroxy-3-(2'-methyl-1,1'-biphenyl-4-yl)-6-oxo-6,7-dihydrothieno[2,3-b]pyridine-5-carbonitrile;
2-chloro-4-hydroxy-3-(3'-hydroxy-1,1'-biphenyl-4-yl)-6-oxo-6,7-dihydrothieno[2,3-b]pyridine-5-carbonitrile;
3-{4-[bis(3,3-dimethylbutyl)amino]phenyl}-4-hydroxy-6-oxo-6,7-dihydrothieno[2,3-b]pyridine-5-carbonitrile;
2,5-dichloro-3-(3,5-dichloro-4-hydroxyphenyl)-4-hydroxythieno[2,3-b]pyridin-6(7H)-one;
3-(2',6'-dihydroxy-1,1'-biphenyl-4-yl)-4-hydroxy-6-oxo-6,7-dihydrothieno[2,3-b]pyridine-5-carbonitrile;
3-[5-(4-aminophenyl)thien-2-yl]-4-hydroxy-6-oxo-6,7-dihydrothieno[2,3-b]pyridine-5-carbonitrile;
N-{4-[5-(2-chloro-5-cyano-4-hydroxy-6-oxo-6,7-dihydrothieno[2,3-b]pyridin-3-yl)thien-2-yl]phenyl}methanesulfonamide;
2-bromo-3-(3,5-dibromo-4-hydroxyphenyl)-4-hydroxy-6-oxo-6,7-dihydrothieno[2,3-b]pyridine-5-carbonitrile;
3-(2',3'-dihydroxy-1,1'-biphenyl-4-yl)-4-hydroxy-6-oxo-6,7-dihydrothieno[2,3-b]pyridine-5-carbonitrile;
2,5-dibromo-3-(3,5-dibromo-4-hydroxyphenyl)-4-hydroxythieno[2,3-b]pyridin-6(7H)-one;
3-(2',4'-dihydroxy-1,1'-biphenyl-4-yl)-4-hydroxy-6-oxo-6,7-dihydrothieno[2,3-b]pyridine-5-carbonitrile;
N-{4-[5-(5-cyano-4-hydroxy-6-oxo-6,7-dihydrothieno[2,3-b]pyridin-3-yl)thien-2-yl]phenyl}methanesulfonamide;
4-hydroxy-3-[5-(4-hydroxyphenyl)thien-2-yl]-6-oxo-6,7-dihydrothieno[2,3-b]pyridine-5-carbonitrile;
2-chloro-3-[4-(2,3-dihydroxypropoxy)phenyl]-4-hydroxy-6-oxo-6,7-dihydrothieno[2,3-b]pyridine-5-carbonitrile;
4-[5-(5-cyano-4-hydroxy-6-oxo-6,7-dihydrothieno[2,3-b]pyridin-3-yl)thien-2-yl]benzenesulfonamide;
3-(2'-amino-1,1'-biphenyl-4-yl)-4-hydroxy-6-oxo-6,7-dihydrothieno[2,3-b]pyridine-5-carbonitrile;
4-hydroxy-6-oxo-3-(5-pyridin-4-ylthien-2-yl)-6,7-dihydrothieno[2,3-b]pyridine-5-carbonitrile;
2-chloro-4-hydroxy-3-[5-(4-hydroxyphenyl)thien-2-yl]-6-oxo-6,7-dihydrothieno[2,3-b]pyridine-5-carbonitrile;
4-hydroxy-3-{5-[4-(hydroxymethyl)phenyl]thien-2-yl}-6-oxo-6,7-dihydrothieno[2,3-b]pyridine-5-carbonitrile;
2-chloro-4-hydroxy-3-{4-[(1-hydroxycyclopent-3-en-1-yl)methoxy]phenyl}-6-oxo-6,7-dihydrothieno[2,3-b]pyridine-5-carbonitrile;
2-chloro-4-hydroxy-3-(4-hydroxyphenyl)-6-oxo-6,7-dihydrothieno[2,3-b]pyridine-5-carbonitrile;
4-hydroxy-3-{5-[4-(methylsulfonyl)phenyl]thien-2-yl}-6-oxo-6,7-dihydrothieno[2,3-b]pyridine-5-carbonitrile;
N-{4-[5-(5-cyano-4-hydroxy-6-oxo-6,7-dihydrothieno[2,3-b]pyridin-3-yl)thien-2-yl]phenyl}acetamide;
4-hydroxy-6-oxo-3-(5-phenylthien-2-yl)-6,7-dihydrothieno[2,3-b]pyridine-5-carbonitrile;
3-(2,2'-bithien-5-yl)-4-hydroxy-6-oxo-6,7-dihydrothieno[2,3-b]pyridine-5-carbonitrile;
3-(3'-fluoro-2'-hydroxy-1,1'-biphenyl-4-yl)-4-hydroxy-6-oxo-6,7-dihydrothieno[2,3-b]pyridine-5-carbonitrile;
3-[5-(2-aminophenyl)thien-2-yl]-4-hydroxy-6-oxo-6,7-dihydrothieno[2,3-b]pyridine-5-carbonitrile;
3-[5-(4-fluorophenyl)thien-2-yl]-4-hydroxy-6-oxo-6,7-dihydrothieno[2,3-b]pyridine-5-carbonitrile;
3-[5-(2,4-difluorophenyl)thien-2-yl]-4-hydroxy-6-oxo-6,7-dihydrothieno[2,3-b]pyridine-5-carbonitrile;
4-hydroxy-6-oxo-3-(4-thien-3-ylphenyl)-6,7-dihydrothieno[2,3-b]pyridine-5-carbonitrile;
4-hydroxy-3-[5-(3-methoxyprop-1-ynyl)-4-methylthien-2-yl]-6-oxo-6,7-dihydrothieno[2,3-b]pyridine-5-carbonitrile;
4-hydroxy-3-(4-hydroxyphenyl)-6-oxo-6,7-dihydrothieno[2,3-b]pyridine-5-carbonitrile;
2-bromo-3-(3-bromo-4-hydroxyphenyl)-4-hydroxy-6-oxo-6,7-dihydrothieno[2,3-b]pyridine-5-carbonitrile;
2,5-dichloro-4-hydroxy-3-(4-hydroxyphenyl)thieno[2,3-b]pyridin-6(7H)-one;
methyl 4-[5-(5-cyano-4-hydroxy-6-oxo-6,7-dihydrothieno[2,3-b]pyridin-3-yl)thien-2-yl]phenylcarbamate;
2-chloro-4-hydroxy-3-[4-(2-hydroxy-2-methylpropoxy)phenyl]-6-oxo-6,7-dihydrothieno[2,3-b]pyridine-5-carbonitrile;
2-chloro-4-hydroxy-3-{4-[(1-hydroxycyclopentyl)methoxy]phenyl}-6-oxo-6,7-dihydrothieno[2,3-b]pyridine-5-carbonitrile;
2-bromo-4-hydroxy-3-(4-hydroxyphenyl)-6-oxo-6,7-dihydrothieno[2,3-b]pyridine-5-carbonitrile;
2-chloro-4-hydroxy-3-[4-(hydroxymethyl)phenyl]-6-oxo-6,7-dihydrothieno[2,3-b]pyridine-5-carbonitrile;
4-hydroxy-3-[5-(4-methoxyphenyl)thien-2-yl]-6-oxo-6,7-dihydrothieno[2,3-b]pyridine-5-carbonitrile;
4-hydroxy-2-methyl-6-oxo-3-(phenylethynyl)-6,7-dihydrothieno[2,3-b]pyridine-5-carbonitrile;
2-chloro-3-{4-[(1-ethyl-4-hydroxypiperidin-4-yl)methoxy]phenyl}-4-hydroxy-6-oxo-6,7-dihydrothieno[2,3-b]pyridine-5-carbonitrile;
4-hydroxy-3-[5-(3-methoxyprop-1-ynyl)thien-2-yl]-6-oxo-6,7-dihydrothieno[2,3-b]pyridine-5-carbonitrile;
4-hydroxy-3-[5-(5-hydroxypent-1-ynyl)thien-2-yl]-6-oxo-6,7-dihydrothieno[2,3-b]pyridine-5-carbonitrile;
3-{4-[(1-acetyl-4-hydroxypiperidin-4-yl)methoxy]phenyl}-2-chloro-4-hydroxy-6-oxo-6,7-dihydrothieno[2,3-b]pyridine-5-carbonitrile;
2-bromo-4-hydroxy-3-[4-(4-hydroxybut-1-ynyl)phenyl]-6-oxo-6,7-dihydrothieno[2,3-b]pyridine-5-carbonitrile;
4-hydroxy-3-[5-(3-hydroxyprop-1-ynyl)thien-2-yl]-6-oxo-6,7-dihydrothieno[2,3-b]pyridine-5-carbonitrile;
2-chloro-4-hydroxy-3-{4-[(4-hydroxy-1-isobutylpiperidin-4-yl)methoxy]phenyl}-6-oxo-6,7-dihydrothieno[2,3-b]pyridine-5-carbonitrile;
4-hydroxy-3-{4-[(1E)-4-hydroxybut-1-enyl]phenyl}-6-oxo-6,7-dihydrothieno[2,3-b]pyridine-5-carbonitrile;
4-hydroxy-6-oxo-3-[5-(1,2,3,6-tetrahydropyridin-4-yl)thien-2-yl]-6,7-dihydrothieno[2,3-b]pyridine-5-carbonitrile;
4-hydroxy-6-oxo-3-(5-phenyl-4-pyridin-3-ylthien-2-yl)-6,7-dihydrothieno[2,3-b]pyridine-5-carbonitrile;
3-[4-(allyloxy)phenyl]-2-chloro-4-hydroxy-6-oxo-6,7-dihydrothieno[2,3-b]pyridine-5-carbonitrile;

7-[4-(5-cyano-4-hydroxy-6-oxo-6,7-dihydrothieno[2,3-b]pyridin-3-yl)phenyl]-N,N-diethylhept-6-ynamide;

4-hydroxy-6-oxo-3-[5-(2-oxo-2,3-dihydro-1H-indol-5-yl)thien-2-yl]-6,7-dihydrothieno[2,3-b]pyridine-5-carbonitrile;

3-[5-(4-cyanophenyl)thien-2-yl]-4-hydroxy-6-oxo-6,7-dihydrothieno[2,3-b]pyridine-5-carbonitrile;

2-chloro-3-{4-[(1-cyclopropyl-4-hydroxypiperidin-4-yl)methoxy]phenyl}-4-hydroxy-6-oxo-6,7-dihydrothieno[2,3-b]pyridine-5-carbonitrile;

3-(4'-fluoro-2'-hydroxy-1,1'-biphenyl-4-yl)-4-hydroxy-6-oxo-6,7-dihydrothieno[2,3-b]pyridine-5-carbonitrile;

4-hydroxy-3-[4-(methoxymethoxy)phenyl]-6-oxo-6,7-dihydrothieno[2,3-b]pyridine-5-carbonitrile;

4-[5-(5-cyano-4-hydroxy-6-oxo-6,7-dihydrothieno[2,3-b]pyridin-3-yl)thien-2-yl]benzoic acid;

3-[5-(3-aminophenyl)thien-2-yl]-4-hydroxy-6-oxo-6,7-dihydrothieno[2,3-b]pyridine-5-carbonitrile;

4-hydroxy-3-(2'-hydroxy-1,1'-biphenyl-4-yl)thieno[2,3-b]pyridin-6(7H)-one;

methyl 4-(2-chloro-5-cyano-4-hydroxy-6-oxo-6,7-dihydrothieno[2,3-b]pyridin-3-yl)benzoate;

2-chloro-4-hydroxy-6-oxo-3-(2-phenylcyclopropyl)-6,7-dihydrothieno[2,3-b]pyridine-5-carbonitrile;

3-[5-(4-acetylphenyl)thien-2-yl]-4-hydroxy-6-oxo-6,7-dihydrothieno[2,3-b]pyridine-5-carbonitrile;

4-hydroxy-6-oxo-3-(4-vinylphenyl)-6,7-dihydrothieno[2,3-b]pyridine-5-carbonitrile;

3-[5-(2,4-dihydroxyphenyl)thien-2-yl]-4-hydroxy-6-oxo-6,7-dihydrothieno[2,3-b]pyridine-5-carbonitrile;

3-[3-(allyloxy)phenyl]-2-bromo-4-hydroxy-6-oxo-6,7-dihydrothieno[2,3-b]pyridine-5-carbonitrile;

3-{5-[3-(dimethylamino)prop-1-ynyl]thien-2-yl}-4-hydroxy-6-oxo-6,7-dihydrothieno[2,3-b]pyridine-5-carbonitrile;

4-hydroxy-3-[2'-(hydroxymethyl)-1,1'-biphenyl-4-yl]-6-oxo-6,7-dihydrothieno[2,3-b]pyridine-5-carbonitrile;

3-(4-bromophenyl)-2-chloro-4-hydroxy-6-oxo-6,7-dihydrothieno[2,3-b]pyridine-5-carbonitrile;

4-hydroxy-3-[4-(4-hydroxybut-1-ynyl)phenyl]-6-oxo-6,7-dihydrothieno[2,3-b]pyridine-5-carbonitrile;

4-hydroxy-6-oxo-3-(5-pyridin-2-ylthien-2-yl)-6,7-dihydrothieno[2,3-b]pyridine-5-carbonitrile;

4-hydroxy-3-(2'-hydroxy-1,1'-biphenyl-4-yl)-6-oxo-6,7-dihydrothieno[2,3-b]pyridine-5-carbaldehyde oxime;

3-[3-(allyloxy)phenyl]-2-chloro-4-hydroxy-6-oxo-6,7-dihydrothieno[2,3-b]pyridine-5-carbonitrile;

3-(5'-bromo-2',4'-dihydroxy-1,1'-biphenyl-4-yl)-4-hydroxy-6-oxo-6,7-dihydrothieno[2,3-b]pyridine-5-carbonitrile;

4-hydroxy-3-(2'-hydroxy-4',6'-dimethyl-1,1'-biphenyl-4-yl)-6-oxo-6,7-dihydrothieno[2,3-b]pyridine-5-carbonitrile;

N-{4-[5-(5-cyano-4-hydroxy-6-oxo-6,7-dihydrothieno[2,3-b]pyridin-3-yl)thien-2-yl]-2-fluorophenyl}acetamide;

2-[({(1E)-[4-(5-cyano-4-hydroxy-6-oxo-6,7-dihydrothieno[2,3-b]pyridin-3-yl)phenyl]methylene}amino)oxy]-N-(pyridin-2-ylmethyl)acetamide;

2-chloro-4-hydroxy-3-(5-methyl-2-furyl)-6,7-dihydrothieno[2,3-b]pyridine-5-carbonitrile;

4-hydroxy-3-(3-hydroxyphenyl)-6-oxo-6,7-dihydrothieno[2,3-b]pyridine-5-carbonitrile;

2-chloro-3-{4-[(1-cyclopentyl-4-hydroxypiperidin-4-yl)methoxy]phenyl}-4-hydroxy-6-oxo-6,7-dihydrothieno[2,3-b]pyridine-5-carbonitrile;

3-(2',5'-dihydroxy-1,1'-biphenyl-4-yl)-4-hydroxy-6-oxo-6,7-dihydrothieno[2,3-b]pyridine-5-carbonitrile;

3-(2'-formyl-1,1'-biphenyl-4-yl)-4-hydroxy-6-oxo-6,7-dihydrothieno[2,3-b]pyridine-5-carbonitrile;

3-[4-(2,3-dihydroxypropoxy)phenyl]-4-hydroxy-2-methyl-6-oxo-6,7-dihydrothieno[2,3-b]pyridine-5-carbonitrile;

3-[4-(allyloxy)phenyl]-2-bromo-4-hydroxy-6-oxo-6,7-dihydrothieno[2,3-b]pyridine-5-carbonitrile;

3-[5-(1-acetyl-1,2,3,6-tetrahydropyridin-4-yl)thien-2-yl]-4-hydroxy-6-oxo-6,7-dihydrothieno[2,3-b]pyridine-5-carbonitrile;

3-{5-[4-(allyloxy)phenyl]thien-2-yl}-4-hydroxy-6-oxo-6,7-dihydrothieno[2,3-b]pyridine-5-carbonitrile;

7-[3-(5-cyano-4-hydroxy-6-oxo-6,7-dihydrothieno[2,3-b]pyridin-3-yl)phenyl]hept-6-ynoic acid;

4-hydroxy-3-[5-(3-methoxyprop-1-ynyl)-4-vinylthien-2-yl]-6-oxo-6,7-dihydrothieno[2,3-b]pyridine-5-carbonitrile;

3-(2'-chloro-6'-hydroxy-1,1'-biphenyl-4-yl)-4-hydroxy-6-oxo-6,7-dihydrothieno[2,3-b]pyridine-5-carbonitrile;

2-chloro-4-hydroxy-3-(3'-hydroxy-1,1'-biphenyl-4-yl)-6-oxo-6,7-dihydrothieno[2,3-b]pyridine-5-carbonitrile;

2-chloro-3-{4-[(1-cyclobutyl-4-hydroxypiperidin-4-yl)methoxy]phenyl}-4-hydroxy-6-oxo-6,7-dihydrothieno[2,3-b]pyridine-5-carbonitrile;

7-[4-(5-cyano-4-hydroxy-6-oxo-6,7-dihydrothieno[2,3-b]pyridin-3-yl)phenyl]hept-6-ynoic acid;

3-(3,5-dichloro-4-hydroxyphenyl)-4-hydroxy-6-oxo-6,7-dihydrothieno[2,3-b]pyridine-5-carbonitrile;

2-[({(1E)-[4-(5-cyano-4-hydroxy-6-oxo-6,7-dihydrothieno[2,3-b]pyridin-3-yl)phenyl]methylene}amino)oxy]-N-[(2S)-2,3-dihydroxypropyl]acetamide;

4-hydroxy-6-oxo-3-[4-(1H-pyrazol-3-yl)phenyl]-6,7-dihydrothieno[2,3-b]pyridine-5-carbonitrile;

3-{5-[4-(2,3-dihydroxypropoxy)phenyl]thien-2-yl}-4-hydroxy-6-oxo-6,7-dihydrothieno[2,3-b]pyridine-5-carbonitrile;

2-bromo-4-hydroxy-3-[4-(5-hydroxypent-1-ynyl)phenyl]-6-oxo-6,7-dihydrothieno[2,3-b]pyridine-5-carbonitrile;

4-hydroxy-6-oxo-3-(5,6,7,8-tetrahydronaphthalen-2-yl)-6,7-dihydrothieno[2,3-b]pyridine-5-carbonitrile;

2-[({(1E)-[4-(5-cyano-4-hydroxy-6-oxo-6,7-dihydrothieno[2,3-b]pyridin-3-yl)phenyl]methylene}amino)oxy]-N-[2-(4-methylpiperazin-1-yl)ethyl]acetamide;

N-{3-chloro-4-[5-(5-cyano-4-hydroxy-6-oxo-6,7-dihydrothieno[2,3-b]pyridin-3-yl)thien-2-yl]phenyl}acetamide;

4-hydroxy-3-[4-(5-hydroxypent-1-ynyl)phenyl]-6-oxo-6,7-dihydrothieno[2,3-b]pyridine-5-carbonitrile;

3-[4-bromo-5-(3-methoxyprop-1-ynyl)thien-2-yl]-4-hydroxy-6-oxo-6,7-dihydrothieno[2,3-b]pyridine-5-carbonitrile;

2-[4-(2-chloro-5-cyano-4-hydroxy-6-oxo-6,7-dihydrothieno[2,3-b]pyridin-3-yl)phenoxy]-N-(3-hydroxypropyl)acetamide;

2-chloro-3-[4-(cyanomethoxy)phenyl]-4-hydroxy-6-oxo-6,7-dihydrothieno[2,3-b]pyridine-5-carbonitrile;

4-hydroxy-3-[4-(3-methoxyprop-1-ynyl)phenyl]-6-oxo-6,7-dihydrothieno[2,3-b]pyridine-5-carbonitrile;

4-hydroxy-6-oxo-3-{4-[(1E)-4-pyrrolidin-1-ylbut-1-enyl]phenyl}-6,7-dihydrothieno[2,3-b]pyridine-5-carbonitrile;

tert-butyl 4-[5-(5-cyano-4-hydroxy-6-oxo-6,7-dihydrothieno[2,3-b]pyridin-3-yl)thien-2-yl]phenylcarbamate;
4-hydroxy-3-[5-(4-hydroxyphenyl)-4-methylthien-2-yl]-6-oxo-6,7-dihydrothieno[2,3-b]pyridine-5-carbonitrile;
2-chloro-3-[4-(diallylamino)phenyl]-4-hydroxy-6-oxo-6,7-dihydrothieno[2,3-b]pyridine-5-carbonitrile;
4-hydroxy-3-[5-(1H-indol-5-yl)thien-2-yl]-6-oxo-6,7-dihydrothieno[2,3-b]pyridine-5-carbonitrile;
2-bromo-3-(5'-bromo-2'-hydroxy-1,1'-biphenyl-4-yl)-4-hydroxy-6-oxo-6,7-dihydrothieno[2,3-b]pyridine-5-carbonitrile;
3-[4-(5-cyanopent-1-ynyl)phenyl]-4-hydroxy-6-oxo-6,7-dihydrothieno[2,3-b]pyridine-5-carbonitrile;
2-[4-(2-chloro-5-cyano-4-hydroxy-6-oxo-6,7-dihydrothieno[2,3-b]pyridin-3-yl)phenoxy]acetamide;
2-[({(1E)-[4-(5-cyano-4-hydroxy-6-oxo-6,7-dihydrothieno[2,3-b]pyridin-3-yl)phenyl]methylene}amino)oxy]-N-(2-pyridin-2-ylethyl)acetamide;
2-chloro-4-hydroxy-3-{4-[(4-hydroxypiperidin-4-yl)methoxy]phenyl}-6-oxo-6,7-dihydrothieno[2,3-b]pyridine-5-carbonitrile;
3-(2'-amino-1,1'-biphenyl-4-yl)-2-chloro-4-hydroxy-6-oxo-6,7-dihydrothieno[2,3-b]pyridine-5-carbonitrile;
4-hydroxy-6-oxo-3-(1,2,3,4-tetrahydronaphthalen-2-yl)-6,7-dihydrothieno[2,3-b]pyridine-5-carbonitrile;
3-(5-bromothien-2-yl)-4-hydroxy-6-oxo-6,7-dihydrothieno[2,3-b]pyridine-5-carbonitrile;
4-hydroxy-3-[5-(4-nitrophenyl)thien-2-yl]-6-oxo-6,7-dihydrothieno[2,3-b]pyridine-5-carbonitrile;
6-[4-(5-cyano-4-hydroxy-6-oxo-6,7-dihydrothieno[2,3-b]pyridin-3-yl)phenyl]hex-5-ynoic acid;
3-[4-(4-cyanobut-1-ynyl)phenyl]-4-hydroxy-6-oxo-6,7-dihydrothieno[2,3-b]pyridine-5-carbonitrile;
2-[({(1E)-[4-(5-cyano-4-hydroxy-6-oxo-6,7-dihydrothieno[2,3-b]pyridin-3-yl)phenyl]methylene}amino)oxy]-N-(pyridin-3-ylmethyl)acetamide;
3-(2,3-dihydro-1,4-benzodioxin-6-yl)-4-hydroxy-6-oxo-6,7-dihydrothieno[2,3-b]pyridine-5-carbonitrile;
N-{4-[5-(5-cyano-4-hydroxy-6-oxo-6,7-dihydrothieno[2,3-b]pyridin-3-yl)-2-phenylthien-3-yl]phenyl}methanesulfonamide;
4-hydroxy-6-oxo-3-(5-vinylthien-2-yl)-6,7-dihydrothieno[2,3-b]pyridine-5-carbonitrile;
4-hydroxy-6-oxo-3-(5-pyrazin-2-ylthien-2-yl)-6,7-dihydrothieno[2,3-b]pyridine-5-carbonitrile;
2-[({(1E)-[4-(5-cyano-4-hydroxy-6-oxo-6,7-dihydrothieno[2,3-b]pyridin-3-yl)phenyl]methylene}amino)oxy]-N-[(1R)-1-(hydroxymethyl)-3-methylbutyl]acetamide;
3-[4-(2-formylthien-3-yl)phenyl]-4-hydroxy-6-oxo-6,7-dihydrothieno[2,3-b]pyridine-5-carbonitrile;
4-hydroxy-3-{4-[(E)-({2-[(2R)-2-(hydroxymethyl)pyrrolidin-1-yl]-2-oxoethoxy}imino)methyl]phenyl}-6-oxo-6,7-dihydrothieno[2,3-b]pyridine-5-carbonitrile;
3-(2,3-dihydro-1H-inden-5-yl)-4-hydroxy-6-oxo-6,7-dihydrothieno[2,3-b]pyridine-5-carbonitrile;
4-hydroxy-3-[5-(4-hydroxybut-1-ynyl)thien-2-yl]-6-oxo-6,7-dihydrothieno[2,3-b]pyridine-5-carbonitrile;
2-[({(1E)-[4-(5-cyano-4-hydroxy-6-oxo-6,7-dihydrothieno[2,3-b]pyridin-3-yl)phenyl]methylene}amino)oxy]-N-[3-(dimethylamino)propyl]acetamide;
2-[4-(2-chloro-5-cyano-4-hydroxy-6-oxo-6,7-dihydrothieno[2,3-b]pyridin-3-yl)phenoxy]-N-methylacetamide;
3-[4-(allyloxy)phenyl]-4-hydroxy-6-oxo-6,7-dihydrothieno[2,3-b]pyridine-5-carbonitrile;
{[4'-(5-cyano-4-hydroxy-6-oxo-6,7-dihydrothieno[2,3-b]pyridin-3-yl)-1,1'-biphenyl-2-yl]oxy}acetic acid;
4-hydroxy-3-(4-methylthien-2-yl)-6-oxo-6,7-dihydrothieno[2,3-b]pyridine-5-carbonitrile;
N-{4-[5-(5-cyano-4-hydroxy-6-oxo-6,7-dihydrothieno[2,3-b]pyridin-3-yl)-3-methylthien-2-yl]phenyl}methanesulfonamide;
4-hydroxy-3-[4-(3-hydroxy-3-methylbut-1-ynyl)phenyl]-6-oxo-6,7-dihydrothieno[2,3-b]pyridine-5-carbonitrile;
N-[2-(acetylamino)ethyl]-2-[({(1E)-[4-(5-cyano-4-hydroxy-6-oxo-6,7-dihydrothieno[2,3-b]pyridin-3-yl)phenyl]methylene}amino)oxy]acetamide;
2-[({(1E)-[4-(5-cyano-4-hydroxy-6-oxo-6,7-dihydrothieno[2,3-b]pyridin-3-yl)phenyl]methylene}amino)oxy]-N-(pyrimidin-4-ylmethyl)acetamide;
4-hydroxy-3-(5-iodo-4-methylthien-2-yl)-6-oxo-6,7-dihydrothieno[2,3-b]pyridine-5-carbonitrile;
5-(5-cyano-4-hydroxy-6-oxo-6,7-dihydrothieno[2,3-b]pyridin-3-yl)-N-[2-(dimethylamino)ethyl]thiophene-2-carboxamide;
4-hydroxy-3-{4-[3-(methylamino)prop-1-ynyl]phenyl}-6-oxo-6,7-dihydrothieno[2,3-b]pyridine-5-carbonitrile;
2-[({(1E)-[4-(5-cyano-4-hydroxy-6-oxo-6,7-dihydrothieno[2,3-b]pyridin-3-yl)phenyl]methylene}amino)oxy]-N-[3-(1H-imidazol-1-yl)propyl]acetamide;
3-{5-[(1E)-N-ethoxyethanimidoyl]thien-2-yl}-4-hydroxy-6-oxo-6,7-dihydrothieno[2,3-b]pyridine-5-carbonitrile;
4-hydroxy-6-oxo-3-(5-pyridin-3-ylthien-2-yl)-6,7-dihydrothieno[2,3-b]pyridine-5-carbonitrile;
7-(5-cyano-4-hydroxy-6-oxo-3-phenyl-6,7-dihydrothieno[2,3-b]pyridin-2-yl)hept-6-ynoic acid;
3-[4-(allyloxy)phenyl]-4-hydroxy-2-methyl-6-oxo-6,7-dihydrothieno[2,3-b]pyridine-5-carbonitrile;
2-[4-(2-chloro-5-cyano-4-hydroxy-6-oxo-6,7-dihydrothieno[2,3-b]pyridin-3-yl)phenoxy]-N-[3-(2-oxopyrrolidin-1-yl)propyl]acetamide;
4-hydroxy-3-[4-(4-hydroxyphenyl)-5-phenylthien-2-yl]-6-oxo-6,7-dihydrothieno[2,3-b]pyridine-5-carbonitrile;
3-(3,5-dibromo-4-hydroxyphenyl)-4-hydroxy-6-oxo-6,7-dihydrothieno[2,3-b]pyridine-5-carbonitrile;
2-[({(1E)-[4-(5-cyano-4-hydroxy-6-oxo-6,7-dihydrothieno[2,3-b]pyridin-3-yl)phenyl]methylene}amino)oxy]-N-[2-(1-methylpyrrolidin-2-yl)ethyl]acetamide;
4-hydroxy-6-oxo-3-{4-[3-(tetrahydrofuran-3-yloxy)prop-1-ynyl]phenyl}-6,7-dihydrothieno[2,3-b]pyridine-5-carbonitrile;
2-[4-(2-chloro-5-cyano-4-hydroxy-6-oxo-6,7-dihydrothieno[2,3-b]pyridin-3-yl)phenoxy]-N-[3-(1H-imidazol-1-yl)propyl]acetamide;
3-(1,3-benzodioxol-5-yl)-4-hydroxy-6-oxo-6,7-dihydrothieno[2,3-b]pyridine-5-carbonitrile;
5-ethanimidoyl-4-hydroxy-3-(2'-hydroxy-1,1'-biphenyl-4-yl)thieno[2,3-b]pyridin-6(7H)-one;
4-hydroxy-3-{5-[(1E)-N-hydroxyethanimidoyl]thien-2-yl}-6-oxo-6,7-dihydrothieno[2,3-b]pyridine-5-carbonitrile;
4-hydroxy-3-(3-methyl-1-benzothien-2-yl)-6-oxo-6,7-dihydrothieno[2,3-b]pyridine-5-carbonitrile;

4-hydroxy-6-oxo-3-[(E)-2-phenylvinyl]-6,7-dihydrothieno[2,3-b]pyridine-5-carbonitrile;
4-hydroxy-6-oxo-3-(phenylethynyl)-6,7-dihydrothieno[2,3-b]pyridine-5-carbonitrile;
N-{3-[4-(5-cyano-4-hydroxy-6-oxo-6,7-dihydrothieno[2,3-b]pyridin-3-yl)phenyl]prop-2-ynyl}methanesulfonamide;
4-hydroxy-3-[4-(4-hydroxybutyl)phenyl]-6-oxo-6,7-dihydrothieno[2,3-b]pyridine-5-carbonitrile;
3-[4-(4-azidobut-1-ynyl)phenyl]-4-hydroxy-6-oxo-6,7-dihydrothieno[2,3-b]pyridine-5-carbonitrile;
4-hydroxy-3-[4-(5-hydroxypentyl)phenyl]-6-oxo-6,7-dihydrothieno[2,3-b]pyridine-5-carbonitrile;
ethyl 4-hydroxy-3-(2'-hydroxy-1,1'-biphenyl-4-yl)-6-oxo-6,7-dihydrothieno[2,3-b]pyridine-5-carboxylate; and
3-(2'-fluoro-6'-hydroxy-1,1'-biphenyl-4-yl)-4-hydroxy-6-oxo-6,7-dihydrothieno[2,3-b]pyridine-5-carbonitrile.

11. A pharmaceutical composition comprising a therapeutically effective amount of a compound of formula (I) of claim 1 in combination with a pharmaceutically suitable carrier.

12. A pharmaceutical composition comprising a therapeutically effective amount of a compound of formula (II) of claim 6 in combination with a pharmaceutically suitable carrier.

13. A method of treating diabetes mellitis in a mammal, comprising administering to said mammal in need thereof a therapeutically effective amount of a compound of formula (I) of claim 1.

14. A method of treating diabetes mellitis in a mammal, comprising administration to mammal in need thereof a therapeutically effective amount of a compound of formula (II) of claim 6.

* * * * *